US012780852B2

(12) United States Patent
Chang et al.

(10) Patent No.: US 12,780,852 B2
(45) Date of Patent: Nov. 3, 2026

(54) PROCESS OF PREPARING HIV CAPSID INHIBITOR

(71) Applicant: Gilead Sciences, Inc., Foster City, CA (US)

(72) Inventors: Yueh Hwa S. Chang, Alberta (CA); Jason A. Davy, Alberta (CA); Maria M. Esanu, Alberta (CA); Julie Farand, San Mateo, CA (US); Karan S. Gandhi, Alberta (CA); Tezcan Guney, Foster City, CA (US); Huy V. Huynh, Alberta (CA); Darryl Kato, San Francisco, CA (US); Youri Kim, Edmonton (CA); Lennie J.K. Lin, Alberta (CA); Yu-Hsuan Liu, Alberta (CA); James B.C. Mack, San Mateo, CA (US); Jaspal S. Phull, Alberta (CA); Ho-Yan Sun, Alberta (CA); Tram T. Truong, Sherwood Park (CA); Sergiy Vshyvenko, Alberta (CA); Lihong Wang, Edmonton (CA); Tao Wu, Edmonton (CA); Di Wu, Alberta (CA); Yao Zou, Alberta (CA)

(73) Assignee: Gilead Sciences, Inc., Foster City, CA (US)

( * ) Notice: Subject to any disclaimer, the term of this patent is extended or adjusted under 35 U.S.C. 154(b) by 280 days.

(21) Appl. No.: 18/678,775

(22) Filed: May 30, 2024

(65) Prior Publication Data

US 2025/0011353 A1 Jan. 9, 2025

Related U.S. Application Data

(60) Provisional application No. 63/505,320, filed on May 31, 2023.

(51) Int. Cl.
*C07F 9/6558* (2006.01)
*B01J 31/22* (2006.01)
*B01J 31/24* (2006.01)
*C07D 311/18* (2006.01)
*C07F 5/02* (2006.01)
*C07F 9/06* (2006.01)

(52) U.S. Cl.
CPC ....... *C07F 9/65583* (2013.01); *B01J 31/2208* (2013.01); *B01J 31/2291* (2013.01); *B01J 31/2404* (2013.01); *C07D 311/18* (2013.01); *C07F 5/027* (2013.01); *C07F 9/062* (2013.01); *B01J 2231/4211* (2013.01); *B01J 2531/004* (2013.01); *B01J 2531/824* (2013.01)

(58) Field of Classification Search
None
See application file for complete search history.

(56) References Cited

U.S. PATENT DOCUMENTS

| | | | |
|---|---|---|---|
| 9,540,343 | B2 | 1/2017 | Bondy et al. |
| 9,944,619 | B2 | 4/2018 | Bondy et al. |
| 9,951,043 | B2 | 4/2018 | Brizgys et al. |
| 10,071,985 | B2 | 9/2018 | Graupe et al. |
| 10,294,234 | B2 | 5/2019 | Bacon et al. |
| 10,370,358 | B2 | 8/2019 | Bondy et al. |
| 10,654,827 | B2 | 5/2020 | Graupe et al. |
| 10,696,657 | B2 | 6/2020 | Vandehey et al. |
| 10,752,636 | B2 | 8/2020 | Bacon et al. |
| 10,836,746 | B2 | 11/2020 | Brizgys et al. |
| 10,849,892 | B2 | 12/2020 | Houston et al. |
| 11,034,668 | B2 | 6/2021 | Bondy et al. |
| 11,078,208 | B1 | 8/2021 | Bacon et al. |
| 11,117,886 | B2 | 9/2021 | Vandehey et al. |
| 11,266,638 | B2 | 3/2022 | Houston et al. |
| 11,267,799 | B2 | 3/2022 | Shi |
| 11,267,801 | B2 | 3/2022 | Brizgys et al. |
| 11,680,064 | B2 | 6/2023 | Chou et al. |
| 11,753,399 | B2 | 9/2023 | Brizgys et al. |
| 11,760,746 | B2 | 9/2023 | Dhar et al. |
| 11,787,825 | B2 | 10/2023 | Farand et al. |
| 11,807,625 | B2 | 11/2023 | Bekerman et al. |
| 11,833,143 | B2 | 12/2023 | Houston et al. |
| 11,845,739 | B2 | 12/2023 | Shi |
| 11,944,611 | B2 | 4/2024 | Bauer et al. |
| 11,993,583 | B2 | 5/2024 | Graupe et al. |
| 12,077,537 | B2 | 9/2024 | Chou et al. |
| 12,084,455 | B2 | 9/2024 | Bacon et al. |
| 12,084,467 | B2 | 9/2024 | Du et al. |
| 2007/0083045 | A1 | 4/2007 | Di Francesco et al. |
| 2014/0142085 | A1 | 5/2014 | Bondy et al. |
| 2014/0303164 | A1 | 10/2014 | Brizgys et al. |
| 2015/0366872 | A1 | 12/2015 | Carra et al. |
| 2016/0108030 | A1 | 4/2016 | Brizgys et al. |
| 2017/0137405 | A1 | 5/2017 | Bondy et al. |

(Continued)

FOREIGN PATENT DOCUMENTS

| | | |
|---|---|---|
| WO | WO 2005123680 | 12/2005 |
| WO | WO 2008011117 | 1/2008 |

(Continued)

OTHER PUBLICATIONS

[No Author], "Highlights of Prescribing Information: SUNLENCA," Gilead Sciences, Dec. 2022, 29 pages.

(Continued)

*Primary Examiner* — Joseph R Kosack
(74) *Attorney, Agent, or Firm* — Fish & Richardson P.C.

(57) ABSTRACT

The present disclosure relates generally to processes for preparing a compound useful in the prevention or treatment of a Retroviridae viral infection, including an infection caused by the human immunodeficiency virus (HIV).

26 Claims, No Drawings

(56) References Cited

U.S. PATENT DOCUMENTS

| | | | |
|---|---|---|---|
| 2018/0051005 | A1 | 2/2018 | Graupe et al. |
| 2018/0194746 | A1 | 7/2018 | Bondy et al. |
| 2018/0258097 | A1 | 9/2018 | Bacon et al. |
| 2018/0273508 | A1 | 9/2018 | Brizgys et al. |
| 2018/0370950 | A1 | 12/2018 | Graupe et al. |
| 2019/0083478 | A1 | 3/2019 | Houston et al. |
| 2019/0084963 | A1 | 3/2019 | Shi |
| 2019/0300505 | A1 | 10/2019 | Vandehey et al. |
| 2019/0308983 | A1 | 10/2019 | Bacon et al. |
| 2019/0345136 | A1 | 11/2019 | Brizgys et al. |
| 2019/0375726 | A1 | 12/2019 | Bondy et al. |
| 2020/0038389 | A1 | 2/2020 | Bauer et al. |
| 2020/0262815 | A1 | 8/2020 | Graupe et al. |
| 2020/0369647 | A1 | 11/2020 | Vandehey et al. |
| 2020/0397772 | A1 | 12/2020 | Houston et al. |
| 2021/0009555 | A1 | 1/2021 | Brizgys et al. |
| 2021/0171498 | A1 | 6/2021 | Brizgys et al. |
| 2021/0188815 | A1 | 6/2021 | Bekerman et al. |
| 2021/0393631 | A1 | 12/2021 | Bekerman et al. |
| 2022/0009904 | A1 | 1/2022 | Dhar et al. |
| 2022/0249460 | A1 | 8/2022 | Houston et al. |
| 2022/0251069 | A1 | 8/2022 | Shi |
| 2022/0267302 | A1 | 8/2022 | Brizgys et al. |
| 2023/0012449 | A1 | 1/2023 | Bondy et al. |
| 2023/0027055 | A1 | 1/2023 | Bacon et al. |
| 2023/0038823 | A1 | 2/2023 | Chou et al. |
| 2023/0203069 | A1 | 6/2023 | Farand et al. |
| 2023/0203071 | A1 | 6/2023 | Du et al. |
| 2023/0212148 | A1 | 7/2023 | Brizgys et al. |
| 2023/0312567 | A1 | 10/2023 | Chou et al. |
| 2024/0034724 | A1 | 2/2024 | Meng et al. |
| 2024/0051941 | A1 | 2/2024 | Bekerman et al. |
| 2024/0067629 | A1 | 2/2024 | Brizgys et al. |
| 2024/0101533 | A1 | 3/2024 | Wagner et al. |
| 2024/0132527 | A1 | 4/2024 | Farand et al. |
| 2024/0245669 | A1 | 7/2024 | Houston et al. |
| 2024/0254104 | A1 | 8/2024 | Shi |

FOREIGN PATENT DOCUMENTS

| | | |
|---|---|---|
| WO | WO 2013006792 | 1/2013 |
| WO | WO 2014134566 | 9/2014 |
| WO | WO 2015196116 | 12/2015 |
| WO | WO 2016033243 | 3/2016 |
| WO | WO 2017007689 | 1/2017 |
| WO | WO 2018035359 | 2/2018 |
| WO | WO 2018145021 | 8/2018 |
| WO | WO 2018203235 | 11/2018 |
| WO | WO 2019035904 | 2/2019 |
| WO | WO 2019035973 | 2/2019 |
| WO | WO 2019161017 | 8/2019 |
| WO | WO 2019161280 | 8/2019 |
| WO | WO 2020018459 | 1/2020 |
| WO | WO 2020061163 | 3/2020 |
| WO | WO 2021108544 | 6/2021 |
| WO | WO 2021262990 | 12/2021 |
| WO | WO 2013006738 | 1/2023 |
| WO | WO 2023102239 | 6/2023 |
| WO | WO 2023102523 | 6/2023 |
| WO | WO 2023102529 | 6/2023 |
| WO | WO 2024006982 | 1/2024 |

OTHER PUBLICATIONS

[No Author], "Sunlenca (lenacapavir) Administration Outside the Dosing Window," Gilead Sciences, Aug. 11, 2023, 7 pages.

aidsmap.com [online], "Oral lenacapavir can bridge gaps if injections must be missed," Jul. 27, 2023, retrieved on Jun. 24, 2024, retrieved from URL<https://www.aidsmap.com/news/jul-2023/oral-lenacapavir-can-bridge-gaps-if-injections-must-be-missed>, 6 pages.

Anonymous, "Gilead Announces Phase 3 Results for Investigational Fixed-Dose Combination of Bictegravir, Emtricitabine, and Tenofovir Alafenamide for Treatment of HIV," Conference Reports for NATAP, IAS 2014: Conference on HIV Pathogenesis Treatment and Prevention, 2017, retrieved on Jun. 9, 2021, retrieved from URL <"http://www.natap.org/2017/IAS/IAS_04.htm">, 3 pages.

Bernice et al., "Novel and Investigational HIV Therapies for Treatment and Prevention: Focus on Cabotegravir, Islatravir, and Lenacapavir," Current Infections Disease Reports, May 23, 2022, 24(7):89-96.

Cihlar et al., "Suppression of HIV-1 Protease Inhibitor Resistance by Phosphonemediated Solvent Anchoring," Journal of Molecular Biology, 2006, 363(3):635-647.

ClinicalTrials.gov [online], "A Study of GS-5423 and GS-2872 in Combination with Capsid Inhibitor Lenacapavir in Virologically Suppressed Adults with HIV-1 Infection," NCT05729568, Feb. 6, 2023, last updated on Jan. 16, 2024, retrieved on Feb. 29, 2024, retrieved from URL<https://clinicaltrials.gov/study/NCT05729568?term=lenacapavir&rank=2&tab=history&a-8>, 17 pages.

ClinicalTrials.gov [online], "Study Evaluating the Safety and Efficacy of Islatravir in Combination with Lenacapavir in Virologically Suppressed People with HIV," NCT05052996, Sep. 13, 2021, last updated Jan. 19, 2024, retrieved on Feb. 8, 2024, retrieved from URL<https://clinicaltrials.gov/study/NCT05052996?intr+lenacapavir&term=NCT05052996&rank=1&tab=history&a=11>, 14 pages.

DailyMed.nlm.nih.gov [online], "Label: SUNLENCA-lenacapavir sodium tablet, film coated; SUNLENCA-lenacapavir sodium kit," Available on or before Jan. 21, 2023 via Internet Archive: Wayback Machine URL<https://web.archive.org/web/20230121044750/https://dailymed.nlm.nih.gov/dailymed/drugInfo.cfm?setid=e5652804-29c4-40d7-aeb2-0142ed2a7b5b>, retrieved on Feb. 7, 2024, 17 pages.

Dvory-Sobol et al., "Lenacapavir: a first-in-class HIV-1 capsid inhibitor," Current Opinion in HIV and AIDS, Jan. 2022, 17(1):15-21.

EMA.Europa.eu [online], "Sunlenca: Epar—Product Information," Jun. 27, 2023, retrieved on Feb. 8, 2024, retrieved from URL<https://www.ema.europa.eu/en/documents/product-information/sunlenca-epar-product-information_en.pdf>, 63 pages.

Hanack et al., "cis- und trans bicyclo [3.1.0] hexano-(2)," Chemische Berichte, 1964, 97(6):1669-1672, XP055573746 (with English translation).

Jarvis et al., "Conquering HIV's capsid", C&EN Chicago, Jul. 2017, 95(31): 23-25.

Jeong, "Synthesis of Tetrasubstituted Pyrazones and Pyrazone N-Oxides," Tetrahedron Letters, 2010, 51 (6):974-976.

Jogiraju et al., "Pharmacokinetic Bridging with Oral Lenacapavir for Missed Subcutaneous Q6M Dosing," Presented at Proceedings of the 12th IAS Conference on HIV Science, Brisbane, Australia, Jul. 23-26, 2023, 1 page.

Markham, "Bictegravir: First Global Approval," Drugs, Mar. 2018, 78:601-606.

Palombo et al., "Prodrug and conjugate drug delivery strategies for improving HIV/ADS therapy," Journal of drug delivery science and technology, Jan. 2009, 19(1): 31 pages.

Shaik et al., "Impact of Intrinsic and Extrinsic Factors on the Pharmacokinetics of Long-Acting Lenacapavir for Treatment of HIV," Presented at Proceedings of AIDS 2022, Montreal, Quebec, Canada, Jul. 29-Aug. 2, 2022; Journal of Virus Eradication, Dec. 2022, 8(S):PP5.1-00045, 3 pages.

Shaik et al., "Simulations for Once-Weekly Dosing of Oral Lenacapavir," Presented at Proceedings of AIDS 2022, Montreal, Quebec, Canada, Jul. 29-Aug. 2, 2022; Journal of Virus Eradication, Dec. 2022, 8(S):PP5.2-00072, 3 pages.

Tanaka et al., "One-Pot Synthesis of Metalated Pyridines from Two Acetylenes, a Nitrile, and a Titanium(II) Alkoxide," J. Am. Chem. Soc., 2005, 127(21):7774-7780.

Tse et al., "Discovery of Novel Potent HIV Capsid Inhibitors with Long-Acting Potential," Abstract for Oral Presentation at the Conference on Retroviruses and Opportunistic Infections (CROI), Seattle, WA, 2017, 18 pages.

Wohl et al., "Patient-Reported Symptoms Over 48 Weeks Among Participants in Randomized, Double-Blind, Phase III Non-Inferiority Trials of Adults with HIV on Co-formulated Bictegravir, Emtricitabine, and Tenofovir Alafenamide versus Co-formulated Abacavir, Dolutegravir, and Lamivudine," The Patient-Patient-Centered Outcomes Research, 2018, 11: 561-573.

PROCESS OF PREPARING HIV CAPSID INHIBITOR

CROSS-REFERENCE TO RELATED APPLICATIONS

This application claims the benefit of U.S. Provisional Application No. 63/505,320, filed on May 31, 2023, the entire contents of which is hereby incorporated by reference in its entirety.

TECHNICAL FIELD

This disclosure relates generally to processes for preparing a compound useful in the prevention or treatment of a Retroviridae viral infection, including an infection caused by the human immunodeficiency virus (HIV).

BACKGROUND

Positive-single stranded RNA viruses comprising the Retroviridae family include those of the subfamily Orthoretrovirinae and genera Alpharetrovirus, Betaretrovirus, Gammaretrovirus, Deltaretrovirus, Epsilonretrovirus, Lentivirus, and Spumavirus which cause many human and animal diseases. Among the Lentivirus, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments could lead to the emergence of HIV strains that are resistant to current therapies (Taiwo, B., *International Journal of Infectious Diseases* 2009, 13:552-559; Smith, R. J., et al., *Science* 2010, 327: 697-701). Therefore, there is a pressing need to discover new antiretroviral agents that are active against emerging drug-resistant HIV variants.

Also of interest in the area of HIV therapies and treatments is providing regimens to patients with improved pharmacokinetic properties, including, for example, increased potency, long-acting pharmacokinetics, low solubility, low clearance, and/or other properties. While current regimens for treating HIV have progressed enough that patients no longer have to take multiple pills multiple times a day, patients today still are required to take a pill every day for the foreseeable span of their life. Thus, it would be beneficial to have HIV therapies that require patients take medication less than once a day (e.g. once every couple of days, once a week, once every other week, once a month, and so forth) or take a smaller effective dose of the medication(s) on a daily, weekly, monthly, or longer basis.

SUMMARY

The present disclosure provides, inter alia, a process of preparing a compound of Formula XIII:

XIII

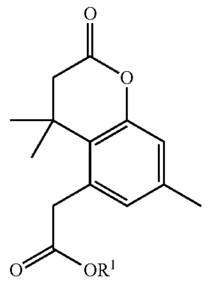

or a salt thereof, comprising reacting a compound of Formula XIV:

XIV

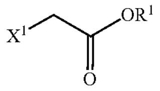

or a salt thereof, with an activator in the presence of zinc and optionally an alkali metal halide to form a first mixture; and mixing the first mixture with a compound of Formula XI-a:

XI-a

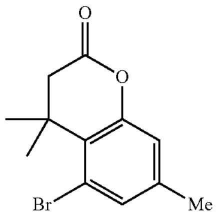

or a salt thereof, in the presence of a coupling catalyst, wherein the constituent members are defined herein.

The present disclosure provides, inter alia, a process of preparing a compound of Formula XIII:

XIII

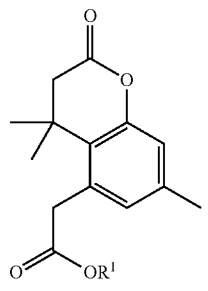

or a salt thereof, comprising reacting a compound of Formula XIV:

XIV

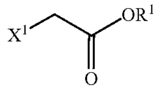

or a salt thereof, with an activator in the presence of zinc and an alkali metal halide to form a first mixture; and mixing the first mixture with a compound of Formula XI-a:

XI-a

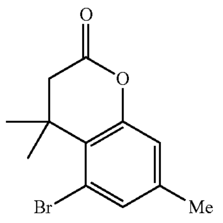

or a salt thereof, in the presence of a coupling catalyst, wherein the constituent members are defined herein.

The present disclosure further provides a process of preparing a compound of Formula VI:

VI

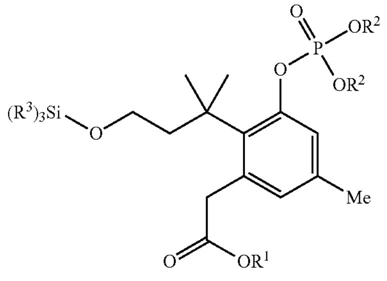

or a salt thereof, comprising reacting a compound of Formula VII:

VII

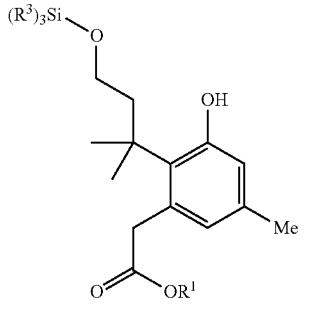

or a salt thereof, with di($C_{1-6}$ alkyl)phosphite in the presence of an oxidizing agent and a base, wherein the constituent members are defined herein.

The present disclosure further provides a process of preparing a compound of Formula VI:

VI

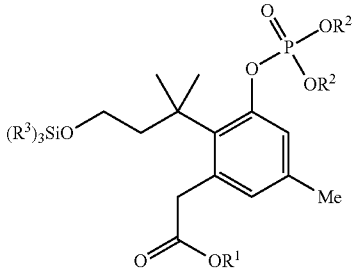

or a salt thereof, comprising reacting a compound of Formula VII:

VII

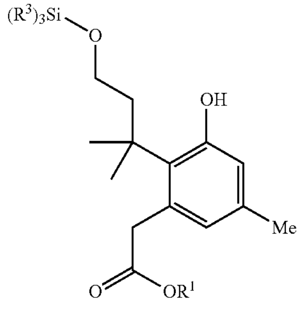

or a salt thereof, with tetra($C_{6-10}$ aryl-$C_{1-6}$ alkyl-)pyrophosphate in the presence of a base, wherein the constituent members are defined herein.

The present disclosure further provides a process of preparing a compound of Formula VI:

VI

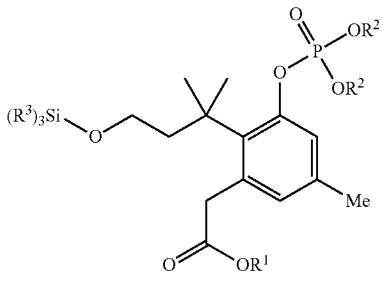

or a salt thereof, comprising reacting a compound of Formula VII:

VII

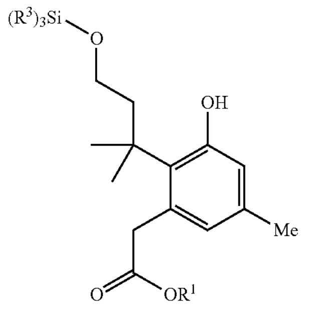

or a salt thereof, with a di($C_{1-6}$ alkyl), N,N-di($C_{1-6}$ alkyl) phosphoramidate in the presence of a base and an acid to form a first mixture; and mixing the first mixture with an oxidizing agent, wherein the constituent members are defined herein.

The present disclosure further provides a process of preparing a compound of Formula I:

I

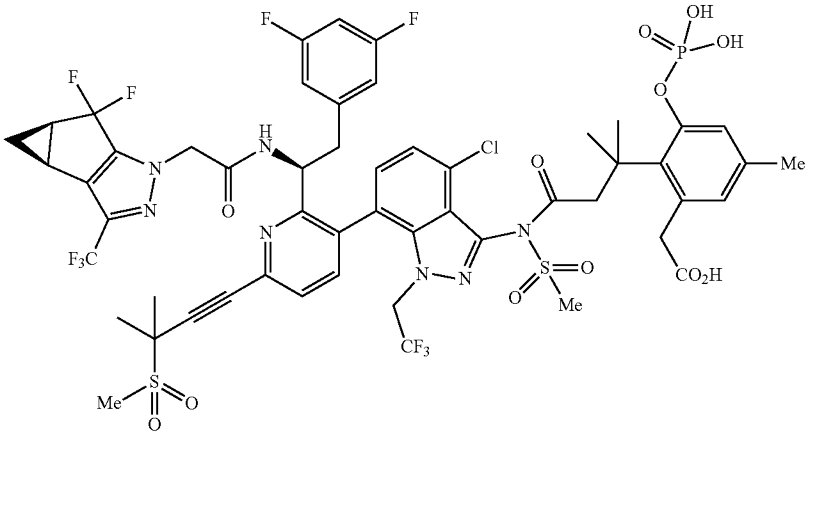

or a salt thereof, comprising:

reacting 3-bromo-5-methylphenol with methyl 3,3-dimethylacrylate in the presence of sulfuric acid to form a compound of Formula XI-a:

XI-a

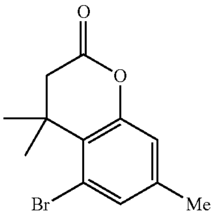

or a salt thereof;

reacting a compound of Formula XIV-a:

XIV-a

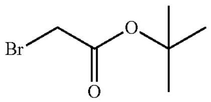

or a salt thereof, with trimethylsilyl chloride in the presence of zinc to form a first mixture; and mixing the first mixture with the compound of Formula XI-a, or a salt thereof, in the presence of bis(dibenzylideneacetone)palladium(0) and 2-dicyclohexylphosphino-2',4',6'-triisopropylbiphenyl to form a compound of Formula XIII-a:

XIII-a

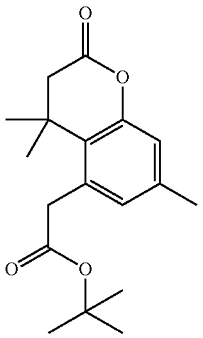

or a salt thereof;

reacting the compound of Formula XIII-a, or a salt thereof, with di-tert-butyl phosphite, bromoform, and sodium trimethylsilanolate to form a compound of Formula IV-a:

IV-a

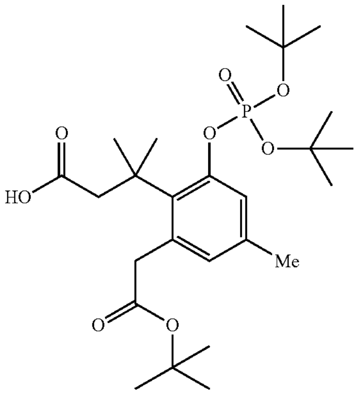

or a salt thereof, coupling the compound of Formula IV-a, or a salt thereof, with a compound of Formula

III

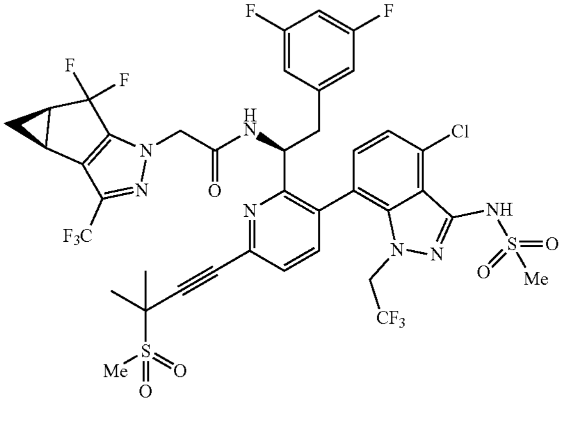

or a salt thereof, in the presence of propanephosphonic acid anhydride and 1-methylimidazole to form a compound of Formula II-a:

II-a
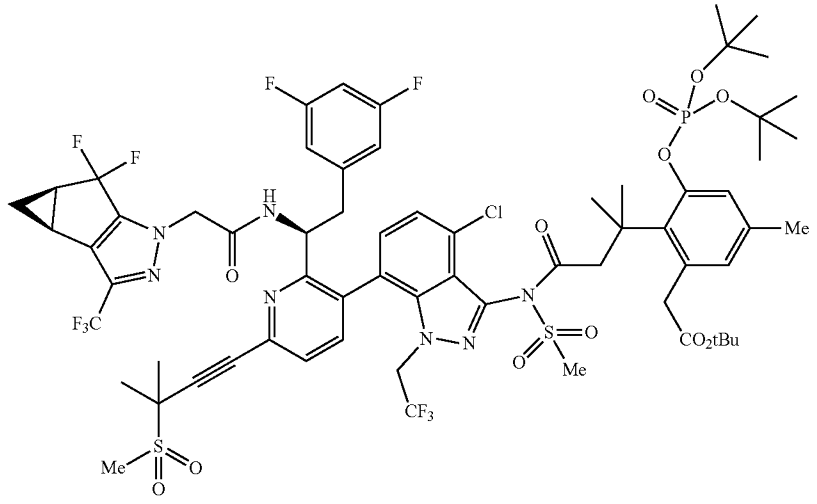
or a salt thereof; and
deprotecting the compound of Formula II-a, or a salt thereof, with phosphoric acid to form the compound of Formula I, or a salt thereof.
The present disclosure further provides a process of preparing a compound of Formula I:
I
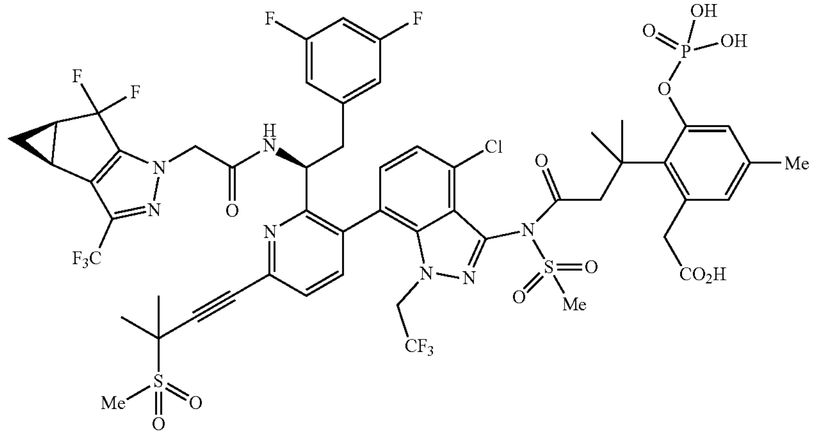

or a salt thereof, comprising:

reacting a compound of Formula XIV-a:

XIV-a

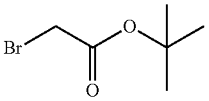

or a salt thereof, with diisobutylaluminium hydride in the presence of zinc and lithium chloride to form a first mixture; and mixing the first mixture with a compound of Formula XI-a:

XI-a

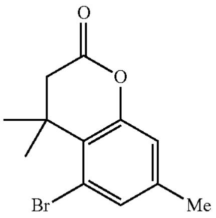

or a salt thereof, in the presence of palladium (II) acetate and 2-dicyclohexylphosphino-2',4',6'-triisopropylbiphenyl to form a compound of Formula XIII-a:

XIII-a

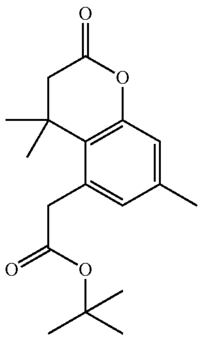

or a salt thereof;

reacting the compound of Formula XIII-a, or a salt thereof, with di-tert-butyl phosphite, bromoform, and trimethylsilanolate to form a compound of Formula IV-a:

IV-a

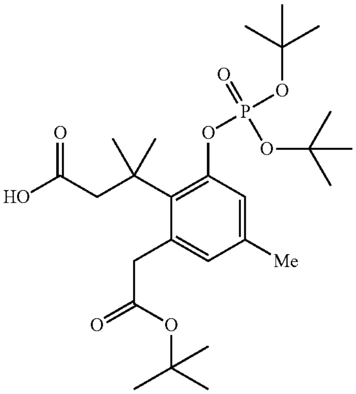

or a salt thereof, coupling the compound of Formula IV-a, or a salt thereof, with a compound of Formula III:

III

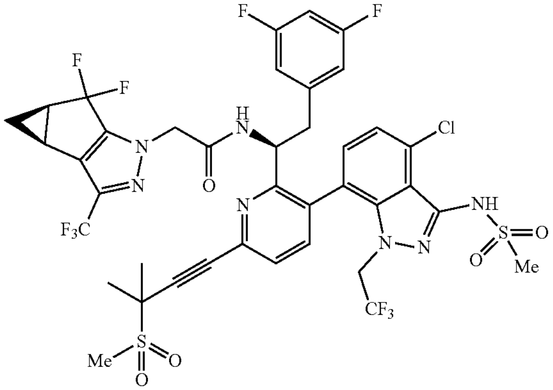

or a salt thereof, in the presence of N,N,N'N'-tetramethylchloroformamidinium hexafluorophosphate and 1-methylimidazole to form a compound of Formula II-a:

II-a
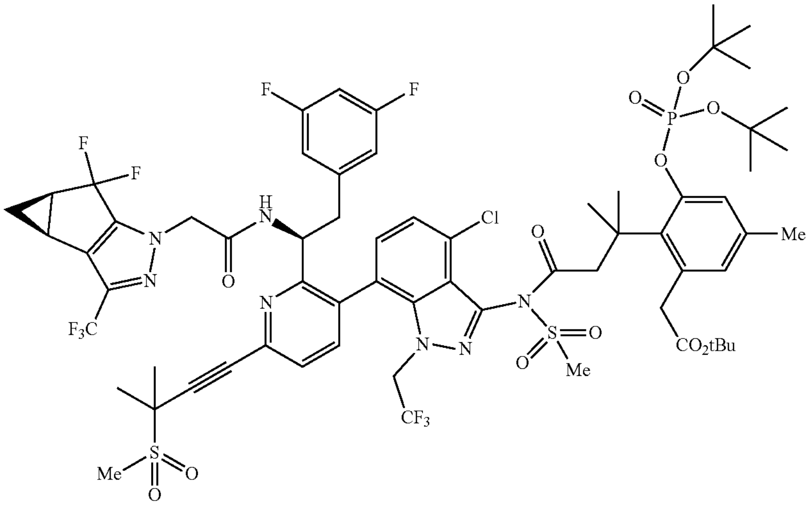
or a salt thereof, and
deprotecting the compound of Formula II-a, or a salt thereof, with phosphoric acid to form the compound of Formula I, or a salt thereof.
The present disclosure further provides a process of preparing a compound of Formula I:
I
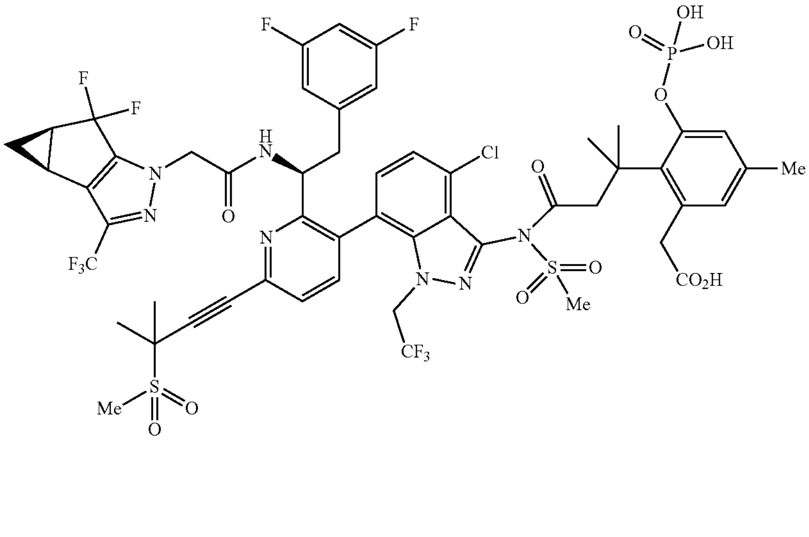

or a salt thereof, comprising:

reacting a compound of Formula VII-a:

VII-a

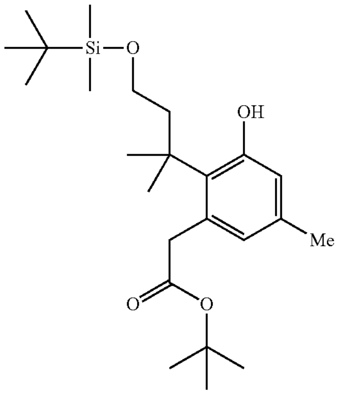

or a salt thereof, with di-tert-butyl phosphite in the presence of bromoform and cesium carbonate to form a compound of Formula VI-a:

VI-a

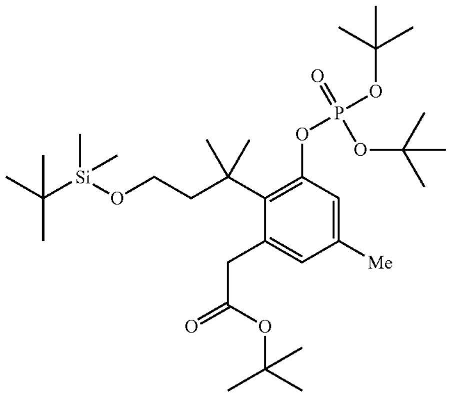

or a salt thereof;

deprotecting the compound of Formula VI-a, or a salt thereof, in the presence of tetrabutylammonium fluoride to form a compound of Formula V-a:

V-a

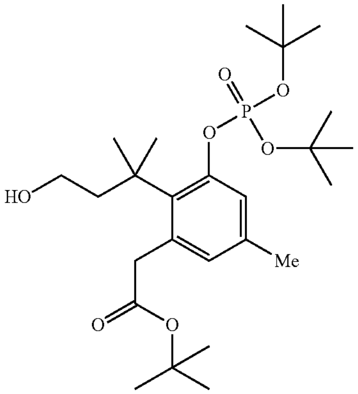

or a salt thereof, oxidizing the compound of Formula V-a, or a salt thereof, in the presence of (diacetoxyiodo)benzene, sodium phosphate dibasic, and 2,2,6,6-tetramethylpiperidine 1-oxyl to form a compound of Formula IV-a:

IV-a

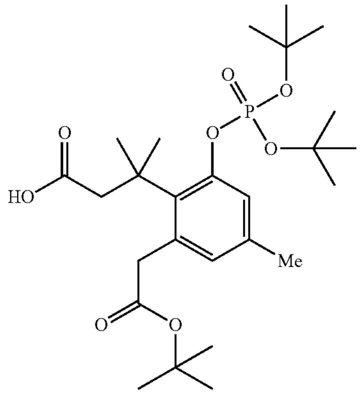

or a salt thereof;

coupling the compound of Formula IV-a, or a salt thereof, with a compound of Formula III:

III

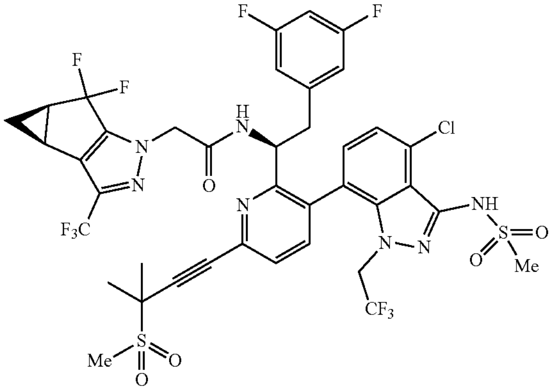

or a salt thereof, in the presence of N,N,N',N'-tetramethylchloroformamidinium hexafluorophosphate and 1-methylimidazole to form a compound of Formula II-a:

II-a
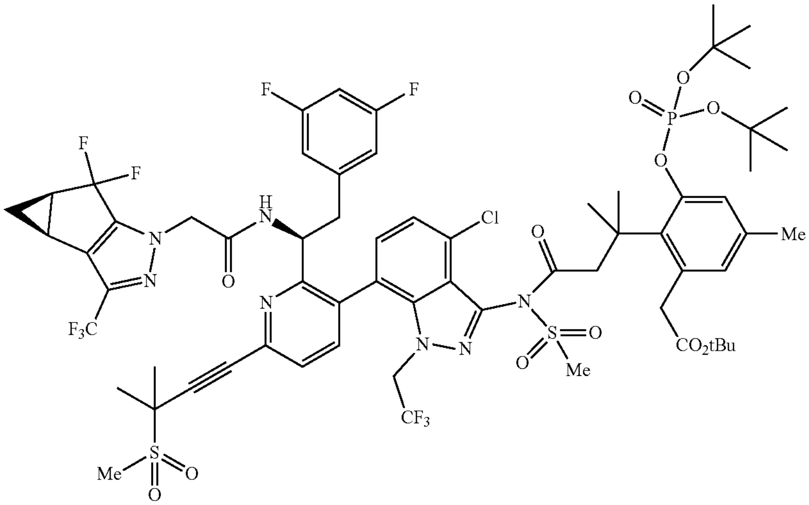
or a salt thereof; and
deprotecting the compound of Formula II-a, or a salt thereof, with phosphoric acid to form the compound of Formula I, or a salt thereof.
The present disclosure further provides a process of preparing a compound of Formula I:
I
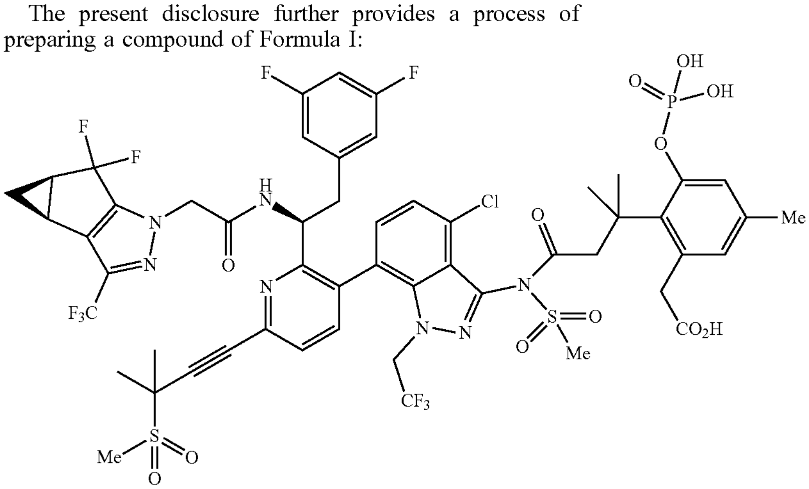
or a salt thereof, comprising:
reacting a compound of Formula VII-a:
VII-a
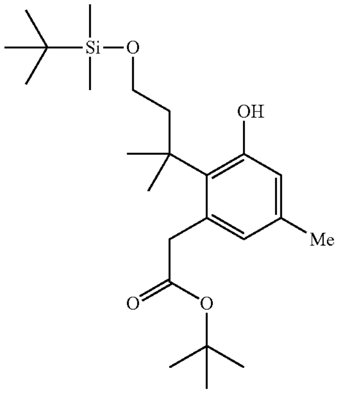

or a salt thereof, with tetrabenzyl pyrophosphate in the presence of sodium hydride to form a compound of Formula VI-b:

VI-b

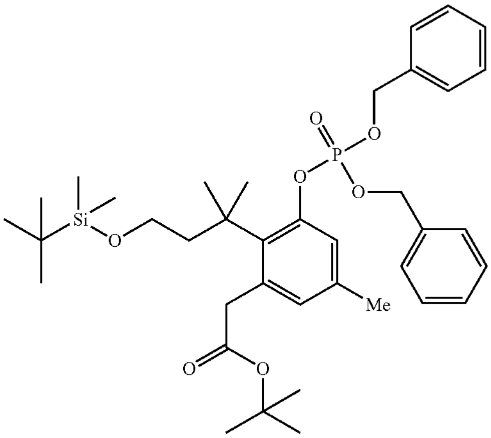

or a salt thereof;

deprotecting the compound of Formula VI-b, or a salt thereof, in the presence of tetrabutylammonium fluoride to form a compound of Formula V-b:

V-b

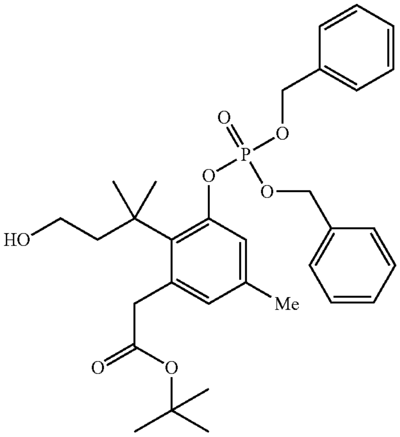

or a salt thereof;

oxidizing the compound of Formula V-b, or a salt thereof, in the presence of (diacetoxyiodo)benzene, sodium phosphate dibasic, and 2,2,6,6-tetramethylpiperidine 1-oxyl to form a compound of Formula IV-b:

IV-b

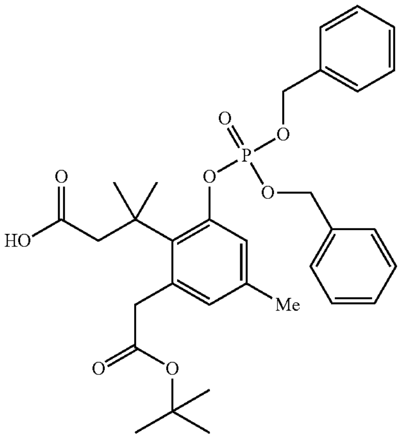

or a salt thereof;

coupling the compound of Formula IV-b, or a salt thereof, with a compound of Formula III:

III

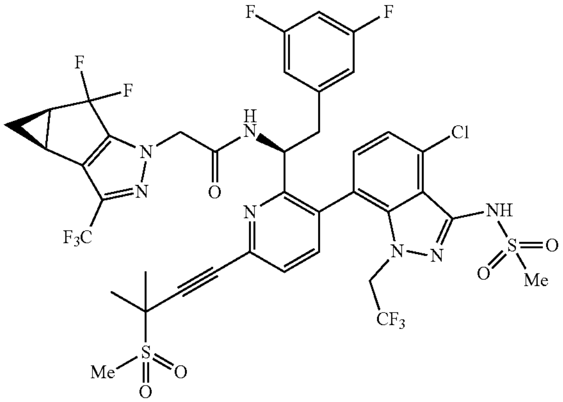

or a salt thereof, in the presence of N,N,N',N'-tetramethylchloroformamidinium hexafluorophosphate and 1-methylimidazole to form a compound of Formula II-b:

II-b
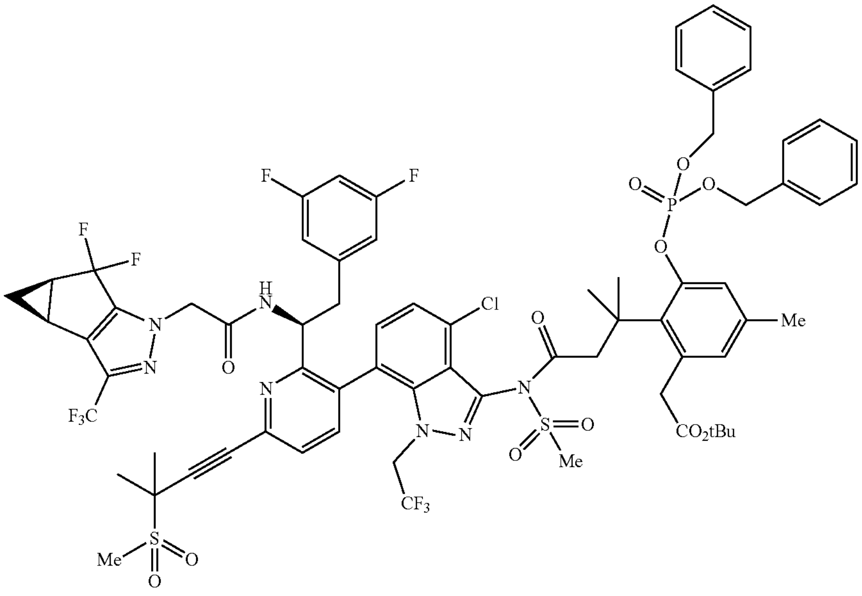
or a salt thereof; and
deprotecting the compound of Formula II-b, or a salt thereof, with phosphoric acid to form the compound of Formula I, or a salt thereof.
The present disclosure further provides a process of preparing a compound of Formula I:
I
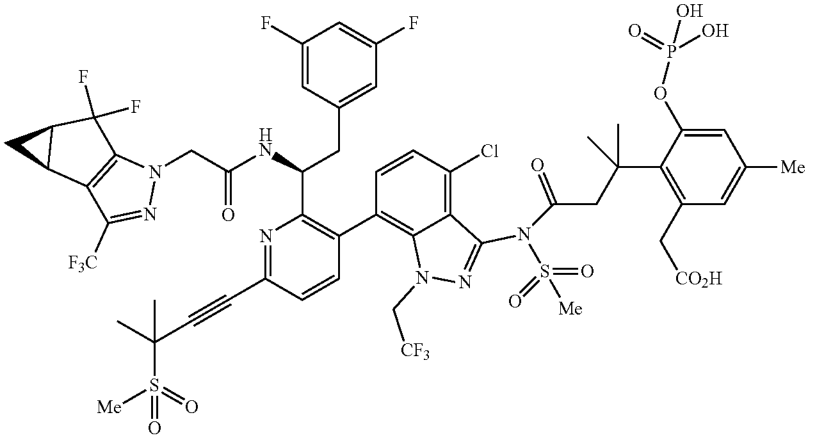

or a salt thereof, comprising:

reacting a compound of Formula VII-a:

VII-a

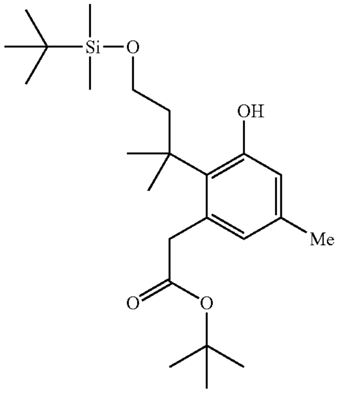

or a salt thereof, with di-tert-butyl N,N-diisopropylphosphoramidate in the presence of a 1-methylimidazole and trifluoroacetic acid to form a first mixture; and mixing the first mixture with hydrogen peroxide to form a compound of Formula VI-a:

VI-a

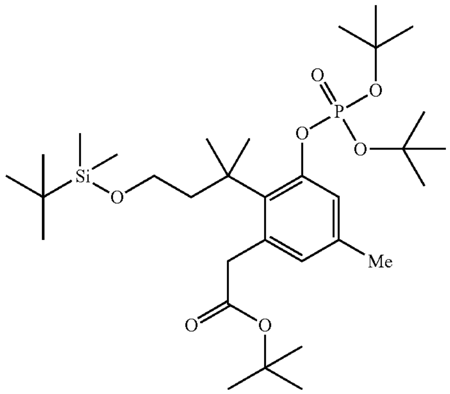

or a salt thereof;

deprotecting the compound of Formula VI-a, or a salt thereof, in the presence of tetrabutylammonium fluoride to form a compound of Formula V-a:

V-a

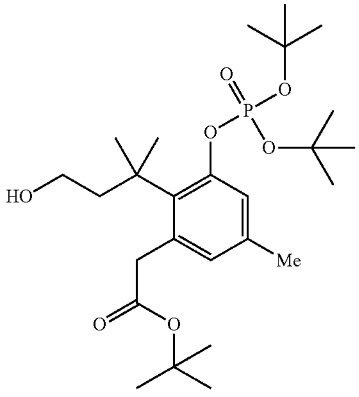

or a salt thereof;

oxidizing the compound of Formula V-a, or a salt thereof, in the presence of (diacetoxyiodo)benzene, sodium phosphate dibasic, and 2,2,6,6-tetramethylpiperidine 1-oxyl to form a compound of Formula IV-a:

IV-a

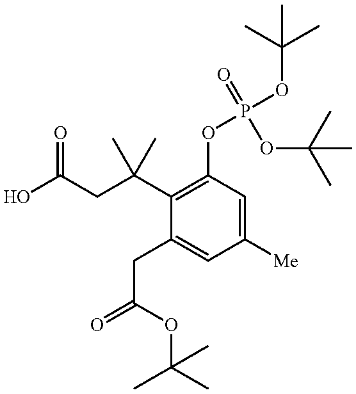

or a salt thereof;

coupling the compound of Formula IV-a, or a salt thereof, with a compound of Formula III:

III

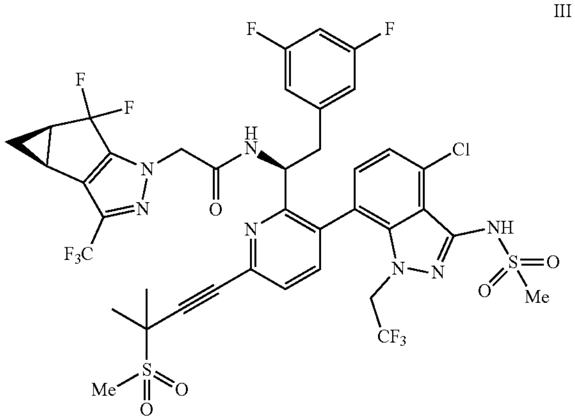 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

or a salt thereof, in the presence of N,N,N',N'-tetramethylchloroformamidinium hexafluorophosphate and 1-methylimidazole to form a compound of Formula II-a:

II-a

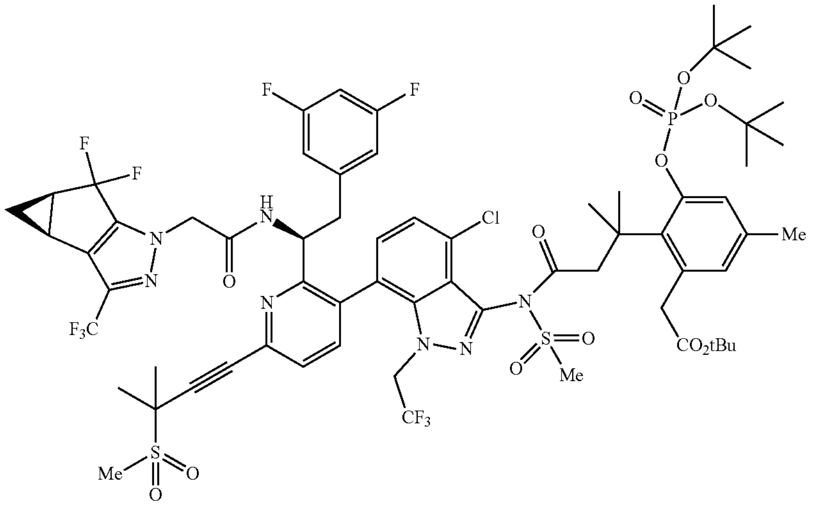

or a salt thereof; and deprotecting the compound of Formula II-a, or a salt thereof, with phosphoric acid to form the compound of Formula I, or a salt thereof.

The present disclosure further provides a process of preparing a compound of Formula XIII:

XIII

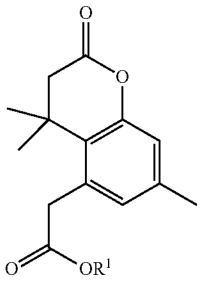

or a salt thereof, comprising reacting a compound of Formula XI-b:

XI-b

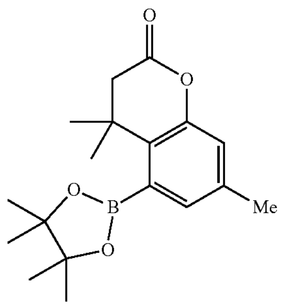

or a salt thereof, with a compound of Formula XIV:

XIV

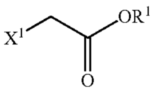

or a salt thereof, under Suzuki coupling conditions, wherein the constituent members are defined herein.

The present disclosure further provides a process of preparing a compound of Formula I:

I

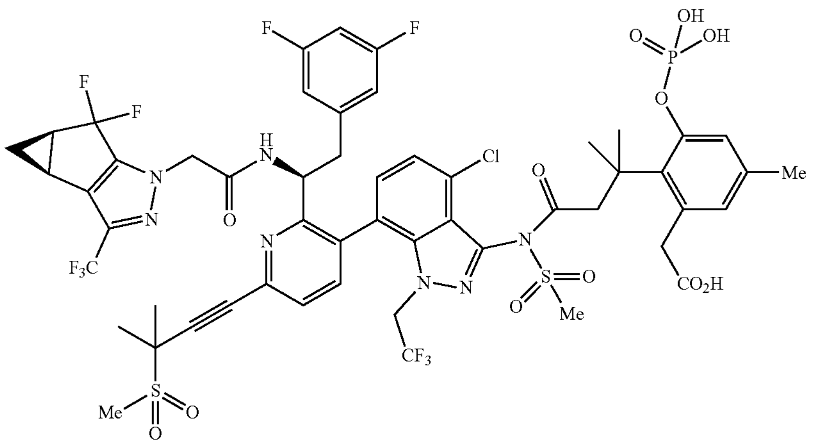

or a salt thereof, comprising:

reacting 3-bromo-5-methylphenol with methyl 3,3-dimethylacrylate in the presence of sulfuric acid to form a compound of Formula XI-a:

XI-a

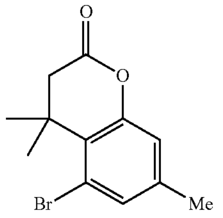

or a salt thereof;

reacting the compound of Formula XI-a, or a salt thereof, with bis(pinacolato)diboron in the presence of bis (dibenzylideneacetone)palladium(0), triphenylphosphine, and potassium propionate to form a compound of Formula XI-b:

XI-b

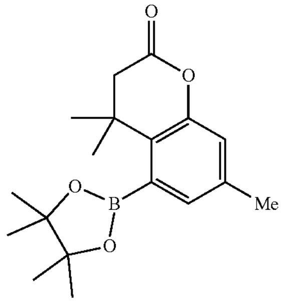

or a salt thereof;

reacting the compound of Formula XI-b, or a salt thereof, with a compound of Formula XIV-a:

XIV-a

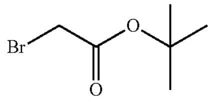

or a salt thereof, in the presence of bis(dibenzylideneacetone)palladium(0), potassium phosphate tribasic, and 1,3,5,7-tetramethyl-6-phenyl-2,4,8-trioxa-6-phosphaadamantane to form a compound of Formula XIII-a:

XIII-a

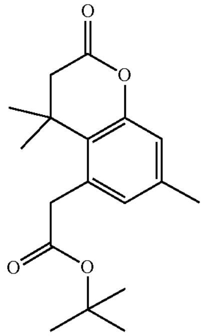

or a salt thereof;

reacting the compound of Formula XIII-a, or a salt thereof, with di-tert-butyl phosphite, bromoform, and sodium trimethylsilanolate to form a compound of Formula IV-a:

IV-a
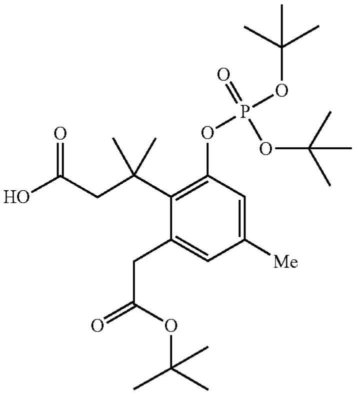
or a salt thereof,
coupling the compound of Formula IV-a, or a salt thereof, with a compound of Formula III:
III
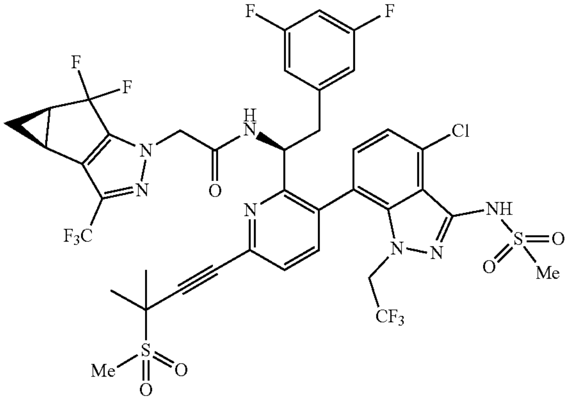
or a salt thereof, in the presence of propanephosphonic acid anhydride and 1-methylimidazole to form a compound of Formula II-a:
II-a
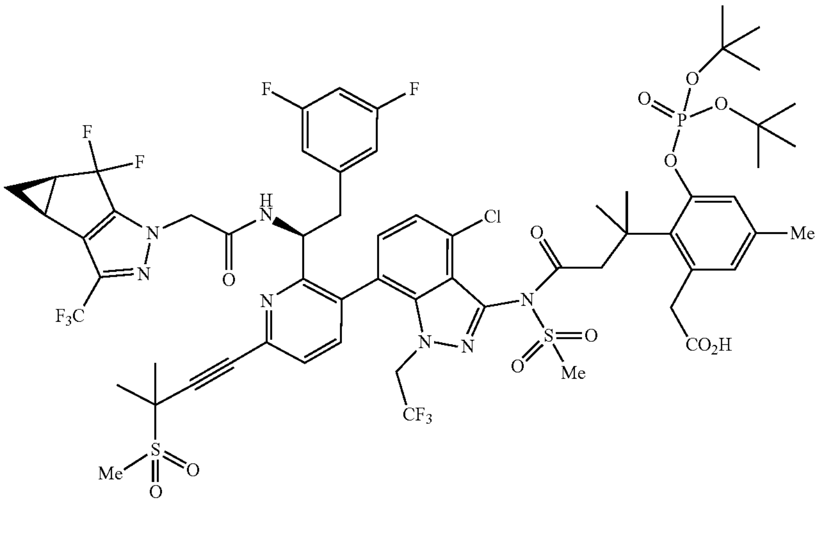

or a salt thereof; and deprotecting the compound of Formula II-a, or a salt thereof, with phosphoric acid to form the compound of Formula I, or a salt thereof.

The present disclosure further provides a process of preparing a compound of Formula VI-a:

VI-a

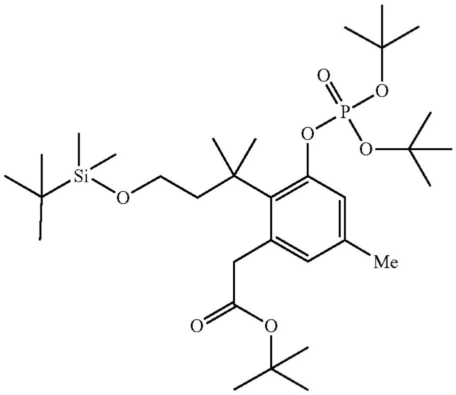

or a salt thereof, comprising reacting a compound of Formula VII-a:

VII-a

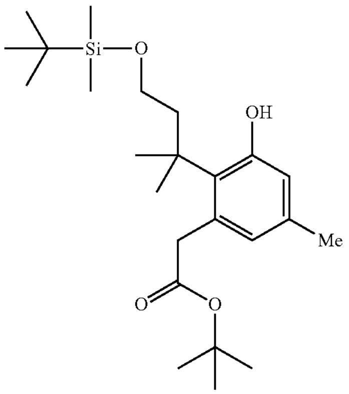

or a salt thereof, with di-tert-butyl N,N-diisopropylphosphoramidate in the presence of 1-methylimidazole and trifluoroacetic acid to form a first mixture; and mixing the first mixture with hydrogen peroxide to form the compound of Formula VI-a, or a salt thereof.

DETAILED DESCRIPTION

The present disclosure relates to processes for preparing 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetic acid (i.e., Compound 1, structure shown below; see e.g. U.S. application Ser. No. 18/061,375, granted on Oct. 17, 2023 as U.S. Pat. No. 11,787,825, the disclosure of which is incorporated herein by reference in its entirety).

Compound 1

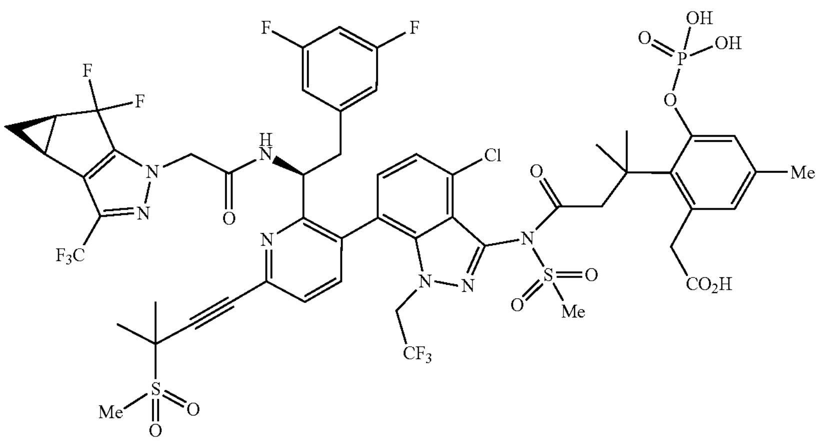

Compound 1 has two restricted rotational axes, resulting in 4 atropisomers, as shown below, that may be detected by $^{19}$F-NMR. In deuterated DMSO at 25° C., the half-life of conversion from the major to the minor atropisomer for the biaryl rotation is about 71.6 hours with equilibrium ratio at about 3:1, and the half-life of interconversion at the 2$^{nd}$ rotational axis is about 7 minutes with equilibrium ratio at about 4:3.

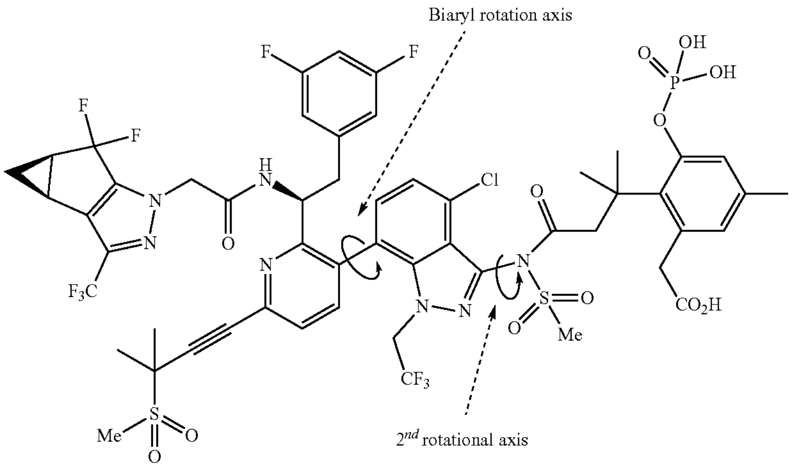

Restricted rotational axes of Compound 1

Compound 1 is a prodrug lenacapavir (compound of Formula III, N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide), an HIV capsid inhibitor that is in development as a long-acting treatment for HIV.

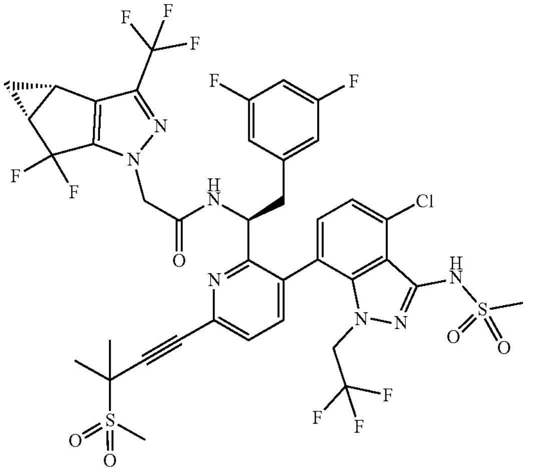

Lenacapavir

Synthesis and characterization of lenacapavir, and salts thereof, are described, for example, in US 20180051005 and US 20190300505, the contents of each of which are hereby incorporated by reference in their entireties. Various forms and/or uses of the compounds of lenacapavir are disclosed, for example, in US 20190083478, US 20190084963, US 20200038389A1, and US 20210188815, the contents of each of which are hereby incorporated by reference in their entireties.

There is currently a need for improved synthetic methods and intermediates that can be used to prepare the compound of Formula I and co-crystals, solvates, salts, and combinations thereof. There is also a need for improved methods for preparing intermediate compounds that can be used to prepare the compound of Formula I and its co-crystals, solvates, salts, and combinations thereof. The improved methods and intermediates may reduce the cost, time, and/or the amount of waste associated with the existing methods for preparing the compound of Formula I and co-crystals, solvates, salts, and combinations thereof.

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading. Unless defined otherwise, all technical and scientific terms used herein have the same meaning as commonly understood by one of ordinary skill in the art.

When trade names are used herein, it is intended to independently include the tradename product and the active pharmaceutical ingredient(s) of the tradename product.

As used herein and in the appended claims, the singular forms "a" and "an", and "the" include plural referents unless the context clearly dictates otherwise. Thus, e.g., reference to "the compound" includes a plurality of such compounds and reference to "the assay" includes reference to one or more assays, and so forth.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and/or hindered rotation about a bond axis and may thus give rise to enantiomers, diastereomers, and other stereoisomeric forms that may be defined, in terms of absolute stereochemistry, as (R)- or (S)-. The present disclosure is meant to include all such possible isomers, including racemic mixtures, scalemic mixtures, diastereomeric mixtures, optically pure forms and intermediate mixtures. Optically active (R)- and (S)-isomers may be prepared using chiral synthons or chiral reagents, or resolved using conventional techniques.

Except as expressly defined otherwise, the present disclosure includes all tautomers of compounds detailed herein, even if only one tautomer is expressly represented (e.g., both tautomeric forms are intended and described by the presentation of one tautomeric form where a pair of two tautomers may exist). For example, if reference is made to a compound containing an amide (e.g., by structure or chemical name), it is understood that the corresponding imidic acid tautomer is included by this disclosure and described the same as if the amide were expressly recited either alone or together with the imidic acid. Where more than two tautomers may exist, the present disclosure includes all such tautomers even if only a single tautomeric form is depicted by chemical name and/or structure.

Compounds described herein may have chiral centers and/or geometric isomeric centers (E- and Z-isomers), and it is to be understood that all such optical, enantiomeric, diastereoisomeric and geometric isomers are encompassed. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

Also provided are pharmaceutically acceptable hydrates, solvates, co-crystals, tautomeric forms, polymorphs, and prodrugs of the compounds described herein.

The term "hydrate" refers to the complex formed by the combining of a compound of Formula I, or any Formula disclosed herein, and water.

The term "solvate" refers to a complex formed by the combining of a compound of Formula I, or any other Formula as disclosed herein, and a solvent or a crystalline solid containing amounts of a solvent incorporated within the crystal structure. As used herein, the term "solvate" includes hydrates.

The term "co-crystal" refers to a crystalline material formed by combining a compound of Formula I, or any Formula disclosed herein and one or more co-crystal formers (i.e., a molecule, ion or atom). In certain instances, co-crystals may have improved properties as compared to the parent form (i.e., the free molecule, zwitterion, etc.) or a salt of the parent compound. Improved properties can be increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like. Methods for making and characterizing co-crystals are known to those of skill in the art.

Any formula or structure given herein, including Formula I, or any Formula disclosed herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula I, or any Formula disclosed herein, in which from 1 to "n" hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal. See, for example, Foster, "Deuterium Isotope Effects in Studies of Drug Metabolism", *Trends Pharmacol. Sci.* 5(12): 524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the Formula I, or any Formula disclosed herein.

The concentration of such a heavier isotope, specifically deuterium, may be defined by an isotopic enrichment factor.

In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The modifier "about" used in connection with a quantity is inclusive of the stated value and has the meaning dictated by the context (e.g., includes the degree of error associated with measurement of the particular quantity).

The term "chiral" refers to molecules which have the property of non-superimposability of the mirror image partner, and the term "achiral" refers to molecules which are superimposable on their mirror image partner.

"Alkyl" is a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms (i.e., ($C_1$-$C_4$)alkyl). Examples of suitable alkyl groups include, but are not limited to, methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$, and octyl ($—(CH_2)_7CH_3$).

The term "halo" or "halogen" as used herein refers to fluoro, chloro, bromo and iodo.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. It is also to be understood that when reference is made to a certain atom-range membered aryl (e.g., 6-12 membered aryl), the atom range is for the total ring atoms of the aryl. For example, a 6-membered aryl would include phenyl and a 10-membered aryl would include naphthyl and 1, 2, 3, 4-tetrahydronaphthyl. Non-limiting examples of aryl groups include, but are not limited to, phenyl, indenyl, naphthyl, 1, 2, 3, 4-tetrahydronaphthyl, anthracenyl, and the like.

As used herein, the term "$C_{n-m}$ alkoxy" refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms. In some embodiments, the $C_{o-p}$ aryl-$C_{n-m}$ alkyl- is $C_{6-10}$ aryl-$C_{1-6}$ alkyl. In some embodiments, the $C_{o-p}$ aryl-$C_{n-m}$ alkyl- or $C_{6-10}$ aryl-$C_{1-6}$ alkyl is benzyl.

As used herein, an "alkylene linking group" is a bivalent straight chain or branched alkyl linking group. For example, "$C_{o-p}$ aryl-$C_{n-m}$ alkyl-", contain alkylene linking groups. Examples of "alkylene linking groups" include methylene, ethan-1,1-diyl, ethan-1,2-diyl, propan-1,3-dilyl, propan-1,2-diyl, propan-1,1-diyl and the like.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

The term "n-membered" where n is an integer typically describes the number of ring-forming atoms in a moiety where the number of ring-forming atoms is n. For example, pyridyl is an example of a 6-membered heteroaryl ring.

As used herein, the term "independently selected from" means that each occurrence of a variable or substituent is independently selected at each occurrence from the applicable list.

Except as otherwise noted, the methods and techniques of the present disclosure are generally performed according to conventional methods well known in the art and as described in various general and more specific references that are cited and discussed throughout the present specification. See, e.g., Loudon, *Organic Chemistry,* 5th edition, New York: Oxford University Press, 2009; Smith, *March's Advanced Organic Chemistry: Reactions, Mechanisms, and Structure,* 7th edition, Wiley-Interscience, 2013.

In certain instances, the processes disclosed herein involve a step of forming a salt of a compound of the present disclosure.

Compounds as described herein can be purified by any of the means known in the art, including chromatographic means, such as high performance liquid chromatography (HPLC), preparative thin layer chromatography, flash column chromatography, supercritical fluid chromatography (SFC), and ion exchange chromatography. Any suitable stationary phase can be used, including normal and reversed phases as well as ionic resins. Most typically the disclosed compounds are purified via silica gel and/or alumina chromatography. See, e.g., *Introduction to Modern Liquid Chromatography,* 2nd ed., ed. L. R. Snyder and J. J. Kirkland, John Wiley and Sons, 1979; and *Thin Layer Chromatography*, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, *Protective Groups in Organic Synthesis,* $4^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. One of skill in the art will recognize that the transformations shown in the schemes below may be performed in any order that is compatible with the functionality of the particular pendant groups. In some embodiments, each of the reactions depicted in the general schemes is run at a temperature from about −80° C. to the reflux temperature of the organic solvent used.

The compounds disclosed herein may display atropisomerism resulting from steric hindrance affecting the axial rotation rate around a single bond. The resultant conformational isomers may each be observed as distinct entities by characterization techniques such as NMR and HPLC. The compounds disclosed herein may exist as a mixture of atropisomers. However, the detection of atropisomers is dependent on factors such as temperature, solvent, conditions of purification, and timescale of spectroscopic technique. The interconversion rate at room temperature has a half-life of minutes to hours, hours to days, or days to years. The ratio of atropisomers at equilibrium may not be unity. Characterization data presented herein may not represent the equilibrium state depending on the conditions of isolation and characterization which may include but not limited to handling, solvents used, and temperature.

The present disclosure provides in some embodiments processes and intermediates for preparing the compound of Formula I, and co-crystals, solvates, salts and combinations thereof. In other embodiments, the disclosure provides processes for preparing intermediates that can be used to prepare the compound of Formula I and co-crystals, solvates, salts and combinations thereof.

Accordingly, the present disclosure provides a process of preparing a compound of Formula XIII:

XIII

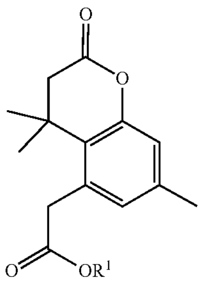

or a co-crystal, solvate, or salt thereof, comprising reacting a compound of Formula XIV:

XIV

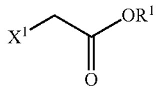

or a co-crystal, solvate, or salt thereof, with an activator in the presence of zinc and optionally an alkali metal halide to form a first mixture; and mixing the first mixture with a compound of Formula XI:

XI

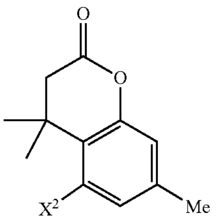

or a co-crystal, solvate, or salt thereof, in the presence of a coupling catalyst, wherein:

$X^1$ is halo;

$X^2$ is selected from the group consisting of halo, (4-methylbenzenesulfonyl)oxyl, (methylsulfonyl)oxyl, (trifluoromethylsulfonyl)oxyl, dihydroxyboranyl, 4,4,5,5-tetramethyl-1,3,2-dioxaborolan-2-yl, 5,5-dimethyl-1,3,2-dioxaborinan-2-yl, and benzo[d][1,3,2]dioxaborol-2-yl; and $R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, the present disclosure provides a process of preparing a compound of Formula XIII:

XIII

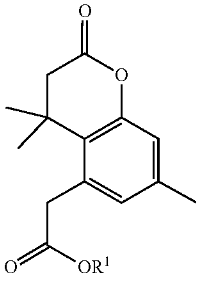

or a co-crystal, solvate, or salt thereof, comprising reacting a compound of Formula XIV:

XIV

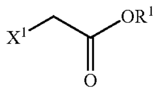

or a co-crystal, solvate, or salt thereof, with an activator in the presence of zinc and an alkali metal halide to form a first mixture; and mixing the first mixture with a compound of Formula XI:

XI

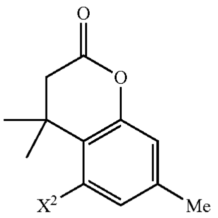

or a co-crystal, solvate, or salt thereof, in the presence of a coupling catalyst, wherein:

$X^1$ is halo;

$X^2$ is selected from the group consisting of halo, (4-methylbenzenesulfonyl)oxyl, (methylsulfonyl)oxyl, and (trifluoromethylsulfonyl)oxyl; and $R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, $X^2$ is halo.

In some embodiments, $X^2$ is bromo, chloro, or iodo.

In some embodiments, $X^2$ is bromo.

In some embodiments, $X^2$ is selected from the group consisting of halo, dihydroxyboranyl, 4,4,5,5-tetramethyl-1,3,2-dioxaborolan-2-yl, 5,5-dimethyl-1,3,2-dioxaborinan-2-yl, and benzo[d][1,3,2]dioxaborol-2-yl.

In some embodiments, $X^2$ is selected from the group consisting of dihydroxyboranyl, 4,4,5,5-tetramethyl-1,3,2-dioxaborolan-2-yl, 5,5-dimethyl-1,3,2-dioxaborinan-2-yl, and benzo[d][1,3,2]dioxaborol-2-yl.

In some embodiments, $X^2$ is 4,4,5,5-tetramethyl-1,3,2-dioxaborolan-2-yl.

In some embodiments, the present disclosure provides a process of preparing a compound of Formula XIII:

XIII

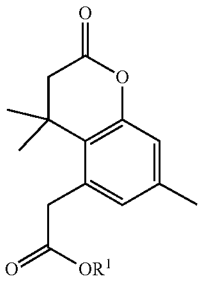

or a co-crystal, solvate, or salt thereof, comprising reacting a compound of Formula XIV:

XIV

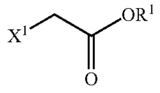

or a co-crystal, solvate, or salt thereof, with an activator in the presence of zinc and an alkali metal halide to form a first mixture; and mixing the first mixture with a compound of Formula XI-a:

XI-a

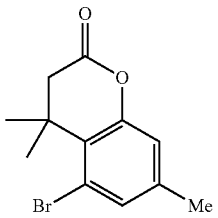

or a co-crystal, solvate, or salt thereof, in the presence of a coupling catalyst, wherein:

$X^1$ is halo; and $R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, the present disclosure provides a process of preparing a compound of Formula XIII:

XIII

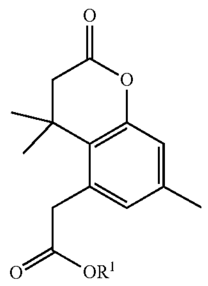

or a co-crystal, solvate, or salt thereof, comprising reacting a compound of Formula XI-b:

XI-b

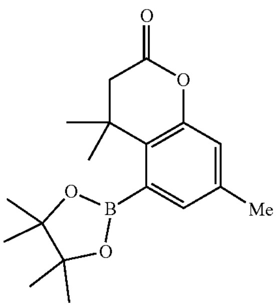

or a co-crystal, solvate, or salt thereof, with a compound of Formula XIV:

XIV

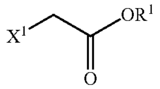

or a co-crystal, solvate, or salt thereof, under Suzuki coupling conditions, wherein:

$X^1$ is halo; and $R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, the present disclosure provides a process of preparing a compound of Formula XIII:

XIII

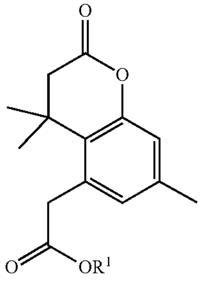

or a salt thereof, comprising reacting a compound of Formula XI-b:

XI-b

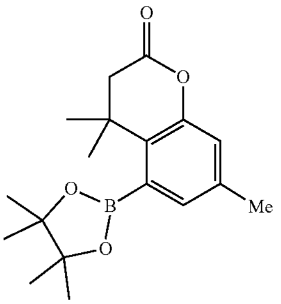

or a salt thereof, with a compound of Formula XIV:

XIV

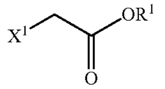

or a salt thereof, under Suzuki coupling conditions, wherein:

$X^1$ is halo; and $R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, $R^1$ is selected from the group consisting of $C_{1-6}$ alkyl, phenyl, pyridyl, and benzyl, wherein the phenyl, pyridyl, and benzyl are each optionally substituted by methoxy.

In some embodiments, $R^1$ is selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, the process of preparing a compound of Formula XIII:

XIII

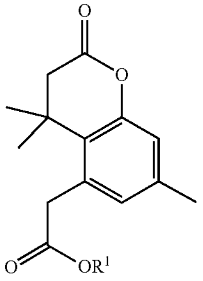

or a salt thereof, comprises reacting a compound of Formula XIV:

XIV

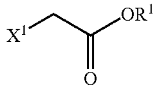

or a salt thereof, with an activator in the presence of zinc and an alkali metal halide to form a first mixture; and mixing the first mixture with a compound of Formula XI-a:

XI-a

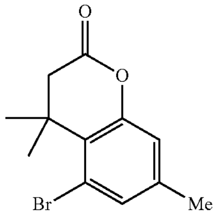

or a salt thereof, in the presence of a coupling catalyst, wherein:

$X^1$ is halo; and $R^1$ is $C_{1-6}$ alkyl.

In some embodiments, $R^1$ is $C_{1-6}$ alkyl. In some embodiments, $R^1$ is selected from the group consisting of methyl, ethyl, isopropyl, and tert-butyl. In some embodiments, $R^1$ is tert-butyl.

In some embodiments, $X^1$ is bromo.

In some embodiments, the activator is selected from the group consisting of a trialkylsilyl halide (e.g., trimethylsilyl chloride, triethylsilyl chloride, trimethylsilyl iodide), a dihaloethane (e.g., dibromoethane, dichloroethane), an alkylaluminum hydride (e.g., diisobutylaluminium hydride), and iodine.

In some embodiments, the activator is selected from the group consisting of diisobutylaluminium hydride, trimethylsilyl chloride, triethylsilyl chloride, trimethylsilyl iodide, dibromoethane, dichloroethane, and iodine. In some embodiments, the activator is diisobutylaluminium hydride. In some embodiments, the activator is trimethylsilyl chloride.

In some embodiments, the alkali metal halide is lithium halide. In some embodiments, the alkali metal halide is lithium chloride. In some embodiments, the alkali metal halide is absent.

In some embodiments, the coupling catalyst comprises a palladium catalyst.

In some embodiments, the palladium catalyst is selected from the group consisting of a palladium(II) salt (e.g., palladium (II) chloride, palladium (II) bromide, palladium (II) acetate, palladium (II) trifluoroacetate), a palladium (0) complex (e.g., bis(dibenzylideneacetone)palladium(0), tris (dibenzylideneacetone)dipalladium(0), tetrakis(triphenylphosphine)palladium(0)), a G3-Pd complex (e.g., (2-dicyclohexylphosphino-2',4',6'-triisopropyl-1,1'-biphenyl)[2-(2'-amino-1,1'-biphenyl)]palladium(II) methanesulfonate (XPhos-Pd-G3)) and a G4-Pd complex (e.g., (SP-4-3)-[dicyclohexyl[2',4',6'-tris(1-methylethyl)[1,1'-biphenyl]-2-yl] phosphine] (methanesulfonato-κO)[2'-(methylamino-κN)[1,1'-biphenyl]-2-yl-κC]palladium (XPhos-Pd-G4)).

In some embodiments, the palladium catalyst is selected from the group consisting of a palladium(II) salt (e.g., palladium (II) chloride, palladium (II) bromide, palladium (II) acetate, palladium (II) trifluoroacetate), a palladium (0) complex (e.g., tris(dibenzylideneacetone)dipalladium(0), tetrakis(triphenylphosphine)palladium(0)), a G3-Pd complex (e.g., (2-dicyclohexylphosphino-2',4',6'-triisopropyl-1,1'-biphenyl)[2-(2'-amino-1,1'-biphenyl)]palladium(II) methanesulfonate (XPhos-Pd-G3)) and a G4-Pd complex (e.g., (SP-4-3)-[dicyclohexyl[2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium (XPhos-Pd-G4)).

In some embodiments, the palladium catalyst is selected from the group consisting of palladium (II) chloride, palladium (II) bromide, palladium (II) acetate, palladium (II) trifluoroacetate, bis(dibenzylideneacetone)palladium(0), tris (dibenzylideneacetone)dipalladium(0), tetrakis(triphenylphosphine)palladium(0), (2-dicyclohexylphosphino-2',4',6'-triisopropyl-1,1'-biphenyl)[2-(2'-amino-1,1'-biphenyl)] palladium(II) methanesulfonate, and (SP-4-3)-[dicyclohexyl [2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium.

In some embodiments, the palladium catalyst is selected from the group consisting of palladium (II) chloride, palladium (II) bromide, palladium (II) acetate, palladium (II) trifluoroacetate, tris(dibenzylideneacetone)dipalladium(0), tetrakis(triphenylphosphine)palladium(0), (2-dicyclohexylphosphino-2',4',6'-triisopropyl-1,1'-biphenyl)[2-(2'-amino-1,1'-biphenyl)]palladium(II) methanesulfonate, and (SP-4-3)-[dicyclohexyl[2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium.

In some embodiments, the palladium catalyst is selected from the group consisting of palladium (II) chloride, palladium (II) bromide, palladium (II) acetate, palladium (II) trifluoroacetate, bis(dibenzylideneacetone)palladium(0), tetrakis(triphenylphosphine)palladium(0), (2-dicyclohexylphosphino-2',4',6'-triisopropyl-1,1'-biphenyl)[2-(2'-amino-1,1'-biphenyl)]palladium(II) methanesulfonate, and (SP-4-3)-[dicyclohexyl[2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium.

In some embodiments, the coupling catalyst comprises a palladium catalyst and, optionally, a phosphine ligand. In some embodiments, the phosphine ligand is absent. In some embodiments, the phosphine ligand is selected from the group consisting of a trialkylphosphine (e.g., tricyclohexylphosphine, tri-tert-butyl phosphine), a triarylphosphine (e.g., triphenyl phosphine), a dialkylarylphosphine (e.g., 2-dicyclohexylphosphino-2',6'-dimethoxybiphenyl (SPhos), 2-dicyclohexylphosphino-2',4',6'-triisopropylbiphenyl) and an alkyldiarylphosphine (e.g., ethylenebis(diphenylphosphine) (DPPE)).

In some embodiments, the phosphine ligand is selected from the group consisting of 2-dicyclohexylphosphino-2',4',6'-triisopropylbiphenyl, tricyclohexylphosphine, tri-tert-butyl phosphine, triphenyl phosphine, 2-dicyclohexylphosphino-2',6'-dimethoxybiphenyl, and ethylenebis (diphenylphosphine). In some embodiments, the phosphine ligand is 2-dicyclohexylphosphino-2',4',6'-triisopropylbiphenyl.

In some embodiments, the coupling catalyst comprises a palladium catalyst and a phosphine ligand. In some embodiments, the coupling catalyst comprises palladium (II) acetate and 2-dicyclohexylphosphino-2',4',6'-triisopropylbiphenyl. In some embodiments, the coupling catalyst comprises bis(dibenzylideneacetone)palladium(0) and 2-dicyclohexylphosphino-2',4',6'-triisopropylbiphenyl.

In some embodiments, the mixing of the first mixture with the compound of Formula XI is performed at a temperature of from about 0° C. to about 100° C. In some embodiments, the mixing of the first mixture with the compound of Formula XI is performed at a temperature of from about 0° C. to about 35° C.

In some embodiments, the mixing of the first mixture and the compound of Formula XI is performed in a solvent selected from the group consisting of an ether (e.g., tetrahydrofuran, 2-methyltetrahydrofuran, tert-butyl methyl ether), a hydrocarbon (e.g., toluene, xylene, trifluorotoluene), a halogenated solvent (e.g., dichloromethane, 1,2-dichloroethane, chloroform, carbon tetrachloride), a nitrile (e.g., acetonitrile, propylnitrile, butylnitrile) and a polar aprotic solvent (e.g., N,N-dimethylformamide, N,N-dimethylacetamide, N-methyl-2-pyrrolidone and dimethyl sulfoxide), or any combination thereof. In some embodiments, the mixing of the first mixture and the compound of Formula XI is performed in a solvent comprising tetrahydrofuran and 2-methyltetrahydrofuran.

In some embodiments, the process of preparing the compound of Formula XIII:

XIII

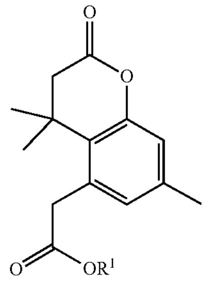

or a co-crystal, solvate, or salt thereof, comprises reacting a compound of Formula XI-b:

XI-b

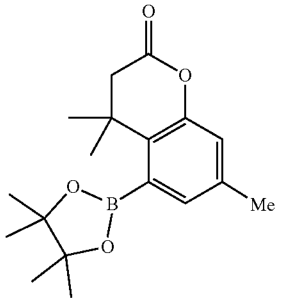

or a co-crystal, solvate, or salt thereof, with a compound of Formula XIV:

XIV

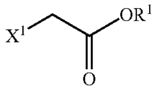

or a co-crystal, solvate, or salt thereof, under Suzuki coupling conditions, wherein:

$X^1$ is halo; and $R^1$ is $C_{1-6}$ alkyl.

In some embodiments, the process of preparing the compound of Formula XIII:

XIII

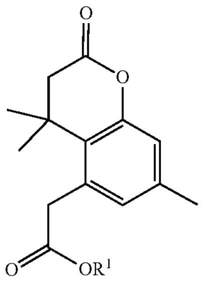

or a salt thereof, comprises reacting a compound of Formula XI-b:

XI-b

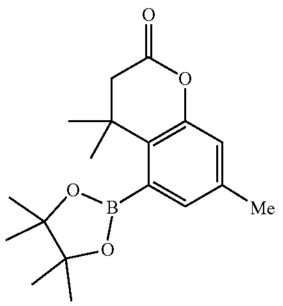

or a salt thereof, with a compound of Formula XIV:

XIV

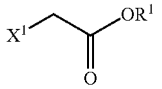

or a salt thereof, under Suzuki coupling conditions, wherein:

$X^1$ is halo; and $R^1$ is $C_{1-6}$ alkyl.

In some embodiments, the Suzuki coupling conditions comprise reacting the compound of Formula XI-b, or a salt thereof, with the compound of Formula XIV, or a salt thereof, in the presence of a palladium catalyst, a base, and optionally in the presence of a ligand.

In some embodiments, the Suzuki coupling conditions comprise reacting the compound of Formula XI-b, or a salt thereof, with the compound of Formula XIV, or a salt thereof, in the presence of a palladium catalyst and a base.

In some embodiments, the palladium catalyst (i.e., the Suzuki coupling palladium catalyst) is selected from a palladium(II) salt (e.g., palladium (II) chloride, palladium (II) bromide, palladium (II) acetate, palladium (II) trifluoroacetate), a palladium (0) complex (e.g., bis(dibenzylideneacetone)palladium(0), tetrakis(triphenylphosphine)palladium(0)), a G3-Pd complex (e.g., (2-dicyclohexylphosphino-2',4',6'-triisopropyl-1,1'-biphenyl)[2-(2'-amino-1,1'-biphenyl)]palladium(II) methanesulfonate (XPhos-Pd-G3)), a G4-Pd complex (e.g., (SP-4-3)-[dicyclohexyl[2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium (XPhos-Pd-G4)).

In some embodiments, the palladium catalyst (i.e., the Suzuki coupling palladium catalyst) is selected from palladium (II) chloride, palladium (II) bromide, palladium (II) acetate, palladium (II) trifluoroacetate, bis(dibenzylideneacetone)palladium(0), tetrakis(triphenylphosphine)palladium (0)), (2-dicyclohexylphosphino-2',4',6'-triisopropyl-1,1'-biphenyl)[2-(2'-amino-1,1'-biphenyl)]palladium(II) methanesulfonate, (SP-4-3)-[dicyclohexyl[2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium. In some embodiments, the palladium catalyst (i.e., the Suzuki coupling palladium catalyst) is bis(dibenzylideneacetone)palladium(0).

In some embodiments, the base (i.e., the Suzuki coupling base) is selected from an inorganic base (e.g., sodium hydroxide, potassium hydroxide, potassium phosphate dibasic, potassium phosphate tribasic, cesium carbonate, potassium propionate), and a tertiary amine base (e.g., triethylamine, N-methylmorpholine, tripropylamine, N,N-diisopropylethylamine).

In some embodiments, the base (i.e., the Suzuki coupling base) is selected from sodium hydroxide, potassium hydroxide, potassium phosphate dibasic, potassium phosphate tribasic, cesium carbonate, potassium propionate, triethylamine, N-methylmorpholine, tripropylamine, and N,N-diisopropylethylamine. In some embodiments, the base (i.e., the Suzuki coupling base) the base is potassium phosphate tribasic.

In some embodiments, the Suzuki coupling of the compound of Formula XI-b, or a salt thereof, and the compound of Formula XIV, is performed in the presence of a ligand.

In some embodiments, the ligand (i.e., the Suzuki coupling ligand) is selected from a trialkylphosphine (e.g., tricyclohexylphosphine, tri-tert-butyl phosphine), a triarylphosphines (e.g., triphenyl phosphine), a dialkylarylphosphine (e.g., 2-dicyclohexylphosphino-2',6'-dimethoxybiphenyl (SPhos)), a alkyldiarylphosphine (e.g., ethylenebis(diphenylphosphine) (DPPE)), and 1,3,5,7-tetramethyl-6-phenyl-2,4,8-trioxa-6-phosphaadamantane.

In some embodiments, the ligand (i.e., the Suzuki coupling ligand) is selected from tricyclohexylphosphine, tri-tert-butyl phosphine, triphenyl phosphine, 2-dicyclohexylphosphino-2',6'-dimethoxybiphenyl, ethylenebis (diphenylphosphine), and 1,3,5,7-tetramethyl-6-phenyl-2,4,8-trioxa-6-phosphaadamantane. In some embodiments, the ligand (i.e., the Suzuki coupling ligand) is 1,3,5,7-tetramethyl-6-phenyl-2,4,8-trioxa-6-phosphaadamantane.

In some embodiments, the reacting of the compound of Formula XI-b, or a salt thereof, and the compound of Formula XIV, or a salt thereof, is performed at a temperature of from about −20° C. to about 150° C. In some embodiments, the reacting of the compound of Formula XI-b, or a salt thereof, and the compound of Formula XIV, or a salt thereof, is performed at a temperature of from about 0° C. to about 90° C. In some embodiments, the reacting of the compound of Formula XI-b, or a salt thereof, and the compound of Formula XIV, or a salt thereof, is performed at a temperature of from about 70° C. to about 90° C. In some embodiments, the reacting of the compound of Formula XI-b, or a salt thereof, and the compound of Formula XIV, or a salt thereof, is performed at a temperature of from about 75° C. to about 85° C.

In some embodiments, the reacting of the compound of Formula XI-b, or a salt thereof, and the compound of Formula XIV, or a salt thereof, is performed in a solvent selected from an ester (e.g., ethyl acetate, n-butyl acetate), an ether (e.g., 2-methyltetrahydrofuran, tert-butyl methyl ether), a hydrocarbon (e.g., toluene, xylene, trifluorotoluene), a halogenated solvent (e.g., dichloromethane, 1,2-dichloroethane, chloroform, carbon tetrachloride), a nitrile (e.g., acetonitrile, propylnitrile, butylnitrile), a polar aprotic solvent (e.g., N,N-dimethylformamide, N,N-dimethylacetamide, N-methyl-2-pyrrolidone, and dimethyl sulfoxide), and a protic solvent (e.g., methanol, ethanol), or any combination thereof.

In some embodiments, the reacting of the compound of Formula XI-b, or a salt thereof, and the compound of Formula XIV, or a salt thereof, is performed in a solvent selected from ethyl acetate, n-butyl acetate, 2-methyltetrahydrofuran, tert-butyl methyl ether, toluene, xylene, trifluorotoluene, dichloromethane, 1,2-dichloroethane, chloroform, carbon tetrachloride, acetonitrile, propylnitrile, butylnitrile, N,N-dimethylformamide, N,N-dimethylacetamide, N-methyl-2-pyrrolidone, dimethyl sulfoxide, methanol, and ethanol, or any combination thereof. In some embodiments, the reacting of the compound of Formula XI-b, or a salt thereof, and the compound of Formula XIV, or a salt thereof, is performed in a solvent comprising isopropyl acetate. In some embodiments, the reacting of the compound of Formula XI-b, or a salt thereof, and the compound of Formula XIV, or a salt thereof, is performed in a solvent comprising isopropyl acetate and water.

In some embodiments, the compound of Formula XI:

XI

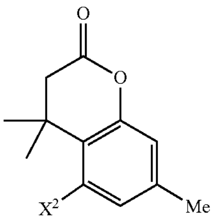

or a co-crystal, solvate, or salt thereof, is prepared by borylating a compound of Formula XI-a:

XI-a

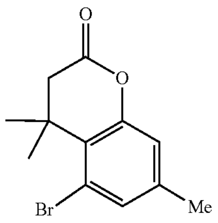

or a co-crystal, solvate, or salt thereof, with a diboron reagent in the presence of a palladium catalyst, a base, and optionally in the presence of a ligand, wherein:

$X^2$ is selected from the group consisting of dihydroxyboranyl, 4,4,5,5-tetramethyl-1,3,2-dioxaborolan-2-yl, 5,5-dimethyl-1,3,2-dioxaborinan-2-yl, and benzo[d][1,3,2]dioxaborol-2-yl.

In some embodiments, the compound of Formula XI:

XI

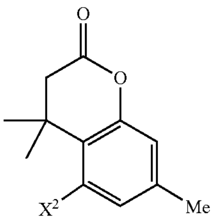

or a salt thereof, is prepared by borylating a compound of Formula XI-a:

XI-a

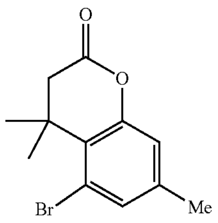

or a salt thereof, with a diboron reagent in the presence of a palladium catalyst, a base, and optionally in the presence of a ligand, wherein:

$X^2$ is selected from the group consisting of dihydroxyboranyl, 4,4,5,5-tetramethyl-1,3,2-dioxaborolan-2-yl, 5,5-dimethyl-1,3,2-dioxaborinan-2-yl, and benzo[d][1,3,2]dioxaborol-2-yl.

In some embodiments, the diboron reagent is selected from bis(pinacolato)diboron, bis(neopentyl glycolato)diboron, tetrahydroxydiboron, 2,2'-bibenzo[d][1,3,2]dioxaborole, and 4,4,4',4',6,6,6',6'-octamethyl-2,2'-bi(1,3,2-dioxaborinane). In some embodiments, the diboron reagent is bis(pinacolato)diboron.

In some embodiments, the compound of Formula XI is a compound of Formula XI-b:

XI-b

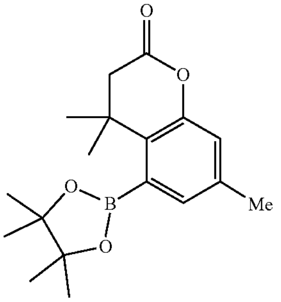

or a co-crystal, solvate, or salt thereof.

In some embodiments, the compound of Formula XI is a compound of Formula XI-b:

XI-b

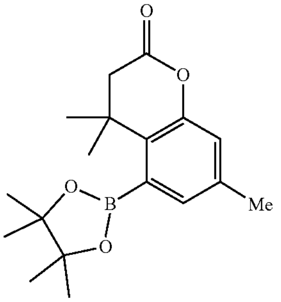

or a salt thereof.

In some embodiments, the compound of Formula XI is a compound of Formula XI-b:

XI-b

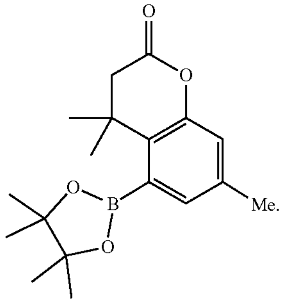

In some embodiments, the compound of Formula XI-b, or a salt thereof, is prepared by borylating a compound of Formula XI-a:

XI-a

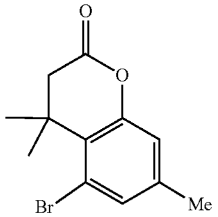

or a co-crystal, solvate, or salt thereof, with a diboron reagent in the presence of a palladium catalyst, a base, and optionally in the presence of a ligand.

In some embodiments, the compound of Formula XI-b, or a salt thereof, is prepared by borylating a compound of Formula XI-a:

XI-a

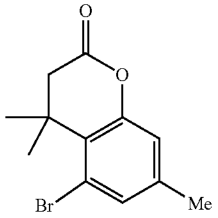

or a salt thereof, with a diboron reagent in the presence of a palladium catalyst, a base, and optionally in the presence of a ligand.

In some embodiments, the diboron reagent is bis(pinacolato)diboron.

In some embodiments, the palladium catalyst (i.e., the borylation palladium catalyst) is selected from the group consisting of a palladium(II) salt (e.g., palladium (II) chloride, palladium (II) bromide, palladium (II) acetate, palladium (II) trifluoroacetate), a palladium (0) complex (e.g., bis(dibenzylideneacetone)palladium(0), tetrakis(triphenylphosphine)palladium(0)), a G3-Pd complex (e.g., (2-dicyclohexylphosphino-2',4',6'-triisopropyl-1,1'-biphenyl)[2-(2'-amino-1,1'-biphenyl)]palladium(II) methanesulfonate (XPhos-Pd-G3)), and a G4-Pd complex (e.g., (SP-4-3)-[dicyclohexyl[2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium (XPhos-Pd-G4)).

In some embodiments, the palladium catalyst (i.e., the borylation palladium catalyst) is selected from palladium (II) chloride, palladium (II) bromide, palladium (II) acetate, palladium (II) trifluoroacetate, tetrakis(triphenylphosphine) palladium(0), (2-dicyclohexylphosphino-2',4',6'-triisopropyl-1,1'-biphenyl)[2-(2'-amino-1,1'-biphenyl)]palladium(II) methanesulfonate, and (SP-4-3)-[dicyclohexyl[2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium. In some embodiments, the palladium catalyst (i.e., the borylation palladium catalyst) is bis(dibenzylideneacetone)palladium(0).

In some embodiments, the borylation of the compound of Formula XI-a, or a salt thereof, is performed in the presence of a ligand.

In some embodiments, the ligand (i.e., the borylation ligand) is selected from a trialkylphosphine (e.g., tricyclohexylphosphine, tri-tert-butyl phosphine), a triarylphosphine (e.g., triphenylphosphine, tri(o-tolyl)phosphine), a dialkylarylphosphine (e.g., 2-dicyclohexylphosphino-2',6'-dimethoxybiphenyl (SPhos)), and a alkyldiarylphosphine (e.g., ethylenebis(diphenylphosphine) (DPPE)).

In some embodiments, the ligand (i.e., the borylation ligand) is selected from tricyclohexylphosphine, tri-tert-butyl phosphine, triphenylphosphine, tri(o-tolyl)phosphine, 2-dicyclohexylphosphino-2',6'-dimethoxybiphenyl, ethylenebis(diphenylphosphine). In some embodiments, the ligand (i.e., the borylation ligand) is triphenylphosphine.

In some embodiments, the base (i.e., the borylation base) is selected from sodium acetate, an inorganic base (e.g., sodium hydroxide, potassium hydroxide, potassium phosphate dibasic, potassium phosphate tribasic, cesium carbonate, potassium propionate), and a tertiary amine base (e.g., triethylamine, N-methylmorpholine, tripropylamine, N,N-diisopropylethylamine).

In some embodiments, the base (i.e., the borylation base) is selected from sodium acetate, sodium hydroxide, potassium hydroxide, potassium phosphate dibasic, potassium phosphate tribasic, cesium carbonate, potassium propionate, triethylamine, N-methylmorpholine, tripropylamine, and N,N-diisopropylethylamine. In some embodiments, the base (i.e., the borylation base) is potassium propionate.

In some embodiments, the borylation of the compound of Formula XI-a, or a salt thereof, is performed at a temperature of from about 0° C. to about 150° C. In some embodiments, the borylation of the compound of Formula XI-a, or a salt thereof, is performed at a temperature of from about 50° C. to about 95° C. In some embodiments, the borylation of the compound of Formula XI-a, or a salt thereof, is performed at a temperature of from about 70° C. to about 90° C. In some embodiments, the borylation of the compound of Formula XI-a, or a salt thereof, is performed at a temperature of from about 80° C. to about 90° C.

In some embodiments, the borylation of the compound of Formula XI-a, or a salt thereof, is performed in a solvent selected from the group consisting of an ester (e.g., ethyl acetate, n-butyl acetate), an ether (e.g., 2-methyltetrahydrofuran, tert-butyl methyl ether), a hydrocarbon (e.g., toluene, xylene), a halogenated solvent (e.g., dichloromethane, 1,2-dichloroethane, chloroform, carbon tetrachloride, trifluorotoluene), a nitrile (e.g., acetonitrile, propylnitrile, butylnitrile), a polar aprotic solvent (e.g., N,N-dimethylformamide, N,N-dimethylacetamide, N-methyl-2-pyrrolidone, and dimethyl sulfoxide), and a protic solvent (e.g., methanol, ethanol)

In some embodiments, the borylation of the compound of Formula XI-a, or a salt thereof, is performed in a solvent selected from the group consisting of ethyl acetate, isopropyl acetate, n-butyl acetate, 2-methyltetrahydrofuran, tert-butyl methyl ether, toluene, xylene, dichloromethane, 1,2-dichloroethane, chloroform, carbon tetrachloride, trifluorotoluene, acetonitrile, propylnitrile, butylnitrile, N,N-dimethylformamide, N,N-dimethylacetamide, N-methyl-2-pyrrolidone, dimethyl sulfoxide, methanol, and ethanol, or any combination thereof. In some embodiments, the borylation of the compound of Formula XI-a, or a salt thereof, is performed in a solvent comprising isopropyl acetate.

In some embodiments, the compound of Formula XIV is a compound of Formula XIV-a:

XIV-a

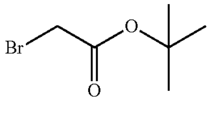

or a co-crystal, solvate, or salt thereof.

In some embodiments, the compound of Formula XIV is a compound of Formula XIV-a:

XIV-a

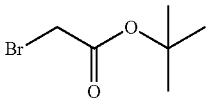

or a salt thereof.

In some embodiments, the compound of Formula XIV is a compound of Formula XIV-a:

XIV-a

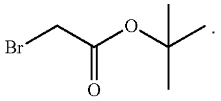

In some embodiments, the compound of Formula XIII is a compound of Formula XIII-a:

XIII-a

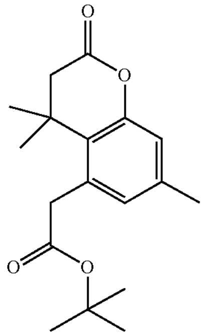

or a co-crystal, solvate, or salt thereof.

In some embodiments, the compound of Formula XIII is a compound of Formula XIII-a:

XIII-a

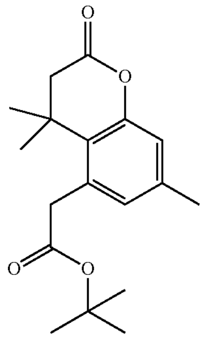

or a salt thereof.

In some embodiments, the compound of Formula XIII is a compound of Formula XIII-a:

XIII-a

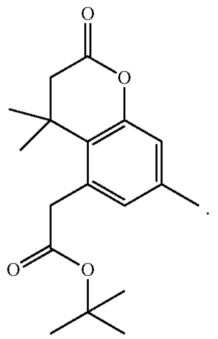

In some embodiments, the process of preparing the compound of Formula XIII, or a co-crystal, solvate, or salt thereof, further comprises phosphorylating the compound of Formula XIII, or a co-crystal, solvate, or salt thereof, to form a compound of Formula IV:

IV

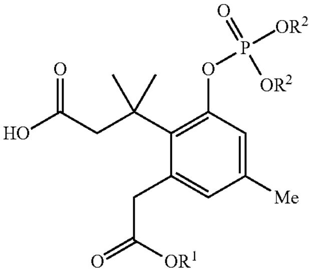

or a co-crystal, solvate, or salt thereof, wherein:

$R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy; and each $R^2$ is independently selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, $R^1$ is selected from the group consisting of $C_{1-6}$ alkyl, phenyl, pyridyl, and benzyl, wherein the phenyl, pyridyl, and benzyl are each optionally substituted by methoxy.

In some embodiments, $R^1$ is selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, each $R^2$ is independently selected from the group consisting of $C_{1-6}$ alkyl, phenyl, pyridyl, and benzyl, wherein the phenyl, pyridyl, and benzyl are each optionally substituted by methoxy.

In some embodiments, each $R^2$ is independently selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, the process of preparing the compound of Formula XIII, or a salt thereof, further comprises phosphorylating the compound of Formula XIII, or a salt thereof, to form a compound of Formula IV:

IV

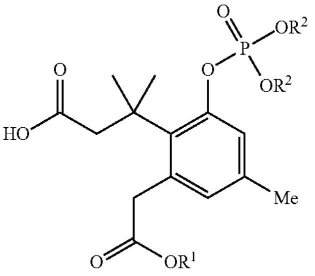

or a salt thereof, wherein:

$R^1$ is $C_{1-6}$ alkyl; and each $R^2$ is independently selected from the group consisting of $C_{1-6}$ alkyl.

In some embodiments, $R^1$ is selected from the group consisting of methyl, ethyl, isopropyl, and tert-butyl. In some embodiments, $R^1$ is tert-butyl.

In some embodiments, each $R^2$ is independently selected from the group consisting of methyl, ethyl, isopropyl, and tert-butyl. In some embodiments, $R^2$ is tert-butyl. In some embodiments, $R^1$ and each $R^2$ is tert-butyl.

In some embodiments, the phosphorylating comprises reacting the compound of Formula XIII, or a co-crystal, solvate, or salt thereof, with phorphorylating agent, optionally in the presence of an oxidizing agent and a base.

In some embodiments, the phosphorylating comprises reacting the compound of Formula XIII, or a salt thereof, with phorphorylating agent, optionally in the presence of an oxidizing agent and a base.

In some embodiments, the phosphorylating comprises reacting the compound of Formula XIII, or a salt thereof, with phorphorylating agent.

In some embodiments, the phosphorylating comprises reacting the compound of Formula XIII, or a salt thereof, with phorphorylating agent in the presence of an oxidizing agent and a base.

In some embodiments, the phosphorylating agent is selected from the group consisting of di-tert-butyl phosphite, a dialkyl phosphoryl halide (e.g., di-t-butyl phosphoryl chloride, di-t-butyl phosphoryl bromide, di-ethyl phosphoryl chloride, di-propyl phosphoryl chloride), dibenzyl phosphorochloridate, and dibenzyl phosphorobromidate.

In some embodiments, the phosphorylating agent is selected from the group consisting of di-tert-butyl phosphite, di-tert-butyl phosphoryl chloride, di-tert-butyl phosphoryl bromide, di-ethyl phosphoryl chloride, di-propyl phosphoryl chloride, dibenzyl phosphorochloridate, and dibenzyl phosphorobromidate. In some embodiments, the phosphorylating agent is di-tert-butyl phosphite.

In some embodiments, the oxidizing agent is absent. In some embodiments, the oxidizing agent is selected from the group consisting of an alkyl halide (e.g., carbontetrabromide, carbon tetrachloride, bromoform, dibromomethane, dibromoethane, bromotrichloromethane), an N-halo succinimide (e.g., N-chlorosuccinimide, N-bromosuccinimide), an N-halo sulfonamides (e.g., N-chlorotosylamide sodium salt), bromine ($Br_2$), chlorine ($Cl_2$), iodine ($I_2$), and a hypochlorite (e.g., sodium hypochlorite).

In some embodiments, the oxidizing agent is selected from the group consisting of bromoform, carbontetrabromide, carbon tetrachloride, dibromomethane, dibromoethane, bromotrichloromethane, N-chlorosuccinimide, N-bromosuccinimide, N-chlorotosylamide sodium salt, bromine, chlorine, iodine, and sodium hypochlorite. In some embodiments, the oxidizing agent is bromoform.

In some embodiments, the base is selected from the group consisting of a hydroxide base (e.g., potassium hydroxide, sodium hydroxide, lithium hydroxide), a siloxide base (e.g., sodium trimethylsilanolate), an alkoxide base (e.g., sodium tert-butoxide), a hydride base (e.g., sodium hydride), a carbonate base (e.g., cesium carbonate).

In some embodiments, the base is selected from the group consisting of sodium trimethylsilanolate, potassium hydroxide, sodium hydroxide, lithium hydroxide, sodium trimethylsilanolate, sodium tert-butoxide, sodium hydride, and cesium carbonate. In some embodiments, the base is sodium trimethylsilanolate. In some embodiments, the base is cesium carbonate.

In some embodiments, the phosphorylating is performed at a temperature of from about 0° C. to about 40° C. In some embodiments, the phosphorylating is performed at a temperature of from about 0° C. to about 35° C. In some embodiments, the phosphorylating is performed at about room temperature.

In some embodiments, the phosphorylating is performed in a solvent selected from the group consisting of an ether (e.g., 2-methyltetrahydrofuran), a hydrocarbon (e.g., toluene, xylene, trifluorotoluene), a halogenated solvent (e.g., dichloromethane, 1,2-dichloroethane, chloroform, carbon tetrachloride), a nitrile (e.g., acetonitrile, propylnitrile, butylnitrile), and a polar aprotic solvent (e.g., N,N-dimethylformamide, N,N-dimethylacetamide, N-methyl-2-pyrrolidone, and dimethyl sulfoxide), or any combination thereof, optionally in combination with water. In some embodiments, the phosphorylating is performed in a solvent comprising 2-methyltetrahydrofuran and water.

In some embodiments, the compound of Formula IV is a compound of Formula IV-a:

IV-a

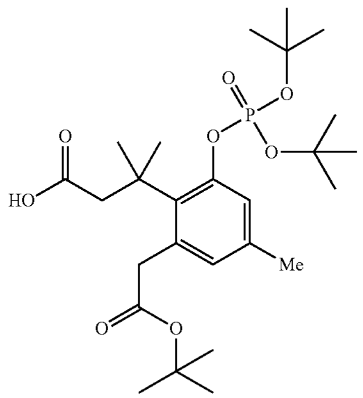

or a co-crystal, solvate, or salt thereof.

In some embodiments, the compound of Formula IV is a compound of Formula IV-a:

IV-a

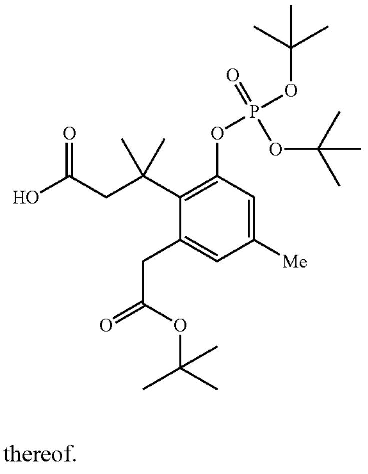

or a salt thereof.

In some embodiments, the compound of Formula IV is a compound of Formula IV-a:

IV-a

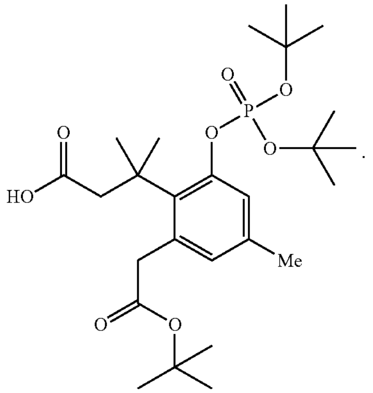

In some embodiments, the present disclosure further provides a process of preparing a compound of Formula VI:

VI

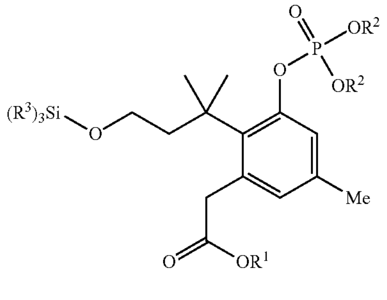

or a co-crystal, solvate, or salt thereof, comprising reacting a compound of Formula VII:

VII

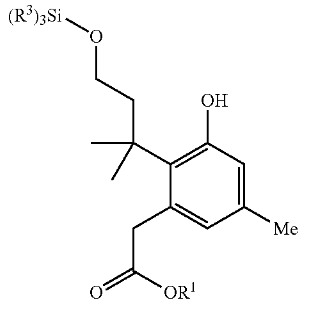

or a co-crystal, solvate, or salt thereof, with di($C_{1-6}$ alkyl) phosphite in the presence of an oxidizing agent and a base, wherein:

$R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy;

each $R^2$ is independently selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy; and each $R^3$ is independently selected from the group consisting of $C_{1-6}$ alkyl and $C_{6-10}$ aryl.

In some embodiments, $R^1$ is selected from the group consisting of $C_{1-6}$ alkyl, phenyl, pyridyl, and benzyl, wherein the phenyl, pyridyl, and benzyl are each optionally substituted by methoxy.

In some embodiments, $R^1$ is selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, each $R^2$ is independently selected from the group consisting of $C_{1-6}$ alkyl, phenyl, pyridyl, and benzyl, wherein the phenyl, pyridyl, and benzyl are each optionally substituted by methoxy.

In some embodiments, each $R^2$ is independently selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, each $R^3$ is independently selected from methyl, ethyl, propyl, isopropyl, tert-butyl, and phenyl.

In some embodiments, the present disclosure further provides a process of preparing a compound of Formula VI:

VI

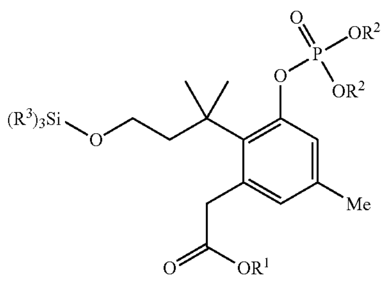

or a salt thereof, comprising reacting a compound of Formula VII:

VII

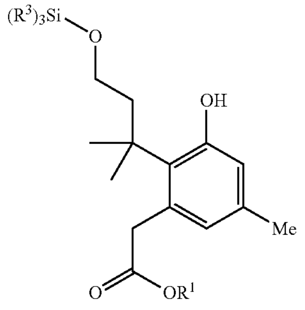

or a salt thereof, with di($C_{1-6}$ alkyl)phosphite in the presence of an oxidizing agent and a base, wherein:

$R^1$ is $C_{1-6}$ alkyl;

each $R^2$ is independently selected from the group consisting of $C_{1-6}$ alkyl; and each $R^3$ is independently selected from the group consisting of $C_{1-6}$ alkyl.

In some embodiments, $R^1$ is selected from the group consisting of methyl, ethyl, isopropyl, and tert-butyl. In some embodiments, $R^1$ is tert-butyl.

In some embodiments, each $R^2$ is independently selected from the group consisting of methyl, ethyl, isopropyl, and tert-butyl. In some embodiments, $R^2$ is tert-butyl. In some embodiments, $R^1$ and each $R^2$ is tert-butyl.

In some embodiments, each $R^3$ is independently selected from methyl and tert-butyl. In some embodiments, the di($C_{1-6}$ alkyl)phosphite is di-tert-butyl phosphite.

In some embodiments, the oxidizing agent is selected from the group consisting of an alkyl halide (e.g., carbontetrabromide, carbon tetrachloride, bromoform, dibromomethane, dibromoethane, bromotrichloromethane), an N-halo succinimide (e.g., N-chlorosuccinimide, N-bromosuccinimide), an N-halo sulfonamide (e.g., N-chlorotosylamide sodium salt), bromine ($Br_2$), chlorine ($Cl_2$), iodine ($I_2$), and a hypochlorite (e.g., sodium hypochlorite).

In some embodiments, the oxidizing agent is selected from the group consisting of bromoform, carbontetrabromide, carbon tetrachloride, dibromomethane, dibromoethane, bromotrichloromethane, N-chlorosuccinimide, N-bromosuccinimide, N-chlorotosylamide sodium salt, bromine, chlorine, iodine, and sodium hypochlorite. In some embodiments, the oxidizing agent is bromoform.

In some embodiments, the base is selected from the group consisting of an inorganic base (e.g., sodium hydroxide, potassium hydroxide, potassium phosphate dibasic, potassium phosphate tribasic, cesium carbonate), a tertiary amine (e.g., triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane (DABCO)), an aromatic amine (e.g., pyridine, 2,6-lutidine, collidine, 1-methylimidazole), and a hydride base (e.g., sodium hydride).

In some embodiments, the base is selected from the group consisting of cesium carbonate, sodium hydroxide, potassium hydroxide, potassium phosphate dibasic, potassium phosphate tribasic, cesium carbonate, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, collidine, 1-methylimidazole, and sodium hydride. In some embodiments, the base is cesium carbonate.

In some embodiments, the reacting is performed a temperature of from about −20° C. to about 100° C. In some embodiments, the reacting is performed a temperature of from about 0° C. to about 40° C. In some embodiments, the reacting is performed a temperature of from about 15° C. to about 25° C.

In some embodiments, the reacting is performed in a solvent selected from the group consisting of an ether (e.g., 2-methyltetrahydrofuran, tert-butyl methyl ether), a ketone (e.g., acetone, 2-butanone) a hydrocarbon (e.g., toluene, xylene, trifluorotoluene), a halogenated solvent (e.g., dichloromethane, 1,2-dichloroethane, chloroform, carbon tetrachloride), a nitrile (e.g., acetonitrile, propylnitrile, butylnitrile), and a polar aprotic solvent (e.g., N,N-dimethylformamide, N,N-dimethylacetamide, N-methyl-2-pyrrolidone, dimethyl sulfoxide), or any combination thereof. In some embodiments, the reacting is performed in a solvent comprising tetrahydrofuran.

In some embodiments, the compound of Formula VI is a compound of Formula VI-a:

VI-a

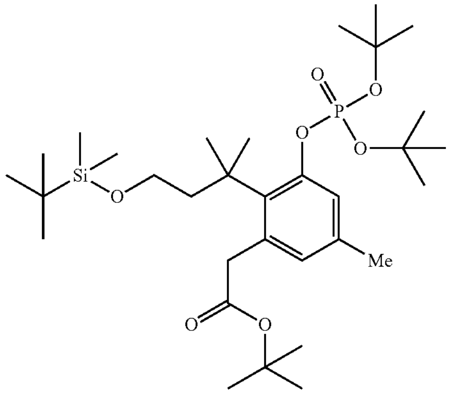

or a co-crystal, solvate, or salt thereof.

In some embodiments, the compound of Formula VI is a compound of Formula VI-a:

VI-a

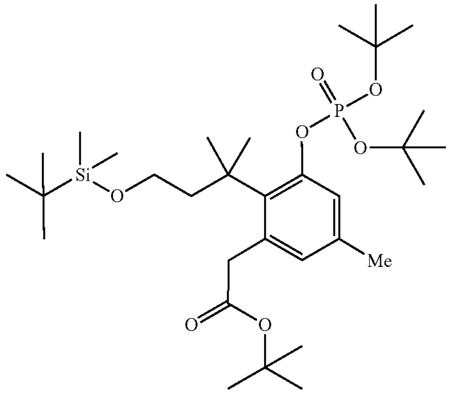

or a salt thereof.

In some embodiments, the compound of Formula VI is a compound of Formula VI-a:

VI-a

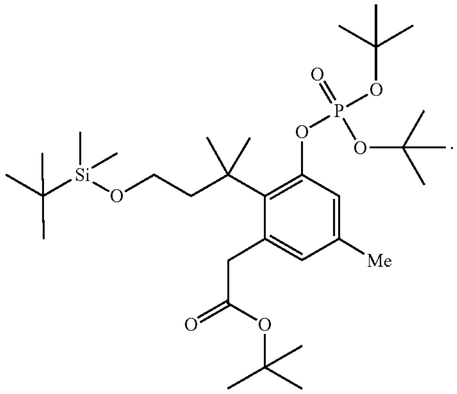

In some embodiments, the present disclosure further provides a process of preparing a compound of Formula VI:

VI

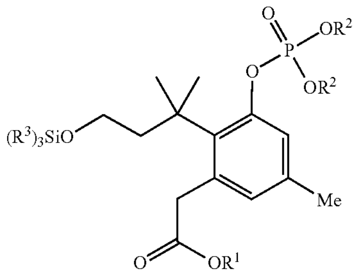

or a co-crystal, solvate, or salt thereof, comprising reacting a compound of Formula VII:

VII

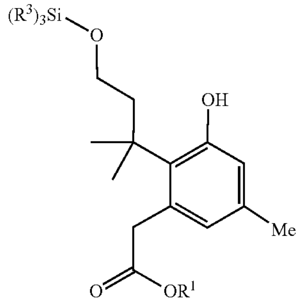

or a co-crystal, solvate, or salt thereof, with a phosphorylating agent selected from tetra($C_{6-10}$ aryl-$C_{1-6}$ alkyl-)pyrophosphate, a tetra($C_{1-6}$ alkyl) pyrophosphates, a di($C_{1-6}$ alkyl) phosphoro halide, a di($C_{1-6}$ alkyl) phosphoro sulfonate, and $(R^4O)_2P(=O)\text{-}LG^2$ in the presence of a base, wherein:

$R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy;

each $R^2$ is independently selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy;

each $R^3$ is independently selected from the group consisting of $C_{1-6}$ alkyl and $C_{6-10}$ aryl;

each $R^4$ is independently selected from the group consisting of $C_{6-10}$ aryl-$C_{1-6}$ alkyl-; and $LG^2$ is selected from the group consisting of halo and 4-methylbenzylsulfonyloxy.

In some embodiments, the present disclosure further provides a process of preparing a compound of Formula VI:

VI

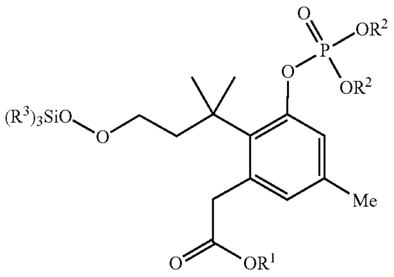

or a co-crystal, solvate, or salt thereof, comprising reacting a compound of Formula VII:

VII

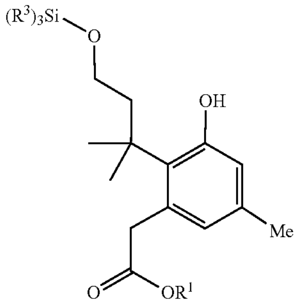

or a co-crystal, solvate, or salt thereof, with tetra($C_{6-10}$ aryl-$C_{1-6}$ alkyl-)pyrophosphate or $(R^4O)_2P(=O)$-$LG^2$ in the presence of a base, wherein:

$R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy;

each $R^2$ is independently selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy;

each $R^3$ is independently selected from the group consisting of $C_{1-6}$ alkyl and $C_{6-10}$ aryl;

each $R^4$ is independently selected from the group consisting of $C_{6-10}$ aryl-$C_{1-6}$ alkyl-; and $LG^2$ is selected from the group consisting of halo and 4-methylbenzylsulfonyloxy.

In some embodiments, the present disclosure further provides a process of preparing a compound of Formula VI:

VI

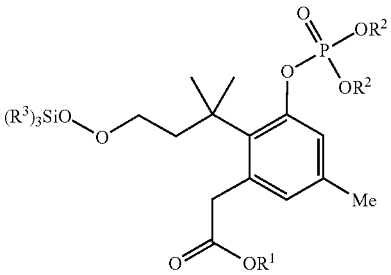

or a co-crystal, solvate, or salt thereof, comprising reacting a compound of Formula VII:

VII

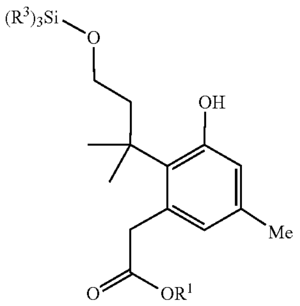

or a co-crystal, solvate, or salt thereof, with tetra($C_{6-10}$ aryl-$C_{1-6}$ alkyl-)pyrophosphate or $(R^4O)_2P(=O)$-$LG^2$ in the presence of a base, wherein:

$R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy;

each $R^2$ is independently selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy;

each $R^3$ is independently selected from the group consisting of $C_{1-6}$ alkyl and $C_{6-10}$ aryl;

each $R^4$ is independently selected from the group consisting of $C_{6-10}$ aryl-$C_{1-6}$ alkyl-; and $LG^2$ is selected from the group consisting of halo and 4-methylbenzylsulfonyloxy.

In some embodiments, the present disclosure further provides a process of preparing a compound of Formula VI:

VI

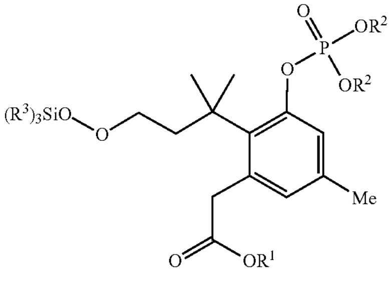

or a salt thereof, comprising reacting a compound of Formula VII:

VII

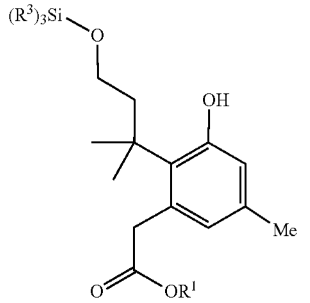

or a salt thereof, with a phosphorylating agent selected from tetra($C_{6-10}$ aryl-$C_{1-6}$ alkyl-)pyrophosphate, a tetra($C_{1-6}$ alkyl) pyrophosphates, a di($C_{1-6}$ alkyl) phosphoro halide, a di($C_{1-6}$ alkyl) phosphoro sulfonate, and $(R^4O)_2P(=O)$-$LG^2$, in the presence of a base, wherein:

$R^1$ is $C_{1-6}$ alkyl;

each $R^2$ is independently selected from the group consisting of $C_{6-10}$ aryl-$C_{1-6}$ alkyl-;

each $R^3$ is independently selected from the group consisting of $C_{1-6}$ alkyl;

each $R^4$ is independently selected from the group consisting of $C_{6-10}$ aryl-$C_{1-6}$ alkyl-; and $LG^2$ is selected from the group consisting of halo and 4-methylbenzylsulfonyloxy.

In some embodiments, the phosphorylating agent is selected from a tetra($C_{6-10}$ aryl-$C_{1-6}$ alkyl-)pyrophosphate, tetramethyl pyrophosphate, tetraethyl pyrophosphate, dimethyl phosphorochloridate, diethyl phosphorochloridate, and dimethyl phosphor methanesulfonate.

In some embodiments, the present disclosure further provides a process of preparing a compound of Formula VI:

VI

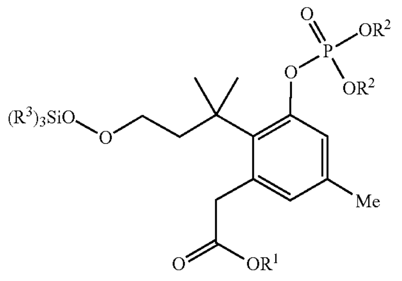

or a salt thereof, comprising reacting a compound of Formula VII:

VII

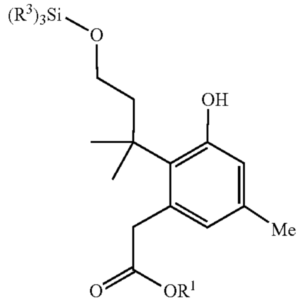

or a salt thereof, with tetra($C_{6-10}$ aryl-$C_{1-6}$ alkyl-)pyrophosphate or $(R^4O)_2P(=O)$-$LG^2$ in the presence of a base, wherein:

$R^1$ is $C_{1-6}$ alkyl;

each $R^2$ is independently selected from the group consisting of $C_{6-10}$ aryl-$C_{1-6}$ alkyl-;

each $R^3$ is independently selected from the group consisting of $C_{1-6}$ alkyl;

each $R^4$ is independently selected from the group consisting of $C_{6-10}$ aryl-$C_{1-6}$ alkyl-; and $LG^2$ is selected from the group consisting of halo and 4-methylbenzylsulfonyloxy.

In some embodiments, $R^1$ is selected from the group consisting of methyl, ethyl, isopropyl, and tert-butyl. In some embodiments, $R^1$ is tert-butyl.

In some embodiments, each $R^2$ is independently selected from the group consisting of phenyl-$C_{1-6}$ alkyl. In some embodiments, each $R^2$ is benzyl.

In some embodiments, $R^1$ is tert-butyl and each $R^2$ is benzyl.

In some embodiments, each $R^3$ is independently selected from methyl and tert-butyl. In some embodiments, the phosphorylating agent is a tetra($C_{6-10}$ aryl-$C_{1-6}$ alkyl-)pyrophosphate. In some embodiments, the tetra($C_{6-10}$ aryl-$C_{1-6}$ alkyl-)pyrophosphate is tetrabenzyl pyrophosphate.

In some embodiments, the phosphorylating agent is $(R^4O)_2P(=O)$-$LG^2$, wherein:

each $R^4$ is independently selected from the group consisting of $C_{6-10}$ aryl-$C_{1-6}$ alkyl-; and $LG^2$ is selected from the group consisting of halo and 4-methylbenzylsulfonyloxy.

In some embodiments, the phosphorylating agent is $(R^4O)_2P(=O)$-$LG^2$, wherein:

each $R^4$ is benzyl; and $LG^2$ is selected from the group consisting of chloro, bromo, iodo, and 4-methylbenzylsulfonyloxy.

In some embodiments, the base is selected from the group consisting of an inorganic base (e.g., sodium hydroxide, potassium hydroxide, potassium phosphate dibasic, potassium phosphate tribasic, cesium carbonate), a tertiary amine (e.g., triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane (DABCO)), and an aromatic amine (e.g., pyridine, 2,6-lutidine, collidine, 1-methylimidazole).

In some embodiments, the base is selected from the group consisting of sodium hydride, sodium hydroxide, potassium hydroxide, potassium phosphate dibasic, potassium phosphate tribasic, cesium carbonate, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, collidine, and 1-methylimidazole. In some embodiments, the base is sodium hydride.

In some embodiments, the reacting is performed at a temperature of from about −40° C. to about 100° C. In some embodiments, the reacting is performed at a temperature of from about −20° C. to about 40° C. In some embodiments, the reacting is performed at a temperature of from about −10° C. to about 10° C.

In some embodiments, the reacting is performed in a solvent selected from the group consisting of an ether (e.g., 2-methyltetrahydrofuran, tert-butyl methyl ether), a ketone (e.g., acetone, 2-butanone), a hydrocarbon (e.g., toluene, xylene, trifluorotoluene), a halogenated solvent (e.g., dichloromethane, 1,2-dichloroethane, chloroform, carbon tetrachloride), a nitrile (e.g., acetonitrile, propylnitrile, butylnitrile), and a polar aprotic solvent (e.g., N,N-dimethylformamide, N,N-dimethylacetamide, N-methyl-2-pyrrolidone, dimethyl sulfoxide), or any combination thereof. In some embodiments, the reacting is performed in a solvent comprising tetrahydrofuran.

In some embodiments, the compound of Formula VI is a compound of Formula VI-b:

VI-b

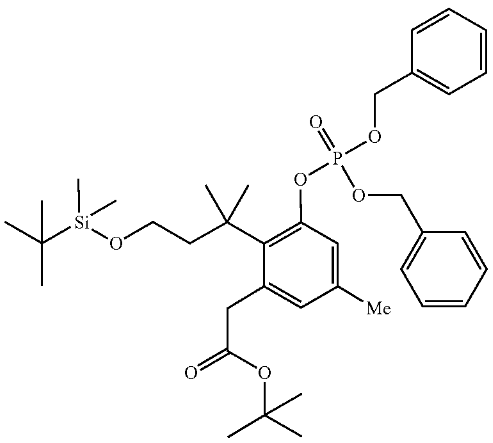

or a co-crystal, solvate, or salt thereof.

In some embodiments, the compound of Formula VI is a compound of Formula VI-b:

VI-b

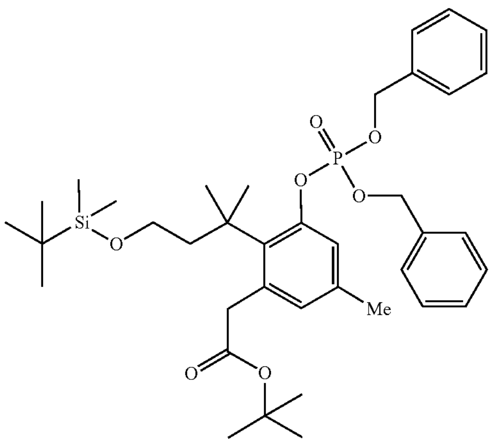

or a salt thereof.

In some embodiments, the compound of Formula VI is a compound of Formula VI-b:

VI-b

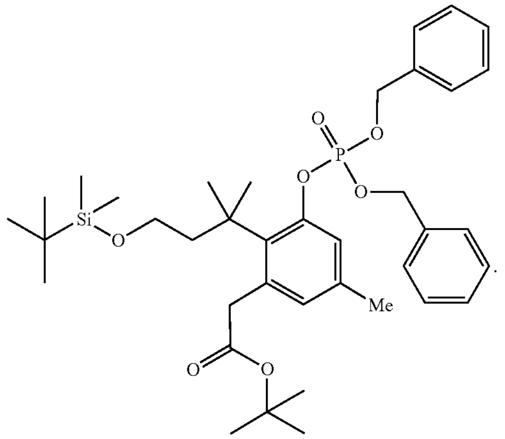

In some embodiments, the present disclosure further provides a process of preparing a compound of Formula VI:

VI

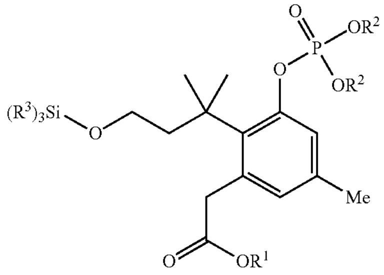

or a co-crystal, solvate, or salt thereof, comprising reacting a compound of Formula VII:

VII

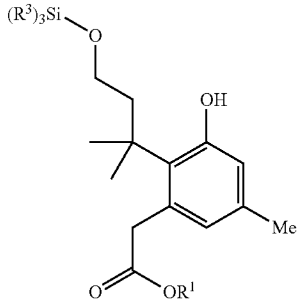

or a co-crystal, solvate, or salt thereof, with a di($C_{1-6}$ alkyl), N,N-di($C_{1-6}$ alkyl)phosphoramidate in the presence of a base and an acid to form a first mixture; and mixing the first mixture with an oxidizing agent; wherein $R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy;

each $R^2$ is independently selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy; and each $R^3$ is independently selected from the group consisting of $C_{1-6}$ alkyl and $C_{6-10}$ aryl-$C_{1-6}$ alkyl-, wherein the $C_{6-10}$ aryl-$C_{1-6}$ alkyl- are each optionally substituted by $C_{1-6}$ alkoxy.

In some embodiments, $R^1$ is selected from the group consisting of $C_{1-6}$ alkyl, phenyl, pyridyl, and benzyl, wherein the phenyl, pyridyl, and benzyl are each optionally substituted by methoxy.

In some embodiments, $R^1$ is selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, each $R^2$ is independently selected from the group consisting of $C_{1-6}$ alkyl, phenyl, pyridyl, and benzyl, wherein the phenyl, pyridyl, and benzyl are each optionally substituted by methoxy.

In some embodiments, each $R^2$ is independently selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, each $R^3$ is independently selected from the group consisting of methyl, ethyl, isopropyl, tert-butyl, benzyl, and methoxybenzyl (e.g., 4-methoxybenzyl).

In some embodiments, the present disclosure further provides a process of preparing a compound of Formula VI:

VI

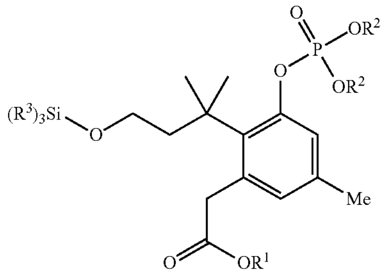

or a salt thereof, comprising reacting a compound of Formula VII:

VII

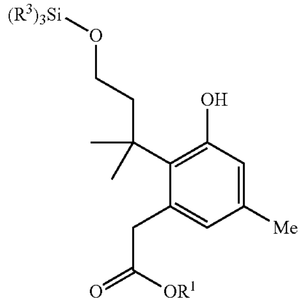

or a salt thereof, with a di($C_{1-6}$ alkyl), N,N-di($C_{1-6}$ alkyl) phosphoramidate in the presence of a base and an acid to form a first mixture; and mixing the first mixture with an oxidizing agent; wherein $R^1$ is $C_{1-6}$ alkyl;

each $R^2$ is independently selected from the group consisting of $C_{1-6}$ alkyl; and each $R^3$ is independently selected from the group consisting of $C_{1-6}$ alkyl.

In some embodiments, $R^1$ is selected from the group consisting of methyl, ethyl, isopropyl, and tert-butyl. In some embodiments, $R^1$ is tert-butyl.

In some embodiments, each $R^2$ is independently selected from the group consisting of methyl, ethyl, isopropyl, and tert-butyl. In some embodiments, $R^2$ is tert-butyl. In some embodiments, $R^1$ and each $R^2$ is tert-butyl.

In some embodiments, each $R^3$ is independently selected from methyl and tert-butyl. In some embodiments, the di($C_{1-6}$ alkyl), N,N-di($C_{1-6}$ alkyl)phosphoramidate is di-tert-butyl N,N-diisopropylphosphoramidate.

In some embodiments, the base is selected from the group consisting of a tertiary amine (e.g., triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane (DABCO)), and an aromatic amine (e.g., pyridine, 2,6-lutidine, collidine, and 1-methylimidazole).

In some embodiments, the base is selected from the group consisting of 1-methylimidazole, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, and collidine. In some embodiments, the base is 1-methylimidazole.

In some embodiments, the acid is selected from the group consisting of a carboxylic acid (e.g., trichloroacetic acid, formic acid), an inorganic acid (e.g., hydrofluoric acid, hydrochloric acid, sulfuric acid, phosphoric acid), an organic acid (e.g., methanesulfonic acid, p-toluenesulfonic acid), a tetrazole (e.g., 1H-tetrazole, 5-phenyltetrazole, an arylsulfonyl tetrazole such as benzylthiotetrazole or ethylthiotetrazole), a phenol (e.g., 2,4-dinitrophenol, 4-cyanophenol), an imidazole (e.g., 2-bromo-4,5-dicyanoimidazole, 4,5-dicyanoimidazole), and saccharin.

In some embodiments, the acid is selected from the group consisting of trifluoroacetic acid, trichloroacetic acid, formic acid, hydrofluoric acid, hydrochloric acid, sulfuric acid, phosphoric acid, methanesulfonic acid, p-toluenesulfonic acid, 1H-tetrazole, 5-phenyltetrazole, benzylthiotetrazole, ethylthiotetrazole, 2,4-dinitrophenol, 4-cyanophenol, 2-bromo-4,5-dicyanoimidazole, 4,5-dicyanoimidazole, and saccharin. In some embodiments, the acid is trifluoroacetic acid.

In some embodiments, the oxidizing agent is selected from the group consisting of an N-halo succinimide (e.g., N-chlorosuccinimide, N-bromosuccinimide), an N-halo sulfonamide (e.g., N-chlorotosylamide sodium salt), bromine ($Br_2$), chlorine ($Cl_2$), iodine ($I_2$), a hypochlorite (e.g., sodium hypochlorite), a peroxide (e.g., sodium peroxide, t-butyl hydrogen peroxide, sodium perborate), and potassium peroxymonosulfate (Oxone).

In some embodiments, the oxidizing agent is selected from the group consisting of hydrogen peroxide, N-chlorosuccinimide, N-bromosuccinimide, N-chlorotosylamide sodium salt, bromine, chlorine, iodine, sodium hypochlorite), sodium peroxide, tert-butyl hydrogen peroxide, sodium perborate, and potassium peroxymonosulfate. In some embodiments, the oxidizing agent is hydrogen peroxide.

In some embodiments, the reacting is performed a temperature of from about −20° C. to about 100° C. In some embodiments, the reacting is performed a temperature of from about 0° C. to about 40° C. In some embodiments, the reacting is performed a temperature of from about 10° C. to about 30° C.

In some embodiments, the reacting is performed in a solvent selected from the group consisting of an ether (e.g., 2-methyltetrahydrofuran, tert-butyl methyl ether), a ketone (e.g., acetone, 2-butanone), a hydrocarbon (e.g., toluene, xylene, trifluorotoluene), a halogenated solvent (e.g., dichloromethane, 1,2-dichloroethane, chloroform, carbon tetrachloride), a nitrile (e.g., acetonitrile, propylnitrile, butylnitrile), and a polar aprotic solvents (e.g., N,N-dimethylformamide, N,N-dimethylacetamide, N-methyl-2-pyrrolidone, dimethyl sulfoxide), or any combination thereof. In some embodiments, the reacting is performed in a solvent comprising tetrahydrofuran and water.

In some embodiments, the compound of Formula VI is a compound of Formula VI-a:

VI-a

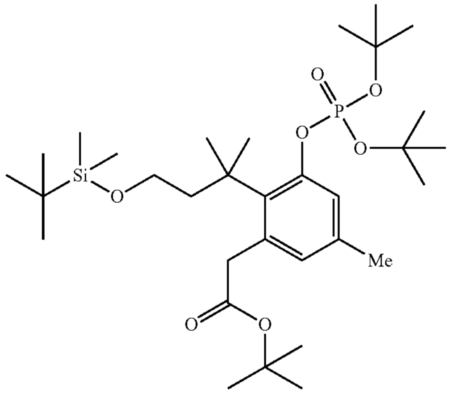

or a co-crystal, solvate, or salt thereof.

In some embodiments, the compound of Formula VI is a compound of Formula VI-a:

VI-a

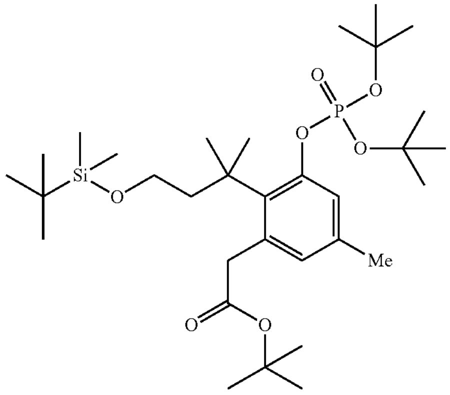

or a salt thereof.

In some embodiments, the compound of Formula VI is a compound of Formula VI-a:

VI-a

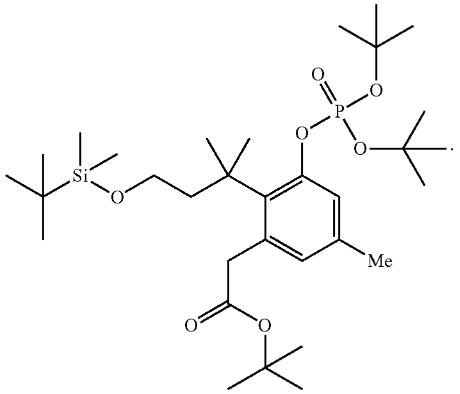

In some embodiments, the compound of Formula VII is a compound of Formula VII-a:

VII-a

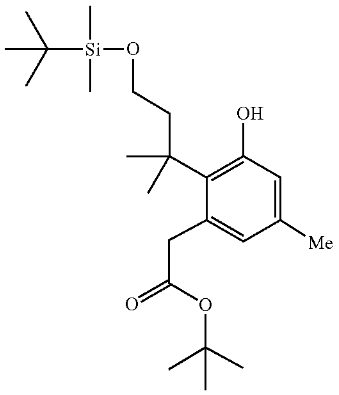

or a co-crystal, solvate, or salt thereof.

In some embodiments, the compound of Formula VII is a compound of Formula VII-a:

VII-a

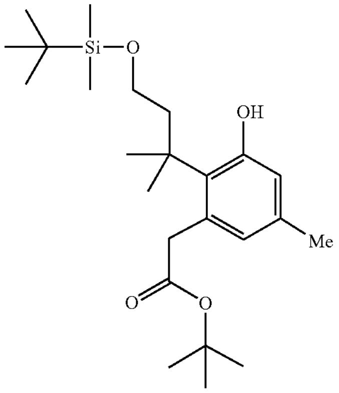

or a salt thereof.

In some embodiments, the compound of Formula VII is a compound of Formula VII-a:

VII-a

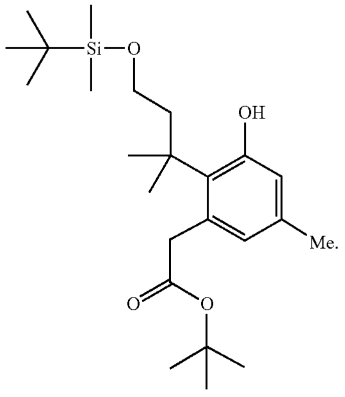

In some embodiments, a process provided herein further comprises deprotecting a compound of Formula VI, or a salt thereof, to form a compound of Formula V:

V

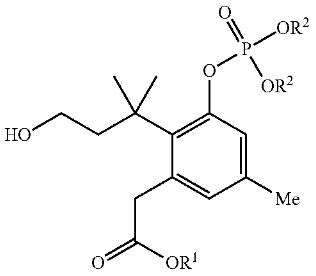

or a co-crystal, solvate, or salt thereof.

In some embodiments, a process provided herein further comprises deprotecting a compound of Formula VI, or a salt thereof, to form a compound of Formula V:

V

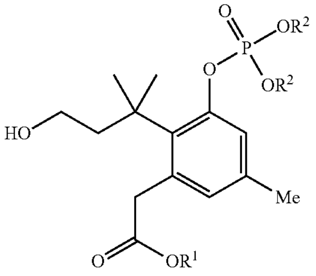

or a salt thereof, wherein:

$R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy; and each $R^2$ is independently selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, $R^1$ is selected from the group consisting of $C_{1-6}$ alkyl, phenyl, pyridyl, and benzyl, wherein the phenyl, pyridyl, and benzyl are each optionally substituted by methoxy.

In some embodiments, $R^1$ is selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, $R^2$ is selected from the group consisting of $C_{1-6}$ alkyl, phenyl, pyridyl, and benzyl, wherein the phenyl, pyridyl, and benzyl are each optionally substituted by methoxy.

In some embodiments, $R^2$ is selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, a process provided herein further comprises deprotecting a compound of Formula VI, or a salt thereof, to form a compound of Formula V:

V

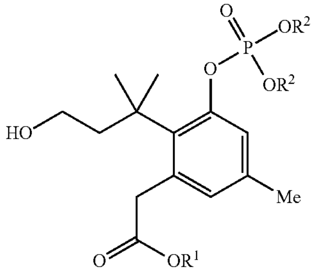

or a salt thereof, wherein:

$R^1$ is $C_{1-6}$ alkyl; and each $R^2$ is independently $C_{1-6}$ alkyl.

In some embodiments, a process provided herein further comprises deprotecting a compound of Formula VI, or a salt thereof, to form a compound of Formula V:

V

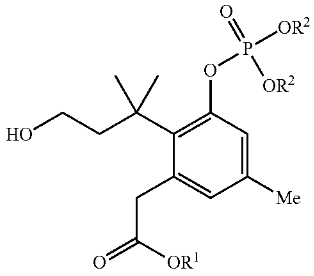

or a salt thereof, wherein:

$R^1$ is $C_{1-6}$ alkyl; and each $R^2$ is independently $C_{1-6}$ alkyl.

In some embodiments, $R^1$ is selected from the group consisting of methyl, ethyl, isopropyl, and tert-butyl. In some embodiments, $R^1$ is tert-butyl.

In some embodiments, each $R^2$ is independently selected from the group consisting of methyl, ethyl, isopropyl, and tert-butyl. In some embodiments, $R^2$ is tert-butyl. In some embodiments, $R^1$ and each $R^2$ is tert-butyl.

In some embodiments, the deprotecting comprises reacting the compound of Formula VI, or a co-crystal, solvate, or salt thereof, with a deprotecting agent selected from the group consisting of tetrabutylammonium fluoride, potassium hydrogen fluoride, potassium fluoride, sodium hydroxide, potassium hydroxide, potassium phosphate dibasic, potassium phosphate tribasic, cesium carbonate, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, collidine, 1-methylimidazole, hydrofluoric acid, hydrochloric acid, sulfuric acid, methanesulfonic acid, N-chlorosuccinimide, potassium peroxymonosulfate, and iodine.

In some embodiments, the deprotecting comprises reacting the compound of Formula VI, or a salt thereof, with a deprotecting agent which is a silyl cleaving agent. In some embodiments, the silyl cleaving agent is selected from a fluoride (e.g., potassium hydrogen fluoride, potassium fluoride, tetrabutylammonium fluoride), an inorganic base (e.g., sodium hydroxide, potassium hydroxide, potassium phosphate dibasic, potassium phosphate tribasic, cesium carbonate), a tertiary amine (e.g., triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane (DABCO)), an aromatic amine (e.g., pyridine, 2,6-lutidine, collidine, 1-methylimidazole), an acid (e.g., hydrofluoric acid, hydrochloric acid, sulfuric acid, methanesulfonic acid) and an oxidant (e.g., N-chlorosuccinimide, potassium peroxymonosulfate (Oxone), iodine).

In some embodiments, the deprotecting comprises reacting the compound of Formula VI, or a salt thereof, with a deprotecting agent (e.g., a silyl cleaving agent) selected from the group consisting of tetrabutylammonium fluoride, potassium hydrogen fluoride, potassium fluoride, sodium hydroxide, potassium hydroxide, potassium phosphate dibasic, potassium phosphate tribasic, cesium carbonate, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, collidine, 1-methylimidazole, hydrofluoric acid, hydrochloric acid, sulfuric acid, methanesulfonic acid, N-chlorosuccinimide, potassium peroxymonosulfate, and iodine. In some embodiments, the deprotecting comprises reacting the compound of Formula VI, or a co-crystal, solvate, or salt thereof, with tetrabutylammonium fluoride. In some embodiments, the deprotecting comprises reacting the compound of Formula VI, or a salt thereof, with tetrabutylammonium fluoride.

In some embodiments, the deprotecting is performed a temperature of from about −20° C. to about 100° C. In some embodiments, the deprotecting is performed a temperature of from about 0° C. to about 60° C. In some embodiments, the deprotecting is performed a temperature of from about 10° C. to about 30° C.

In some embodiments, the deprotecting is performed in a solvent selected from the group consisting of an ether (e.g., 2-methyltetrahydrofuran, tert-butyl methyl ether), a ketone (e.g., acetone, 2-butanone), a hydrocarbon (e.g., toluene, xylene, trifluorotoluene), a halogenated solvent (e.g., dichloromethane, 1,2-dichloroethane, chloroform, carbon tetrachloride), a nitrile (e.g., acetonitrile, propylnitrile, butylnitrile), a polar aprotic solvent (e.g., N,N-dimethylformamide, N,N-dimethylacetamide, N-methyl-2-pyrrolidone, dimethyl sulfoxide), and a protic solvent (e.g., methanol, ethanol, propanol, t-butanol), or any combination thereof, optionally in combination with water. In some embodiments, the deprotecting is performed in a solvent comprising tetrahydrofuran.

In some embodiments, the process provided herein further comprises oxidizing the compound of Formula V, or a co-crystal, solvate, or salt thereof, to form a compound of Formula IV:

IV

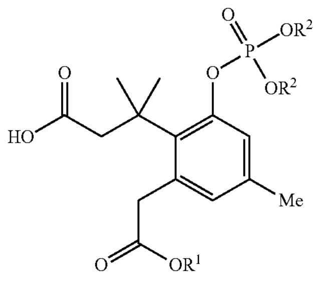

or a co-crystal, solvate, or salt thereof, wherein:

$R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy; and each $R^2$ is independently selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, the process provided herein further comprises oxidizing the compound of Formula V, or a salt thereof, to form a compound of Formula IV:

IV

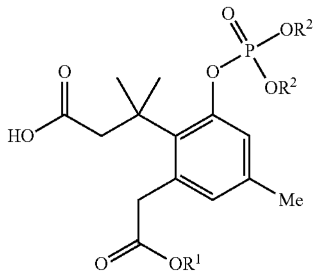

or a salt thereof, wherein:

$R^1$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy; and each $R^2$ is independently selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, $R^1$ is selected from the group consisting of $C_{1-6}$ alkyl, phenyl, pyridyl, and benzyl, wherein the phenyl, pyridyl, and benzyl are each optionally substituted by methoxy.

In some embodiments, $R^1$ is selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, $R^2$ is selected from the group consisting of $C_{1-6}$ alkyl, phenyl, pyridyl, and benzyl, wherein the phenyl, pyridyl, and benzyl are each optionally substituted by methoxy.

In some embodiments, $R^2$ is selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, the process provided herein further comprises oxidizing the compound of Formula V, or a salt thereof, to form a compound of Formula IV:

IV

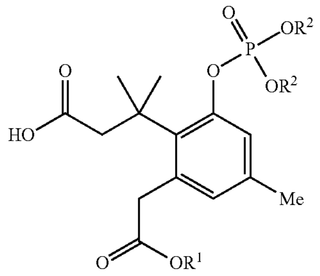

or a salt thereof, wherein:

$R^1$ is $C_{1-6}$ alkyl; and each $R^2$ is independently $C_{1-6}$ alkyl.

In some embodiments, $R^1$ is selected from the group consisting of methyl, ethyl, isopropyl, and tert-butyl. In some embodiments, $R^1$ is tert-butyl.

In some embodiments, each $R^2$ is independently selected from the group consisting of methyl, ethyl, isopropyl, and tert-butyl. In some embodiments, $R^2$ is tert-butyl. In some embodiments, $R^1$ and each $R^2$ is tert-butyl.

In some embodiments, the oxidizing comprises reacting the compound of Formula V, or a co-crystal, solvate, or salt thereof, with an oxidizing agent in the presence of a base and an oxidation catalyst.

In some embodiments, the oxidizing comprises reacting the compound of Formula V, or a salt thereof with an oxidizing agent in the presence of a base and an oxidation catalyst.

In some embodiments, the oxidizing agent is selected from the group consisting of a hypervalent iodine reagent (e.g., (bis(trifluoroacetoxy)iodo)benzene, 2-iodoxybenzoic acid (IBX)), an N-halo succinimide (e.g., N-chlorosuccinimide, N-bromosuccinimide), an N-halo sulfonamide (e.g., N-chlorotosylamide sodium salt), bromine ($Br_2$), chlorine ($Cl_2$), iodine ($I_2$), a hypochlorite (e.g., sodium hypochlorite), a chlorite (e.g., sodium chlorite), a peroxide (e.g., hydrogen peroxide, sodium peroxide, t-butyl hydrogen peroxide, sodium perborate), potassium peroxymonosulfate (Oxone), and a periodate (e.g., sodium periodate), (diacetoxyiodo) benzene, or any combination thereof.

In some embodiments, the oxidizing agent is selected from the group consisting of (diacetoxyiodo)benzene, (bis (trifluoroacetoxy)iodo)benzene, 2-iodoxybenzoic acid, N-chlorosuccinimide, N-bromosuccinimide, N-chlorotosylamide sodium salt, bromine, chlorine, iodine, sodium hypochlorite, sodium chlorite, hydrogen peroxide, sodium peroxide, t-butyl hydrogen peroxide, sodium perborate, potassium peroxymonosulfate, and sodium periodate, or any combination thereof. In some embodiments, the oxidizing agent is (diacetoxyiodo)benzene.

In some embodiments, the base is selected from the group consisting of an inorganic salt (e.g., sodium hydroxide, potassium hydroxide, potassium phosphate monobasic, potassium phosphate dibasic, potassium phosphate tribasic, cesium carbonate), a tertiary amine (e.g., triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane (DABCO)), an aromatic amine (e.g., pyridine, 2,6-lutidine, collidine, 1-methylimidazole), and a tetraalkylammonium salt (e.g., tetrabutylammonium bisulfate, tetrabutylammonium chloride).

In some embodiments, the base is selected from the group consisting of sodium phosphate dibasic, sodium hydroxide, potassium hydroxide, potassium phosphate monobasic, potassium phosphate dibasic, potassium phosphate tribasic, cesium carbonate, triethylamine, N-methylmorpholine, tripropylamine, N,N-diisopropylethylamine, tributylamine, 1,8-diazabicyclo[5.4.0]undec-7-ene, 1,4-diazabicyclo[2.2.2] octane, pyridine, 2,6-lutidine, collidine, 1-methylimidazole, tetrabutylammonium bisulfate, and tetrabutylammonium chloride. In some embodiments, the base is sodium phosphate dibasic.

In some embodiments, the oxidation catalyst is selected from the group consisting of a radical (e.g., 2-azaadamantane N-oxyl, 2,2,6,6-tetramethylpiperidine 1-oxyl) and a metal salt (e.g., ruthenium trichloride, ruthenium tetraoxide, osmium tetraoxide).

In some embodiments, the oxidation catalyst is selected from the group consisting of 2,2,6,6-tetramethylpiperidine 1-oxyl, 2-azaadamantane N-oxyl, ruthenium trichloride, ruthenium tetraoxide, and osmium tetraoxide. In some embodiments, the oxidation catalyst is 2,2,6,6-tetramethylpiperidine 1-oxyl.

In some embodiments, the oxidizing is performed a temperature of from about −20° C. to about 100° C. In some embodiments, the oxidizing is performed a temperature of from about 0° C. to about 40° C. In some embodiments, the oxidizing is performed a temperature of from about 10° C. to about 30° C.

In some embodiments, the oxidizing is performed in a solvent selected from the group consisting of an ether (e.g., 2-methyltetrahydrofuran, tert-butyl methyl ether), a ketone (e.g., acetone, 2-butanone), a hydrocarbon (e.g., toluene, xylene, trifluorotoluene), a halogenated solvent (e.g., dichloromethane, 1,2-dichloroethane, chloroform, carbon tetrachloride), and a polar aprotic solvent (e.g., N,N-dimethylformamide, N,N-dimethylacetamide, N-methyl-2-pyrrolidone, dimethyl sulfoxide), or any combination thereof, optionally in combination with water. In some embodiments, the oxidizing is performed in a solvent comprising methyl tert-butyl ether, acetonitrile, and water.

In some embodiments, the process provided herein further comprises preparing the compound of Formula VII, or a co-crystal, solvate, or salt thereof, by deprotecting a compound of Formula VIII:

VIII

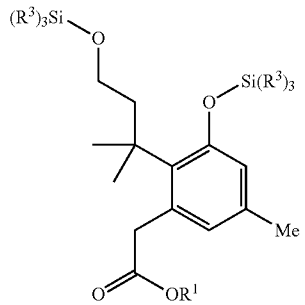

or a co-crystal, solvate, or salt thereof, wherein:

$R^1$ is selected from the group consisting of $C_{1-6}$ alkyl, $C_{6-10}$ aryl, and 5-10 membered heteroaryl, and $C_{6-10}$ aryl-$C_{1-6}$ alkyl-, wherein the $C_{6-10}$ aryl, and 5-10 membered heteroaryl, and $C_{6-10}$ aryl-$C_{1-6}$ alkyl- are each optionally substituted by $C_{1-6}$ alkoxy; and each $R^3$ is independently selected from the group consisting of $C_{1-6}$ alkyl and $C_{6-10}$ aryl.

In some embodiments, the process provided herein further comprises preparing the compound of Formula VII, or a salt thereof, by deprotecting a compound of Formula VIII:

VIII

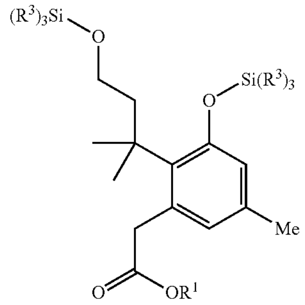

or a salt thereof, wherein:

$R^1$ is selected from the group consisting of $C_{1-6}$ alkyl, $C_{6-10}$ aryl, and 5-10 membered heteroaryl, and $C_{6-10}$ aryl-$C_{1-6}$ alkyl-, wherein the $C_{6-10}$ aryl, and 5-10 membered heteroaryl, and $C_{6-10}$ aryl-$C_{1-6}$ alkyl- are each optionally substituted by $C_{1-6}$ alkoxy; and each $R^3$ is independently selected from the group consisting of $C_{1-6}$ alkyl and $C_{6-10}$ aryl.

In some embodiments, $R^1$ is selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, the process provided herein further comprises preparing the compound of Formula VII, or a salt thereof, by deprotecting a compound of Formula VIII:

VIII

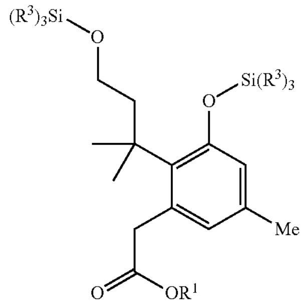

or a salt thereof, wherein:

$R^1$ is $C_{1-6}$ alkyl; and each $R^3$ is independently $C_{1-6}$ alkyl.

In some embodiments, $R^1$ is selected from the group consisting of methyl, ethyl, isopropyl, and tert-butyl. In some embodiments, $R^1$ is tert-butyl.

In some embodiments, each $R^3$ is independently selected from methyl and tert-butyl.

In some embodiments, the deprotecting comprises reacting the compound of Formula VII with a deprotecting agent which is a silyl cleaving agent. In some embodiments, the silyl cleaving agent is selected from a fluoride (e.g., potassium hydrogen fluoride, tetrabutylammonium fluoride, potassium fluoride), an inorganic base (e.g., lithium hydroxide, sodium hydroxide, potassium hydroxide, potassium phosphate dibasic, potassium phosphate tribasic, cesium carbonate), a tertiary amine (e.g., triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane (DABCO)), an aromatic amine (e.g., pyridine, 2,6-lutidine, collidine, 1-methylimidazole), an acid (e.g., hydrofluoric acid, hydrochloric acid, sulfuric acid, methanesulfonic acid), and an oxidant (e.g., N-chlorosuccinimide, potassium peroxymonosulfate (Oxone), iodine), or any combination thereof, optionally in combination with water.

In some embodiments, the deprotecting comprises reacting the compound of Formula VII with a deprotecting agent (e.g., a silyl cleaving agent) selected from the group consisting of lithium hydroxide, potassium hydrogen fluoride, tetrabutylammonium fluoride, potassium fluoride, sodium hydroxide, potassium hydroxide, potassium phosphate dibasic, potassium phosphate tribasic, cesium carbonate, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, collidine, 1-methylimidazole, hydrofluoric acid, hydrochloric acid, sulfuric acid, methanesulfonic acid, N-chlorosuccinimide, potassium peroxymonosulfate, and iodine, or any combination thereof in the presence of water. In some embodiments, the deprotecting agent is lithium hydroxide.

In some embodiments, the deprotecting is performed a temperature of from about 0° C. to about 100° C. In some embodiments, the deprotecting is performed a temperature of from about 20° C. to about 60° C. In some embodiments, the deprotecting is performed a temperature of from about 30° C. to about 50° C.

In some embodiments, the deprotecting is performed in a solvent selected from the group consisting of an ether (e.g., 2-methyltetrahydrofuran, tert-butyl methyl ether), a ketone (e.g., acetone, 2-butanone), a hydrocarbon (e.g., toluene, xylene, trifluorotoluene), a halogenated solvent (e.g., dichloromethane, 1,2-dichloroethane, chloroform, carbon tetrachloride), a polar aprotic solvent (e.g., N,N-dimethylformamide, N,N-dimethylacetamide, N-methyl-2-pyrrolidone, dimethyl sulfoxide), a nitrile (e.g., acetonitrile, propylnitrile, butylnitrile), and a protic solvent (e.g., methanol, ethanol, propanol, t-butanol), or any combination thereof, optionally in combination with of these with water. In some embodiments, the deprotecting is performed in a solvent comprising tetrahydrofuran and water.

In some embodiments, the compound of Formula VIII is a compound of Formula VIII-a:

VIII-a

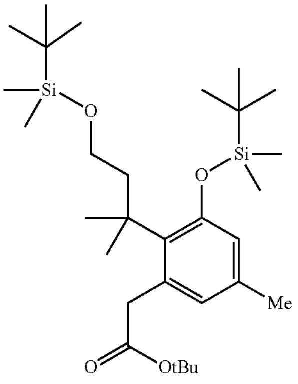

or a co-crystal, solvate, or salt thereof.

In some embodiments, the compound of Formula VIII is a compound of Formula VIII-a:

VIII-a

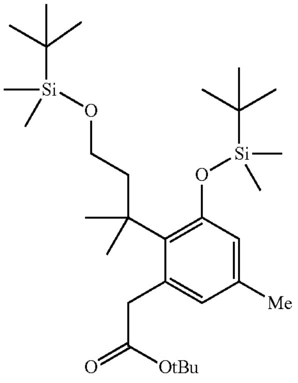

or a salt thereof.

In some embodiments, the compound of Formula VIII is a compound of Formula VIII-a:

VIII-a

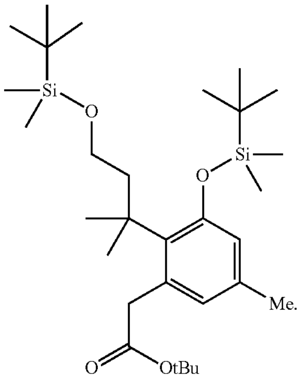

In some embodiments, the process provided herein further comprises preparing the compound of Formula VIII, or a co-crystal, solvate, or salt thereof, by a process comprising reacting a compound of Formula XIV:

XIV

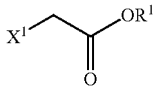

or a co-crystal, solvate, or salt thereof, with an activator in the presence of zinc to form a first mixture; and mixing the first mixture with a compound of Formula IX:

IX

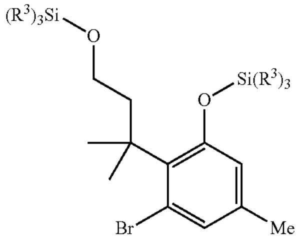

or a co-crystal, solvate, or salt thereof, in the presence of a coupling catalyst, wherein:

$X^1$ is selected from the group consisting of halo and $C_{1-6}$ alkylsulfonate;

$R^1$ is selected from the group consisting of $C_{1-6}$ alkyl, $C_{6-10}$ aryl, and 5-10 membered heteroaryl, and $C_{6-10}$ aryl-$C_{1-6}$ alkyl-, wherein the $C_{6-10}$ aryl, and 5-10 membered heteroaryl, and $C_{6-10}$ aryl-$C_{1-6}$ alkyl- are each optionally substituted by $C_{1-6}$ alkoxy; and each $R^3$ is independently selected from the group consisting of $C_{1-6}$ alkyl and $C_{6-10}$ aryl.

In some embodiments, the process provided herein further comprises preparing the compound of Formula VIII, or a salt thereof, by a process comprising reacting a compound of Formula XIV:

XIV

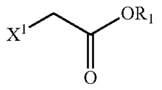

or a salt thereof, with an activator in the presence of zinc to form a first mixture; and mixing the first mixture with a compound of Formula IX:

IX

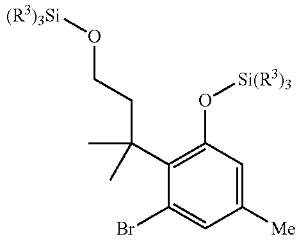

or a salt thereof, in the presence of a coupling catalyst, wherein:

$X^1$ is selected from the group consisting of halo and $C_{1-6}$ alkylsulfonate;

$R^1$ is selected from the group consisting of $C_{1-6}$ alkyl, $C_{6-10}$ aryl, and 5-10 membered heteroaryl, and $C_{6-10}$ aryl-$C_{1-6}$ alkyl-, wherein the $C_{6-10}$ aryl, and 5-10 membered heteroaryl, and $C_{6-10}$ aryl-$C_{1-6}$ alkyl- are each optionally substituted by $C_{1-6}$ alkoxy; and each $R^3$ is independently selected from the group consisting of $C_{1-6}$ alkyl and $C_{6-10}$ aryl.

In some embodiments, $X^1$ is selected from bromo, chloro, iodo, and trifluoromethylsulfonate.

In some embodiments, $R^1$ is selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, the process provided herein further comprises preparing the compound of Formula VIII, or a salt thereof, by a process comprising reacting a compound of Formula XIV:

XIV

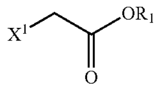

or a salt thereof, with an activator in the presence of zinc to form a first mixture; and mixing the first mixture with a compound of Formula IX:

IX

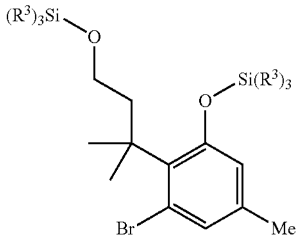

or a salt thereof, in the presence of a coupling catalyst, wherein:

$X^1$ is halo;

$R^1$ is $C_{1-6}$ alkyl; and each $R^3$ is independently $C_{1-6}$ alkyl.

In some embodiments, $X^1$ is bromo.

In some embodiments, $R^1$ is selected from the group consisting of methyl, ethyl, isopropyl, and tert-butyl. In some embodiments, $R^1$ is tert-butyl.

In some embodiments, each $R^3$ is independently selected from methyl and tert-butyl. In some embodiments, the activator is selected from the group consisting of a trialkylsilyl halide (e.g., trimethylsilyl chloride, triethylsilyl chloride, trimethylsilyl iodide), a dihaloethane (e.g., dibromoethane, dichloroethane), an alkylaluminum hydride (e.g., diisobutylaluminium hydride), and iodine.

In some embodiments, the activator is selected from the group consisting of trimethylsilyl chloride, triethylsilyl chloride, trimethylsilyl iodide, dibromoethane, dichloroethane, diisobutylaluminium hydride, and iodine. In some embodiments, the activator is trimethylsilyl chloride.

In some embodiments, the coupling catalyst comprises a palladium catalyst.

In some embodiments, the palladium catalyst is selected from the group consisting of tris(dibenzylideneacetone)dipalladium(0), a palladium(II) salt (such as palladium (II) chloride, palladium (II) bromide, palladium (II) acetate, palladium (II) trifluoroacetate), a palladium (0) complex (e.g., tetrakis(triphenylphosphine)palladium(0)), a G3-Pd complex (e.g., (2-dicyclohexylphosphino-2',4',6'-triisopropyl-1,1'-biphenyl)[2-(2'-amino-1,1'-biphenyl)]palladium(II) methanesulfonate (XPhos-Pd-G3)), and a G4-Pd complex (e.g., (SP-4-3)-[dicyclohexyl[2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium (XPhos-Pd-G4).

In some embodiments, the palladium catalyst is selected from the group consisting of tris(dibenzylideneacetone)dipalladium(0), palladium (II) chloride, palladium (II) bromide, palladium (II) acetate, palladium (II) trifluoroacetate, tetrakis(triphenylphosphine)palladium(0)), (2-dicyclohexylphosphino-2',4',6'-triisopropyl-1,1'-biphenyl)[2-(2'-amino-1,1'-biphenyl)]palladium(II) methanesulfonate, and (SP-4-3)-[dicyclohexyl[2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium. In some embodiments, the palladium catalyst is tris(dibenzylideneacetone)dipalladium(0).

In some embodiments, the coupling catalyst comprises a palladium catalyst and, optionally, a phosphine ligand. In some embodiments, the coupling catalyst comprises a palladium catalyst and a phosphine ligand.

In some embodiments, the phosphine ligand is absent. In some embodiments, the phosphine ligand is selected from the group consisting of a trialkylphosphines (e.g., tricyclohexylphosphine, tri-tert-butyl phosphine), a triarylphosphines (e.g., triphenyl phosphine), a dialkylarylphosphines (e.g., 2-dicyclohexylphosphino-2',6'-dimethoxybiphenyl (SPhos), and a alkyldiarylphosphines (e.g., ethylenebis(diphenylphosphine) (DPPE)).

In some embodiments, the phosphine ligand is selected from the group consisting of 2-dicyclohexylphosphino-2',4',6'-triisopropylbiphenyl, tricyclohexylphosphine, tri-tert-butyl phosphine, triphenyl phosphine), 2-dicyclohexylphosphino-2',6'-dimethoxybiphenyl, and ethylenebis (diphenylphosphine). In some embodiments, the coupling catalyst comprises tris(dibenzylideneacetone)dipalladium and 2-dicyclohexylphosphino-2',4',6'-triisopropylbiphenyl.

In some embodiments, the mixing of the first mixture with the compound of Formula IX is performed at a temperature of from about 0° C. to about 100° C. In some embodiments, the mixing of the first mixture with the compound of Formula IX is performed at a temperature of from about 30°

C. to about 80° C. In some embodiments, the mixing of the first mixture with the compound of Formula IX is performed at a temperature of from about 45° C. to about 65° C.

In some embodiments, the mixing of the first mixture with the compound of Formula IX is performed in a solvent selected from the group consisting of an ether (e.g., tetrahydrofuran, 2-methyltetrahydrofuran, tert-butyl methyl ether), a hydrocarbon (e.g., toluene, xylene, trifluorotoluene), a halogenated solvent (e.g., dichloromethane, 1,2-dichloroethane, chloroform, carbon tetrachloride), a nitrile (e.g., acetonitrile, propylnitrile, butylnitrile) and a polar aprotic solvent (e.g., N,N-dimethylformamide, N,N-dimethylacetamide, N-methyl-2-pyrrolidone and dimethyl sulfoxide), or any combination thereof. In some embodiments, the mixing of the first mixture with the compound of Formula IX is performed in a solvent comprising tetrahydrofuran.

In some embodiments, the process provided herein further comprises preparing a compound of Formula IX, or a co-crystal, solvate, or salt thereof, by silylating a compound of Formula X:

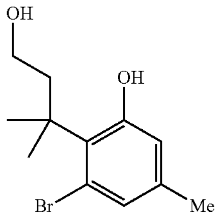

X or a co-crystal, solvate, or salt thereof.

In some embodiments, the process provided herein further comprises preparing a compound of Formula IX, or a salt thereof, by silylating a compound of Formula X:

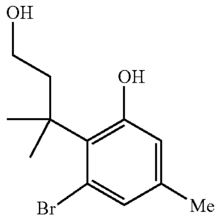

X or a salt thereof.

In some embodiments, the silylating comprises reacting the compound of Formula IX, or a co-crystal, solvate, or salt thereof, with a silylating agent of formula:

$Si(R^3)_3$-LG in the presence of a base and silylating catalyst, wherein each $R^3$ is independently selected from the group consisting of $C_{1-6}$ alkyl and $C_{6-10}$ aryl; and LG is a leaving group.

In some embodiments, the silylating comprises reacting the compound of Formula IX, or a salt thereof, with a silylating agent of formula:

$Si(R^3)_3$-LG in the presence of a base and silylating catalyst, wherein each $R^3$ is independently $C_{1-6}$ alkyl; and LG is a leaving group.

In some embodiments, each $R^3$ is independently selected from the group consisting of methyl and tert-butyl.

In some embodiments, LG is selected from the group consisting of chloride, bromide, iodide, methanesulfonate, trifluoromethanesulfonate, and p-toluenesulfonate. In some embodiments, LG is chloride.

In some embodiments, the silylating agent is tert-butyl (chloro)dimethylsilane.

In some embodiments, the base is selected from the group consisting of a tertiary amine (e.g., triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane (DABCO)), an aromatic amine (e.g., pyridine, 2,6-lutidine, collidine, 1-methylimidazole), and an inorganic base (e.g., lithium carbonate, sodium carbonate, potassium carbonate, calcium carbonate, potassium phosphate (e.g., monobasic, dibasic or tribasic), sodium phosphate (e.g., monobasic, dibasic or tribasic)).

In some embodiments, the base is selected from the group consisting of imidazole, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, collidine, 1-methylimidazole, lithium carbonate, sodium carbonate, potassium carbonate, calcium carbonate, potassium phosphate monobasic, potassium phosphate dibasic, potassium phosphate tribasic, sodium phosphate monobasic, sodium phosphate dibasic, and sodium phosphate tribasic. In some embodiments, the base is imidazole.

In some embodiments, the silylating catalyst is selected from the group consisting of N-methylimidazole, 1-hydroxy-7-azabenzotriazole (HOAt), 1-hydroxybenzotriazole (HOBt), and a tetraalkylammonium halide (e.g., tetrabutyl ammonium bromide, tetrabutyl ammonium iodide).

In some embodiments, the silylating catalyst is selected from the group consisting of 4-dimethylaminopyridine, N-methylimidazole, 1-hydroxy-7-azabenzotriazole, 1-hydroxybenzotriazole, tetrabutyl ammonium bromide, and tetrabutyl ammonium iodide. In some embodiments, the silylating catalyst is 4-dimethylaminopyridine.

In some embodiments, the silylating is performed at a temperature of from about 0° C. to about 100° C. In some embodiments, the silylating is performed at a temperature of from about 45° C. to about 85° C. In some embodiments, the silylating is performed at a temperature of from about 55° C. to about 75° C.

In some embodiments, the silylating is performed in a solvent selected from the group consisting of an ether (e.g., 2-methyltetrahydrofuran, tert-butyl methyl ether), a hydrocarbon (e.g., toluene, xylene, trifluorotoluene), a halogenated solvent (e.g., dichloromethane, 1,2-dichloroethane, chloroform, carbon tetrachloride), a polar aprotic solvent (e.g., N,N-dimethylacetamide, N-methyl-2-pyrrolidone) and a nitrile (e.g., acetonitrile, propylnitrile, butylnitrile), or any combination thereof. In some embodiments, the silylating is performed in a solvent comprising N,N-dimethylformamide.

In some embodiments, the process provided herein further comprises preparing the compound of Formula X, or a co-crystal, solvate, or salt thereof, by reducing a compound of Formula XI:

XI

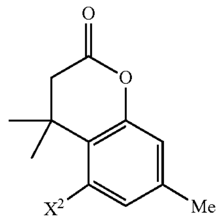

or a co-crystal, solvate, or salt thereof, wherein:

$X^2$ is selected from the group consisting of halo, (4-methylbenzenesulfonyl)oxyl, (methylsulfonyl)oxyl, and (trifluoromethylsulfonyl)oxyl.

In some embodiments, the process provided herein further comprises preparing the compound of Formula X, or a co-crystal, solvate, or salt thereof, by reducing a compound of Formula XI-a:

XI-a

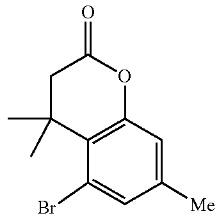

or a co-crystal, solvate, or salt thereof.

In some embodiments, the process provided herein further comprises preparing the compound of Formula X, or a salt thereof, by reducing a compound of Formula XI:

XI

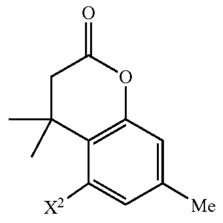

or co-crystal, solvate, or salt thereof, wherein:

$X^2$ is selected from the group consisting of halo, (4-methylbenzenesulfonyl)oxyl, (methylsulfonyl)oxyl, (trifluoromethylsulfonyl)oxyl, dihydroxyboranyl, 4,4,5,5-tetramethyl-1,3,2-dioxaborolan-2-yl, 5,5-dimethyl-1,3,2-dioxaborinan-2-yl, and benzo[d][1,3,2]dioxaborol-2-yl.

In some embodiments, the process provided herein further comprises preparing the compound of Formula X, or a salt thereof, by reducing a compound of Formula XI:

XI

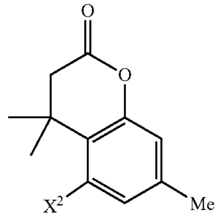

or a salt thereof, wherein:

$X^2$ is selected from the group consisting of halo, (4-methylbenzenesulfonyl)oxyl, (methylsulfonyl)oxyl, (trifluoromethylsulfonyl)oxyl, dihydroxyboranyl, 4,4,5,5-tetramethyl-1,3,2-dioxaborolan-2-yl, 5,5-dimethyl-1,3,2-dioxaborinan-2-yl, and benzo[d][1,3,2]dioxaborol-2-yl.

In some embodiments, the process provided herein further comprises preparing the compound of Formula X, or a salt thereof, by reducing a compound of Formula XI:

XI

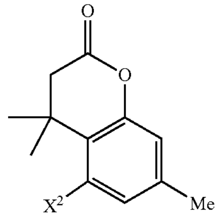

or a salt thereof, wherein:

$X^2$ is selected from the group consisting of halo, (4-methylbenzenesulfonyl)oxyl, (methylsulfonyl)oxyl, and (trifluoromethylsulfonyl)oxyl.

In some embodiments, $X^2$ is selected from the group consisting of halo, dihydroxyboranyl, 4,4,5,5-tetramethyl-1,3,2-dioxaborolan-2-yl, 5,5-dimethyl-1,3,2-dioxaborinan-2-yl, and benzo[d][1,3,2]dioxaborol-2-yl.

In some embodiments, $X^2$ is selected from the group consisting of dihydroxyboranyl, 4,4,5,5-tetramethyl-1,3,2-dioxaborolan-2-yl, 5,5-dimethyl-1,3,2-dioxaborinan-2-yl, and benzo[d][1,3,2]dioxaborol-2-yl.

In some embodiments, $X^2$ is 4,4,5,5-tetramethyl-1,3,2-dioxaborolan-2-yl.

In some embodiments, $X^2$ is halo.

In some embodiments, the reducing comprises reacting the compound of Formula X, or a salt thereof, in the presence of a reducing agent and, optionally, a catalyst.

In some embodiments, the catalyst is selected a Lewis acid catalyst. In some embodiments, the Lewis acid catalyst is selected from the group consisting of boron trifluoride, boron trichloride, boron tribromide, and aluminum trichloride. In some embodiments, the catalyst is absent.

In some embodiments, the reducing comprises reacting the compound of Formula X, or a salt thereof, in the presence of a reducing agent (e.g., in the absence of a catalyst). In some embodiments, the reducing agent is selected from the group consisting of diisobutylaluminum hydride, aluminum hydride, sodium bis(2-methoxyethoxy) aluminum hydride, a borane tetrahydrofuran complex, diborane, $I_2/NaBH_4$, and a borane dimethyl sulfide complex.

In some embodiments, the reducing agent selected from the group consisting of lithium aluminum hydride, diisobutylaluminum hydride, aluminum hydride, sodium bis(2-methoxyethoxy)aluminum hydride, borane tetrahydrofuran complex, diborane, $I_2/NaBH_4$, and borane dimethyl sulfide complex. In some embodiments, the reducing agent is lithium aluminum hydride.

In some embodiments, the reducing is performed at a temperature of from about −20° C. to about 100° C. In some embodiments, the reducing is performed at a temperature of from about 0° C. to about 60° C. In some embodiments, the reducing is performed at a temperature of from about 20° C. to about 40° C.

In some embodiments, the reducing is performed in a solvent selected from the group consisting of an ether (e.g., tetrahydrofuran, 2-methyltetrahydrofuran, tert-butyl methyl ether), a hydrocarbon (e.g., toluene, xylene, trifluorotoluene), a halogenated solvent (e.g., dichloromethane, 1,2-dichloroethane, chloroform, carbon tetrachloride), and a polar aprotic solvent (e.g., N,N-dimethylformamide, N,N-dimethylacetamide, N-methyl-2-pyrrolidone), or any combination thereof, optionally in combination with water. In some embodiments, the reducing is performed in a solvent comprising tetrahydrofuran.

In some embodiments, the process provided herein further comprises preparing the compound of Formula XI, or a co-crystal, solvate, or salt thereof, by reacting 3-bromo-5-methylphenol with methyl 3,3-dimethylacrylate in the presence of an acid.

In some embodiments, the process provided herein further comprises preparing the compound of Formula XI, or a salt thereof, by reacting 3-bromo-5-methylphenol with methyl 3,3-dimethylacrylate in the presence of an acid.

In some embodiments, the acid is selected from the group consisting of sulfuric acid, hydrochloric acid, hydrobromic acid, a carboxylic acid (e.g., acetic acid, pivalic acid), phosphoric acid, a sulfonic acid (e.g., p-toluenesulfonic acid), a metal halide (e.g., boron trichloride, lithium bromide, magnesium chloride, aluminum chloride), and a metal triflate (e.g., lithium triflate, magnesium triflate, aluminum triflate). In some embodiments, the acid is selected from the group consisting of methane sulfonic acid, sulfuric acid, hydrochloric acid, hydrobromic acid, acetic acid, pivalic acid, phosphoric acid, p-toluenesulfonic acid, boron trichloride, lithium bromide, magnesium chloride, aluminum chloride, lithium triflate, magnesium triflate, and aluminum triflate. In some embodiments, the acid is methane sulfonic acid. In some embodiments, the acid is sulfuric acid.

In some embodiments, the reacting is performed at a temperature of from about 0° C. to about 200° C. In some embodiments, the reacting is performed at a temperature of from about 80° C. to about 160° C. In some embodiments, the reacting is performed at a temperature of from about 110° C. to about 130° C.

In some embodiments, the reacting is optionally performed in a solvent selected from the group consisting of a hydrocarbon (e.g., toluene, xylene, trifluorotoluene), a halogenated solvent (e.g., dichloromethane, 1,2-dichloroethane, chloroform, carbon tetrachloride), and a polar aprotic solvent (e.g., N,N-dimethylformamide, N,N-dimethylacetamide, N-methyl-2-pyrrolidone), or any combination thereof, optionally in combination with water. In some embodiments, the reacting is performed in the absence of a solvent.

In some embodiments, the compound of Formula XI, or a co-crystal, solvate, or salt thereof, is a compound of Formula XI-a:

XI-a

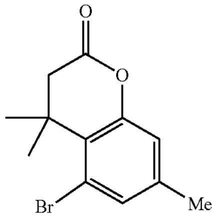

or a co-crystal, solvate, or salt thereof.

In some embodiments, the compound of Formula XI, or a salt thereof, is a compound of Formula XI-a:

XI-a

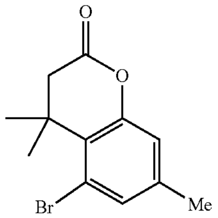

or a salt thereof.

In some embodiments, the compound of Formula XI is a compound of Formula XI-a:

XI-a

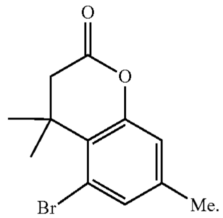

In some embodiments, the present disclosure provides a process of preparing a compound of Formula XV:

XV

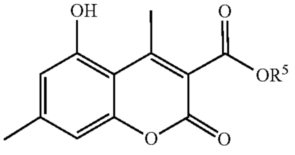

or a co-crystal, solvate, or salt thereof, comprising reacting a compound of Formula XVI:

XVI

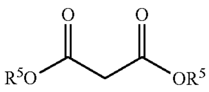

or a co-crystal, solvate, or salt thereof, with 1-(2,6-dihydroxy-4-methylphenyl)ethan-1-one in the presence of a base, wherein:

each $R^5$ is independently selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, the present disclosure provides a process of preparing a compound of Formula XV:

XV

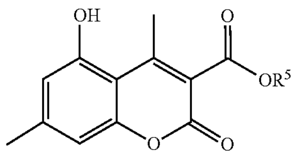

or a salt thereof, comprising reacting a compound of Formula XVI:

XVI

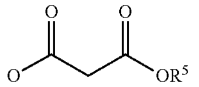

or a salt thereof, with 1-(2,6-dihydroxy-4-methylphenyl)ethan-1-one in the presence of a base, wherein:

each $R^5$ is independently selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, each $R^5$ is independently selected from the group consisting of methyl, ethyl, isopropyl, tert-butyl, phenyl, pyridyl (e.g., 2-pyridyl or 4-pyridyl), benzyl, and methoxybenzyl (e.g., 4-methoxybenzyl).

In some embodiments, each $R^5$ is independently selected from the group consisting of $C_{1-6}$ alkyl.

In some embodiments, each $R^5$ is ethyl.

In some embodiments, the base is selected from the group consisting of an inorganic base (e.g., sodium ethoxide, sodium methoxide, sodium tert-butoxide, potassium ethoxide, potassium methoxide, potassium tert-butoxide, potassium phosphate tribasic, cesium carbonate), a tertiary amine base (e.g., triethylamine, N-methylmorpholine, tripropylamine, N,N-diisopropylethylamine, tributylamine, 1,4-diazabicyclo[2.2.2]octane (DABCO), 1,8-diazabicyclo[5.4.0]undec-7-ene (DBU)), and an aromatic amine base (e.g., pyridine, 2,6-lutidine, collidine, 1-methylimidazole).

In some embodiments, the base is selected from the group consisting of sodium ethoxide, sodium methoxide, sodium tert-butoxide, potassium ethoxide, potassium methoxide, potassium tert-butoxide, potassium phosphate tribasic, cesium carbonate, triethylamine, N-methylmorpholine, tripropylamine, N,N-diisopropylethylamine, tributylamine, 1,4-diazabicyclo[2.2.2]octane (DABCO), 1,8-diazabicyclo[5.4.0]undec-7-ene (DBU), pyridine, 2,6-lutidine, collidine, and 1-methylimidazole. In some embodiments, the base is 1,8-diazabicyclo[5.4.0]undec-7-ene.

In some embodiments, the reacting of the compound of Formula XVI, or a salt thereof, with the 1-(2,6-dihydroxy-4-methylphenyl)ethan-1-one is performed at a temperature of from about 0° C. to about 200° C. In some embodiments, the reacting of the compound of Formula XVI, or a salt thereof, with the 1-(2,6-dihydroxy-4-methylphenyl)ethan-1-one is performed at a temperature of from about 60° C. to about 140° C. In some embodiments, the reacting of the compound of Formula XVI, or a salt thereof, with the 1-(2,6-dihydroxy-4-methylphenyl)ethan-1-one is performed at a temperature of from about 90° C. to about 110° C. In some embodiments, the reacting of the compound of Formula XVI, or a salt thereof, with the 1-(2,6-dihydroxy-4-methylphenyl)ethan-1-one is performed at a temperature of from about 95° C. to about 105° C.

In some embodiments, the reacting of the compound of Formula XVI, or a salt thereof, with the 1-(2,6-dihydroxy-4-methylphenyl)ethan-1-one is performed in the presence of a solvent selected from the group consisting of an ethers (e.g., 2-methyltetrahydrofuran, tert-butyl methyl ether), a hydrocarbon (e.g., toluene, xylene, trifluorotoluene, chlorobenzene), a nitrile (e.g., acetonitrile, propylnitrile, butylnitrile), and a polar aprotic solvent (e.g., N,N-dimethylformamide, N,N-dimethylacetamide, N-methyl-2-pyrrolidone, dimethyl sulfoxide, sulfolane).

In some embodiments, the reacting of the compound of Formula XVI, or a salt thereof, with the 1-(2,6-dihydroxy-4-methylphenyl)ethan-1-one is performed in the absence of a solvent.

In some embodiments, the compound of Formula XVI is a compound of Formula XVI-a:

XVI-a

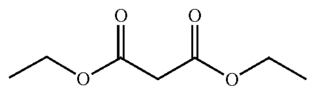

or a co-crystal, solvate, or salt thereof.

In some embodiments, the compound of Formula XVI is a compound of Formula XVI-a:

XVI-a

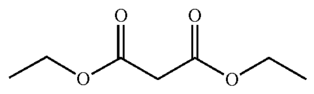

or salt thereof.

In some embodiments, the compound of Formula XVI is a compound of Formula XVI-a:

XVI-a

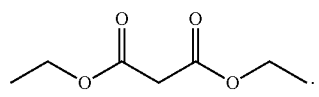

In some embodiments, the compound of Formula XV is a compound of Formula XV-a:

XV-a

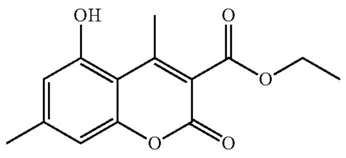

or a co-crystal, solvate, or salt thereof.

In some embodiments, the compound of Formula XV is a compound of Formula XV-a:

XV-a

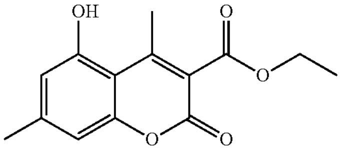

or a salt thereof.

In some embodiments, the compound of Formula XV is a compound of Formula XV-a:

XV-a

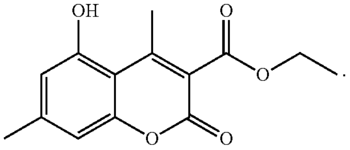

In some embodiments, the present disclosure provides a process of preparing a compound of Formula XVII:

XVII

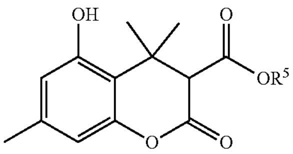

or a co-crystal, solvate, or salt thereof, comprising reacting a compound of Formula XV:

XV

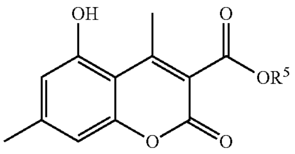

or a co-crystal, solvate, or salt thereof, with a metallated methyl reagent in the presence of a copper reagent and optionally in the presence of an additive, wherein:

$R^5$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, the present disclosure provides a process of preparing a compound of Formula XVII:

XVII

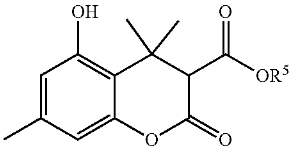

or a salt thereof, comprising reacting a compound of Formula XV:

XV

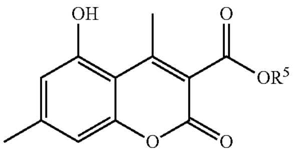

or a salt thereof, with a metallated methyl reagent in the presence of a copper reagent and optionally in the presence of an additive, wherein:

$R^5$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, $R^5$ is selected from the group consisting of methyl, ethyl, isopropyl, tert-butyl, phenyl, pyridyl (e.g., 2-pyridyl or 4-pyridyl), benzyl, and methoxybenzyl (e.g., 4-methoxybenzyl). In some embodiments, $R^5$ is selected from the group consisting of $C_{1-6}$ alkyl. In some embodiments, $R^5$ is ethyl.

In some embodiments, the metallated methyl reagent is selected from the group consisting of methylmagnesium bromide, methylmagnesium chloride, methyllithium, methylzinc chloride, and methylzinc bromide. In some embodiments, the metallated methyl reagent is methylmagnesium bromide.

In some embodiments, the copper reagent is selected from the group consisting of copper (I) iodide, copper (I) chloride, copper (I) bromide, copper (I) cyanide. In some embodiments, the copper reagent is copper (I) iodide.

In some embodiments, the reacting of the compound of Formula XVII, or a salt thereof, with the metallated methyl reagent is performed in the presence of an additive.

In some embodiments, the additive is selected from the group consisting of lithium chloride, lithium bromide, and hexamethylphosphoramide. In some embodiments, the additive is lithium chloride.

In some embodiments, the reacting of the compound of Formula XVII, or a salt thereof, with the metallated methyl reagent is performed at a temperature of from about −78° C. to about 50° C. In some embodiments, the reacting of the compound of Formula XVII, or a salt thereof, with the metallated methyl reagent is performed at a temperature of from about −60° C. to about 0° C. In some embodiments, the reacting of the compound of Formula XVII, or a salt thereof, with the metallated methyl reagent is performed at a temperature of from about −50° C. to about −30° C. In some embodiments, the reacting of the compound of Formula XVII, or a salt thereof, with the metallated methyl reagent is performed at a temperature of from about −45° C. to about −35° C.

In some embodiments, the reacting of the compound of Formula XVII, or a salt thereof, with the metallated methyl reagent is performed in the presence of a solvent selected from the group consisting of an ether (e.g., tert-butyl methyl ether), a hydrocarbon (e.g., toluene, trifluorotoluene), and a polar aprotic solvent (e.g., tetrahydrofuran, 2-methyltetrahydrofuran, N,N-dimethylformamide, N,N-dimethylacetamide, N-methyl-2-pyrrolidone, dimethyl sulfoxide and sulfolane), or any combination thereof. In some embodiments, the reacting of the compound of Formula XVII, or a salt thereof, with the metallated methyl reagent is performed in the presence of a solvent comprising tetrahydrofuran. In some embodiments, the reacting of the compound of Formula XVII, or a salt thereof, with the metallated methyl reagent is performed in the presence of a solvent comprising 2-methyltetrahydrofuran. In some embodiments, the reacting of the compound of Formula XVII, or a salt thereof, with the metallated methyl reagent is performed in the presence of a solvent comprising tetrahydrofuran and 2-methyltetrahydrofuran.

In some embodiments, the compound of Formula XVII is a compound of Formula XVII-a XVII-a

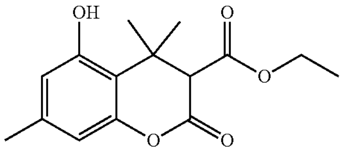

or a co-crystal, solvate, or salt thereof.

In some embodiments, the compound of Formula XVII is a compound of Formula XVII-a XVII-a

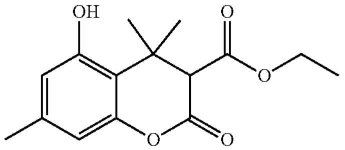

or a salt thereof.

In some embodiments, the compound of Formula XVII is a compound of Formula XVII-a XVII-a

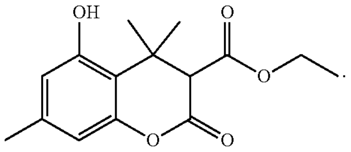

In some embodiments, the present disclosure provides a process of preparing a compound of Formula XVIII:

XVIII

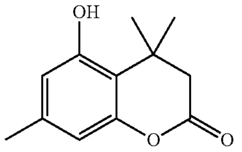

or a co-crystal, solvate, or salt thereof, comprising decarboxylating a compound of Formula XVII.

XVII

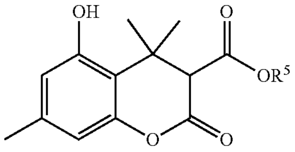

or a co-crystal, solvate, or salt thereof, wherein:

$R^5$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, the present disclosure provides a process of preparing a compound of Formula XVIII:

XVIII

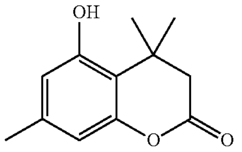

or a salt thereof, comprising decarboxylating a compound of Formula XVII:

XVII

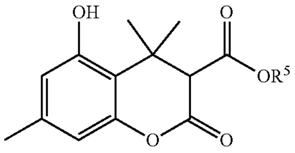

or a salt thereof, wherein:

$R^5$ is selected from the group consisting of $C_{1-6}$ alkyl, $C_{6-10}$ aryl, 5-10 membered heteroaryl, and $C_{6-10}$ aryl-$C_{1-6}$ alkyl-, wherein the $C_{6-10}$ aryl, 5-10 membered heteroaryl, and $C_{6-10}$ aryl-$C_{1-6}$ alkyl- are each optionally substituted by $C_{1-6}$ alkoxy.

In some embodiments, $R^5$ is selected from the group consisting of methyl, ethyl, isopropyl, tert-butyl, phenyl, pyridyl (e.g., 2-pyridyl or 4-pyridyl), benzyl, and methoxybenzyl (e.g., 4-methoxybenzyl). In some embodiments, $R^5$ is selected from the group consisting of $C_{1-6}$ alkyl. In some embodiments, $R^5$ is ethyl.

In some embodiments, the decarboxylation reaction comprises reacting the compound of Formula XVII, or a salt thereof, with a decarboxylation reagent selected from the group consisting of concentrated hydrochloric acid, lithium chloride, lithium bromide, lithium cyanide; or hydrolyzing the compound of Formula XVII, or a salt thereof, with a base selected from the group consisting of lithium hydroxide, sodium hydroxide, and potassium hydroxide, and subsequently acidifying the reaction mixture using an acid selected from the group consisting of hydrochloric acid, sulfuric acid, and trifluoroacetic acid, in the presence of a solvent.

In some embodiments, the decarboxylation reaction comprises reacting the compound of Formula XVII, or a salt thereof, with a decarboxylation reagent selected from the group consisting of concentrated hydrochloric acid, lithium chloride, lithium bromide, and lithium cyanide. In some embodiments, the decarboxylation reaction comprises reacting the compound of Formula XVII, or a salt thereof, with concentrated hydrochloric acid.

In some embodiments, the decarboxylation reaction is performed at a temperature of from about 20° C. to about 130° C. In some embodiments, the decarboxylation reaction is performed in at a temperature of from about 20° C. to about 80° C. In some embodiments, the decarboxylation reaction is performed in at a temperature of from about 50° C. to about 60° C.

In some embodiments, the decarboxylation reaction is performed in a solvent selected from the group consisting of a protic solvent (e.g., water, methanol, ethanol, isopropanol, propanol), an ether (e.g., 2-methyltetrahydrofuran, tetrahydrofuran), a hydrocarbon (e.g., toluene, trifluorotoluene), a nitrile (e.g., acetonitrile, propylnitrile, butylnitrile), and a polar aprotic solvent (e.g., acetone, N,N-dimethylformamide, N,N-dimethylacetamide, N-methyl-2-pyrrolidone, dimethyl sulfoxide, and sulfolane, or any combination thereof. In some embodiments, the decarboxylation reaction is performed in a solvent comprising acetone.

In some embodiments, the compound of Formula XVIII is a compound of Formula XVIII:

XVIII

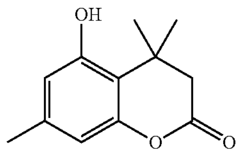

or a co-crystal, solvate, or salt thereof.

In some embodiments, the compound of Formula XVIII is a compound of Formula XVIII:

XVIII

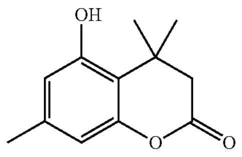

or a salt thereof.

In some embodiments, the compound of Formula XVIII is a compound of Formula XVIII:

XVIII

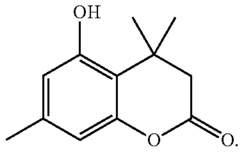

In some embodiments, the present disclosure provides a process of preparing a compound of Formula XIX:

XIX

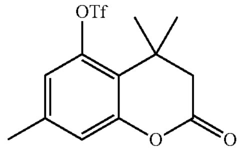

or a co-crystal, solvate, or salt thereof, comprising triflating a compound of Formula XVIII:

XVIII

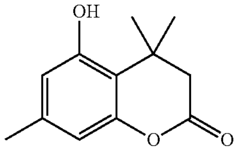

or a co-crystal, solvate, or salt thereof, in the presence of a base.

In some embodiments, the present disclosure provides a process of preparing a compound of Formula XIX:

XIX

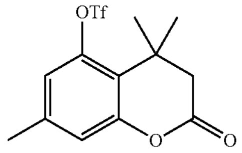

or a salt thereof, comprising triflating a compound of Formula XVIII:

XVIII

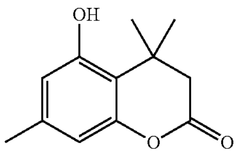

or a salt thereof, in the presence of a base.

In some embodiments, the triflation reaction comprises reacting the compound of Formula XVIII, or a salt thereof, with a triflating reagent selected from the group consisting of trifluoromethanesulfonic anhydride, bis(trifluoromethanesulfonyl)aniline, and N-(5-chloro-2-pyridyl)triflimide, in the presence of a base.

In some embodiments, the triflation reaction comprises reacting the compound of Formula XVIII, or a salt thereof, with trifluoromethanesulfonic anhydride in the presence of a base.

In some embodiments, the base is selected from the group consisting of an amine base (e.g., diisopropylethylamine, 4-methylmorpholine, triethylamine, N,N-diisopropylethylamine), a basic aromatic compound (e.g., pyridine, 2,6-lutidine, 4-dimethylaminopyridine), a carbonate base (e.g., lithium carbonate, sodium carbonate, potassium carbonate, cesium carbonate), a bicarbonate base (e.g., lithium bicarbonate, sodium bicarbonate, potassium bicarbonate), and a phosphate base (e.g., sodium phosphate, potassium phosphate). In some embodiments, the base is pyridine.

In some embodiments, the triflation reaction is performed at a temperature of from about −78° C. to about 80° C. In some embodiments, the triflation reaction is performed at a temperature of from about −20° C. to about 40° C. In some embodiments, the triflation reaction is performed at a temperature of from about −10° C. to about 10° C.

In some embodiments, the triflation reaction is performed in a solvent selected from the group consisting of an ether (e.g., 2-methyltetrahydrofuran, tetrahydrofuran), a hydrocarbon (e.g., toluene, trifluorotoluene), a nitrile (e.g., acetonitrile, propylnitrile, butylnitrile), a halogenated solvent (e.g., dichloromethane) and a polar aprotic solvent (e.g., N,N-dimethylformamide, N,N-dimethylacetamide, N-methyl-2-pyrrolidone, dimethyl sulfoxide, and sulfolane), or any combination thereof. In some embodiments, the triflation reaction is performed in a solvent comprising dichloromethane.

In some embodiments, the compound of Formula XIX is a compound of Formula XIX:

XIX

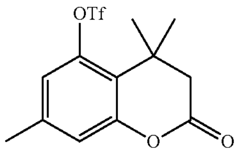

or a co-crystal, solvate, or salt thereof.

In some embodiments, the compound of Formula XIX is a compound of Formula XIX:

XIX

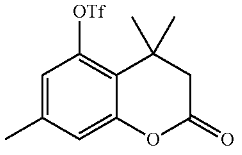

or a salt thereof.

In some embodiments, the compound of Formula XIX is a compound of Formula XIX:

XIX

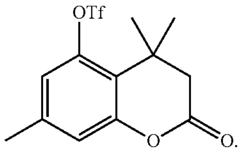

In some embodiments, the present disclosure provides a process of preparing a compound of Formula XIII:

XIII

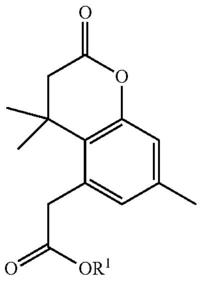

or a co-crystal, solvate, or salt thereof, comprising reacting a compound of Formula XIV:

XIV

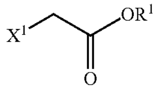

or a co-crystal, solvate, or salt thereof, with an activator in the presence of zinc and an alkali metal halide to form a first mixture; and mixing the first mixture with a compound of Formula XIX:

XIX

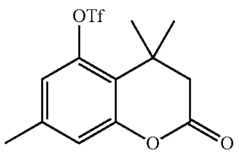

or a co-crystal, solvate, or salt thereof, in the presence of a coupling catalyst, wherein:

$X^1$ is halo; and $R^1$ is $C_{1-6}$ alkyl.

In some embodiments, the present disclosure provides a process of preparing a compound of Formula XIII:

XIII

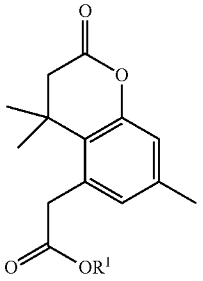

or a salt thereof, comprising reacting a compound of Formula XIV:

XIV

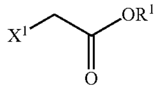

or a salt thereof, with an activator in the presence of zinc and an alkali metal halide to form a first mixture; and mixing the first mixture with a compound of Formula XIX:

XIX

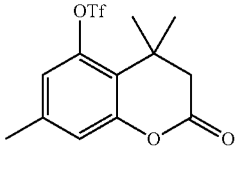

or a salt thereof, in the presence of a coupling catalyst, wherein:

$X^1$ is halo; and $R^1$ is $C_{1-6}$ alkyl.

In some embodiments, $R^1$ is selected from the group consisting of $C_{1-6}$ alkyl, phenyl, pyridyl, and benzyl, wherein the phenyl, pyridyl, and benzyl are each optionally substituted by methoxy.

In some embodiments, $R^1$ is selected from the group consisting of methyl, ethyl, isopropyl, and tert-butyl, phenyl, pyridyl (e.g., 2-pyridyl or 4-pyridyl), benzyl, and methoxybenzyl (e.g., 4-methoxybenzyl).

In some embodiments, $R^1$ is $C_{1-6}$ alkyl. In some embodiments, $R^1$ is selected from the group consisting of methyl, ethyl, isopropyl, and tert-butyl. In some embodiments, $R^1$ is tert-butyl.

In some embodiments, $X^1$ is bromo.

In some embodiments, the activator is selected from the group consisting of a trialkylsilyl halide (e.g., trimethylsilyl chloride, triethylsilyl chloride, trimethylsilyl iodide), a dihaloethane (e.g., dibromoethane, dichloroethane), an alkylaluminum hydride (e.g., diisobutylaluminium hydride), and iodine.

In some embodiments, the activator is selected from the group consisting of diisobutylaluminium hydride, trimethylsilyl chloride, triethylsilyl chloride, trimethylsilyl iodide, dibromoethane, dichloroethane, and iodine. In some embodiments, the activator is diisobutylaluminium hydride.

In some embodiments, the alkali metal halide is lithium halide. In some embodiments, the alkali metal halide is lithium chloride.

In some embodiments, the coupling catalyst comprises a palladium catalyst.

In some embodiments, the palladium catalyst is selected from the group consisting of a palladium(II) salt (e.g., palladium (II) chloride, palladium (II) bromide, palladium (II) acetate, palladium (II) trifluoroacetate), a palladium (0) complex (e.g., tris(dibenzylideneacetone)dipalladium(0), tetrakis(triphenylphosphine)palladium(0)), a G3-Pd complex (e.g., (2-dicyclohexylphosphino-2',4',6'-triisopropyl-1,1'-biphenyl)[2-(2'-amino-1,1'-biphenyl)]palladium(II) methanesulfonate (XPhos-Pd-G3)) and a G4-Pd complex (e.g., (SP-4-3)-[dicyclohexyl[2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium (XPhos-Pd-G4)).

In some embodiments, the palladium catalyst is selected from the group consisting of palladium (II) chloride, palladium (II) bromide, palladium (II) acetate, palladium (II) trifluoroacetate, tris(dibenzylideneacetone)dipalladium(0), tetrakis(triphenylphosphine)palladium(0), (2-dicyclohexylphosphino-2',4',6'-triisopropyl-1,1'-biphenyl)[2-(2'-amino-1,1'-biphenyl)]palladium(II) methanesulfonate, and (SP-4-3)-[dicyclohexyl[2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium.

In some embodiments, the coupling catalyst comprises a palladium catalyst and, optionally, a phosphine ligand. In some embodiments, the phosphine ligand is absent. In some embodiments, the phosphine ligand is selected from the group consisting of a trialkylphosphine (e.g., tricyclohexylphosphine, tri-tert-butyl phosphine), a triarylphosphine (e.g., triphenyl phosphine), a dialkylarylphosphine (e.g., 2-dicyclohexylphosphino-2',6'-dimethoxybiphenyl (SPhos), 2-dicyclohexylphosphino-2',4',6'-triisopropylbiphenyl) and an alkyldiarylphosphine (e.g., ethylenebis(diphenylphosphine) (DPPE)).

In some embodiments, the phosphine ligand is selected from the group consisting of 2-dicyclohexylphosphino-2',4',6'-triisopropylbiphenyl, tricyclohexylphosphine, tri-tert-butyl phosphine, triphenyl phosphine, 2-dicyclohexylphosphino-2',6'-dimethoxybiphenyl, and ethylenebis(diphenylphosphine). In some embodiments, the phosphine ligand is 2-dicyclohexylphosphino-2',4',6'-triisopropylbiphenyl.

In some embodiments, the coupling catalyst comprises a palladium catalyst and a phosphine ligand. In some embodiments, the coupling catalyst comprises palladium (II) acetate and 2-dicyclohexylphosphino-2',4',6'-triisopropylbiphenyl.

In some embodiments, the mixing of the first mixture with the compound of Formula XIX is performed at a temperature of from about 0° C. to about 100° C. In some embodiments, the mixing of the first mixture with the compound of Formula XIX is performed at a temperature of from about 0° C. to about 70° C. In some embodiments, the mixing of the first mixture with the compound of Formula XIX is performed at a temperature of from about 45° C. to about 65° C.

In some embodiments, the mixing of the first mixture and the compound of Formula XIX is performed in a solvent selected from the group consisting of an ether (e.g., tetrahydrofuran, 2-methyltetrahydrofuran, tert-butyl methyl ether), a hydrocarbon (e.g., toluene, xylene, trifluorotoluene), a halogenated solvent (e.g., dichloromethane, 1,2-dichloroethane, chloroform, carbon tetrachloride), a nitrile (e.g., acetonitrile, propylnitrile, butylnitrile) and a polar aprotic solvent (e.g., N,N-dimethylformamide, N,N-dimethylacetamide, N-methyl-2-pyrrolidone and dimethyl sulfoxide), or any combination thereof. In some embodiments, the mixing of the first mixture and the compound of Formula XIX is performed in a solvent comprising tetrahydrofuran and 2-methyltetrahydrofuran.

In some embodiments, the process provided herein further comprises coupling the compound of Formula IV, or a co-crystal, solvate, or salt thereof, with a compound of Formula III:

III

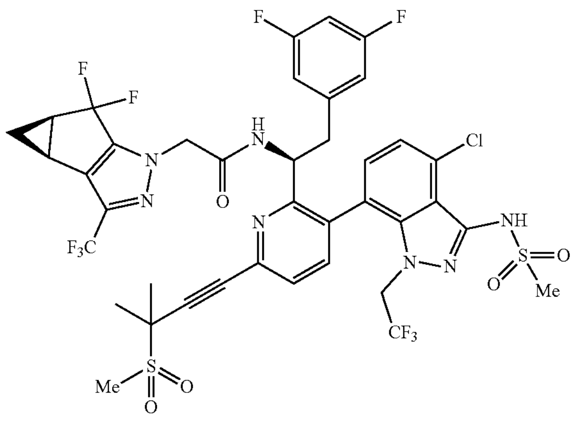

or a co-crystal, solvate, or salt thereof, to form a compound of Formula II:

II

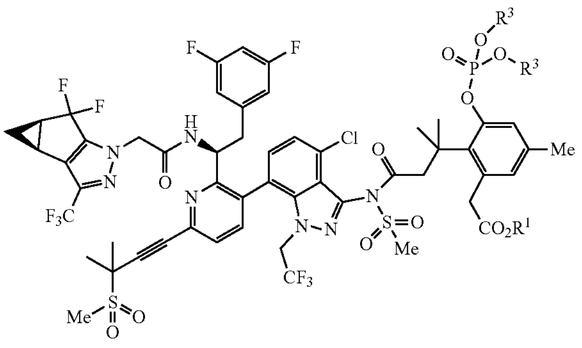

or a co-crystal, solvate, or salt thereof, wherein:

$R^1$ is selected from the group consisting of $C_{1-6}$ alkyl, $C_{6-10}$ aryl, and 5-10 membered heteroaryl, and $C_{6-10}$ aryl-$C_{1-6}$ alkyl-, wherein the $C_{6-10}$ aryl, and 5-10 membered heteroaryl, and $C_{6-10}$ aryl-$C_{1-6}$ alkyl- are each optionally substituted by $C_{1-6}$ alkoxy; and each $R^3$ is independently selected from the group consisting of $C_{1-6}$ alkyl and $C_{6-10}$ aryl.

In some embodiments, the process provided herein further comprises coupling the compound of Formula IV, or a salt thereof, with a compound of Formula III:

III

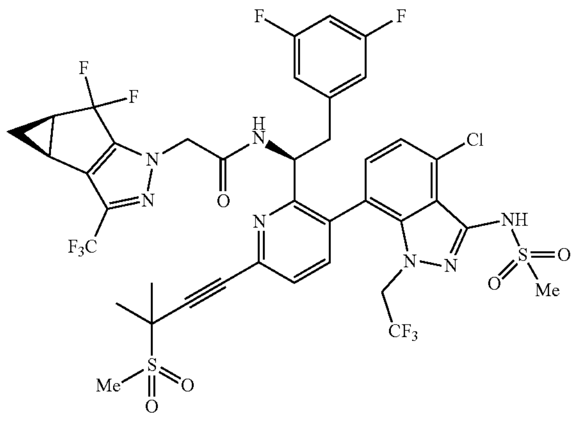

or a salt thereof, to form a compound of Formula II:

II

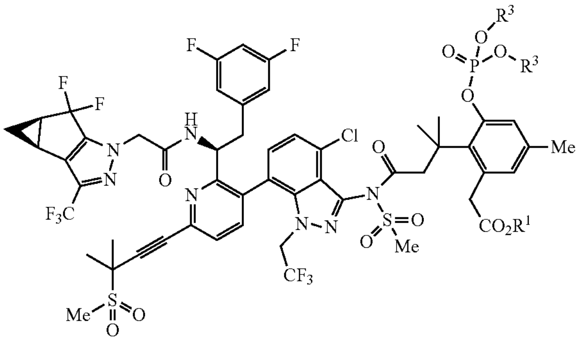

or a salt thereof, wherein:

$R^1$ is selected from the group consisting of $C_{1-6}$ alkyl, $C_{6-10}$ aryl, and 5-10 membered heteroaryl, and $C_{6-10}$ aryl-$C_{1-6}$ alkyl-, wherein the $C_{6-10}$ aryl, and 5-10 membered heteroaryl, and $C_{6-10}$ aryl-$C_{1-6}$ alkyl- are each optionally substituted by $C_{1-6}$ alkoxy; and each $R^3$ is independently selected from the group consisting of $C_{1-6}$ alkyl and $C_{6-10}$ aryl.

In some embodiments, the process provided herein further comprises coupling the compound of Formula IV, or a salt thereof, with a compound of Formula III:

III

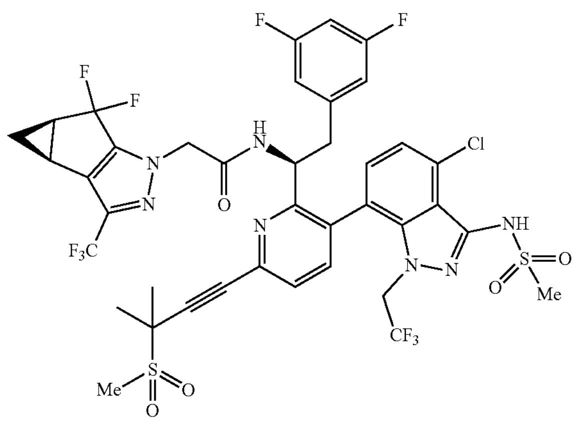

or a salt thereof, to form a compound of Formula II:

II

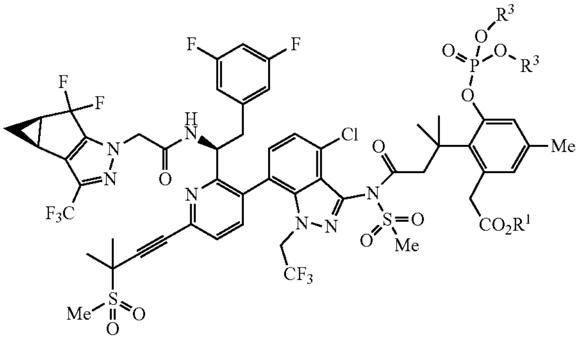

or a salt thereof, wherein:

$R^1$ is $C_{1-6}$ alkyl; and each $R^3$ is independently selected from $C_{1-6}$ alkyl.

In some embodiments, $R^1$ is selected from the group consisting of methyl, ethyl, isopropyl, and tert-butyl. In some embodiments, $R^1$ is tert-butyl.

In some embodiments, each $R^3$ is independently selected from methyl and tert-butyl.

In some embodiments, the coupling comprises reacting the compound of Formula IV, or a salt thereof, with the compound of Formula III, or a salt thereof, in the presence of a coupling agent, a base, and, optionally, a catalyst.

In some embodiments, the catalyst is selected from the group consisting of dimethylaminopyridine (DMAP), 1-hydroxybenzotriazole (HOBt), and 1-hydroxy-7-azabenzotriazole (HOAt). In some embodiments, the catalyst is absent.

In some embodiments, the coupling comprises reacting the compound of Formula IV, or a salt thereof, with the compound of Formula III, or a salt thereof, in the presence of a coupling agent and a base (e.g., in the absence of a catalyst).

In some embodiments, the coupling agent is selected from the group consisting of 1,1'-carbonyldiimidazole, thionyl chloride, phosgene, triphosgene, an alkyl chloroformate (e.g., ethyl chloroformate, isobutyl chloroformate), a carbodiimide (e.g., dicyclohexylcarbodiimide, diisopropylcarbodiimide, 1-ethyl-3-(3-dimethylaminopropyl)carbodiimide), propanephosphonic acid anhydride (T3P), and a peptide coupling reagent (e.g., HATU, HBTU, TATU, TBTU, HCTU, BOP, PyBOP, COMU).

In some embodiments, the coupling agent is selected from the group consisting of N,N,N',N'-tetramethylchloroformamidinium hexafluorophosphate, 1,1'-carbonyldiimidazole, thionyl chloride, phosgene, triphosgene, ethyl chloroformate, isobutyl chloroformate, dicyclohexylcarbodiimide, diisopropylcarbodiimide, 1-ethyl-3-(3-dimethylaminopropyl)carbodiimide), propanephosphonic acid anhydride, HATU, HBTU, TATU, TBTU, HCTU, BOP, PyBOP, and COMU. In some embodiments, the coupling agent is N,N,N',N'-tetramethylchloroformamidinium hexafluorophosphate. In some embodiments, the coupling agent is propanephosphonic acid anhydride.

In some embodiments, the base is selected from the group consisting of an amine (e.g., diisopropylethylamine, 4-methylmorpholine), a basic aromatic compound (e.g., pyridine, 2,6-lutidine, imidazole), a carbonate (e.g., lithium carbonate, sodium carbonate, potassium carbonate, cesium carbonate), a bicarbonate (e.g., lithium bicarbonate, sodium bicarbonate, potassium bicarbonate), and a phosphate (e.g., sodium phosphate, potassium phosphate).

In some embodiments, the base is selected from the group consisting of 1-methylimidazole, diisopropylethylamine, 4-methylmorpholine, pyridine, 2,6-lutidine, imidazole, lithium carbonate, sodium carbonate, potassium carbonate, cesium carbonate, lithium bicarbonate, sodium bicarbonate, potassium bicarbonate, sodium phosphate, and potassium phosphate. In some embodiments, the base is 1-methylimidazole.

In some embodiments, the coupling is performed at a temperature of from about −30° C. to about 60° C. In some embodiments, the coupling is performed at a temperature of from about 0° C. to about 30° C. In some embodiments, the coupling is performed at a temperature of from about 0° C. to about 20° C.

In some embodiments, the coupling is performed in a solvent selected from the group consisting of an ester (e.g., ethyl acetate, isopropyl acetate), an ether (e.g., tetrahydrofuran, 2-methyltetrahydrofuran, tert-butyl methyl ether), a halogenated solvent (e.g., dichloromethane, 1,2-dichloroethane, chlorobenzene), a hydrocarbon (e.g., toluene, n-heptane), a nitrile (e.g., propylnitrile, butylnitrile), and a polar aprotic solvent (e.g., N,N-dimethylformamide, N,N-dimethylacetamide, N-methyl-2-pyrrolidone), or any combination thereof, optionally in combination with water. In some embodiments, the coupling is performed in a solvent comprising acetonitrile.

In some embodiments, the compound of Formula II is a compound of Formula II-a:

II-a

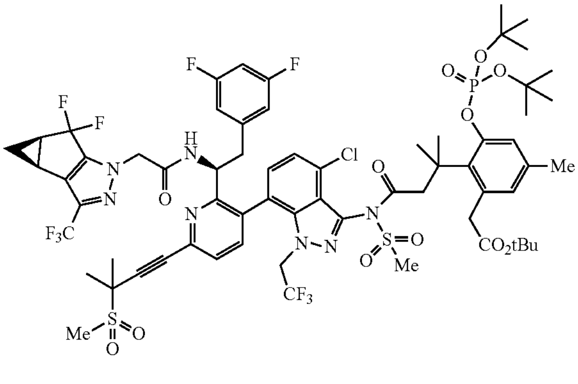

or a co-crystal, solvate, or salt thereof.

In some embodiments, the compound of Formula II is a compound of Formula II-a:

II-a

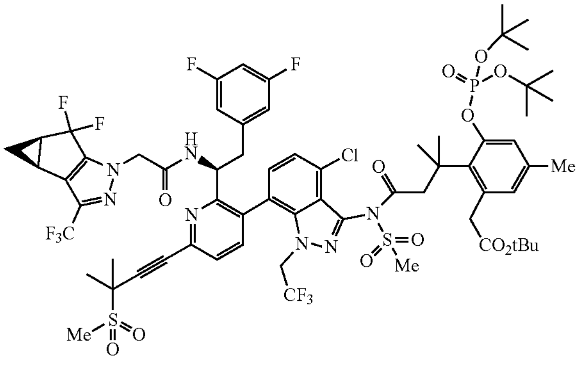

or a salt thereof.

In some embodiments, the compound of Formula II is a compound of Formula II-a:

II-a

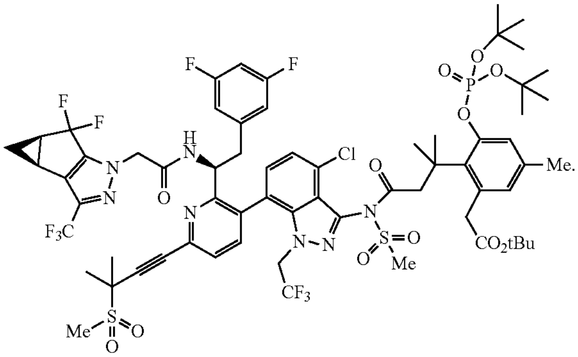

In some embodiments, the process provided herein further comprises deprotecting the compound of Formula II, or a co-crystal, solvate, or salt thereof, to form a compound of Formula I:

I

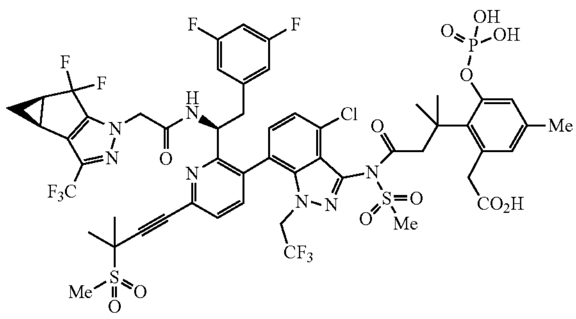

or a co-crystal, solvate, or salt thereof.

In some embodiments, the process provided herein further comprises deprotecting the compound of Formula II, or a salt thereof, to form a compound of Formula I.

I

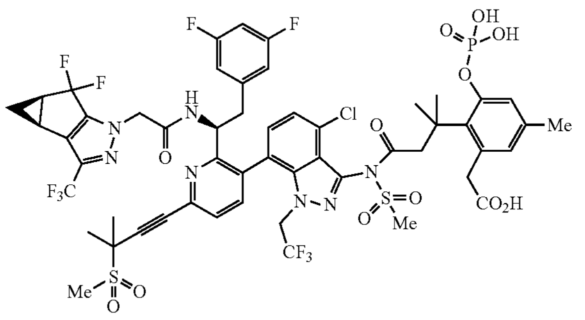

or a salt thereof.

In some embodiments, the deprotecting comprises reacting the compound of Formula II, or a co-crystal, solvate, or salt thereof, in the presence of an acid. In some embodiments, the deprotecting comprises reacting the compound of Formula II, or a salt thereof, in the presence of an acid.

In some embodiments, the acid is selected from the group consisting of a carboxylic acid (e.g., trifluoroacetic acid, trichloroacetic acid, formic acid), an inorganic acid (e.g., hydrofluoric acid, hydrochloric acid, sulfuric acid), and an organic acid (e.g., methanesulfonic acid, p-toluenesulfonic acid, camphorsulfonic acid).

In some embodiments, the acid is selected from the group consisting of phosphoric acid, trifluoroacetic acid, trichloroacetic acid, formic acid, hydrofluoric acid, hydrochloric acid, sulfuric acid, methanesulfonic acid, p-toluenesulfonic acid, and camphorsulfonic acid. In some embodiments, the acid is phosphoric acid.

In some embodiments, the deprotecting comprises reacting the compound of Formula II, or a co-crystal, solvate, or salt thereof, in the presence of an oxidant. In some embodiments, the deprotecting comprises reacting the compound of Formula II, or a salt thereof, in the presence of an oxidant.

In some embodiments, the oxidant is selected from the group consisting of an N-halo succinimide (e.g., N-chlorosuccinimide, N-bromosuccinimide), an N-halo sulfonamide (e.g., N-chlorotosylamide sodium salt), bromine ($Br_2$), chlorine ($Cl_2$), iodine ($I_2$), a hypochlorite (e.g., sodium hypochlorite), a peroxide (e.g., sodium peroxide, t-butyl hydrogen peroxide, sodium perborate), and potassium peroxymonosulfate (Oxone). In some embodiments, the deprotecting is performed at a temperature of from about −20° C. to about 100° C. In some embodiments, the deprotecting is performed at a temperature of from about 0° C. to about 40° C. In some embodiments, the deprotecting is performed at a temperature of from about 10° C. to about 30° C.

In some embodiments, the coupling is performed in a solvent selected from the group consisting of an ether (e.g., 2-methyltetrahydrofuran, tert-butyl methyl ether), a ketone (e.g., acetone, 2-butanone), a hydrocarbon (e.g., toluene, xylene, trifluorotoluene), a halogenated solvent (e.g., dichloromethane, 1,2-dichloroethane, chloroform, carbon tetrachloride), a nitrile (e.g., acetonitrile, propylnitrile, butylnitrile), a protic solvent (e.g., methanol, ethanol, propanol, t-butanol), and a polar aprotic solvent (e.g., N,N-dimethylformamide, N,N-dimethylacetamide, N-methyl-2-pyrrolidone, dimethyl sulfoxide), or any combination thereof, optionally in combination with water. In some embodiments, the coupling is performed in a solvent comprising acetonitrile and water.

In some embodiments, the present disclosure provides a process of preparing a compound of Formula I:

I

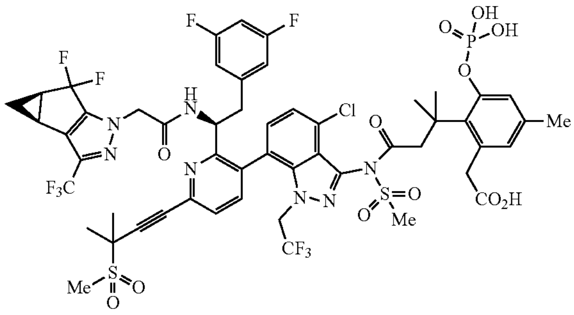

or a co-crystal, solvate, or salt thereof, comprising:

reacting a compound of Formula XIV-a:

XIV-a

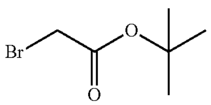

or a co-crystal, solvate, or salt thereof, with trimethylsilyl chloride in the presence of zinc to form a first mixture; and mixing the first mixture with a compound of Formula XI-a:

XI-a

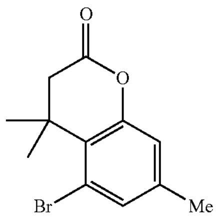

or a co-crystal, solvate, or salt thereof, in the presence of bis(dibenzylideneacetone)palladium(0) and 2-dicyclohexylphosphino-2',4',6'-triisopropylbiphenyl to form a compound of Formula XIII-a:

XIII-a

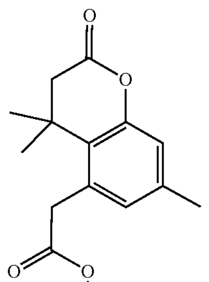

or a co-crystal, solvate, or salt thereof;

reacting the compound of Formula XIII-a, or a co-crystal, solvate, or salt thereof, with di-tert-butyl phosphite, bromoform, and sodium trimethylsilanolate to form a compound of Formula IV-a:

IV-a

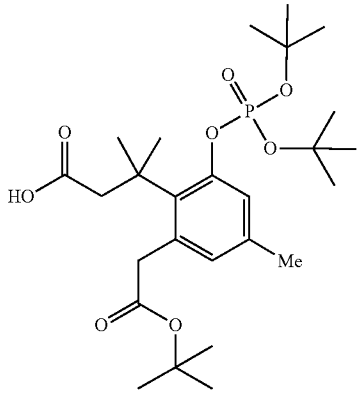

or a salt thereof, coupling the compound of Formula IV-a, or a co-crystal, solvate, or salt thereof, with a compound of Formula III:

III

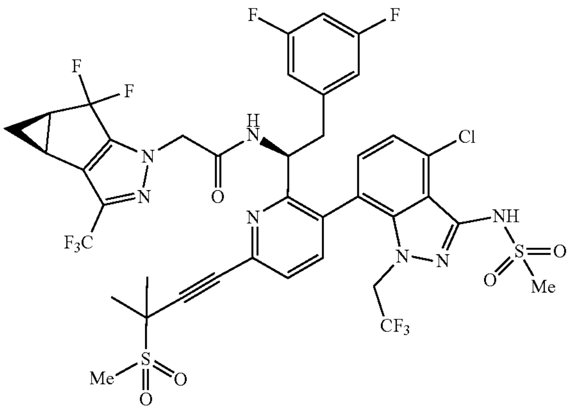

or a co-crystal, solvate, or salt thereof, in the presence of propanephosphonic acid anhydride and 1-methylimidazole to form a compound of Formula II-a:

II-a
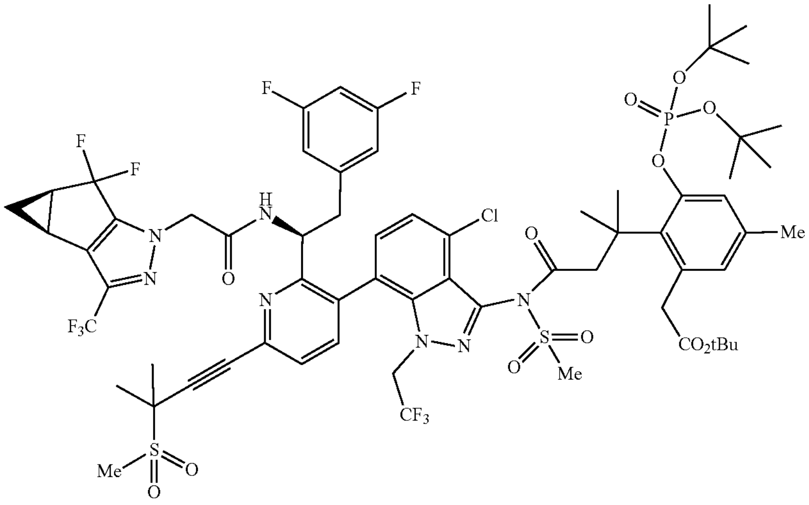
or a co-crystal, solvate, or salt thereof; and
deprotecting the compound of Formula II-a, or a co-crystal, solvate, or salt thereof, with phosphoric acid to form the compound of Formula I, or a co-crystal, solvate, or salt thereof.
In some embodiments, the present disclosure provides a process of preparing a compound of Formula I:
I
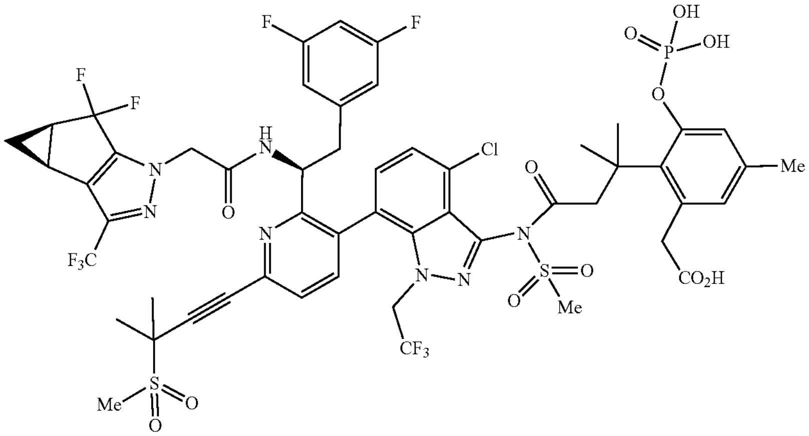

or a salt thereof, comprising:

reacting 3-bromo-5-methylphenol with methyl 3,3-dimethylacrylate in the presence of sulfuric acid to form a compound of Formula XI-a:

XI-a

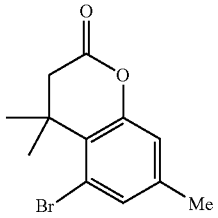

or a salt thereof;

reacting a compound of Formula XIV-a:

XIV-a

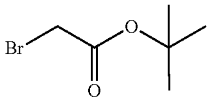

or a salt thereof, with trimethylsilyl chloride in the presence of zinc to form a first mixture; and mixing the first mixture with the compound of Formula XI-a, or a salt thereof, in the presence of bis(dibenzylideneacetone)palladium(0) and 2-dicyclohexylphosphino-2',4',6'-triisopropylbiphenyl to form a compound of Formula XIII-a:

XIII-a

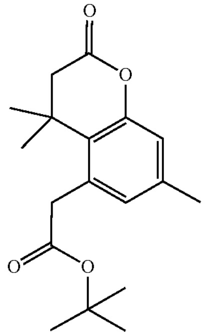

or a salt thereof;

reacting the compound of Formula XIII-a, or a salt thereof, with di-tert-butyl phosphite, bromoform, and sodium trimethylsilanolate to form a compound of Formula IV-a:

IV-a

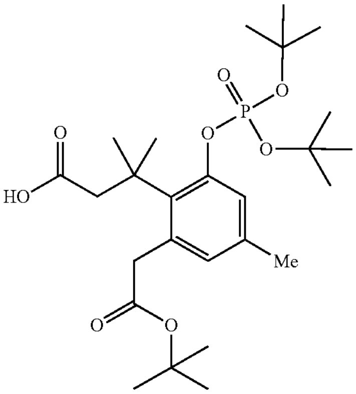

or a salt thereof, coupling the compound of Formula IV-a, or a salt thereof, with a compound of Formula III:

III

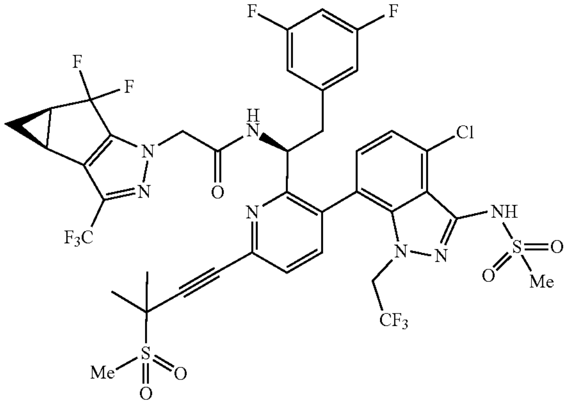

or a salt thereof, in the presence of propanephosphonic acid anhydride and 1-methylimidazole to form a compound of Formula II-a:

II-a
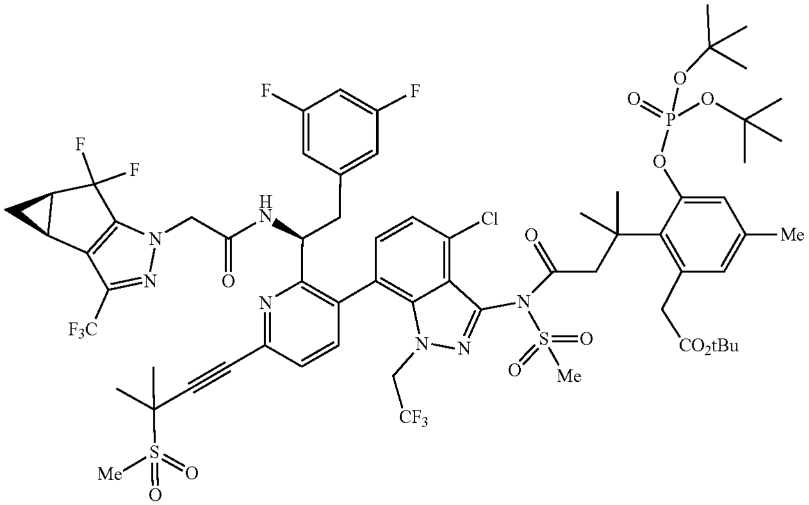
or a salt thereof; and
deprotecting the compound of Formula II-a, or a salt thereof, with phosphoric acid to form the compound of Formula I, or a salt thereof.
In some embodiments, the present disclosure provides a process of preparing a compound of Formula I:
I
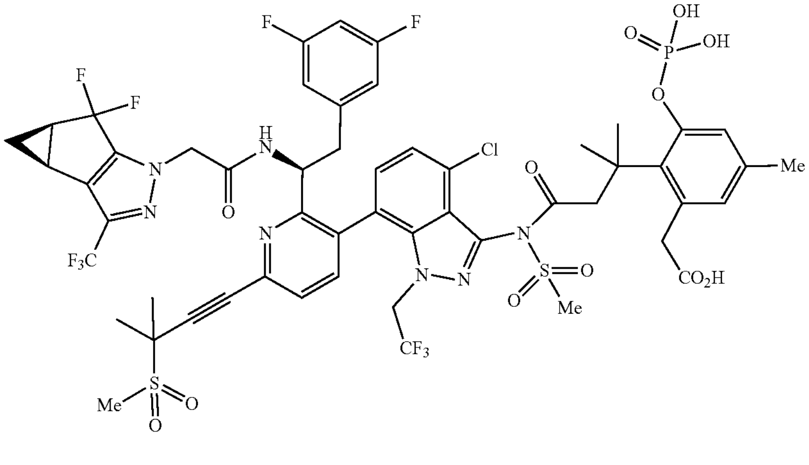

or a salt thereof, comprising:

reacting a compound of Formula XIV-a:

XIV-a

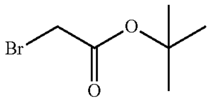

or a salt thereof, with trimethylsilyl chloride in the presence of zinc to form a first mixture; and mixing the first mixture with a compound of Formula XI-a, XI-a

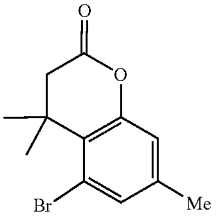

or a salt thereof, in the presence of bis(dibenzylideneacetone)palladium(0) and 2-dicyclohexylphosphino-2',4',6'-triisopropylbiphenyl to form a compound of Formula XIII-a:

XIII-a

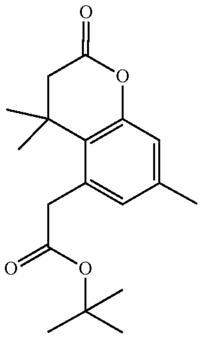

or a salt thereof;

reacting the compound of Formula XIII-a, or a salt thereof, with di-tert-butyl phosphite, bromoform, and sodium trimethylsilanolate to form a compound of Formula IV-a:

IV-a

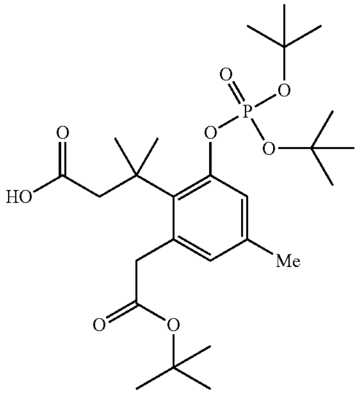

or a salt thereof, coupling the compound of Formula IV-a, or a salt thereof, with a compound of Formula III:

III

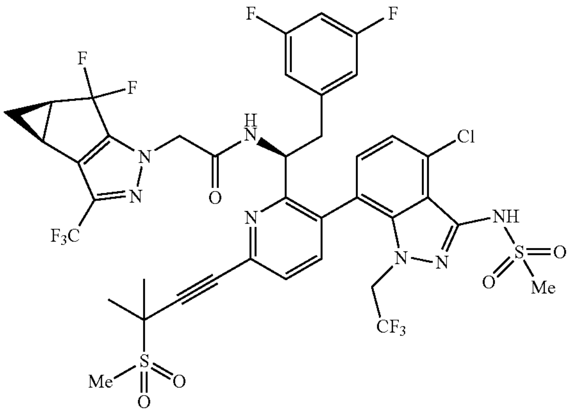

or a salt thereof, in the presence of propanephosphonic acid anhydride and 1-methylimidazole to form a compound of Formula II-a:

II-a
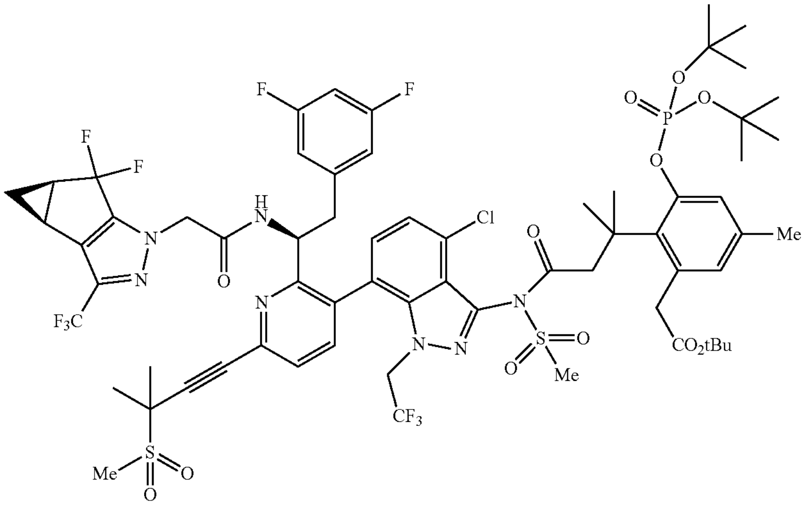
or a salt thereof; and
deprotecting the compound of Formula II-a, or a salt thereof, with phosphoric acid to form the compound of Formula I, or a salt thereof.
In some embodiments, the present disclosure provides a process of preparing a compound of Formula I:
I
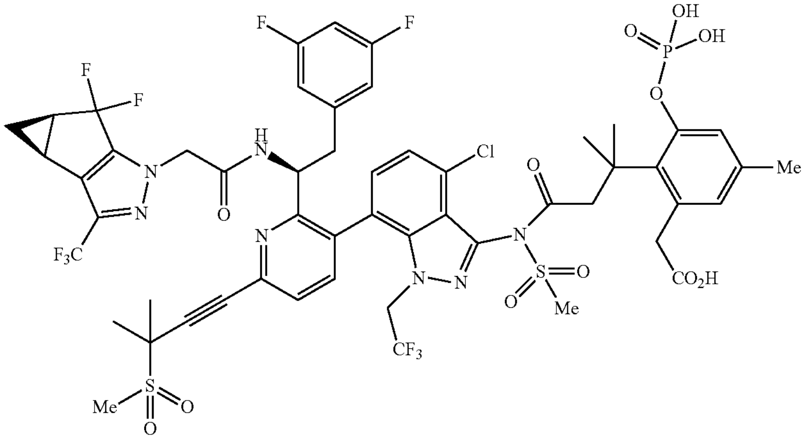

or a co-crystal, solvate, or salt thereof, comprising:

reacting 3-bromo-5-methylphenol with methyl 3,3-dimethylacrylate in the presence of sulfuric acid to form a compound of Formula XI-a:

XI-a

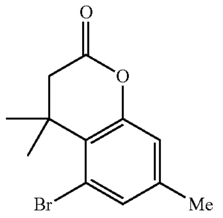

or a salt thereof;

reacting the compound of Formula XI-a, or a co-crystal, solvate, or salt thereof, with bis(pinacolato)diboron in the presence of bis(dibenzylideneacetone)palladium (0), triphenylphosphine, and potassium propionate to form a compound of Formula XI-b:

XI-b

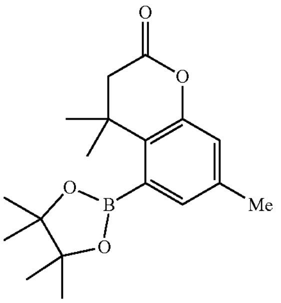

or a co-crystal, solvate, or salt thereof;

reacting the compound of Formula XI-b, or a co-crystal, solvate, or salt thereof, with a compound of Formula XIV-a:

XIV-a

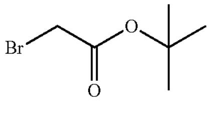

or a co-crystal, solvate, or salt thereof, in the presence of bis(dibenzylideneacetone)palladium(0), potassium phosphate tribasic, and 1,3,5,7-tetramethyl-6-phenyl-2,4,8-trioxa-6-phosphaadamantane to form a compound of Formula XIII-a:

XIII-a

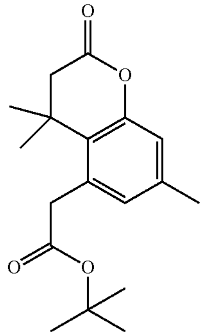

or a co-crystal, solvate, or salt thereof;

reacting the compound of Formula XIII-a, or a co-crystal, solvate, or salt thereof, with di-tert-butyl phosphite, bromoform, and sodium trimethylsilanolate to form a compound of Formula IV-a:

IV-a

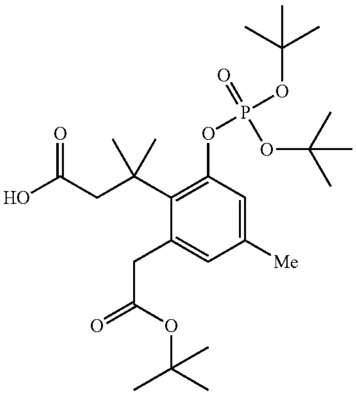

or a co-crystal, solvate, or salt thereof, coupling the compound of Formula IV-a, or a co-crystal, solvate, or salt thereof, with a compound of Formula III:

III

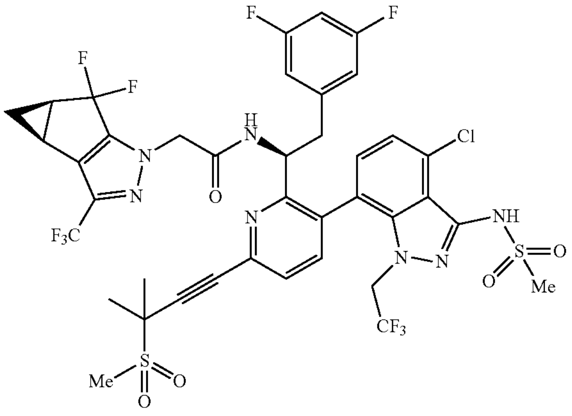

or a co-crystal, solvate, or salt thereof, in the presence of propanephosphonic acid anhydride and 1-methylimidazole to form a compound of Formula II-a:

II-a
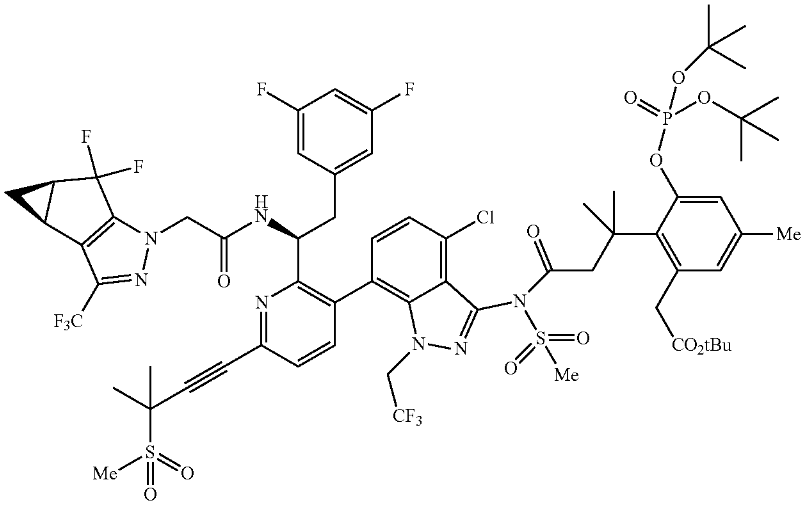
or a co-crystal, solvate, or salt thereof; and
deprotecting the compound of Formula II-a, or a co-crystal, solvate, or salt thereof, with phosphoric acid to form the compound of Formula I, or a co-crystal, solvate, or salt thereof.
In some embodiments, the present disclosure provides a process of preparing a compound of Formula I:
I
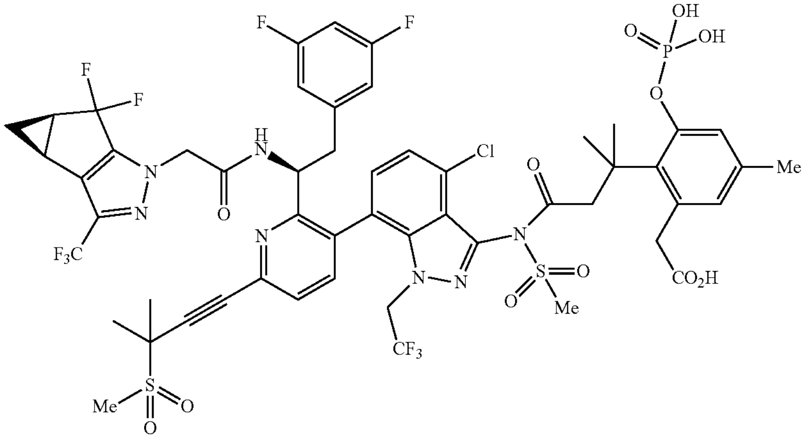

or a salt thereof, comprising:

reacting 3-bromo-5-methylphenol with methyl 3,3-dimethylacrylate in the presence of sulfuric acid to form a compound of Formula XI-a:

XI-a

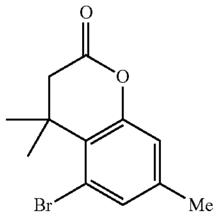

or a salt thereof;

reacting the compound of Formula XI-a, or a salt thereof, with bis(pinacolato)diboron in the presence of bis(dibenzylideneacetone)palladium(0), triphenylphosphine, and potassium propionate to form a compound of Formula XI-b:

XI-b

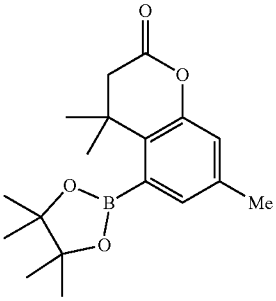

or a salt thereof;

reacting the compound of Formula XI-b, or a salt thereof, with a compound of Formula XIV-a:

XIV-a

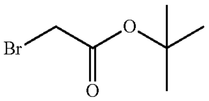

or a salt thereof, in the presence of bis(dibenzylideneacetone)palladium(0), potassium phosphate tribasic, and 1,3,5,7-tetramethyl-6-phenyl-2,4,8-trioxa-6-phosphaadamantane to form a compound of Formula XIII-a:

XIII-a

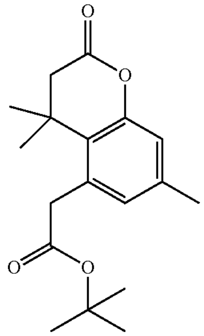

or a salt thereof;

reacting the compound of Formula XIII-a, or a salt thereof, with di-tert-butyl phosphite, bromoform, and sodium trimethylsilanolate to form a compound of Formula IV-a:

IV-a

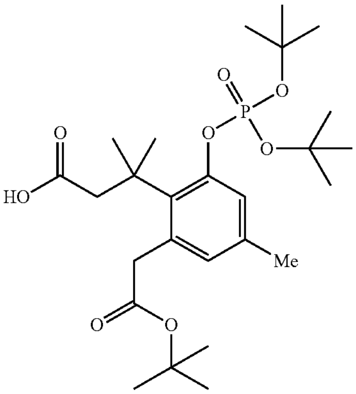

or a salt thereof, coupling the compound of Formula IV-a, or a salt thereof, with a compound of Formula

III

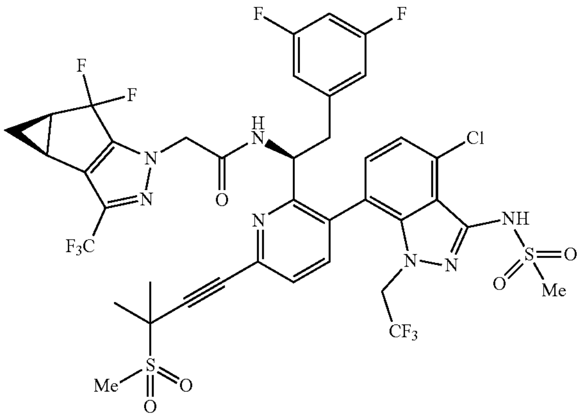

or a salt thereof, in the presence of propanephosphonic acid anhydride and 1-methylimidazole to form a compound of Formula II-a:

II-a
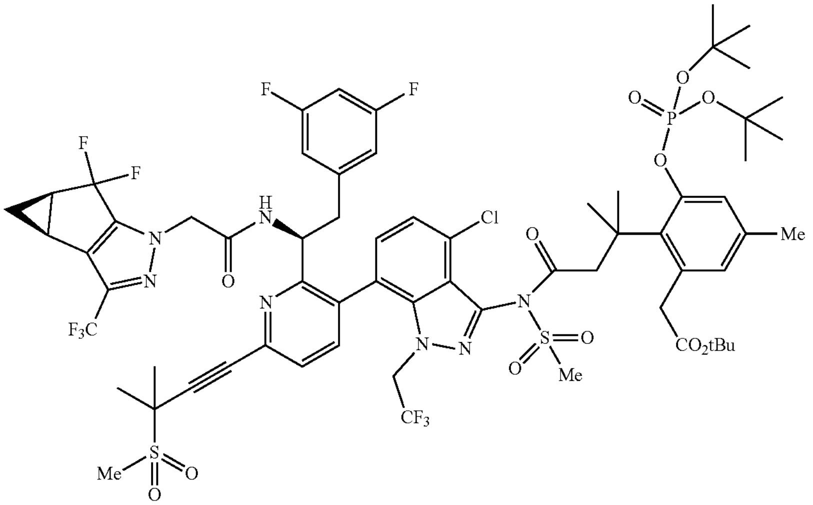
or a salt thereof; and
deprotecting the compound of Formula II-a, or a salt thereof, with phosphoric acid to form the compound of Formula I, or a salt thereof.
In some embodiments, the present disclosure provides a process of preparing a compound of Formula I:
I
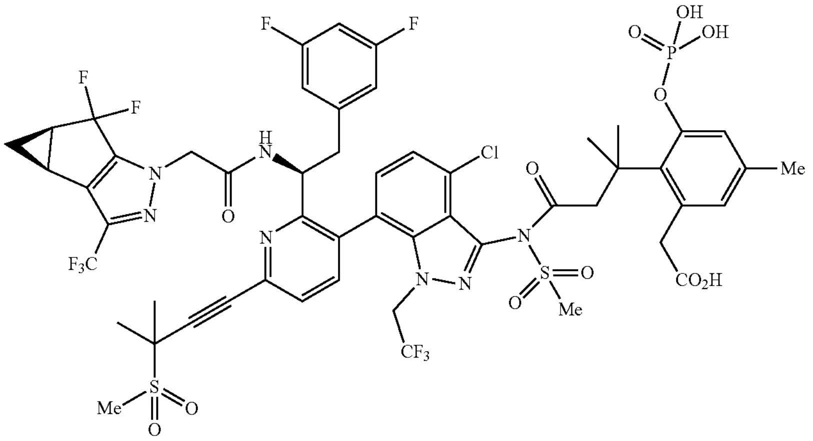

or a salt thereof, comprising:

reacting a compound of Formula XI-a:

XI-a

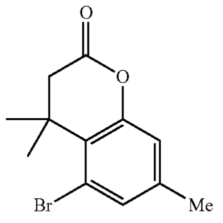

or a salt thereof, with bis(pinacolato)diboron in the presence of bis(dibenzylideneacetone)palladium(0), triphenylphosphine, and potassium propionate to form a compound of Formula XI-b:

XI-b

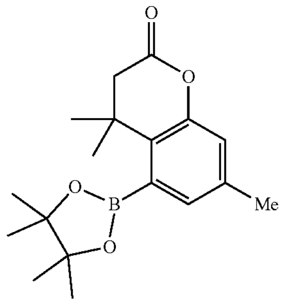

or a salt thereof;

reacting the compound of Formula XI-b, or a salt thereof, with a compound of Formula XIV-a:

XIV-a

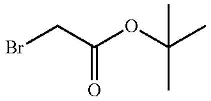

or a salt thereof, in the presence of bis(dibenzylideneacetone)palladium(0), potassium phosphate tribasic, and 1,3,5,7-tetramethyl-6-phenyl-2,4,8-trioxa-6-phosphaadamantane to form a compound of Formula XIII-a:

XIII-a

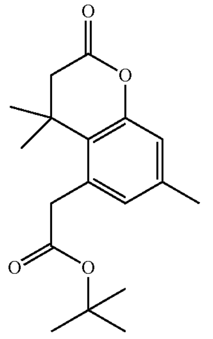

or a salt thereof;

reacting the compound of Formula XIII-a, or a salt thereof, with di-tert-butyl phosphite, bromoform, and sodium trimethylsilanolate to form a compound of Formula IV-a:

IV-a

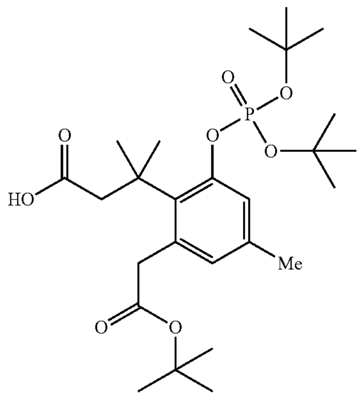

or a salt thereof, coupling the compound of Formula IV-a, or a salt thereof, with a compound of Formula III:

III

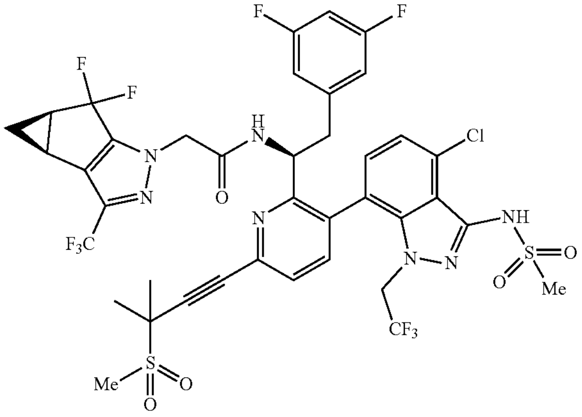

or a salt thereof, in the presence of propanephosphonic acid anhydride and 1-methylimidazole to form a compound of Formula II-a:

II-a
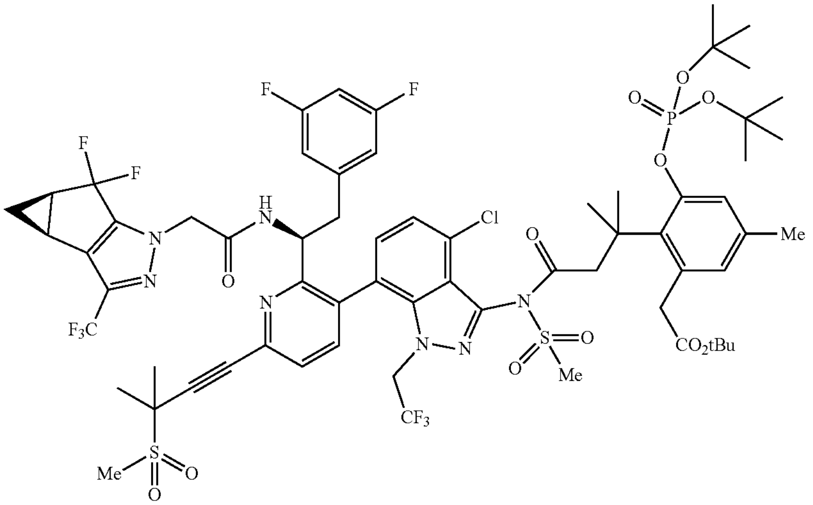
or a salt thereof; and
deprotecting the compound of Formula II-a, or a salt thereof, with phosphoric acid to form the compound of Formula I, or a salt thereof.
In some embodiments, the present disclosure provides a process of preparing a compound of Formula I:
I
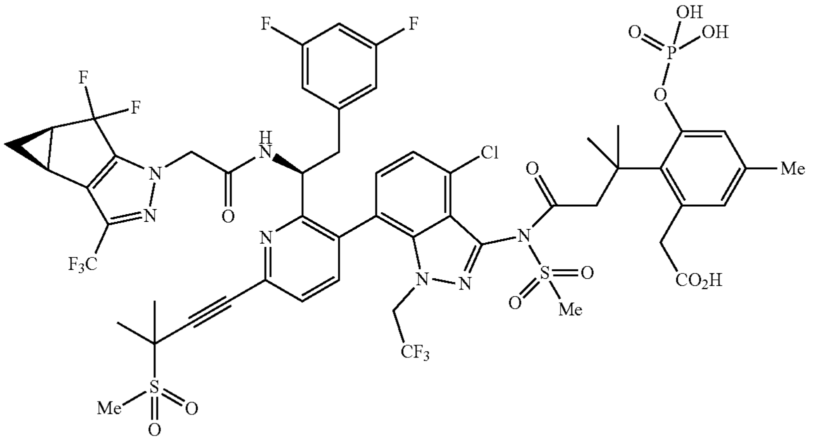

or a salt thereof, comprising:

reacting a compound of Formula XIV-a:

XIV-a

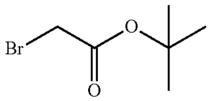

or a salt thereof, with diisobutylaluminium hydride in the presence of zinc and lithium chloride to form a first mixture; and mixing the first mixture with a compound of Formula XI-a:

XI-a

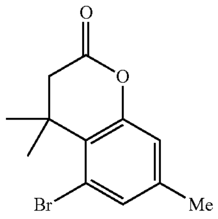

or a salt thereof, in the presence of palladium (II) acetate and 2-dicyclohexylphosphino-2',4',6'-triisopropylbiphenyl to form a compound of Formula XIII-a:

XIII-a

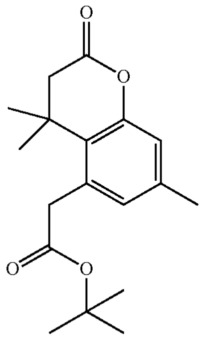

or a salt thereof;

reacting the compound of Formula XIII-a, or a salt thereof, with di-tert-butyl phosphite, bromoform, and trimethylsilanolate to form a compound of Formula IV-a:

IV-a

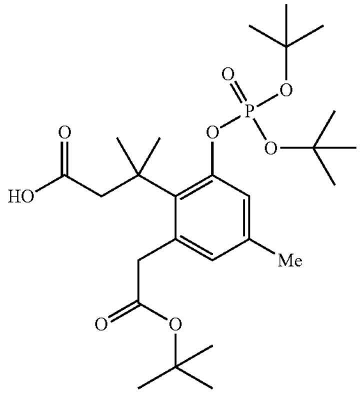

or a salt thereof, coupling the compound of Formula IV-a, or a salt thereof, with a compound of Formula III:

III

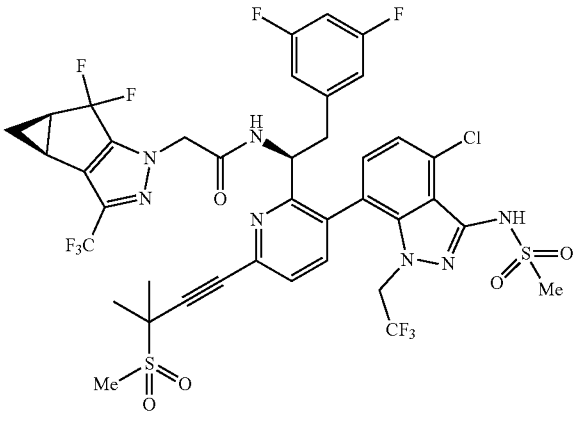

or a salt thereof, in the presence of N,N,N',N'-tetramethylchloroformamidinium hexafluorophosphate and 1-methylimidazole to form a compound of Formula II-a:

II-a
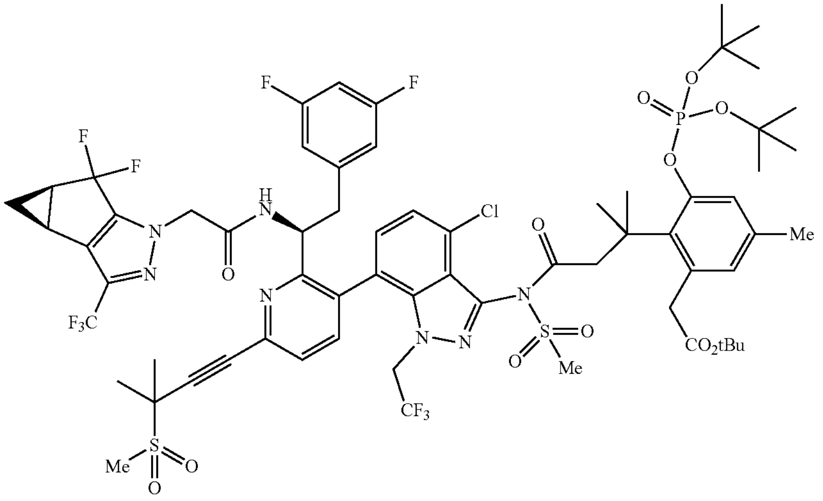
or a salt thereof; and
deprotecting the compound of Formula II-a, or a salt thereof, with phosphoric acid to form the compound of Formula I, or a salt thereof.
In some embodiments, the present disclosure provides a process of preparing a compound of Formula I:
I
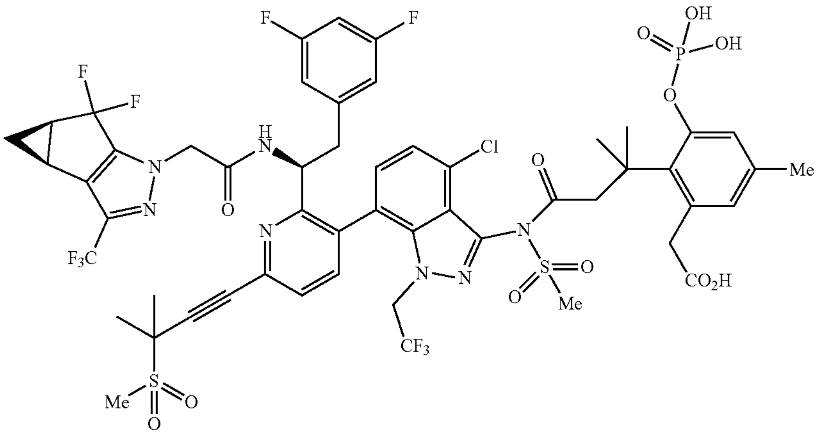

or a salt thereof, comprising:

reacting a compound of Formula VII-a:

VII-a

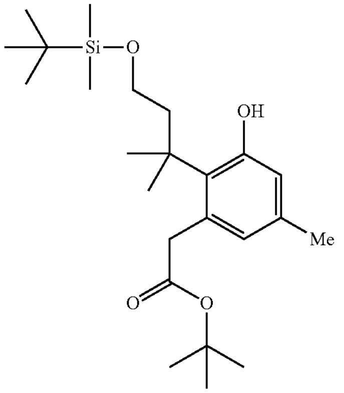

or a salt thereof, with di-tert-butyl phosphite in the presence of bromoform and cesium carbonate to form a compound of Formula VI-a:

VI-a

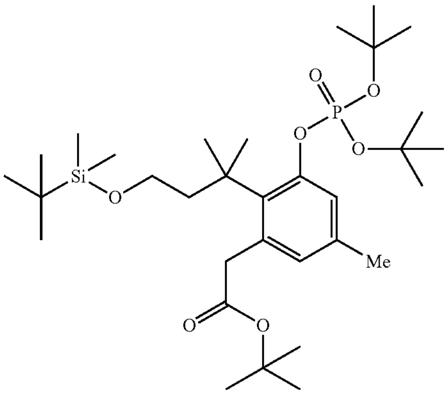

or a salt thereof;

deprotecting the compound of Formula VI-a, or a salt thereof, in the presence of tetrabutylammonium fluoride to form a compound of Formula V-a:

V-a

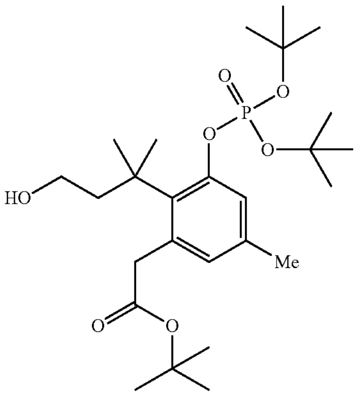

or a salt thereof;

oxidizing the compound of Formula V-a, or a salt thereof, in the presence of (diacetoxyiodo)benzene, sodium phosphate dibasic, and 2,2,6,6-tetramethylpiperidine 1-oxyl to form a compound of Formula IV-a:

IV-a

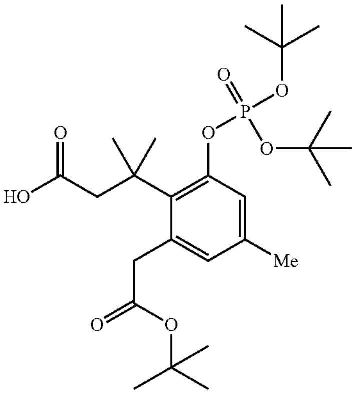

or a salt thereof, coupling the compound of Formula IV-a, or a salt thereof, with a compound of Formula III:

III

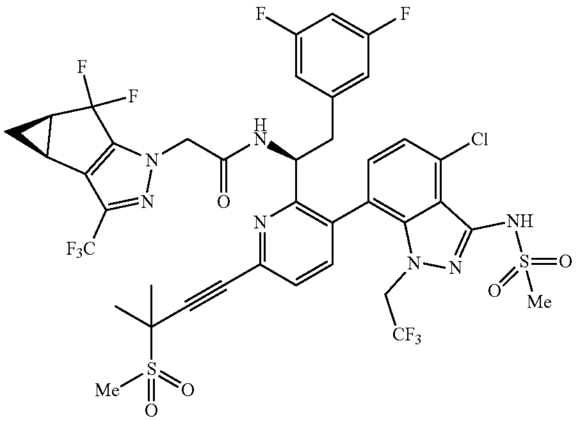

or a salt thereof, in the presence of N,N,N',N'-tetramethylchloroformamidinium hexafluorophosphate and 1-methylimidazole to form a compound of Formula II-a:

II-a
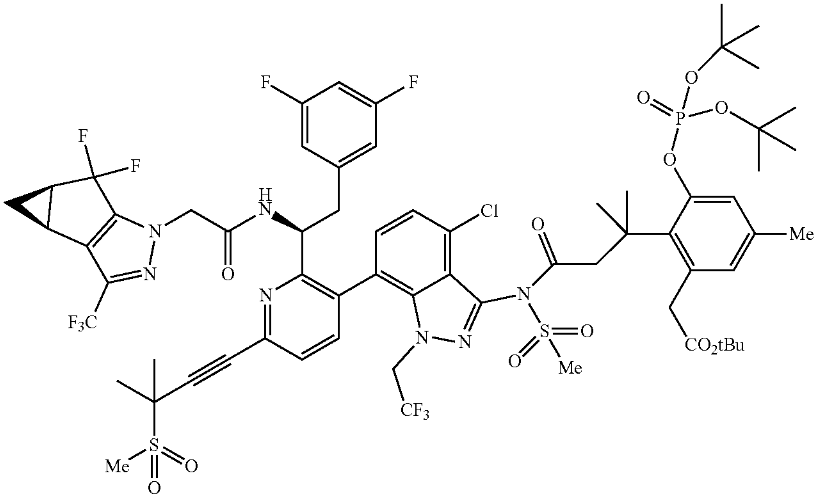
or a salt thereof; and
deprotecting the compound of Formula II-a, or a salt thereof, with phosphoric acid to form the compound of Formula I, or a salt thereof.
In some embodiments, the present disclosure provides a process of preparing a compound of Formula I:
I
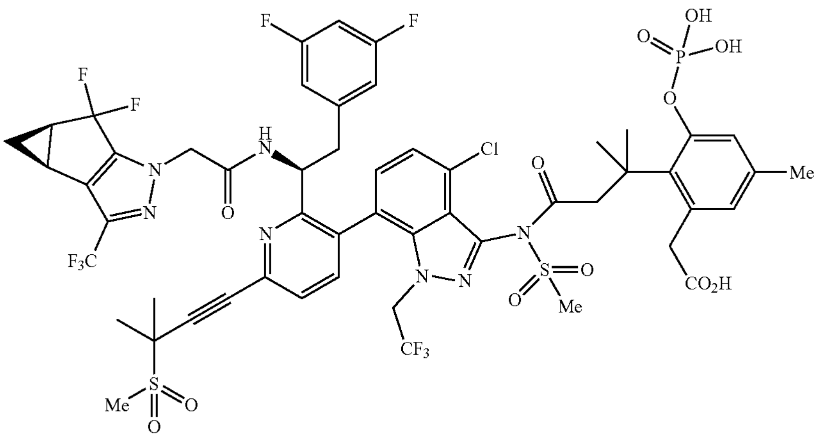

or a salt thereof, comprising:

reacting a compound of Formula VII-a:

VII-a

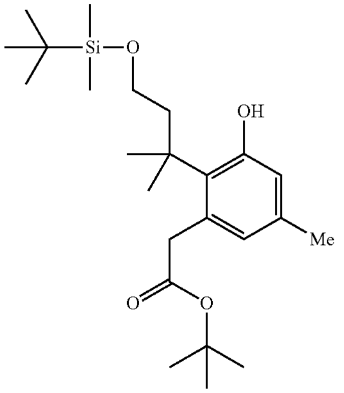

or a salt thereof, with tetrabenzyl pyrophosphate in the presence of sodium hydride to form a compound of Formula VI-b:

VI-b

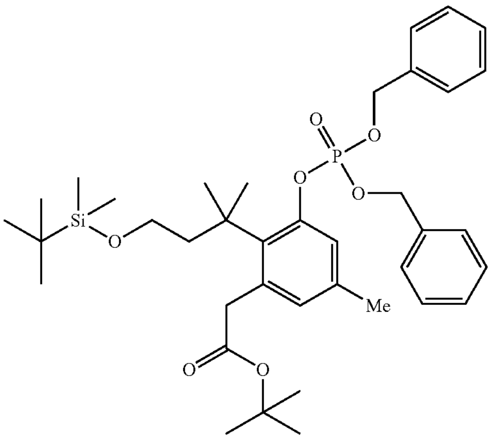

or a salt thereof;

deprotecting the compound of Formula VI-b, or a salt thereof, in the presence of tetrabutylammonium fluoride to form a compound of Formula V-b:

V-b

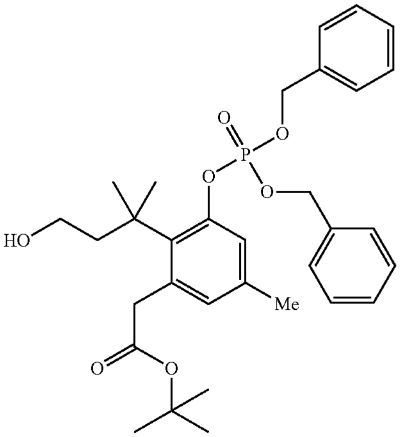

or a salt thereof;

oxidizing the compound of Formula V-b, or a salt thereof, in the presence of (diacetoxyiodo)benzene, sodium phosphate dibasic, and 2,2,6,6-tetramethylpiperidine 1-oxyl to form a compound of Formula IV-b:

IV-b

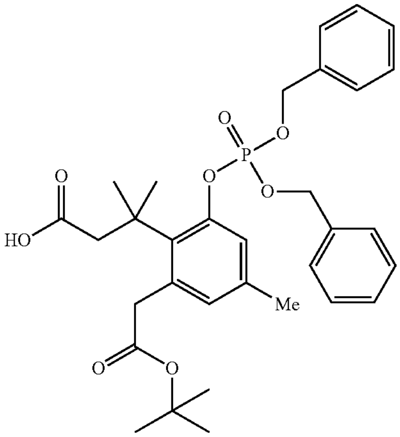

or a salt thereof;

coupling the compound of Formula IV-b, or a salt thereof, with a compound of Formula III:

III

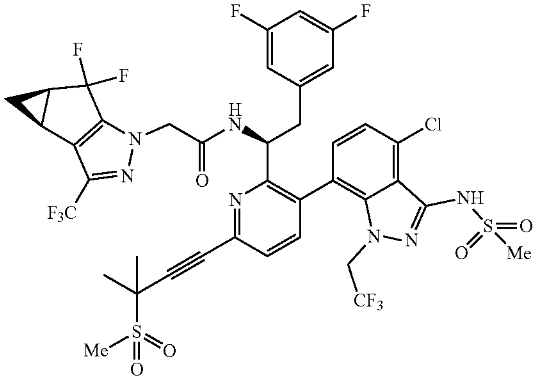

or a salt thereof, in the presence of N,N,N',N'-tetramethylchloroformamidinium hexafluorophosphate and 1-methylimidazole to form a compound of Formula II-b:

II-b

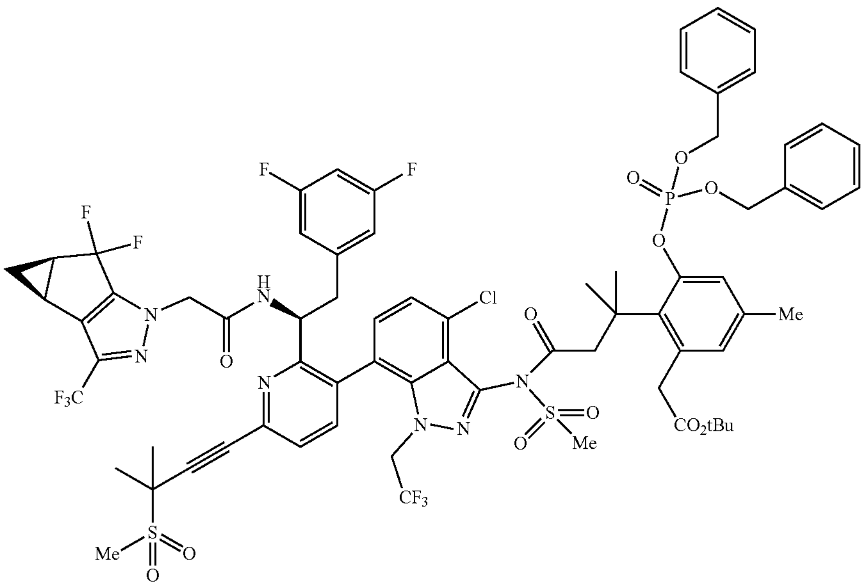

or a salt thereof, and deprotecting the compound of Formula II-b, or a salt thereof, with phosphoric acid to form the compound of Formula I, or a salt thereof.

In some embodiments, the present disclosure provides a process of preparing a compound of Formula I:

I

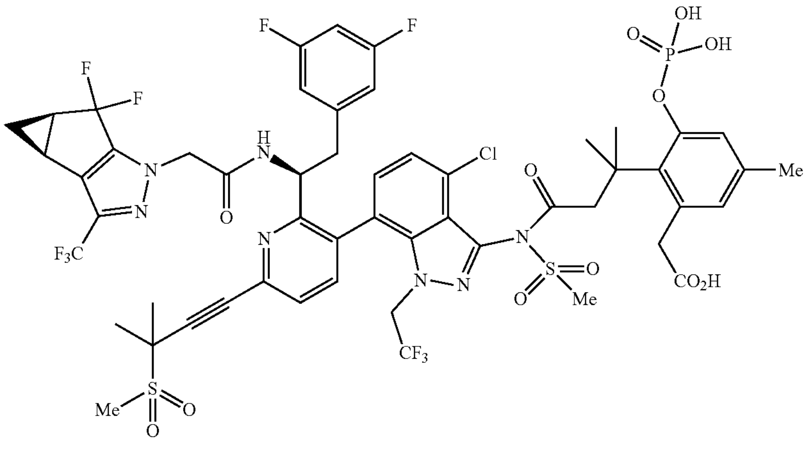

or a salt thereof, comprising:

reacting a compound of Formula VII-a:

VII-a

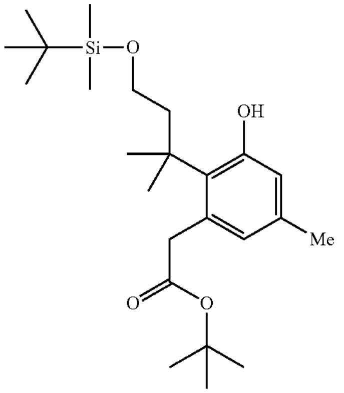

or a salt thereof, with di-tert-butyl N,N-diisopropylphosphoramidate in the presence of a 1-methylimidazole and trifluoroacetic acid to form a first mixture; and mixing the first mixture with hydrogen peroxide to form a compound of Formula VI-a:

VI-a

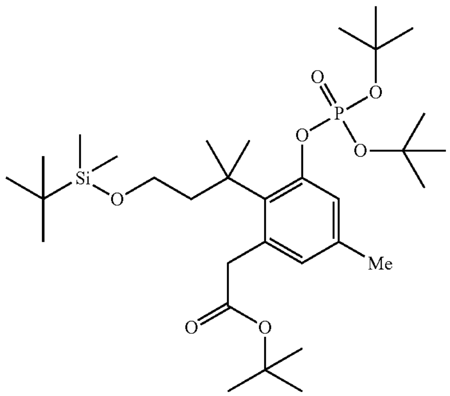

or a salt thereof;

deprotecting the compound of Formula VI-a, or a salt thereof, in the presence of tetrabutylammonium fluoride to form a compound of Formula V-a:

V-a

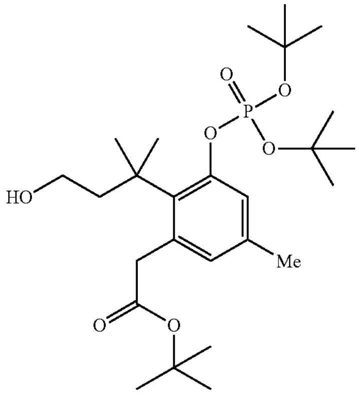

or a salt thereof;

oxidizing the compound of Formula V-a, or a salt thereof, in the presence of (diacetoxyiodo)benzene, sodium phosphate dibasic, and 2,2,6,6-tetramethylpiperidine 1-oxyl to form a compound of Formula IV-a:

IV-a

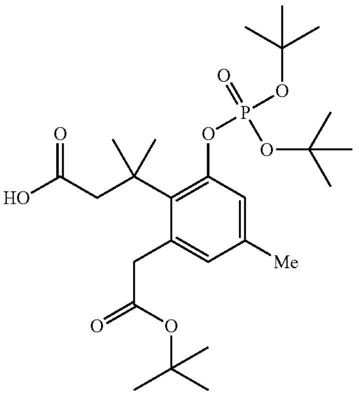

or a salt thereof;

coupling the compound of Formula IV-a, or a salt thereof, with a compound of Formula III:

III

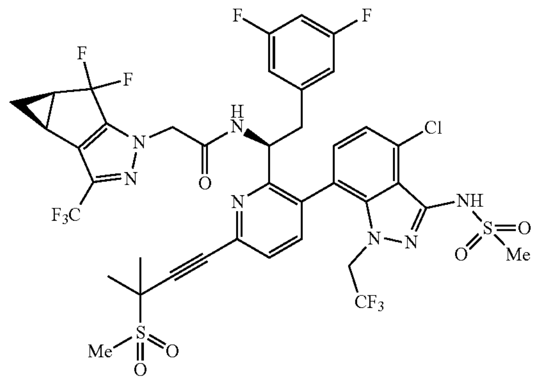

or a salt thereof, in the presence of N,N,N',N'-tetramethylchloroformamidinium hexafluorophosphate and 1-methylimidazole to form a compound of Formula II-a:

II-a

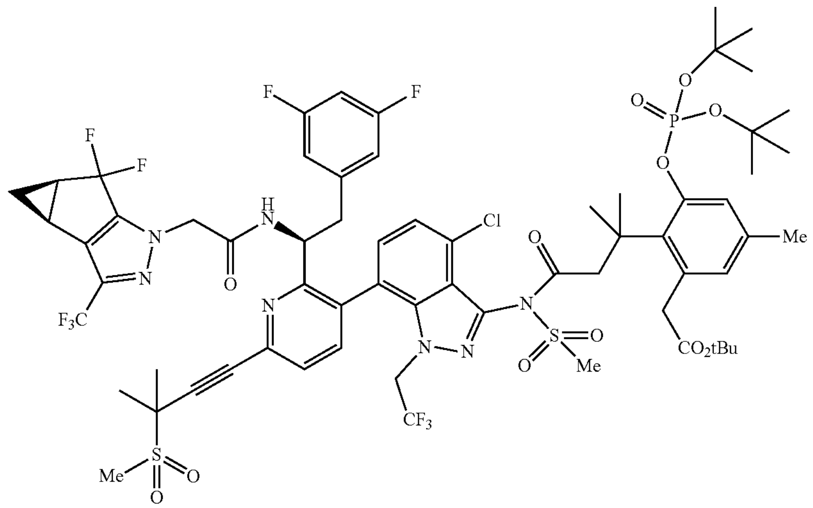

or a salt thereof; and deprotecting the compound of Formula II-a, or a salt thereof, with phosphoric acid to form the compound of Formula I, or a salt thereof.

In some embodiments, the compound of Formula III, or a co-crystal, solvate, or salt thereof, is a sodium salt of the compound of Formula III.

In some embodiments, the compound of Formula III, or a salt thereof, is a sodium salt of the compound of Formula III.

In some embodiments, the present disclosure provides a process of preparing a compound of Formula VI-a:

VI-a

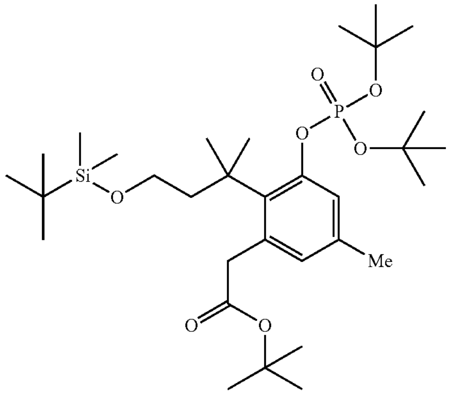

or a co-crystal, solvate, or salt thereof, comprising reacting a compound of Formula VII-a:

VII-a

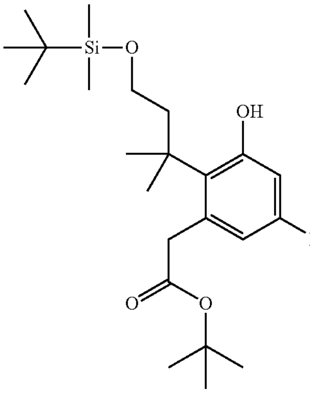

or a co-crystal, solvate, or salt thereof, with di-tert-butyl N,N-diisopropylphosphoramidate in the presence of 1-methylimidazole and trifluoroacetic acid to form a first mixture; and mixing the first mixture with hydrogen peroxide.

In some embodiments, the present disclosure provides a process of preparing a compound of Formula VI-a:

VI-a

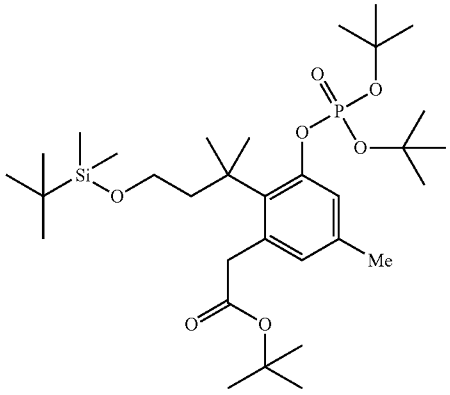

or a salt thereof, comprising reacting a compound of Formula VII-a:

VII-a

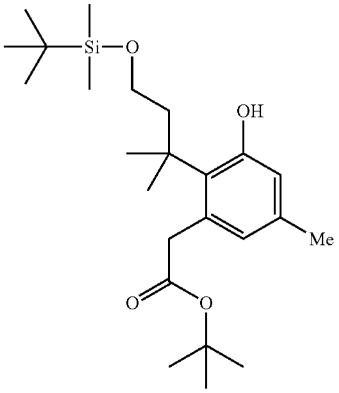

or a salt thereof, with di-tert-butyl N,N-diisopropylphosphoramidate in the presence of 1-methylimidazole and trifluoroacetic acid to form a first mixture; and mixing the first mixture with hydrogen peroxide to form the compound of Formula VI-a, or a salt thereof.

In some embodiments, the present disclosure provides an intermediate compound provided herein (e.g., an intermediate compounds prepared according to a process provided herein).

In some embodiments, the present disclosure provides a compound of Formula XIII-a:

XIII-a

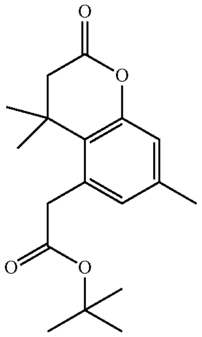

or a co-crystal, solvate, or salt thereof. In some embodiments, the present disclosure provides a compound of Formula XIII-a, or a salt thereof. In some embodiments, the present disclosure provides a compound of Formula XIII-a.

The present disclosure further provides a compound of Formula VI-b:

VI-b

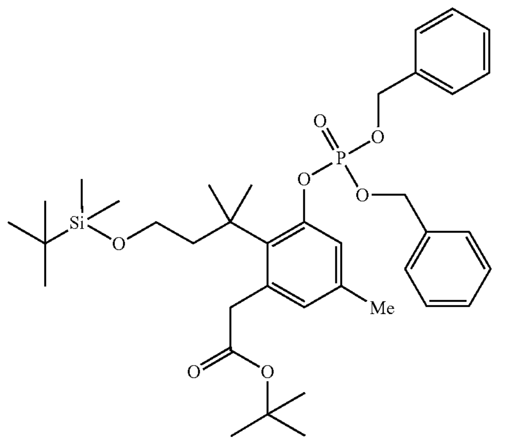

or a co-crystal, solvate, or salt thereof. In some embodiments, the present disclosure provides a compound of Formula VI-b, or a salt thereof. In some embodiments, the present disclosure provides a compound of Formula VI-b.

EXAMPLES

Representative syntheses of compounds of the present disclosure are described in schemes below, and the particular examples that follow. The following examples are merely illustrative, and not intended to limit this disclosure in any way. It is to be understood that individual steps described herein may be combined. It is also to be understood that separate batches of a compound may be combined and carried forth in the next synthetic step.

Example 1. Synthesis of 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetic acid

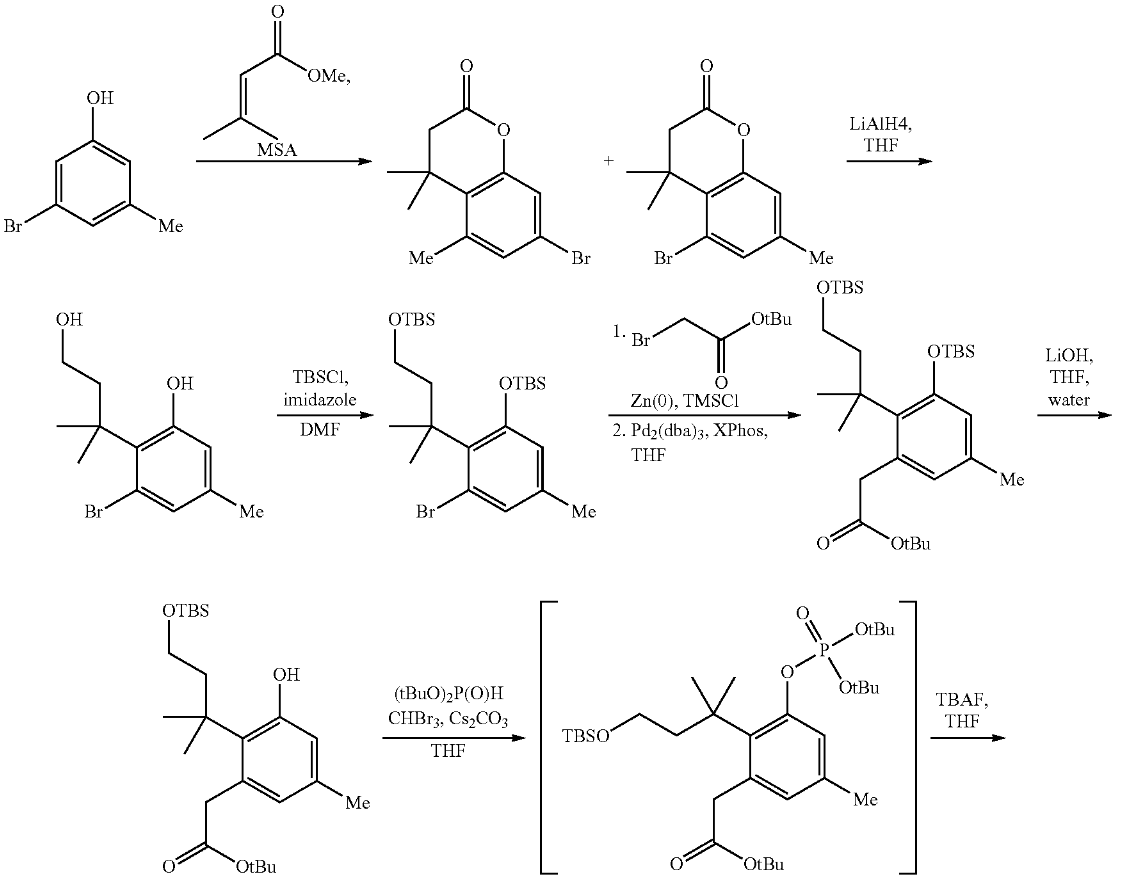

-continued

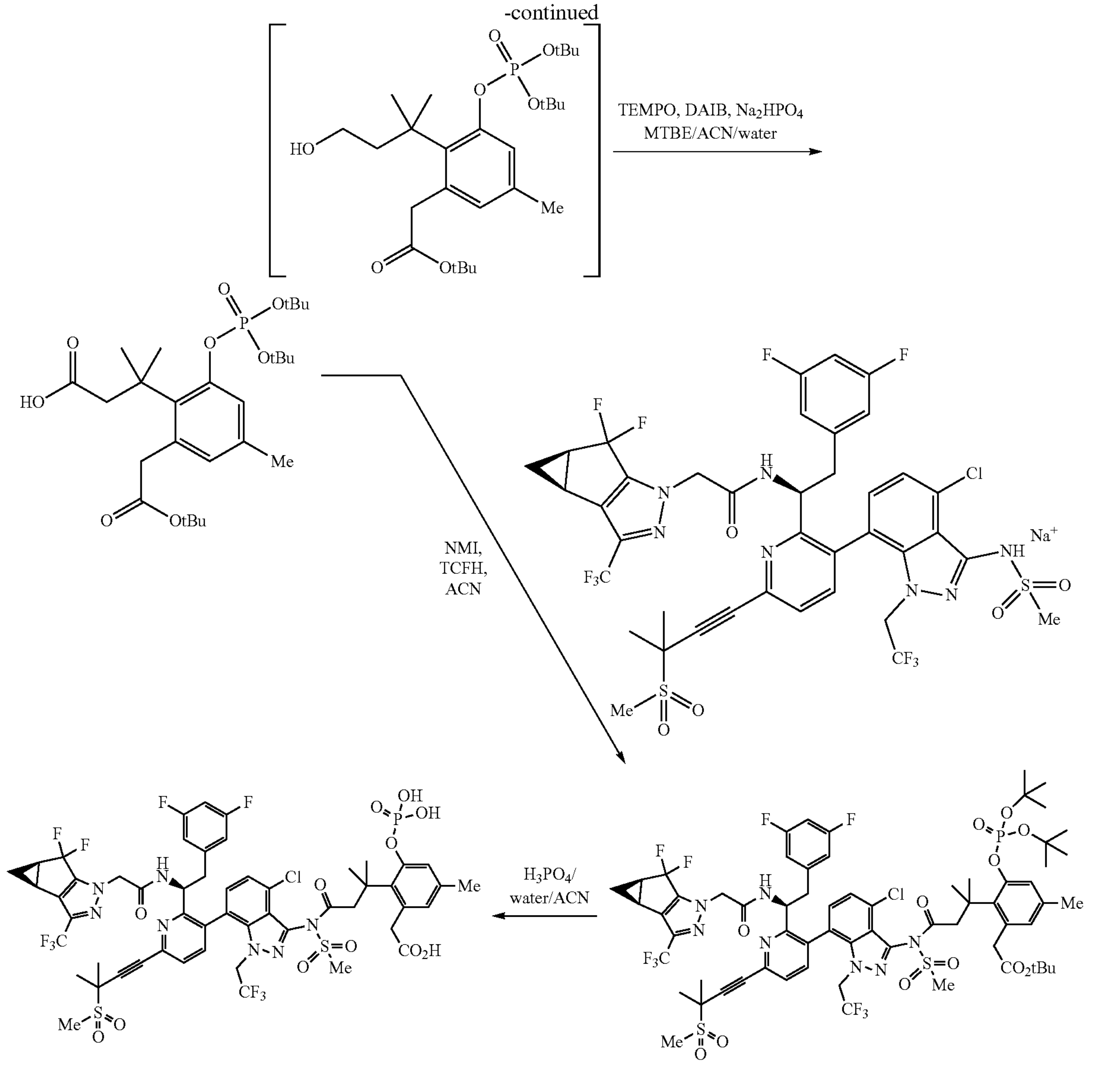

Step 1. Synthesis of 5-bromo-4,4,7-trimethylchroman-2-one

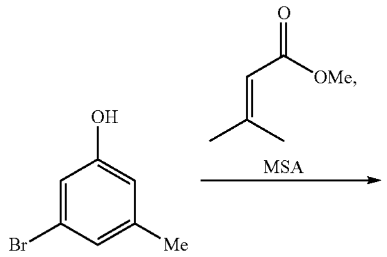

-continued

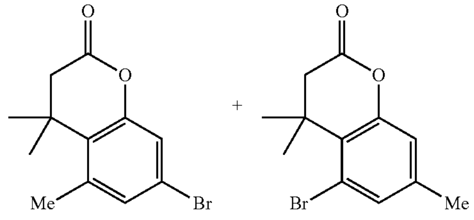

3-Bromo-5-methylphenol (1.00 equiv, scaling factor), methane sulfonic acid (MSA, 2.00 equiv) were charged to a reactor. The mixture was heated to about 110° C. and methyl 3,3-dimethylacrylate (2.00 equiv) was charged portion-wise. The mixture was agitated at about 110° C. until the reaction was deemed complete. The mixture was cooled to about 20° C. then charged to another reactor than contained water (2.7 volumes). The mixture was extracted with ethyl acetate (4.1 volumes) twice and the combined organic layers were washed successively with saturated sodium bicarbonate solution (4.3 volumes) and 10% brine solution (2.3 volumes). The organic layer was dried over sodium sulfate and concentrated to a minimum volume. The crude product was triturated with a mixture of n-heptane (2.0 volumes) and ethyl acetate (0.2 volumes) at about 0° C. for about 1 hour. The slurry was filtered and the filtrate was concentrated to a minimum volume then purified by column chromatography on silica to afford 5-bromo-4,4,7-trimethylchroman-2-one. $^1$H NMR (400 MHz, $CDCl_3$): δ 7.14 (s, 1H), 6.75 (s, 1H), 2.56 (s, 2H), 2.21 (s, 3H), 1.48 (s 6H) ppm.

Step 2. Synthesis of 3-bromo-2-(4-hydroxy-2-methylbutan-2-yl)-5-methylphenol

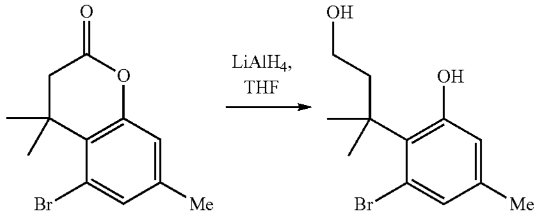

5-bromo-4,4,7-trimethylchroman-2-one (1.00 equiv, scaling factor) and tetrahydrofuran (3.0 volumes) were charged to reactor A. Lithium aluminum hydride solution (2.5 M in tetrahydrofuran, 2.00 equiv) was charged to reactor B. The reactor A contents and reactor B contents were simultaneously pumped through a flow reactor (pre-heated to about 35° C.) at about 82 mL/min and 115 mL/min, respectively. The reaction mixture exiting the flow reactor was quenched in reactor C that contained a pre-cooled hydrochloric acid (1.0 M, 35.0 volumes) at about 0° C. The reaction mixture was extracted with ethyl acetate (10.0 volumes) and the organic layer was washed successively with saturated sodium bicarbonate solution (11.6 volumes) and 10% brine solution (5.8 volumes). The organic layer was dried over sodium sulfate and concentrated to a minimum volume. The crude product was triturated with a mixture of n-heptane (1.8 volumes) and methyl t-butyl ether (0.2 volumes) at about 0° C. for about 5 hours. The slurry was filtered then dried to afford 3-bromo-2-(4-hydroxy-2-methylbutan-2-yl)-5-methylphenol. $^1$H NMR (400 MHz, $CDCl_3$): δ 7.05 (s, 1H), 6.48 (s, 1H), 3.65 (t, J=6.8 Hz, 2H), 2.29 (t, J=6.8 Hz, 2H), 2.19 (s, 3H), 1.68 (s, 6H) ppm.

Step 3. Synthesis of (3-bromo-2-(4-((tert-butyldimethylsilyl)oxy)-2-methylbutan-2-yl)-5-methylphenoxy)(tert-butyl)dimethylsilane

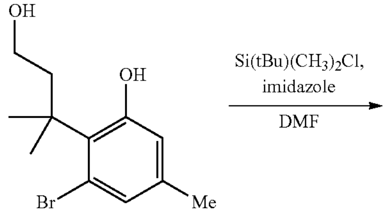

-continued

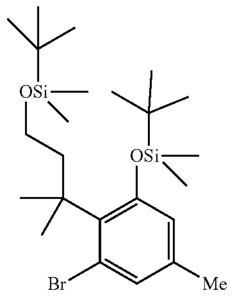

3-bromo-2-(4-hydroxy-2-methylbutan-2-yl)-5-methylphenol (1.00 equiv, scaling factor) and N,N-dimethyl formamide (4.0 volumes) were charged in a reactor, followed by 4-dimethylaminopyridine (DMAP, 0.10 equiv), imidazole (5.00 equiv) and t-butyldimethylsilyl chloride (5.20 equiv). The mixture was agitated at about 60° C. until the reaction was deemed complete. The mixture was quenched with water (7.0 volumes), then extracted with n-heptane (6.0 volumes). The organic layer was washed with 10% brine solution (3 volumes), dried over sodium sulfate then concentrated to afford (3-bromo-2-(4-((tert-butyldimethylsilyl)oxy)-2-methylbutan-2-yl)-5-methylphenoxy)(tert-butyl)dimethylsilane. $^1$H NMR (400 MHz, $CDCl_3$): δ 7.06 (s, 1H), 6.55 (s, 1H), 3.50 (t, J=7.8 Hz, 2H), 2.27 (t, J=7.8 Hz, 2H), 2.19 (s, 3H), 1.62 (s, 6H), 1.02 (s, 9H), 0.86 (s, 9H), 0.31 (s, 6H), −0.01 (s, 6H) ppm.

Step 4. Synthesis of tert-butyl 2-(3-((tert-butyldimethylsilyl)oxy)-2-(4-((tert-butyldimethylsilyl)oxy)-2-methylbutan-2-yl)-5-methylphenyl)acetate

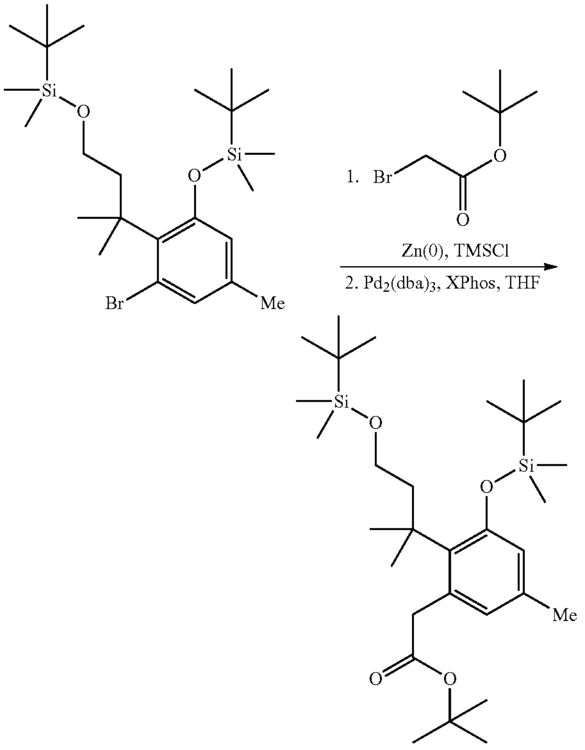

Formation of Reformatsky reagent: Zinc (15.0 equiv), tetrahydrofuran (14.0 volumes) and chlorotrimethylsilane (0.25 equiv) were charged in a reactor. 1,2-Dibromoethane (0.25 equiv) was charged, and the resultant suspension was warmed to about 50° C. for about 2 hours. The reaction mixture was cooled to about 40° C. and t-butyl bromoacetate (5.00 equiv) was charged in portions. The reaction mixture was agitated at about 50° C. for about 0.5 hours, then allowed to settle at about 20° C. for about 3 hours. The supernatant was transferred to another reactor and diluted with a lithium chloride solution in tetrahydrofuran (0.5 M, 12.0 volumes).

Negishi coupling: To the reactor containing the Reformatsky reagent were charged a solution of (3-bromo-2-(4-((tert-butyldimethylsilyl)oxy)-2-methylbutan-2-yl)-5-methylphenoxy)(tert-butyl)dimethylsilane (1.00 equiv, scaling factor) in tetrahydrofuran (7.0 volumes), 2-dicyclohexylphosphino-2',4',6'-triisopropylbiphenyl (XPhos, 0.05 equiv), and tris(dibenzylideneacetone)dipalladium ($Pd_2(dba)_3$, 0.02 equiv). The reaction mixture was agitated at about 50° C. for about 3 hours. The reaction mixture was quenched into a 0.5 M aqueous citric acid solution (20.0 volumes) and extracted with n-heptane (8.0 volumes). The organic layer was washed successively with 10% brine solution (3.0 volumes), saturated sodium bicarbonate solution (5.0 volumes) and 10% brine solution (3.0 volumes). The organic layer was concentrated to a minimum volume then purified by column chromatography on silica to afford tert-butyl 2-(3-((tert-butyldimethylsilyl)oxy)-2-(4-((tert-butyldimethylsilyl)oxy)-2-methylbutan-2-yl)-5-methylphenyl)acetate. $^1H$ NMR (400 MHz, $CDCl_3$): δ 6.55 (s, 1H), 6.49 (s, 1H), 3.77 (s, 2H), 3.46 (t, J=7.2 Hz, 2H), 2.21 (s, 3H), 2.17 (t, J=7.2 Hz, 2H), 1.49 (s, 6H), 1.47 (s, 9H), 1.03 (s, 9H), 0.84 (s, 9H), 0.30 (s, 6H), −0.03 (s, 6H) ppm.

-continued

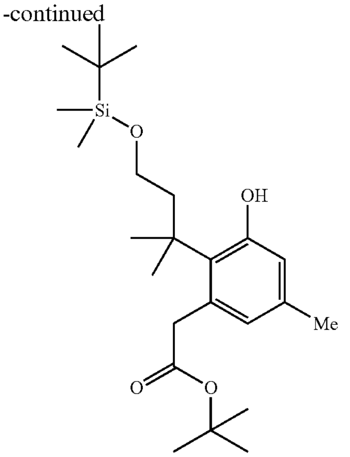

tert-Butyl 2-(3-((tert-butyldimethylsilyl)oxy)-2-(4-((tert-butyldimethylsilyl)oxy)-2-methylbutan-2-yl)-5-methylphenyl)acetate (1.00 equiv, scaling factor) and tetrahydrofuran (6.0 volumes) were charged in a reactor, followed by lithium hydroxide monohydrate (5.00 equiv) and water (6.0 volumes). The mixture was agitated at about 40° C. until the reaction was deemed complete. The reaction mixture was diluted with 0.5 M aqueous citric acid solution (4.8 volumes) and extracted with methyl t-butyl ether (4.1 volumes). The organic layer was washed successively with saturated sodium bicarbonate solution (5.0 volumes) and 10% brine solution (3.0 volumes), then dried over sodium sulfate. The organic layer was concentrated to a minimum volume then triturated with n-heptane. The slurry was filtered and the filter cake was dried under vacuum to afford tert-butyl 2-(2-(4-((tert-butyldimethylsilyl)oxy)-2-methylbutan-2-yl)-3-hydroxy-5-methylphenyl)acetate. $^1H$ NMR (400 MHz, $CDCl_3$): δ 6.48 (s, 1H), 5.85 (s, 1H), 3.75 (s, 2H), 3.58 (t, J=7.2 Hz, 2H), 2.20 (s, 3H), 2.14 (t, J=7.2 Hz, 2H), 1.52 (s, 6H), 1.46 (s, 9H), 0.88 (s, 9H), 0.03 (s, 6H) ppm.

Step 5. Synthesis of tert-butyl 2-(2-(4-((tert-butyldimethylsilyl)oxy)-2-methylbutan-2-yl)-3-hydroxy-5-methylphenyl)acetate

Step 6. Synthesis of tert-butyl 2-(2-(4-((tert-butyldimethylsilyl)oxy)-2-methylbutan-2-yl)-3-((di-tert-butoxyphosphoryl)oxy)-5-methylphenyl)acetate

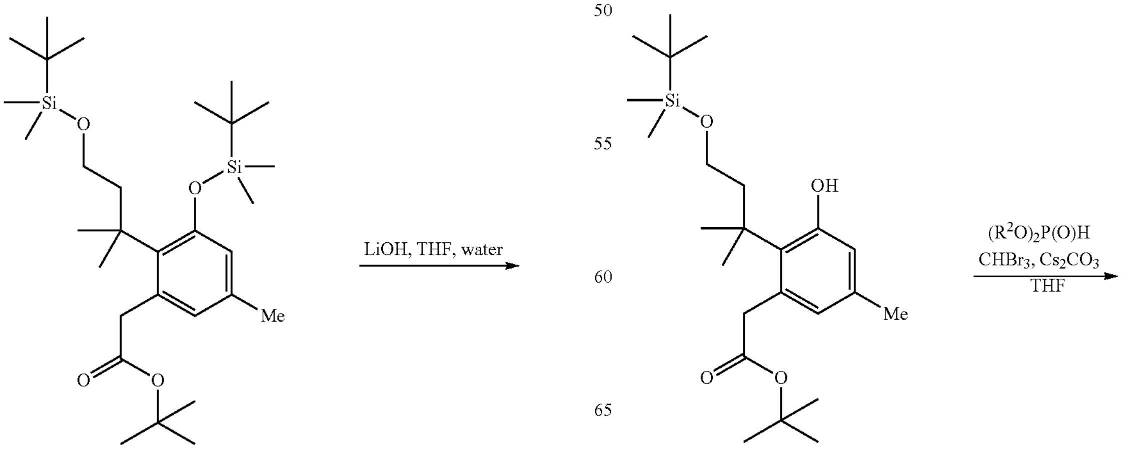

-continued

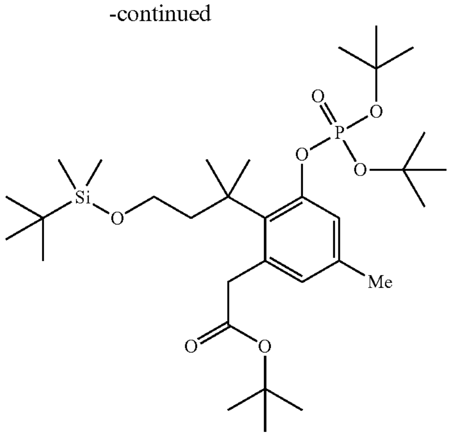

-continued

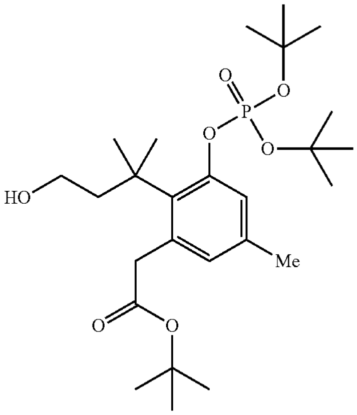

Di-t-butyl phosphite (1.20 equiv) and tetrahydrofuran (2.0 volumes) were charged in a reactor, followed by bromoform (1.22 equiv) at about 15° C. The mixture was agitated at about 15° C. for about 1 hour before charging to another reactor containing tert-butyl 2-(2-(4-((tert-butyldimethylsilyl)oxy)-2-methylbutan-2-yl)-3-hydroxy-5-methylphenyl) acetate (1.00 equiv, scaling factor), cesium carbonate (1.70 eq) and tetrahydrofuran (4.0 volumes) at about 15° C. The mixture was agitated at about 25° C. until the reaction was deemed complete. The reaction mixture was diluted with 5% aqueous potassium phosphate dibasic solution (5.0 volumes) and methyl t-butyl ether (5.0 volumes). The biphasic mixture was agitated at about 25° C. for about 16 hours. The organic layer was separated and washed with 10% brine solution (3.0 volumes), then concentrated to a minimum volume to afford tert-butyl 2-(2-(4-((tert-butyldimethylsilyl) oxy)-2-methylbutan-2-yl)-3-((di-tert-butoxyphosphoryl) oxy)-5-methylphenyl)acetate. $^1$H NMR (400 MHz, $CDCl_3$): δ 7.33 (s, 1H), 6.69 (s, 1H), 3.80 (s, 2H), 3.50 (t, J=7.2 Hz, 2H), 2.24 (s, 3H), 2.09 (t, J=7.2 Hz, 2H), 1.53 (s, 24H), 1.49 (s, 18H), 1.45 (s, 9H), 0.84 (s, 9H), −0.03 (s, 6H) ppm.

Step 7. Synthesis of tert-butyl 2-(3-((di-tert-butoxyphosphoryl)oxy)-2-(4-hydroxy-2-methylbutan-2-yl)-5-methylphenyl)acetate tert-Butyl 2-(2-(4-((tert-butyldimethylsilyl)oxy)-2-methylbutan-2-yl)-3-((di-tert-butoxyphosphoryl)oxy)-5-methylphenyl)acetate (1.00 equiv, scaling factor) and tetrahydrofuran (6.0 volumes) were charged in a reactor, followed by 1 M tetrabutylammonium fluoride solution in tetrahydrofuran (2.00 equiv). The mixture was agitated at about 25° C. until the reaction was deemed complete. The reaction mixture was quenched with water (4.0 volumes) and extracted with methyl t-butyl ether (6.0 volumes). The organic layer was separated and washed successively with 5% potassium phosphate dibasic solution (6.0 volumes), 10% sodium bicarbonate solution (4.0 volumes) and 10% brine solution (4.0 volumes). The organic layer was concentrated to a minimum volume to afford tert-butyl 2-(3-((di-tert-butoxyphosphoryl)oxy)-2-(4-hydroxy-2-methylbutan-2-yl)-5-methylphenyl)acetate. $^1$H NMR (400 MHz, $CDCl_3$): δ 7.33 (s, 1H), 6.70 (s, 1H), 3.83 (s, 2H), 3.52 (t, J=6.8 Hz 2H), 2.24 (s, 3H), 2.17 (t, J=6.8 Hz, 2H), 1.51 (s, 24H), 1.46 (s, 9H) ppm.

Step 8. Synthesis of 3-(2-(2-(tert-butoxy)-2-oxoethyl)-6-((di-tert-butoxyphosphoryl)oxy)-4-methylphenyl)-3-methylbutanoic acid

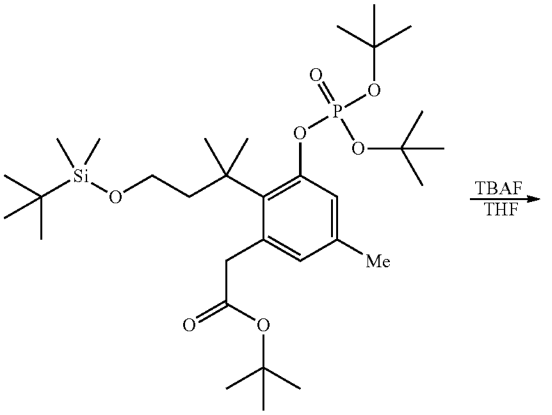

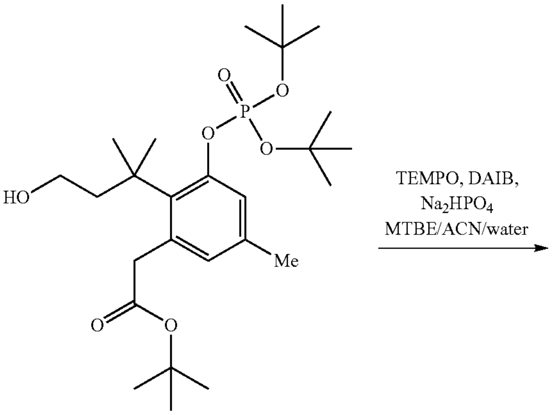

-continued

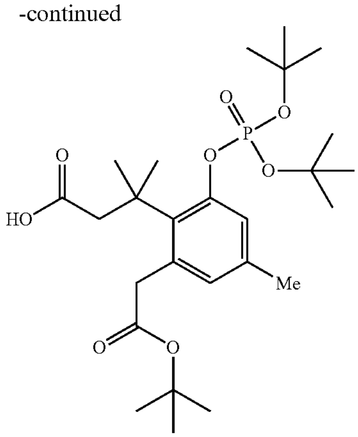

tert-butyl 2-(3-((di-tert-butoxyphosphoryl)oxy)-2-(4-hydroxy-2-methylbutan-2-yl)-5-methylphenyl)acetate (1.00 equiv, scaling factor), acetonitrile (2.7 volumes), methyl t-butyl ether (5.4 volumes) were charged in a reactor, followed by 2,2,6,6-tetramethylpiperidine 1-oxyl (TEMPO, 0.50 equiv), water (8.0 volumes), sodium phosphate dibasic (6.00 equiv) and (diacetoxyiodo)benzene (DAIB, 2.80 equiv). The mixture was agitated at about 25° C. until the reaction was deemed complete. The reaction mixture was diluted with methyl t-butyl ether (6.5 volumes) and the organic layer was separated. The organic layer was washed successively with 10% sodium thiosulfate solution (8.6 volumes) and 10% brine solution (5.4 volumes). The organic layer was concentrated to a minimum volume then crystallized twice in a mixture of dichloromethane (1.1 volumes) and n-heptane (16.2 volumes). The slurry was filtered and the filter cake was washed with n-heptane (0.6 volumes) and then dried to afford 3-(2-(2-(tert-butoxy)-2-oxoethyl)-6-((di-tert-butoxyphosphoryl)oxy)-4-methylphenyl)-3-methylbutanoic acid. $^1H$ NMR (400 MHz, $d_6$-DMSO): δ 11.69 (s, 1H), 7.19 (s, 1H), 6.70 (s, 1H), 3.82 (s, 2H), 2.83 (s, 2H), 2.18 (s, 3H), 1.47 (s, 6H), 1.42 (s, 18H), 1.40 (s, 9H) ppm.

Step 9. Synthesis of tert-butyl 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((di-tert-butoxyphosphoryl)oxy)-5-methylphenyl)acetate

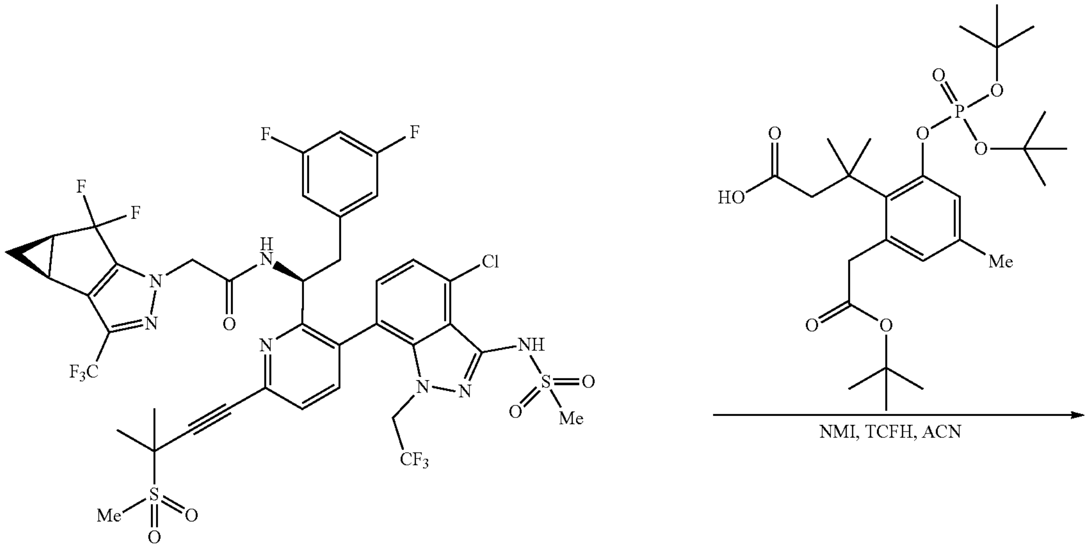

-continued

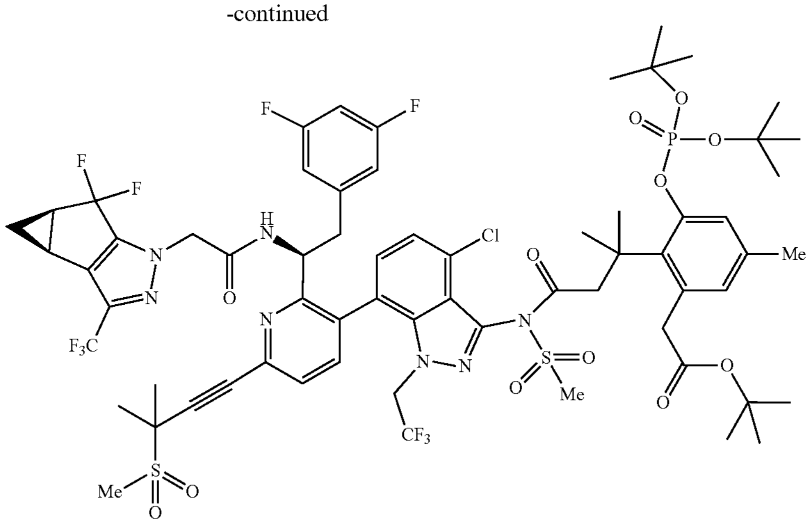

3-(2-(2-(tert-Butoxy)-2-oxoethyl)-6-((di-tert-butoxy-phosphoryl)oxy)-4-methylphenyl)-3-methylbutanoic acid (1.15 equiv), acetonitrile (2.7 volumes), 1-methylimidazole (9.00 equiv) were charged in a reactor, followed by chloro-N,N,N',N'-tetramethylformamidinium hexafluorophosphate (TCFH, 1.40 equiv) at about 10° C. The mixture was agitated at about 10° C. for about 2 hours then GS-6207-02 (1.00 equiv, scaling factor) was charged. The mixture was agitated at about 10° C. until the reaction was deemed complete. The reaction mixture was diluted with methyl t-butyl ether (12.8 volumes) then quenched with an aqueous solution that contained 2% potassium phosphate dibasic and 5% potassium chloride (10 volumes). The biphasic mixture was diluted with cyclohexane (2.6 volumes), then the organic layer was separated. The organic layer was washed with an aqueous solution that contained 2% potassium phosphate dibasic and 5% potassium chloride (10 volumes), then twice with 5% potassium chloride solution (10 volumes). The organic layer was diluted with methyl t-butyl ether (4.0 volumes) then evaporated to about 2.0 volumes. The residue was co-evaporated with methyl t-butyl ether (12.0 volumes) to about 2.0 volumes twice. The residue was diluted with methyl t-butyl ether (3.0 volumes) then charged to n-heptane (14.6 volumes). The slurry was agitated at about 25° C. for about 4 hours then filtered. The filter cake was washed twice with n-heptane (7.3 volumes) and then dried to afford tert-butyl 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((di-tert-butoxyphosphoryl)oxy)-5-methylphenyl)acetate. $^{1}H$ NMR (400 MHz, $d_6$-DMSO, all atropisomers): δ 9.25-8.84 (m, 1H), 8.02-6.41 (m, 9H), 5.04-4.50 (m, 4H), 4.25-2.82 (m, 13H), 2.61-2.42 (m, 2H), 2.18 (s, 3H), 1.75 (s, 6H), 1.53-0.92 (m, 35H) ppm. $^{19}F$ NMR (377 MHz, $d_6$-DMSO, all atropisomers): δ −60.28-−60.43 (m, 3F), −68.84-−69.17 (m, 3F), −79.25-−80.41 (m, 1F), −101.96-−103.31 (m, 1F), −110.05-−110.43 (m, 2F) ppm. $^{31}P$ NMR (162 MHz, $d_6$-DMSO, all atropisomers): −16.88, −17.07, −17.18, −17.56 ppm.

Step 10. Synthesis of 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetic acid

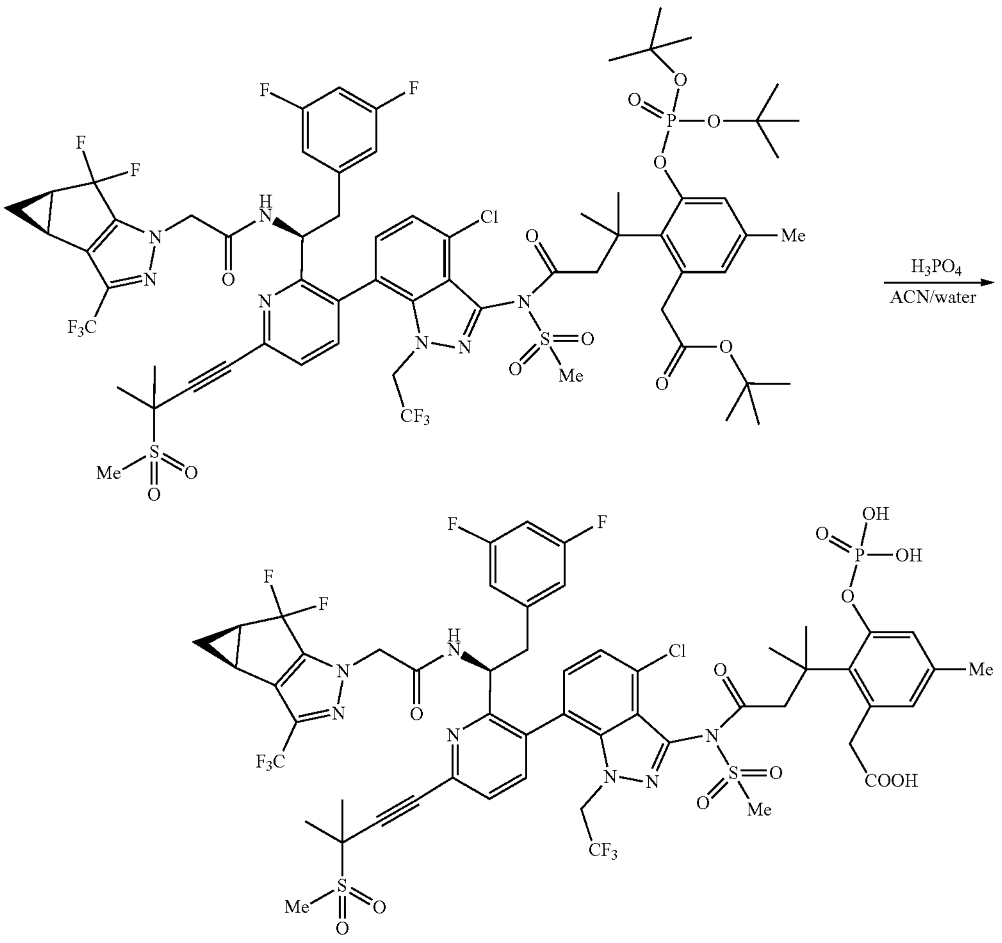

I tert-Butyl 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((di-tert-butoxyphosphoryl)oxy)-5-methylphenyl)acetate (1.00 equiv, scaling factor) and acetonitrile (1.4 volumes) were charged to a reactor and adjusted to about 22° C. Phosphoric acid (85 wt %, 37 equiv) was charged while maintaining the mixture at below 27° C., followed by acetonitrile (0.45 volumes). The mixture was agitated at about 22° C. until the reaction was deemed complete. Acetonitrile (5.3 volumes) was added, then the mixture was washed twice with 14% aq NaCl (5 volumes). Acetonitrile (5.3 volumes) was added, then the mixture was washed twice with 8% aq NaCl (5 volumes). Acetonitrile (2.6 volumes) was added, then the mixture was washed with 8% aq NaCl-4% aq $NaHSO_4$ (5 volumes). The mixture was concentrated under reduced pressure to about 3.0 volumes. The residue was co-evaporated with acetonitrile (8.7 volumes) to about 3.0 volumes twice. Acetonitrile (6.9 volumes) was charged, and the mixture was polish filtered into another reactor. The mixture concentrated under reduced pressure to about 3.0 volumes. Trifluoroacetic acid (0.26 equiv), acetonitrile (1.0 volume) and seeds of the compound of Formula I (0.0017 equiv) were charged, and the mixture was agitated for about 16 hours. Di-n-butyl ether (8.0 volumes) was charged over about 4 hours at about 22° C., and the resulting slurry was agitated for about 24 hours. The slurry was filtered, the filter cake rinsed with 23% solution of acetonitrile in diisopropyl ether (3.3 volumes), and then dried to afford 2-(2-(4-(N-(4-chloro-7-(2-((S)-1-(2-((3bS,4aR)-5,5-difluoro-3-(trifluoromethyl)-3b,4,4a,5-tetrahydro- 1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetic acid. $^{1}H$ NMR (400 MHz, $d_6$-DMSO, major atropisomers): δ 9.18 (d, 1H, J 8.2 Hz), 9.16 (m, 1H), 7.87 (d, 1H, J=8.0 Hz), 7.83 (d, 1H, J=8.1 Hz), 7.77 (d, 1H, J=8.3 Hz), 7.75 (m, 1H), 7.44 (d, 1H, J=7.7 Hz), 7.36 (d, 1H, J=7.7 Hz), 7.15 (s, 1H), 7.02 (m, 1H), 7.01 (m, 1H), 6.66 (s, 1H), 6.63 (s, 1H), 6.61 (m, 1H), 6.48 (m, 2H), 4.93 (d, 1H, J=16.4 Hz), 4.85 (d, 1H, J=16.5 Hz), 4.77 (m, 1H), 4.76 (d, 1H, J=16.7 Hz), 4.71 (m, 1H), 4.68 (m, 1H), 4.66 (d, 1H, J=16.4 Hz), 4.63 (m, 1H), 4.24 (dq, 1H, J=16.3, 8.2 Hz), 4.01 (dq, 1H, J=16.4, 8.1 Hz), 3.87 (d, 1H, J=17.7 Hz), 3.86 (d, 1H, J=17.5 Hz), 3.72 (d, 1H, J=17.8 Hz), 3.59 (d, 1H, J=17.7 Hz), 3.48 (s, 3H), 3.46 (s, 3H), 3.44 (br m, 1H), 3.27 (s, 3H), 3.27 (s, 3H), 3.22 (br m, 1H), 3.06 (dd, 1H, J=13.5, 7.2 Hz), 2.99 (m, 1H), 2.57 (m, 1H), 2.53 (m, 1H), 2.53 (m, 1H), 2.18 (s, 3H), 1.75 (s, 3H), 1.75 (s, 3H), 1.75 (s, 3H), 1.75 (s, 3H), 1.45 (s, 3H), 1.38 (m, 1H), 1.34 (s, 3H), 1.30 (s, 3H), 1.18 (s, 3H), 1.02 (m, 1H), 0.97 (m, 1H). $^{13}C$ NMR (101 MHz, $d_6$-DMSO, major atropisomers): δ 173.7, 173.6, 171.8, 171.6, 164.6, 164.4, 162.1, 158.8, 158.5, 150.7, 142.8, 142.7, 142.4, 142.1, 141.9, 141.7, 140.0, 139.6, 139.3, 137.6, 134.9, 134.6, 134.5, 134.5, 134.0, 133.7, 132.5, 132.2, 132.2, 132.0, 131.8, 131.3, 130.5, 130.3, 129.9, 129.8, 126.9, 126.7, 125.6, 125.5, 123.1, 122.8, 122.8, 120.7, 120.7, 120.0, 119.9, 119.7, 119.6, 119.4, 119.2, 118.8, 118.7, 112.1, 102.2, 88.5, 88.3, 84.5, 57.3, 57.3, 53.2, 53.0, 53.0, 52.7, 52.7, 52.1, 50.8, 50.8, 50.4, 50.4, 47.3, 42.2, 42.2, 42.0, 42.0, 41.6, 41.5, 39.7, 39.2, 35.1, 35.1, 30.6, 30.3, 30.3, 30.2, 27.6, 23.2, 22.4, 22.4, 22.3, 22.3, 20.0, 11.7, 11.6. $^{19}F$ NMR (376 MHz, $d_6$-DMSO, major atropisomers): δ −60.32 (s, 3F), −60.38 (s, 3F), −68.98 (t, 3F, J=8.2 Hz), −69.22 (t, 3F, J=8.3 Hz), −79.59 (dd, 1F, J 253.6, 12.7 Hz), −80.00 (m, 1F), −101.82 (m, 1F), −103.03 (dd, 1F, J=253.6, 9.6 Hz), −109.96 (m, 2F), −110.06 (m, 2F). $^{31}P$ NMR (162 MHz, $d_6$-DMSO, major atropisomers): δ −7.10 (s, 1P), −7.14 (s, 1P). IR (ATR): 2931, 1735, 1624-1477, 1448, 1381-1315, 1259-1107, 1057-1032 $cm^{-1}$. HRMS (ESI) $[M+Na]^+$ calcd for $C_{53}H_{49}ClF_{10}N_7NaO_{12}PS_2^+$: 1318.20393, found: 1318.20239.

Example 2. Synthesis of tert-Butyl 2-(3-((bis(benzyloxy)phosphoryl)oxy)-2-(4-((tert-butyldimethylsilyl)oxy)-2-methylbutan-2-yl)-5-methylphenyl)acetate

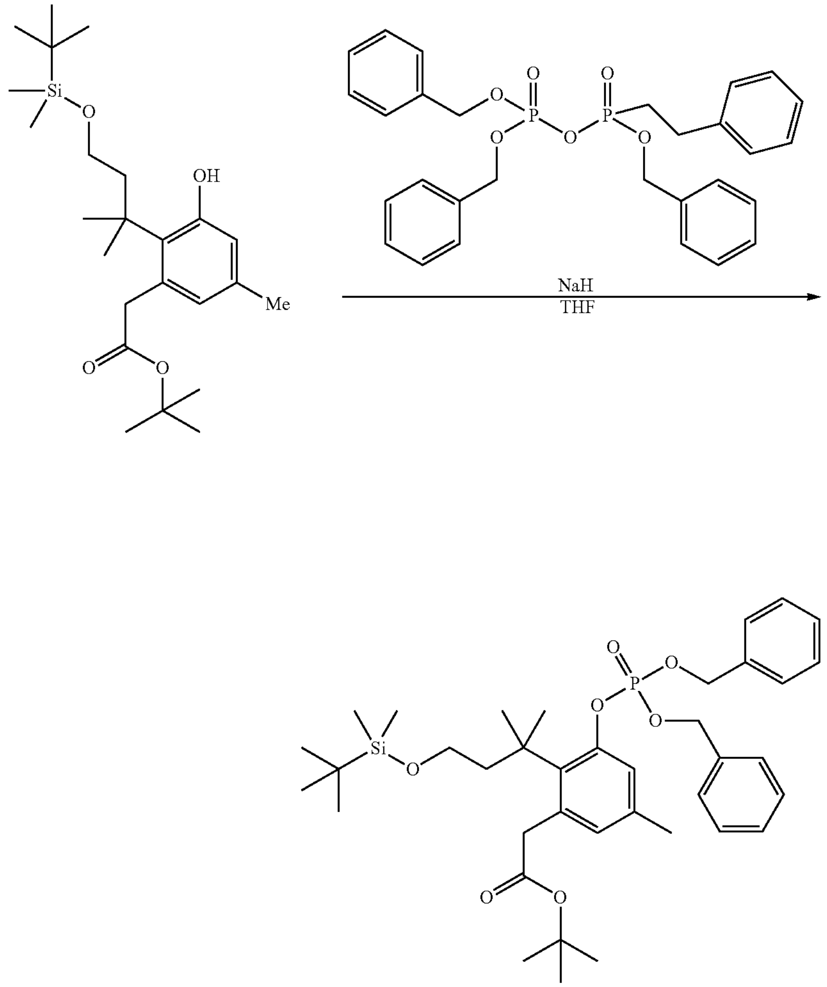

tert-butyl 2-(2-(4-((tert-butyldimethylsilyl)oxy)-2-methylbutan-2-yl)-3-hydroxy-5-methylphenyl)acetate (1.00 equiv, scaling factor) was dissolved in tetrahydrofuran (10 volumes). Sodium hydride (3.40 equiv) and tetrabenzyl pyrophosphate (1.52 equiv) were charged at about 0° C. The mixture was agitated at about 25° C. until the reaction was deemed complete. The reaction mixture was diluted with water and methyl t-butyl ether (17 volumes). The biphasic mixture was agitated at about 25° C. until the residual tetrabenzyl pyrophosphate was fully consumed. The organic layer was separated and washed twice with water (17 volumes), then concentrated to a minimum volume to afford the desired phosphate product. MS (ESI) after TBS removal: $[M+H]^+$ calcd for $C_{32}H_{42}O_7P^+$: 569.27, found: 569.11.

Example 3. Alternative Synthesis of tert-butyl 2-(2-(4-((tert-butyldimethylsilyl)oxy)-2-methylbutan-2-yl)-3-((di-tert-butoxyphosphoryl)oxy)-5-methylphenyl)acetate

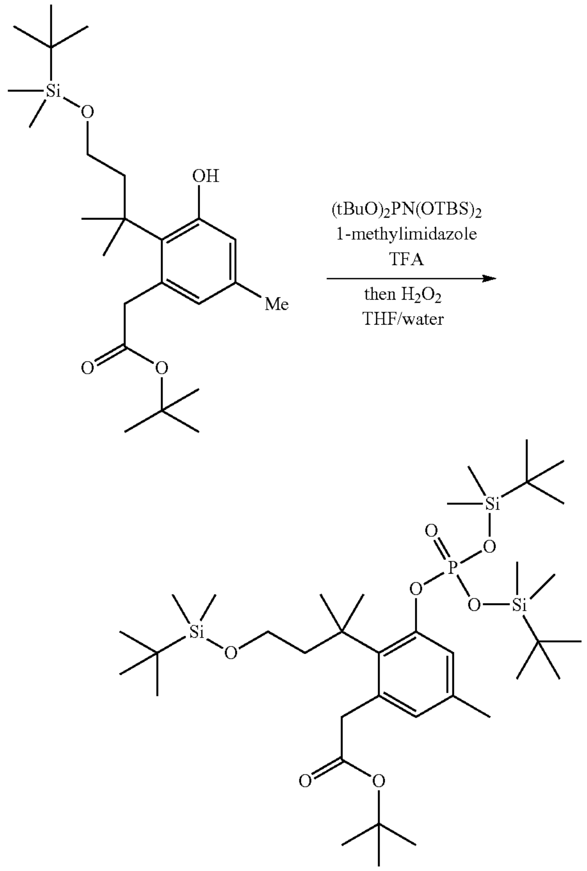

tert-Butyl 2-(2-(4-((tert-butyldimethylsilyl)oxy)-2-methylbutan-2-yl)-3-hydroxy-5-methylphenyl)acetate (1.00 equiv, scaling factor) and tetrahydrofuran (23.0 volumes) were charged in a reactor followed by 1-methylimidazole (3.50 equiv) and trifluoroacetic acid (2.00 equiv) and di-t-butyl N,N-diisopropylphosphoramidate (2.00 equiv). The reaction was agitated until the reaction was deemed complete. The reaction mixture was cooled to about 0° C. and 35% aqueous hydrogen peroxide (2.80 equiv) was charged. The reaction mixture was agitated for about 3 hours, then quenched with sodium sulfite (2.00 equiv). The reaction mixture was filtered and the filter cake was rinsed with tetrahydrofuran (11.0 volumes). The combined filtrate and rinse were diluted with n-heptane (44.0 volumes) and passed through a silica gel pad. The filtrate was then evaporated to a minimum volume to afford tert-butyl 2-(2-(4-((tert-butyldimethylsilyl)oxy)-2-methylbutan-2-yl)-3-((di-tert-butoxyphosphoryl)oxy)-5-methylphenyl)acetate. $^1H$ NMR (400 MHz, $CDCl_3$): δ 7.33 (s, 1H), 6.69 (s, 1H), 3.80 (s, 2H), 3.50 (t, J=7.2 Hz, 2H), 2.24 (s, 3H), 2.09 (t, J=7.2 Hz, 2H), 1.53 (s, 24H), 1.49 (s, 18H), 1.45 (s, 9H), 0.84 (s, 9H), −0.03 (s, 6H) ppm.

Example 4. Alternative Synthesis of 3-(2-(2-(tert-butoxy)-2-oxoethyl)-6-((di-tert-butoxyphosphoryl)oxy)-4-methylphenyl)-3-methylbutanoic acid

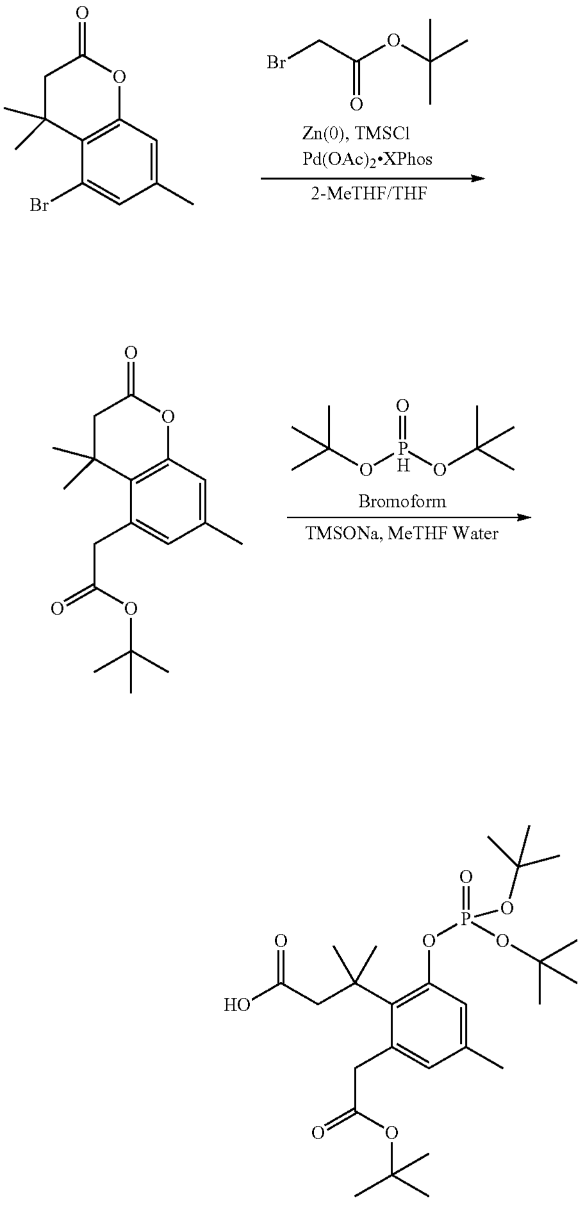

Step 1. Synthesis of tert-butyl 2-(4,4,7-trimethyl-2-oxochroman-5-yl)acetate

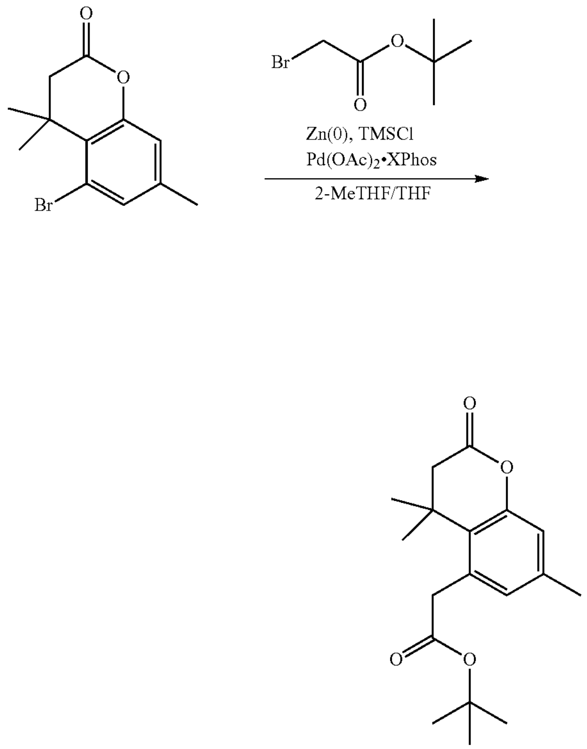

Formation of Reformatsky reagent: Zinc (3 equiv), and lithium chloride in tetrahydrofuran solution (0.5 M, 5 volumes) were charged to a reactor and warmed to about 35° C. To the reactor was charged tert-butyl bromoacetate (0.09 equiv) and diisobutylaluminium hydride (0.07 equiv). The reactor was then warmed to about 40° C. and tert-butyl bromoacetate (2 equiv) was charged in portions and agitated for about 1.5 hours then cooled to about 22° C. and was used for the Negishi coupling.

Negishi coupling: To a separate reactor was charged palladium (II) acetate (0.015 equiv), 2-Dicyclohexylphosphino-2',4',6'-triisopropylbiphenyl (XPhos, 0.015 equiv), GS-1178687 (1.00 equiv, scaling factor), 2-methyltetrahydrofuran (10 volumes), and the Reformatsky reagent solution (1.3 equiv). The reaction mixture was agitated at about 55° C. for about 1 h then cooled to about 22° C. and quenched with acetic acid (1.1 equiv). The organic layer was washed successively with 10% NAC solution (10 volumes), 20% ammonium chloride solution (10 volumes), and 10% brine solution (10 volumes). The organic layer was then concentrated to about 3 volumes then 2-propanol (10 volumes) was charged. The resulting solution was filtered, concentrated to about 3 volumes, then 2-propanol (3 volumes) was charged followed by water (3 volumes). The resulting slurry was cooled to about 0° C. then filtered. The filter cake was washed with a solution of 2-propanol (1.6 volumes) and water (3 volumes) then dried to afford tert-butyl 2-(4,4,7-trimethyl-2-oxochroman-5-yl)acetate. $^1$H NMR (400 MHz, $CDCl_3$): δ 6.81 (s, 1H), δ 6.79 (s, 1H), δ 3.70 (s, 2H), δ 2.57 (s, 2H), δ 2.29 (s, 3H), δ 1.47 (s, 9H), δ 1.41 (s, 6H).

Step 2. Synthesis of 3-(2-(2-(tert-butoxy)-2-oxoethyl)-6-((di-tert-butoxyphosphoryl)oxy)-4-methylphenyl)-3-methylbutanoic acid

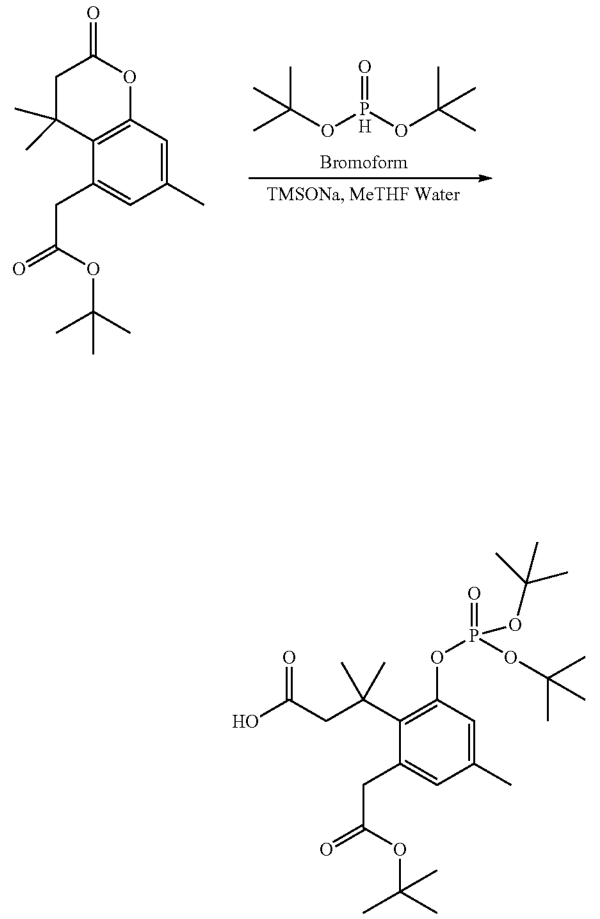

tert-Butyl 2-(4,4,7-trimethyl-2-oxochroman-5-yl)acetate (1.00 equiv, scaling factor), sodium trimethylsilanolate (4 equiv) 2-methyltetrahydrofuran (20 volumes), and water (0.08 volumes) were charged in a reactor, followed by bromoform (2 equiv) and di-tert-butyl phosphite (2 equiv). The mixture was agitated at about 22° C. until the reaction was deemed complete. The reaction mixture was washed with 10% potassium dihydrogen phosphate (10 volumes) and 10% brine solution (10 volumes). The organic layer was concentrated to about 5 volumes then n-heptane (10 volumes) was charged. The resulting slurry was cooled to about 0° C. then filtered. The filter cake was washed with a solution of n-heptane (1.5 volumes) and 2-methyltetrahydrofuran (1.5 volumes) then dried to afford 3-(2-(2-(tert-butoxy)-2-oxoethyl)-6-((di-tert-butoxyphosphoryl)oxy)-4-methylphenyl)-3-methylbutanoic acid. $^1$H NMR (400 MHz, $d_6$-DMSO): δ 11.74 (s, 1H), 7.23 (s, 1H), 6.74 (s, 1H), 3.86 (s, 2H), 2.87 (s, 2H), 2.22 (s, 3H), 1.51 (s, 6H), 1.46 (s, 18H), 1.44 (s, 9H) ppm.

Example 5. Alternative Synthesis of 2-(2-(4-(N-(4-Chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetic acid
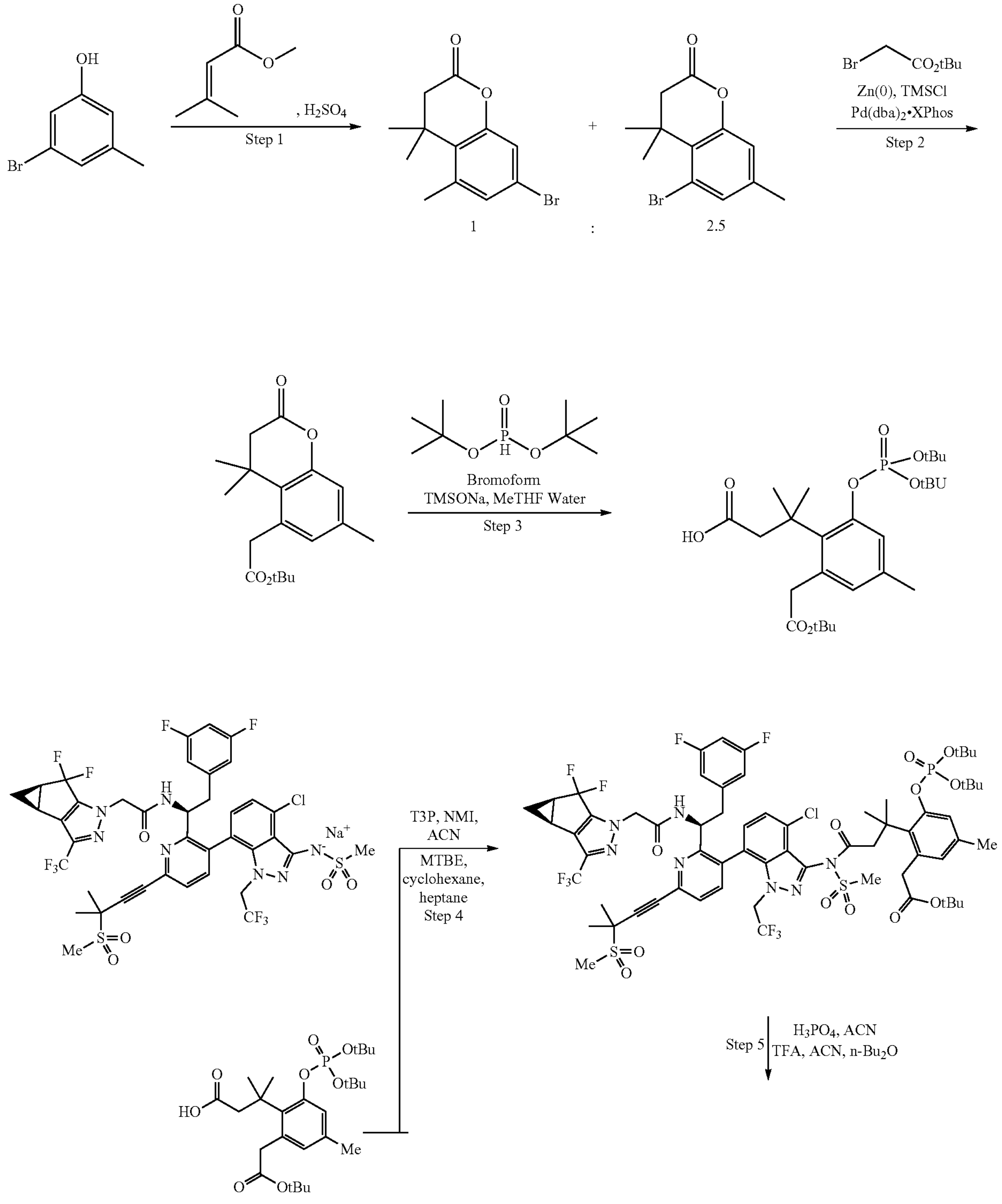

-continued

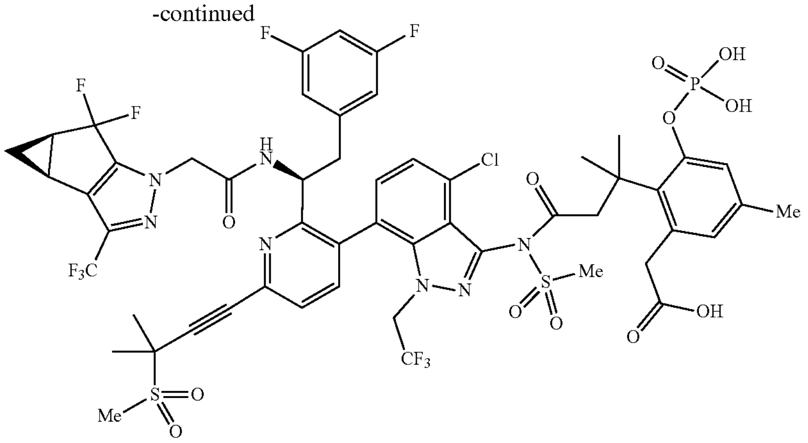

Step 1. Synthesis of 5-bromo-4,4,7-trimethylchroman-2-one

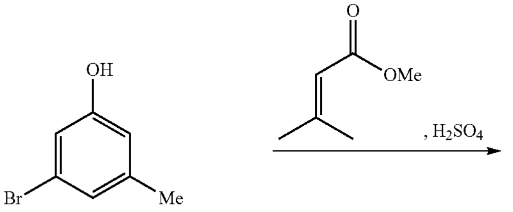

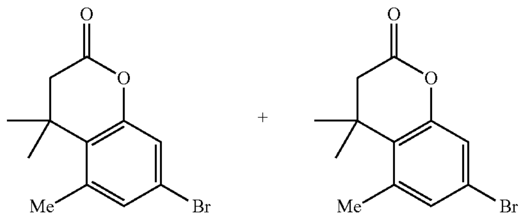

1 : 2 (desired)

3-Bromo-5-methylphenol (1.00 equiv, scaling factor) and 3,3-dimethylacrylate (1.70 equiv) were charged to a reactor. The mixture was agitated and adjusted to about 10° C. Sulfuric acid (2.00 equiv.) was charged, while maintaining the mixture temperature below 35° C. The reaction mixture was heated to 90° C. and agitated until the reaction was complete. The mixture was cooled to 0-10° C., dichloromethane (2 volumes) was charged, and the mixture was agitated for about 10 min to homogenize. Water (3 volumes) was charged to another reactor, agitated, and cooled to about 10° C. The solution was transferred to the pre-cooled water and rinsed with additional dichloromethane (2 volumes). The mixture was adjusted to about 22° C. for not less than 30 minutes, and the layers were separated after settling. The organic layer was washed with an aqueous solution of 1.9 wt % sodium hydroxide and 5 wt % sodium chloride (5.4 volumes) and 10% brine (5.0 volumes). If required, a charcoal treatment was performed to remove dark color of the mixture by mixing with charcoal powder (0.03 parts) at 20-30° C. for about 45 minutes, followed by filtration through a celite pad to remove charcoal. The organic solution was concentrated to about 2 volumes under vacuum with the reactor jacket at not more than 50° C. 2-Propanol (8 volumes) was added, and the mixture was adjusted to about 65° C. and agitated for not less than 1 hour. The resultant slurry was cooled to 0-5° C. over not less than 5 hours. The slurry was filtered, and the wet cake was rinsed with n-heptane twice (3 volumes for each rinse). The filtrate was concentrated to about 3 volumes under vacuum with a jacket temperature of not more than 50° C. Water (1 volume) was charged and the mixture was adjusted to about 22° C. and agitated for not less than 1 hour. Water (2 volumes) was charged over not less than 1 hour. The slurry was cooled to about 0° C. over about 4 hours and agitated for about 5 hours. Filtration of the slurry, rinsing the wet cake with a mixture of water (1 volume) and 2-propanol (2 volumes), and drying of the wet cake afforded 5-bromo-4,4,7-trimethylchroman-2-one. $^1H$ NMR (400 MHz, $CDCl_3$): δ 7.14 (s, 1H), 6.75 (s, 1H), 2.56 (s, 2H), 2.21 (s, 3H), 1.48 (s 6H) ppm.

Step 2: Synthesis of tert-butyl 2-(4,4,7-trimethyl-2-oxochroman-5-yl)acetate

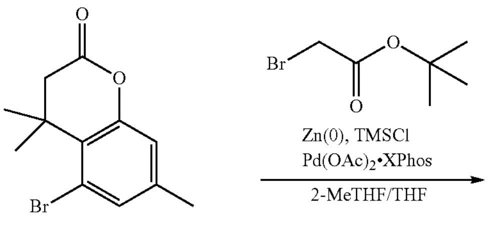

-continued

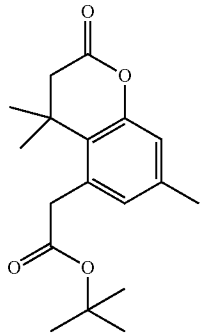

Tetrahydrofuran (15 volumes) and zinc granules (20-30 mesh) (4.50 equiv.) were charged to a reactor under nitrogen. The reactor was degassed for three cycles by putting the reactor under vacuum and back filling with nitrogen for each cycle. The mixture was agitated and adjusted to 35-45° C. TMSCl (0.20 equiv.) was charged, followed by addition of tert-butyl bromoacetate (1.5 equiv.) while keeping the reactor at constant temperature at not more than 50° C. The mixture was adjusted to 40° C. and agitated until reaction was complete. The mixture was adjusted to about 22° C. 5-Bromo-4,4,7-trimethylchroman-2-one (1.0 equiv., scaling factor) and $Pd(dba)_2$ (0.02 equiv.) and Xphos (0.02 equiv.) were charged, and the reaction mixture was degassed for three cycles by putting the reactor under vacuum and back filling with nitrogen for each cycle. The mixture was adjusted to about 40° C. and agitated. Upon reaction completion, the mixture was adjusted to about 22° C., transferred to another reactor via a filter, and rinsed with 2-MeTHF (6 volumes). Acetic acid (1.10 equiv.) was charged, followed by an aqueous solution of 10 wt % N-acetyl-L-cysteine (10 volumes). The mixture was heated to about 50° C., agitated for about 14 hours, and then cooled to about 22° C. The agitation was stopped, and the aqueous layer was removed after phase separation. The organic layer was washed with an aqueous solution of 33.3 wt % $NH_4Cl$ (6 volumes) and 10% brine (10 volumes) sequentially. The organic layer was concentrated to about 3 volumes under vacuum with a jacket temperature of not more than 50° C. 2-Propanol (2 volumes) was charged, and the mixture was again concentrated to 3 volumes. The mixture was adjusted to about 22° C. and diluted with 2-propanol (2.5 volumes). Water (2.5 volumes) was charged over not less than 1.5 hours, and the mixture was adjusted to about 0° C. over about 1 hour and agitated for about 2 hours. The slurry was filtered, and the wet cake was rinsed with a mixture of water (3.0 volumes) and 2-propanol (1.6 volumes). Drying of the wet cake under vacuum at 50° C. afforded tert-butyl 2-(4,4,7-trimethyl-2-oxochroman-5-yl)acetate. $^1H$ NMR (400 MHz, $CDCl_3$): δ 6.81 (s, 1H), δ 6.79 (s, 1H), δ 3.70 (s, 2H), δ 2.57 (s, 2H), δ 2.29 (s, 3H), δ 1.47 (s, 9H), δ 1.41 (s, 6H).

Step 3. Synthesis of 3-(2-(2-(tert-butoxy)-2-oxoethyl)-6-((di-tert-butoxyphosphoryl)oxy)-4-methylphenyl)-3-methylbutanoic acid

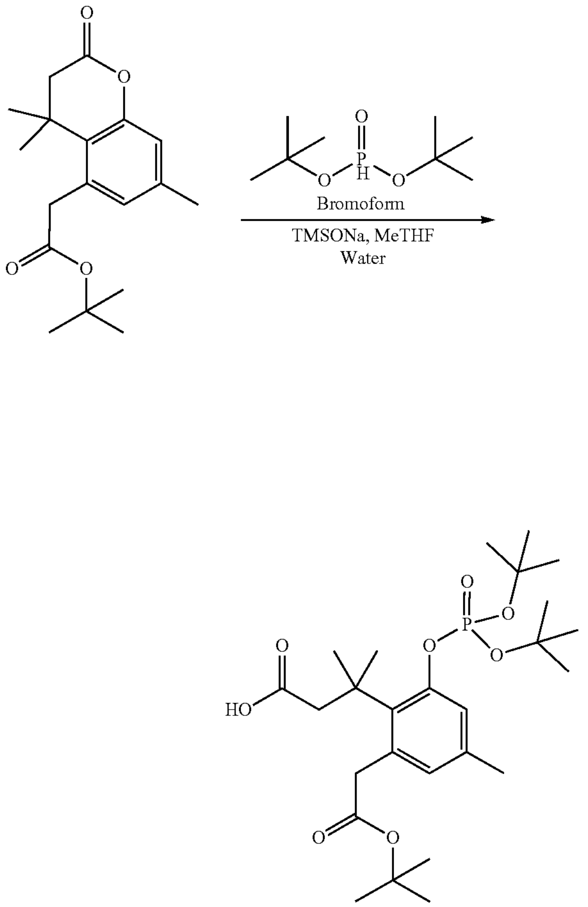

tert-Butyl 2-(4,4,7-trimethyl-2-oxochroman-5-yl)acetate (1.00 equiv, scaling factor), sodium trimethylsilanolate (4 equiv), 2-methyltetrahydrofuran (20 volumes), and water (0.08 volumes) were charged in a reactor, followed by bromoform (2 equiv) and di-tert-butyl phosphite (2 equiv). The mixture was agitated at about 22° C. until the reaction was deemed complete. The reaction mixture was washed with 10% potassium dihydrogen phosphate (10 volumes) and 10% brine solution (10 volumes). The organic layer was concentrated to about 5 volumes then n-heptane (10 volumes) was charged. The resulting slurry was cooled to about 0° C. then filtered. The filter cake was washed with a solution of n-heptane (1.5 volumes) and 2-methyltetrahydrofuran (1.5 volumes) then dried to afford 3-(2-(2-(tert-butoxy)-2-oxoethyl)-6-((di-tert-butoxyphosphoryl)oxy)-4-methylphenyl)-3-methylbutanoic acid. $^1H$ NMR (400 MHz, $d_6$-DMSO): δ 11.74 (s, 1H), 7.23 (s, 1H), 6.74 (s, 1H), 3.86 (s, 2H), 2.87 (s, 2H), 2.22 (s, 3H), 1.51 (s, 6H), 1.46 (s, 18H), 1.44 (s, 9H) ppm.

Step 4: Synthesis of tert-butyl 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((di-tert-butoxyphosphoryl)oxy)-5-methylphenyl) acetate

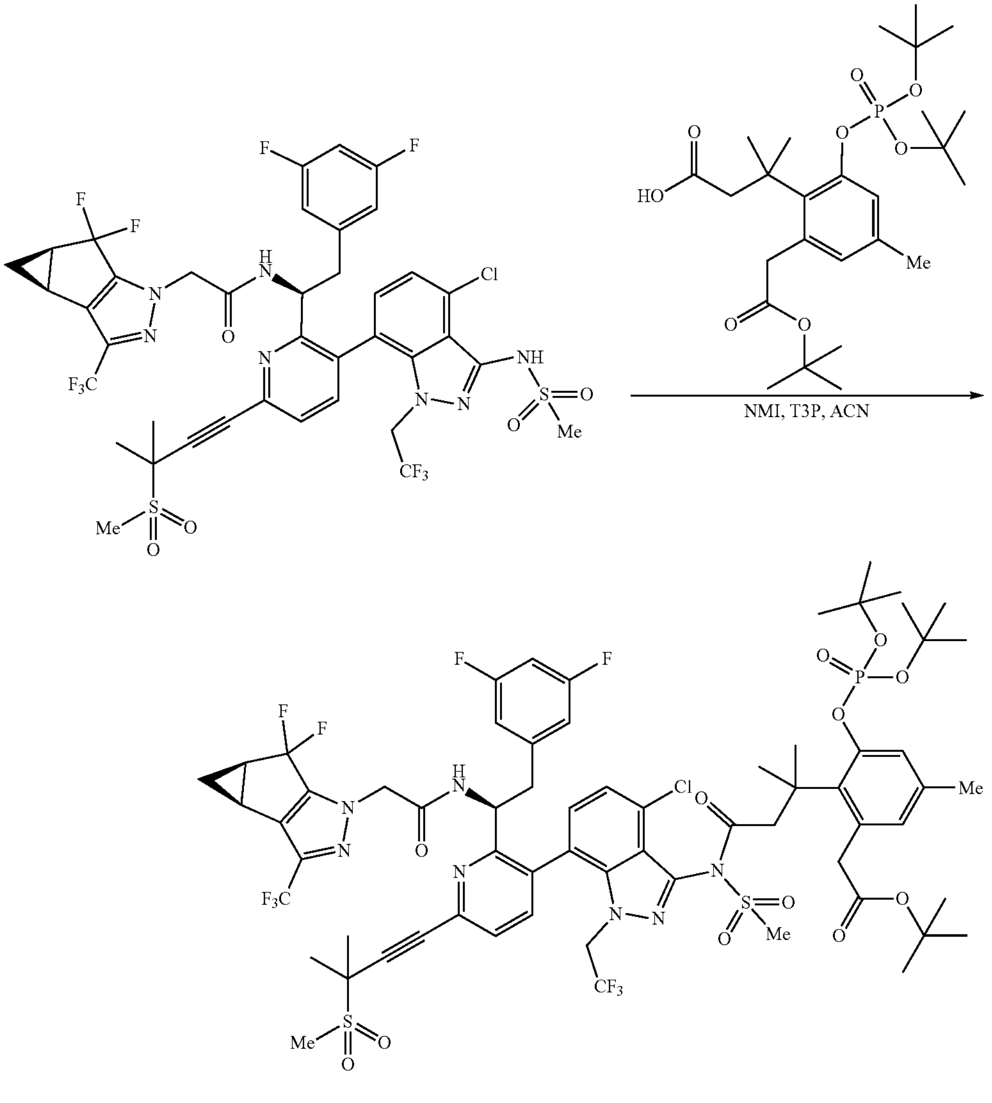

3-(2-(2-(tert-Butoxy)-2-oxoethyl)-6-((di-tert-butoxyphosphoryl)oxy)-4-methylphenyl)-3-methylbutanoic acid (1.10 equiv), acetonitrile (5.3 volumes), 1-methylimidazole (7.00 equiv), propanephosphonic acid anhydride (T3P) 50 wt % in acetonitrile (T3P, 2.00 equiv) were charged to a reactor at 10° C., followed by GS-6207-02 (i.e., lenacapavir sodium, 1.00 equiv, scaling factor). The mixture was agitated at about 10° C. until the reaction was deemed complete. The reaction mixture was diluted with methyl t-butyl ether (12.8 volumes) then quenched with 5% aqueous potassium chloride solution (10 volumes). The biphasic mixture was diluted with cyclohexane (2.6 volumes), then the organic layer was separated. The organic layer was washed with 5% aqueous potassium chloride solution for additional 3 times (10.0 volumes each time). The organic layer was evaporated to about 2.5 volumes. The residue was co-evaporated with methyl t-butyl ether (12.2 volumes) to about 3.0 volumes twice. The residue was diluted with methyl t-butyl ether (4.1 volumes) then charged to n-heptane (14.6 volumes). The slurry was agitated at about 22° C. for about 4 hours then filtered. The filter cake was washed with n-heptane (7.3 volumes) and then dried to afford tert-butyl 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((di-tert-butoxyphosphoryl)oxy)-5-methylphenyl) acetate. $^{1}H$ NMR (400 MHz, $d_6$-DMSO, all atropisomers): δ 9.25-8.84 (m, 1H), 8.02-6.41 (m, 9H), 5.04-4.50 (m, 4H), 4.25-2.82 (m, 13H), 2.61-2.42 (m, 2H), 2.18 (s, 3H), 1.75 (s, 6H), 1.53-0.92 (m, 35H) ppm. $^{19}F$ NMR (377 MHz, $d_6$-DMSO, all atropisomers): δ −60.28--60.43 (m, 3F), −68.84--69.17 (m, 3F), −79.25--80.41 (m, 1F), −101.96--103.31 (m, 1F), −110.05--110.43 (m, 2F) ppm. $^{31}P$ NMR (162 MHz, $d_6$-DMSO, all atropisomers): −16.88, −17.07, −17.18, −17.56 ppm.

Step 5. Synthesis of 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy phenyl)acetic acid

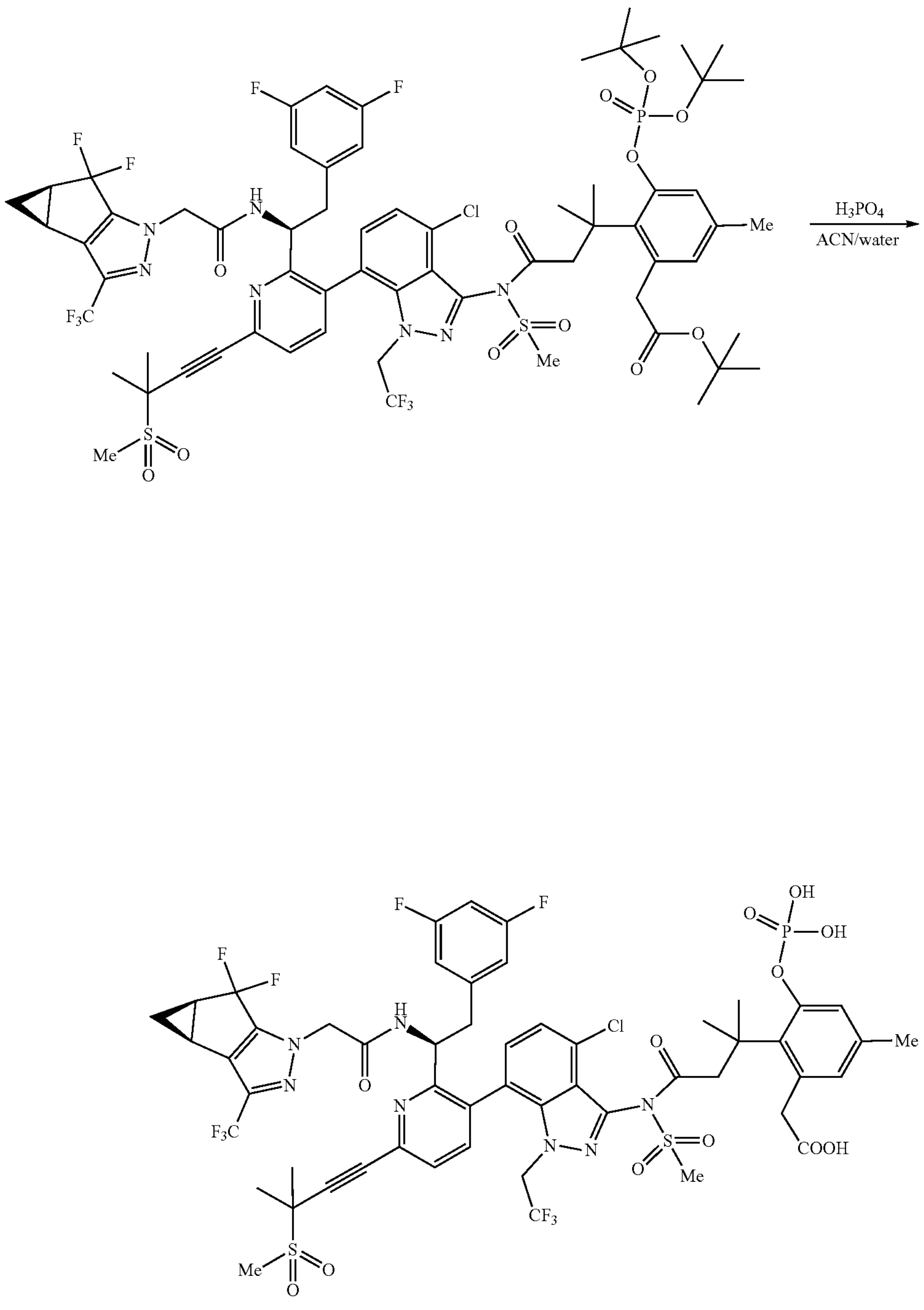

tert-Butyl 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((di-tert-butoxyphosphoryl)oxy)-5-methylphenyl)acetate (1.00 equiv, scaling factor) and acetonitrile (1.4 volumes) were charged to a reactor and adjusted to about 10° C. Phosphoric acid (85 wt %, 37 equiv) was charged while maintaining the mixture over about 30 min, followed by acetonitrile (0.45 volumes). The mixture was agitated at about 22° C. until the reaction was deemed complete. 2-Methyltetrahydrofuran (9.4 volumes) and cyclohexane (1.9 volumes) were added, then the mixture was washed twice with 3% aq NaCl solution (6 volumes each time) and once with 4% aq $NaHSO_4$ solution (8 volumes). The mixture was concentrated under reduced pressure to about 3.0 volumes. The residue was co-evaporated with acetonitrile (10.2 volumes) to about 3.0 volumes. Acetonitrile (7.9 volumes) was charged, and the mixture was polish filtered into another reactor, followed by a rinse with acetonitrile (1.8 volumes). The mixture concentrated under reduced pressure to about 3.0 volumes. Trifluoroacetic acid (1.09 equiv), acetonitrile (1.0 volume) and 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetic acid seeds (0.0014 equiv) were charged, and the mixture was agitated for about 18 hours. Di-n-butyl ether (8.1 volumes) was charged over about 2 hours at about 22° C., and the resulting slurry was agitated for about 24 hours. The slurry was filtered, the filter cake rinsed with a mixture of acetonitrile (1.0 volume) and di-n-butyl ether (2.3 volumes), and then dried to afford 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetic acid. $^1$H NMR (400 MHz, $d_6$-DMSO, major atropisomers): δ 9.18 (d, 1H, J 8.2 Hz), 9.16 (m, 1H), 7.87 (d, 1H, J=8.0 Hz), 7.83 (d, 1H, J=8.1 Hz), 7.77 (d, 1H, J=8.3 Hz), 7.75 (m, 1H), 7.44 (d, 1H, J=7.7 Hz), 7.36 (d, 1H, J=7.7 Hz), 7.15 (s, 1H), 7.02 (m, 1H), 7.01 (m, 1H), 6.66 (s, 1H), 6.63 (s, 1H), 6.61 (m, 1H), 6.48 (m, 2H), 4.93 (d, 1H, J=16.4 Hz), 4.85 (d, 1H, J=16.5 Hz), 4.77 (m, 1H), 4.76 (d, 1H, J=16.7 Hz), 4.71 (m, 1H), 4.68 (m, 1H), 4.66 (d, 1H, J=16.4 Hz), 4.63 (m, 1H), 4.24 (dq, 1H, J=16.3, 8.2 Hz), 4.01 (dq, 1H, J=16.4, 8.1 Hz), 3.87 (d, 1H, J=17.7 Hz), 3.86 (d, 1H, J=17.5 Hz), 3.72 (d, 1H, J=17.8 Hz), 3.59 (d, 1H, J=17.7 Hz), 3.48 (s, 3H), 3.46 (s, 3H), 3.44 (br m, 1H), 3.27 (s, 3H), 3.27 (s, 3H), 3.22 (br m, 1H), 3.06 (dd, 1H, J=13.5, 7.2 Hz), 2.99 (m, 1H), 2.57 (m, 1H), 2.53 (m, 1H), 2.53 (m, 1H), 2.18 (s, 3H), 1.75 (s, 3H), 1.75 (s, 3H), 1.75 (s, 3H), 1.75 (s, 3H), 1.45 (s, 3H), 1.38 (m, 1H), 1.34 (s, 3H), 1.30 (s, 3H), 1.18 (s, 3H), 1.02 (m, 1H), 0.97 (m, 1H). $^{13}$C NMR (101 MHz, $d_6$-DMSO, major atropisomers): δ 173.7, 173.6, 171.8, 171.6, 164.6, 164.4, 162.1, 158.8, 158.5, 150.7, 142.8, 142.7, 142.4, 142.1, 141.9, 141.7, 140.0, 139.6, 139.3, 137.6, 134.9, 134.6, 134.5, 134.5, 134.0, 133.7, 132.5, 132.2, 132.2, 132.0, 131.8, 131.3, 130.5, 130.3, 129.9, 129.8, 126.9, 126.7, 125.6, 125.5, 123.1, 122.8, 122.8, 120.7, 120.7, 120.0, 119.9, 119.7, 119.6, 119.4, 119.2, 118.8, 118.7, 112.1, 102.2, 88.5, 88.3, 84.5, 57.3, 57.3, 53.2, 53.0, 53.0, 52.7, 52.7, 52.1, 50.8, 50.8, 50.4, 50.4, 47.3, 42.2, 42.2, 42.0, 42.0, 41.6, 41.5, 39.7, 39.2, 35.1, 35.1, 30.6, 30.3, 30.3, 30.2, 27.6, 23.2, 22.4, 22.4, 22.3, 22.3, 20.0, 11.7, 11.6. $^{19}$F NMR (376 MHz, $d_6$-DMSO, major atropisomers): δ −60.32 (s, 3F), −60.38 (s, 3F), −68.98 (t, 3F, J=8.2 Hz), −69.22 (t, 3F, J=8.3 Hz), −79.59 (dd, 1F, J 253.6, 12.7 Hz), −80.00 (m, 1F), −101.82 (m, 1F), −103.03 (dd, 1F, J=253.6, 9.6 Hz), −109.96 (m, 2F), −110.06 (m, 2F). $^{31}$P NMR (162 MHz, $d_6$-DMSO, major atropisomers): δ −7.10 (s, 1P), −7.14 (s, 1P). IR (ATR): 2931, 1735, 1624-1477, 1448, 1381-1315, 1259-1107, 1057-1032 cm$^{-1}$. HRMS (ESI) [M+Na]$^+$ calcd for $C_{53}H_{49}ClF_{10}N_7NaO_{12}PS_2^+$: 1318.20393, found: 1318.20239.

Example 6. Alternative Synthesis of 2-(2-(4-(N-(4-Chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetic acid

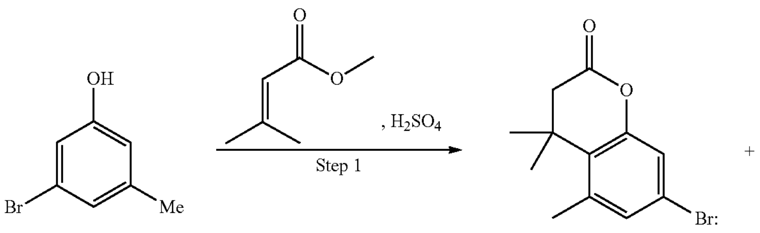

1

-continued
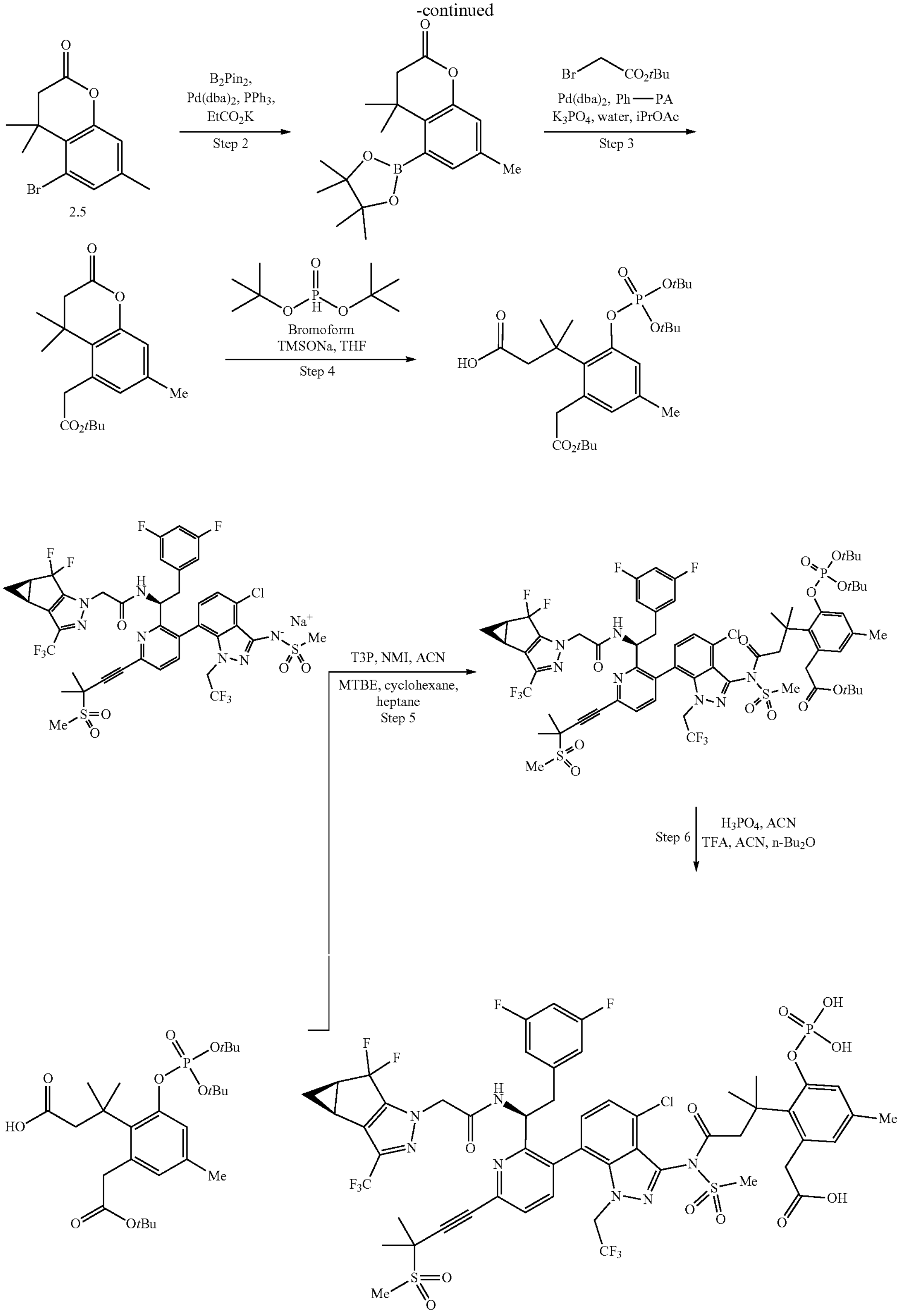

Step 1. Synthesis of 5-bromo-4,4,7-trimethylchroman-2-one

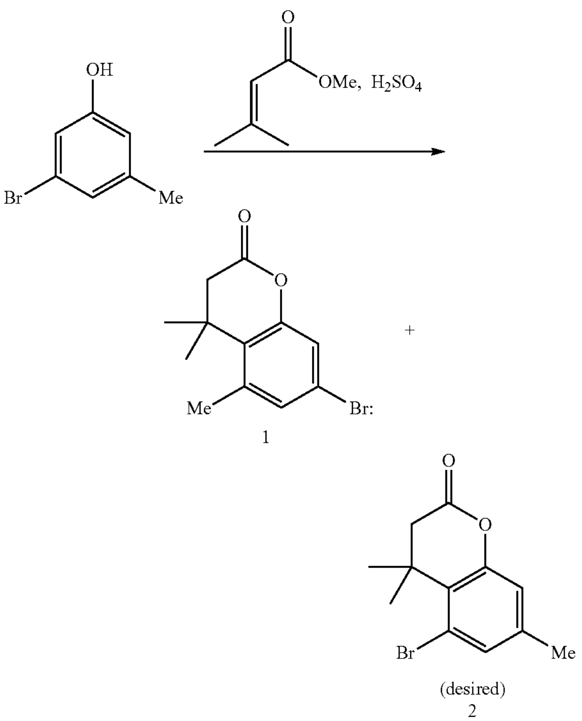

1

(desired)
2

3-Bromo-5-methylphenol (1.00 equiv, scaling factor) and 3,3-dimethylacrylate (1.70 equiv) were charged to a reactor. The mixture was agitated and adjusted to about 10° C. Sulfuric acid (2.00 equiv.) was charged, while maintaining the mixture temperature below 35° C. The reaction mixture was heated to 90° C. and agitated until the reaction was complete. The mixture was cooled to 0-10° C., dichloromethane (2 volumes) was charged, and the mixture was agitated for about 10 min to homogenize. Water (3 volumes) was charged to another reactor, agitated, and cooled to about 10° C. The solution was transferred to the pre-cooled water and rinsed with additional dichloromethane (2 volumes). The mixture was adjusted to about 22° C. for not less than 30 minutes, and the layers were separated after settling. The organic layer was washed with an aqueous solution of 1.9 wt % sodium hydroxide and 5 wt % sodium chloride (5.4 volumes) and 10% brine (5.0 volumes). If required, a charcoal treatment was performed to remove dark color of the mixture by mixing with charcoal powder (0.03 parts) at 20-30° C. for about 45 minutes, followed by filtration through a celite pad to remove charcoal. The organic solution was concentrated to about 2 volumes under vacuum with the reactor jacket at not more than 50° C. 2-Propanol (8 volumes) was added, and the mixture was adjusted to about 65° C. and agitated for not less than 1 hour. The resultant slurry was cooled to 0-5° C. over not less than 5 hours. The slurry was filtered, and the wet cake was rinsed with n-heptane twice (3 volumes for each rinse). The filtrate was concentrated to about 3 volumes under vacuum with a jacket temperature of not more than 50° C. Water (1 volume) was charged and the mixture was adjusted to about 22° C. and agitated for not less than 1 hour. Water (2 volumes) was charged over not less than 1 hour. The slurry was cooled to about 0° C. over about 4 hours and agitated for about 5 hours. Filtration of the slurry, rinsing the wet cake with a mixture of water (1 volume) and 2-propanol (2 volumes), and drying of the wet cake afforded 5-bromo-4,4,7-trimethylchroman-2-one. $^1H$ NMR (400 MHz, $CDCl_3$): δ 7.14 (s, 1H), 6.75 (s, 1H), 2.56 (s, 2H), 2.21 (s, 3H), 1.48 (s 6H) ppm.

Step 2. Synthesis of 4,4,7-trimethyl-5-(4,4,5,5-tetramethyl-1,3,2-dioxaborolan-2-yl)chroman-2-one

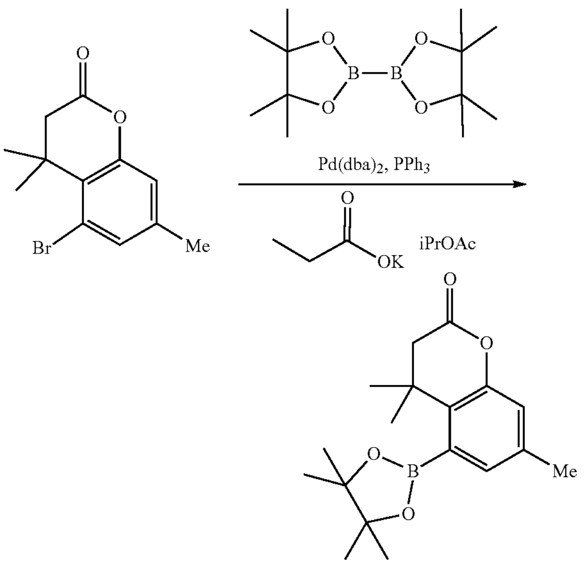

To a reactor was charged 5-bromo-4,4,7-trimethylchroman-2-one (1.00 equiv, scaling factor), bis(pinacolato)diboron (1.3 equiv.), potassium propanoate (2.9 equiv.), and isopropyl acetate (12 volumes). The mixture was distilled to 3 volumes under vacuum with a jacket temperature of 45° C. Isopropyl acetate (9 volumes) was then added and the distillation was repeated to a concentration of 3 volumes under vacuum. Isopropyl acetate (9 volumes) was then added, followed by bis(dibenzylideneacetone)dipalladium (0) (0.015 equiv.) and triphenylphosphine (0.015 equiv.). The mixture was degassed three times, each time by putting the reactor under vacuum for about 30 seconds and filing the reactor with nitrogen to atmospheric pressure. The reaction mixture was then agitated at about 85° C. for about 21 h. Upon reaction completion, the mixture was cooled to about 60° C., and a solution of N-acetyl cysteine (0.1 parts) in water (9 volumes) was added. The mixture was adjusted to about 60° C. and agitated for about 12 h. The mixture was then cooled to about 22° C., followed by cease of agitation, settling, and layer separation. The organic layer was washed with a solution of sodium chloride (1 parts) in water (9 volumes). The organic layer was filtered, concentrated to about 3 volumes, and diluted with ethanol (10 volumes). The mixture was concentrated to 3 volumes under vacuum and diluted with ethanol (1 volume). Water (1.5 volumes) was added, the resulting slurry was cooled to about 0° C., and then filtered. The filter cake was washed using a mixture of ethanol (2 volumes) and water (1 volume) and then n-heptane (2 volumes). The wet case was dried to afford 4,4,7-trimethyl-5-(4,4,5,5-tetramethyl-1,3,2-dioxaborolan-2-yl)

chroman-2-one. $^1H$ NMR (400 MHz, $d_6$-DMSO): δ 7.12 (s, 1H), δ 6.89 (s, 1H), δ 2.55 (s, 2H), δ 2.31 (s, 3H), δ 1.45 (s, 6H), δ 1.38 (s, 12H).

Step 3. Synthesis of tert-butyl 2-(4,4,7-trimethyl-2-oxochroman-5-yl)acetate

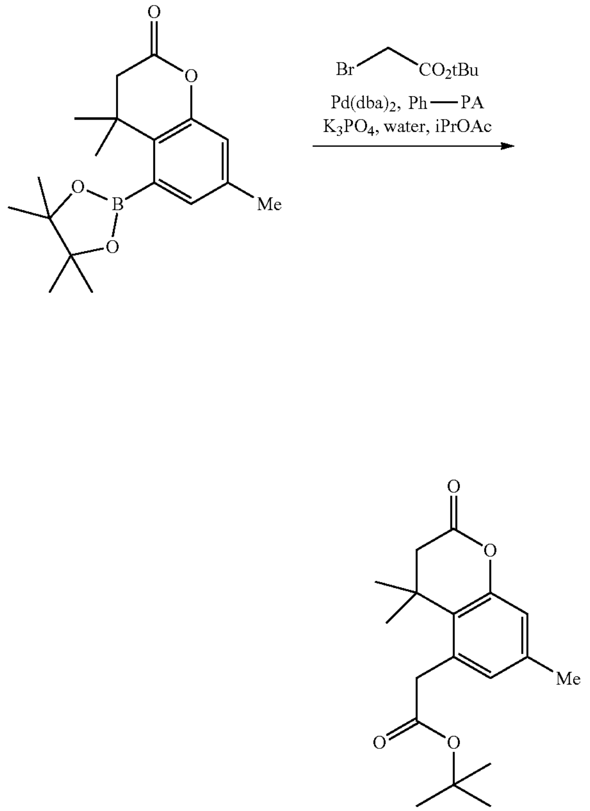

To a reactor was charged 4,4,7-trimethyl-5-(4,4,5,5-tetramethyl-1,3,2-dioxaborolan-2-yl)chroman-2-one (1.00 equiv, scaling factor), potassium phosphoate tribasic (4 equiv), Bis(dibenzylideneacetone)palladium(0) (0.033 equiv), 1,3,5,7-tetramethyl-6-phenyl-2,4,8-trioxa-6-phosphaadamantane (Ph-PA, 0.06 equiv), isopropyl acetate (11.4 volumes), tert-butyl bromoacetate (2.5 equiv), and water (2 volumes). The reaction mixture was agitated at about 81° C. for about 2 h then cooled to about 22° C. The organic layer was washed successively with 10% N-acetyl-L-cysteine (NAC) solution (10 volumes), 20% ammonium chloride solution (10 volumes), and 10% brine solution (10 volumes). The organic layer was then concentrated to about 3 volumes then 2-propanol (10 volumes) was charged. The resulting solution was filtered, concentrated to about 3 volumes, then 2-propanol (3 volumes) was charged followed by water (2.5 volumes). The resulting slurry was cooled to about 0° C. then filtered. The filter cake was washed with a solution of 2-propanol (2.5 volumes) and water (4 volumes) then dried to afford tert-butyl 2-(4,4,7-trimethyl-2-oxochroman-5-yl) acetate. $^1H$ NMR (400 MHz, $CDCl_3$): δ 6.81 (s, 1H), δ 6.79 (s, 1H), δ 3.70 (s, 2H), δ 2.57 (s, 2H), δ 2.29 (s, 3H), δ 1.47 (s, 9H), δ 1.41 (s, 6H).

Step 4. Synthesis of 3-(2-(2-(tert-butoxy)-2-oxoethyl)-6-((di-tert-butoxyphosphoryl)oxy)-4-methylphenyl)-3-methylbutanoic acid

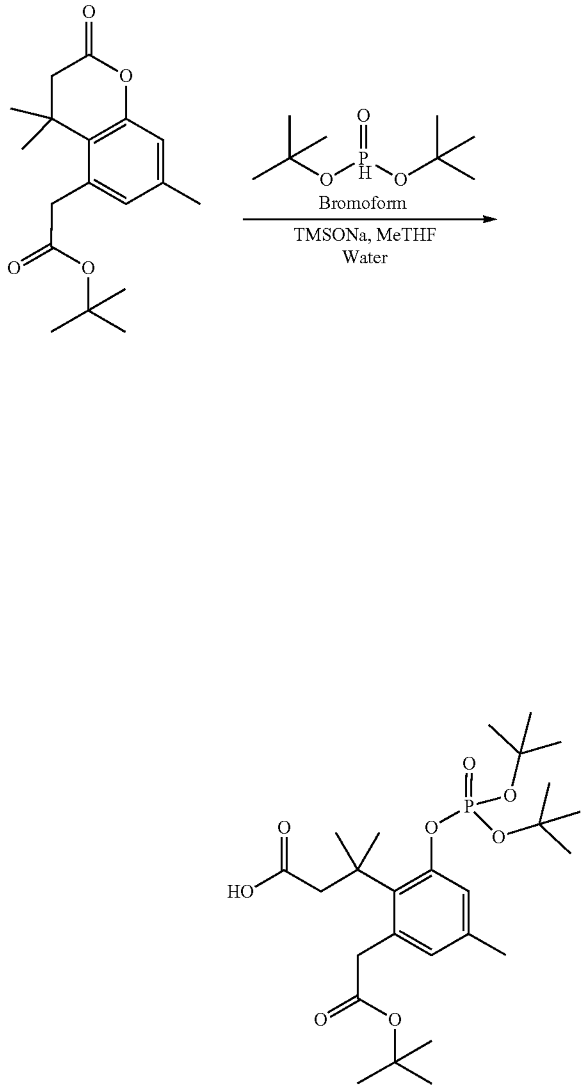

tert-Butyl 2-(4,4,7-trimethyl-2-oxochroman-5-yl)acetate (1.00 equiv, scaling factor), sodium trimethylsilanolate (4 equiv), 2-methyltetrahydrofuran (20 volumes), and water (0.08 volumes) were charged in a reactor, followed by bromoform (2 equiv) and di-tert-butyl phosphite (2 equiv). The mixture was agitated at about 22° C. until the reaction was deemed complete. The reaction mixture was washed with 10% potassium dihydrogen phosphate (10 volumes) and 10% brine solution (10 volumes). The organic layer was concentrated to about 5 volumes then n-heptane (10 volumes) was charged. The resulting slurry was cooled to about 0° C. then filtered. The filter cake was washed with a solution of n-heptane (1.5 volumes) and 2-methyltetrahydrofuran (1.5 volumes) then dried to afford 3-(2-(2-(tert-butoxy)-2-oxoethyl)-6-((di-tert-butoxyphosphoryl)oxy)-4-methylphenyl)-3-methylbutanoic acid. $^1H$ NMR (400 MHz, $d_6$-DMSO): δ 11.74 (s, 1H), 7.23 (s, 1H), 6.74 (s, 1H), 3.86 (s, 2H), 2.87 (s, 2H), 2.22 (s, 3H), 1.51 (s, 6H), 1.46 (s, 18H), 1.44 (s, 9H) ppm.

Step 5: Synthesis of tert-butyl 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((di-tert-butoxyphosphoryl)oxy)-5-methylphenyl)acetate

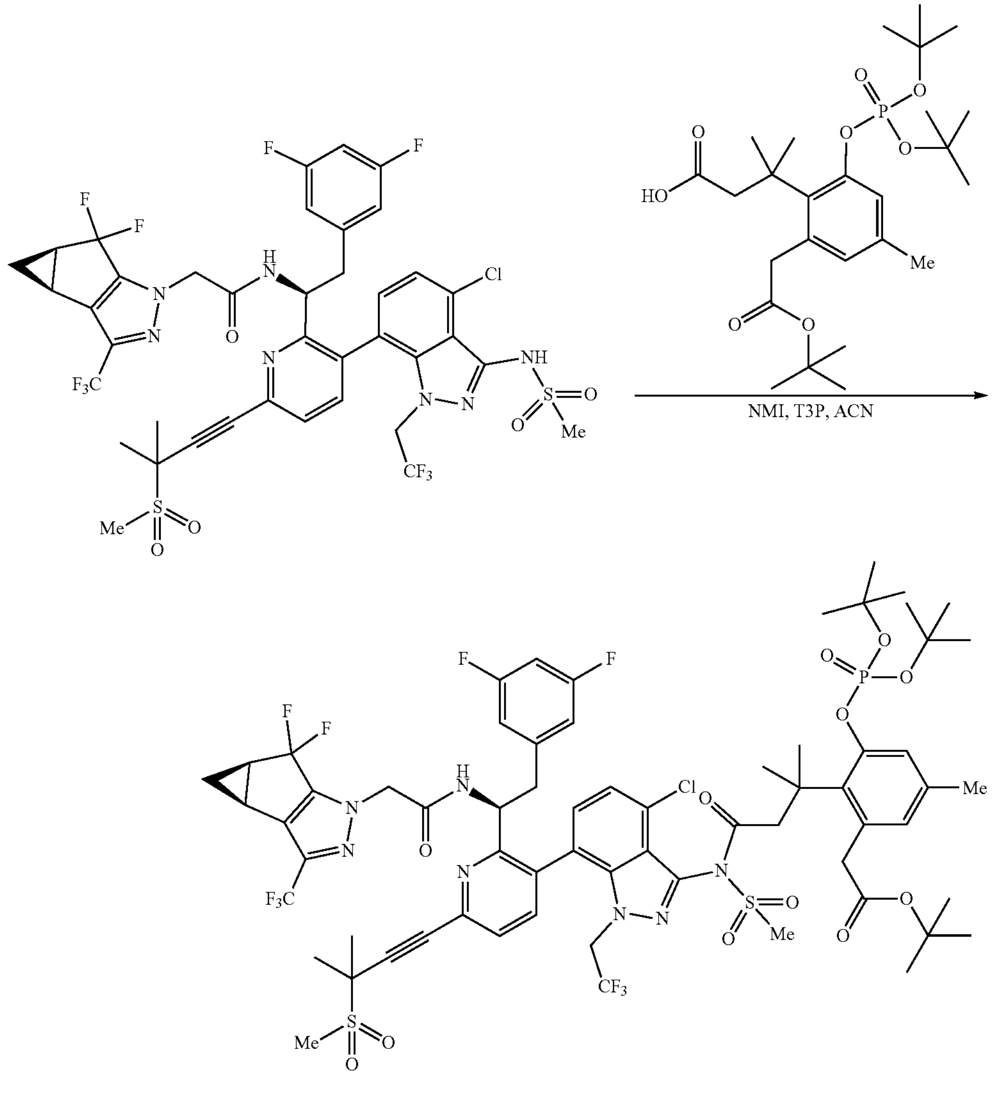

3-(2-(2-(tert-Butoxy)-2-oxoethyl)-6-((di-tert-butoxyphosphoryl)oxy)-4-methylphenyl)-3-methylbutanoic acid (1.10 equiv), acetonitrile (5.3 volumes), 1-methylimidazole (7.00 equiv), propanephosphonic acid anhydride (T3P) 50 wt % in acetonitrile (T3P, 2.00 equiv) were charged to a reactor at 10° C., followed by GS-6207-02 (i.e., lenacapavir sodium, 1.00 equiv, scaling factor). The mixture was agitated at about 10° C. until the reaction was deemed complete. The reaction mixture was diluted with methyl t-butyl ether (12.8 volumes) then quenched with 5% aqueous potassium chloride solution (10 volumes). The biphasic mixture was diluted with cyclohexane (2.6 volumes), then the organic layer was separated. The organic layer was washed with 5% aqueous potassium chloride solution for additional 3 times (10.0 volumes each time). The organic layer was evaporated to about 2.5 volumes. The residue was co-evaporated with methyl t-butyl ether (12.2 volumes) to about 3.0 volumes twice. The residue was diluted with methyl t-butyl ether (4.1 volumes) then charged to n-heptane (14.6 volumes). The slurry was agitated at about 22° C. for about 4 hours then filtered. The filter cake was washed with n-heptane (7.3 volumes) and then dried to afford tert-butyl 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((di-tert-butoxyphosphoryl)oxy)-5-methylphenyl) acetate. $^{1}H$ NMR (400 MHz, $d_6$-DMSO, all atropisomers): δ 9.25-8.84 (m, 1H), 8.02-6.41 (m, 9H), 5.04-4.50 (m, 4H), 4.25-2.82 (m, 13H), 2.61-2.42 (m, 2H), 2.18 (s, 3H), 1.75 (s, 6H), 1.53-0.92 (m, 35H) ppm. $^{19}F$ NMR (377 MHz, $d_6$-DMSO, all atropisomers): δ −60.28--60.43 (m, 3F), −68.84--69.17 (m, 3F), −79.25--80.41 (m, 1F), −101.96--103.31 (m, 1F), −110.05--110.43 (m, 2F) ppm. $^{31}P$ NMR (162 MHz, $d_6$-DMSO, all atropisomers): −16.88, −17.07, −17.18, −17.56 ppm.

Step 6. Synthesis of 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetic acid

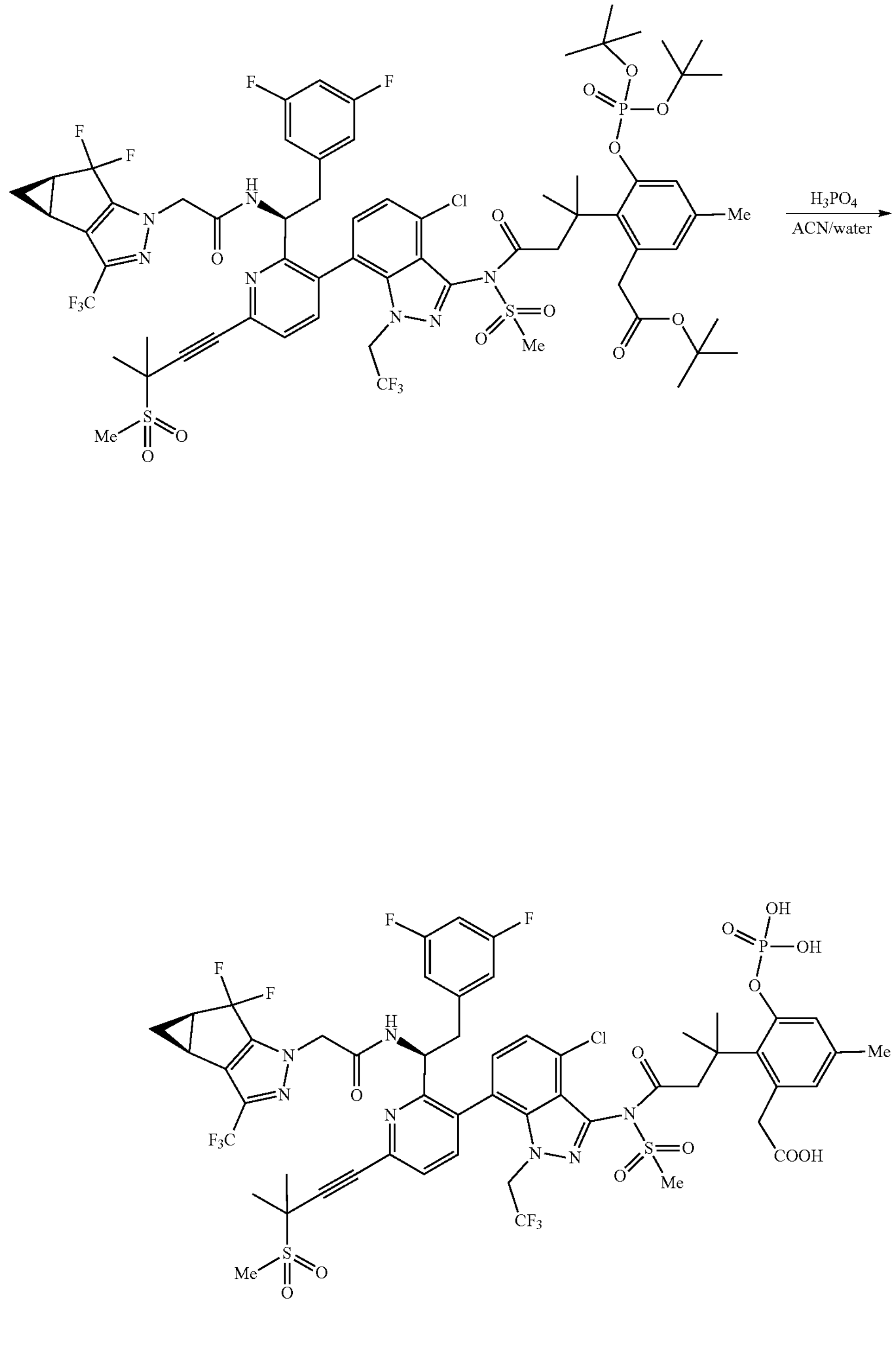

tert-Butyl 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((di-tert-butoxyphosphoryl)oxy)-5-methylphenyl)acetate (1.00 equiv, scaling factor) and acetonitrile (1.4 volumes) were charged to a reactor and adjusted to about 10° C. Phosphoric acid (85 wt %, 37 equiv) was charged while maintaining the mixture over about 30 min, followed by acetonitrile (0.45 volumes). The mixture was agitated at about 22° C. until the reaction was deemed complete. 2-Methyltetrahydrofuran (9.4 volumes) and cyclohexane (1.9 volumes) were added, then the mixture was washed twice with 3% aq NaCl solution (6 volumes each time) and once with 4% aq $NaHSO_4$ solution (8 volumes). The mixture was concentrated under reduced pressure to about 3.0 volumes. The residue was co-evaporated with acetonitrile (10.2 volumes) to about 3.0 volumes. Acetonitrile (7.9 volumes) was charged, and the mixture was polish filtered into another reactor, followed by a rinse with acetonitrile (1.8 volumes). The mixture concentrated under reduced pressure to about 3.0 volumes. Trifluoroacetic acid (1.09 equiv), acetonitrile (1.0 volume) and 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetic acid seeds (0.0014 equiv) were charged, and the mixture was agitated for about 18 hours. Di-n-butyl ether (8.1 volumes) was charged over about 2 hours at about 22° C., and the resulting slurry was agitated for about 24 hours. The slurry was filtered, the filter cake rinsed with a mixture of acetonitrile (1.0 volume) and di-n-butyl ether (2.3 volumes), and then dried to afford 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetic acid. $^1H$ NMR (400 MHz, $d_6$-DMSO, major atropisomers): δ 9.18 (d, 1H, J 8.2 Hz), 9.16 (m, 1H), 7.87 (d, 1H, J=8.0 Hz), 7.83 (d, 1H, J=8.1 Hz), 7.77 (d, 1H, J=8.3 Hz), 7.75 (m, 1H), 7.44 (d, 1H, J=7.7 Hz), 7.36 (d, 1H, J=7.7 Hz), 7.15 (s, 1H), 7.02 (m, 1H), 7.01 (m, 1H), 6.66 (s, 1H), 6.63 (s, 1H), 6.61 (m, 1H), 6.48 (m, 2H), 4.93 (d, 1H, J=16.4 Hz), 4.85 (d, 1H, J=16.5 Hz), 4.77 (m, 1H), 4.76 (d, 1H, J=16.7 Hz), 4.71 (m, 1H), 4.68 (m, 1H), 4.66 (d, 1H, J=16.4 Hz), 4.63 (m, 1H), 4.24 (dq, 1H, J=16.3, 8.2 Hz), 4.01 (dq, 1H, J=16.4, 8.1 Hz), 3.87 (d, 1H, J=17.7 Hz), 3.86 (d, 1H, J=17.5 Hz), 3.72 (d, 1H, J=17.8 Hz), 3.59 (d, 1H, J=17.7 Hz), 3.48 (s, 3H), 3.46 (s, 3H), 3.44 (br m, 1H), 3.27 (s, 3H), 3.27 (s, 3H), 3.22 (br m, 1H), 3.06 (dd, 1H, J=13.5, 7.2 Hz), 2.99 (m, 1H), 2.57 (m, 1H), 2.53 (m, 1H), 2.53 (m, 1H), 2.18 (s, 3H), 1.75 (s, 3H), 1.75 (s, 3H), 1.75 (s, 3H), 1.75 (s, 3H), 1.45 (s, 3H), 1.38 (m, 1H), 1.34 (s, 3H), 1.30 (s, 3H), 1.18 (s, 3H), 1.02 (m, 1H), 0.97 (m, 1H). $^{13}C$ NMR (101 MHz, $d_6$-DMSO, major atropisomers): δ 173.7, 173.6, 171.8, 171.6, 164.6, 164.4, 162.1, 158.8, 158.5, 150.7, 142.8, 142.7, 142.4, 142.1, 141.9, 141.7, 140.0, 139.6, 139.3, 137.6, 134.9, 134.6, 134.5, 134.5, 134.0, 133.7, 132.5, 132.2, 132.2, 132.0, 131.8, 131.3, 130.5, 130.3, 129.9, 129.8, 126.9, 126.7, 125.6, 125.5, 123.1, 122.8, 122.8, 120.7, 120.7, 120.0, 119.9, 119.7, 119.6, 119.4, 119.2, 118.8, 118.7, 112.1, 102.2, 88.5, 88.3, 84.5, 57.3, 57.3, 53.2, 53.0, 53.0, 52.7, 52.7, 52.1, 50.8, 50.8, 50.4, 50.4, 47.3, 42.2, 42.2, 42.0, 42.0, 41.6, 41.5, 39.7, 39.2, 35.1, 35.1, 30.6, 30.3, 30.3, 30.2, 27.6, 23.2, 22.4, 22.4, 22.3, 22.3, 20.0, 11.7, 11.6. $^{19}F$ NMR (376 MHz, $d_6$-DMSO, major atropisomers): δ −60.32 (s, 3F), −60.38 (s, 3F), −68.98 (t, 3F, J=8.2 Hz), −69.22 (t, 3F, J=8.3 Hz), −79.59 (dd, 1F, J 253.6, 12.7 Hz), −80.00 (m, 1F), −101.82 (m, 1F), −103.03 (dd, 1F, J=253.6, 9.6 Hz), −109.96 (m, 2F), −110.06 (m, 2F). $^{31}P$ NMR (162 MHz, $d_6$-DMSO, major atropisomers): δ −7.10 (s, 1P), −7.14 (s, 1P). IR (ATR): 2931, 1735, 1624-1477, 1448, 1381-1315, 1259-1107, 1057-1032 $cm^{-1}$. HRMS (ESI) $[M+Na]^+$ calcd for $C_{53}H_{49}ClF_{10}N_7NaO_{12}PS_2^+$: 1318.20393, found: 1318.20239.

Example 7. Synthesis of Ethyl 5-hydroxy-4,7-dimethyl-2-oxo-2H-chromene-3-carboxylate

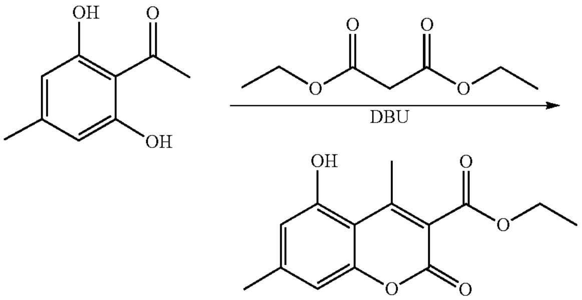

1-(2,6-Dihydroxy-4-methylphenyl)ethan-1-one (1.00 equiv, scaling factor) and DBU (3.8 volumes) were charged to a reactor. Diethyl malonate (1.40 equiv) was added dropwise. The reaction mixture was stirred at about 100° C. for about 14 hours. Additional diethyl malonate (0.60 equiv) was added, and the reaction mixture was stirred at about 100° C. for about 2. The reaction mixture was acidified by adding 1M aq. HCl (25 volumes) and then diluted with water (50 volumes). The resulting slurry was filtered, and the residue was dried in vacuum oven at about 45° C. overnight to give a crude solid. The crude solid was purified by column chromatography on silica gel to afford ethyl 5-hydroxy-4,7-dimethyl-2-oxo-2H-chromene-3-carboxylate. $^1H$ NMR (300 MHz, DMSO-$d_6$): δ 10.85 (s, 1H), 6.71-6.66 (m, 1H), 6.65-6.60 (m, 1H), 4.30 (q, J=7.2 Hz, 2H), 2.53 (s, 3H), 2.30 (s, 3H), 1.28 (t, J=7.1 Hz, 3H).

Example 8. Synthesis of Ethyl 5-hydroxy-4,4,7-trimethyl-2-oxochromane-3-carboxylate

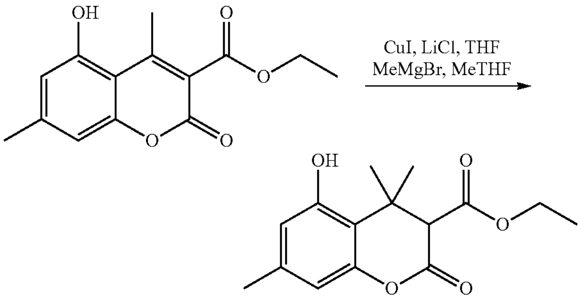

To a reactor was charged LiCl (8.50 equiv). The LiCl was dried under the vacuum with heating for about 3 minutes. CuI (6.00 equiv) and dry THE (38.2 volumes) were added under $N_2$. The slurry was stirred at room temperature for about 10 minutes until the solids were dissolved. The flask was cooled to about −40° C. A solution of 3.4M MeMgBr in 2-MeTHF (8.2 equiv) was added dropwise via a syringe and stirred for about 10 minutes. Ethyl 5-hydroxy-4,7-dimethyl-2-oxo-2H-chromene-3-carboxylate (1.00 equiv, scaling factor) was dissolved in dry THE (38.1 volumes) and the solution was added dropwise via an addition funnel over about 1 hour. The reaction mixture was stirred at about −40° C. for about 5 minutes and was warmed up naturally by removing the dry ice. The reaction was quenched by adding an aqueous solution of saturated $NH_4Cl$ (11.5 volumes), acetone (7.6 volumes), EtOAc (19 volumes), and water (7.6 volumes). The resulting mixture was stirred for about 1 hour. The dark blue aqueous layer was extracted with EtOAc. The combined organic layers were washed with brine, dried with $Na_2SO_4$, and evaporated to dryness. The residue was purified by column chromatography on silica gel to provide ethyl 5-hydroxy-4,4,7-trimethyl-2-oxochromane-3-carboxylate. $^1$H NMR (300 MHz, DMSO-$d_6$) δ 9.70 (s, 1H), 6.48-6.41 (m, 1H), 6.39-6.33 (m, 1H), 4.11 (qd, J=7.1, 0.7 Hz, 2H), 3.79 (s, 1H), 2.17 (s, 3H), 1.45 (s, 3H), 1.39 (s, 3H), 1.14 (t, J=7.1 Hz, 3H).

Example 9. Synthesis of 5-Hydroxy-4,4,7-trimethylchroman-2-one

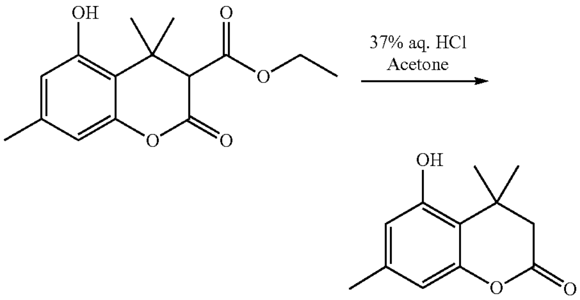

To a reactor were charged ethyl 5-hydroxy-4,4,7-trimethyl-2-oxochromane-3-carboxylate (1.00 equiv, scaling factor) and acetone (6.2 volumes). 37% aq. HCl (16.9 volumes) was added, and the reaction mixture was refluxed for about 7 hours, followed by agitation at room temperature overnight. The mixture was extracted with EtOAc three times. The combined organic layer was washed with sat. aq. $NaHCO_3$, dried with $Na_2SO_4$, and evaporated to dryness to afford 5-hydroxy-4,4,7-trimethylchroman-2-one. $^1$H NMR (300 MHz, DMSO-$d_6$) δ 9.63 (s, 1H), 6.46-6.39 (m, 1H), 6.35-6.28 (m, 1H), 2.62 (s, 2H), 2.16 (s, 3H), 1.34 (s, 6H).

Example 10. Synthesis of 4,4,7-Trimethyl-2-oxochroman-5-yl trifluoromethanesulfonate

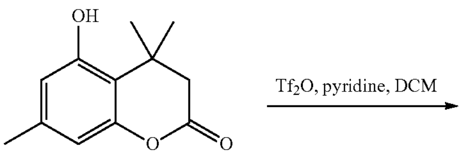

-continued

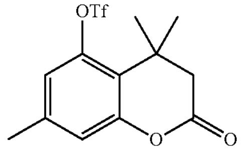

To a reactor was charged 5-hydroxy-4,4,7-trimethylchroman-2-one (1.00 equiv, scaling factor) and dry DCM (22.7 volumes). Pyridine (2.00 equiv) was added at about 0° C., followed by the dropwise addition of $Tf_2O$ (1.50 equiv). The reaction mixture was stirred at about 22° C. for about 1.5 hours. The mixture was washed with aqueous solution of 1M HCl, aqueous solution of saturated $NaHCO_3$ and brine. The organic layer was dried with $Na_2SO_4$ and evaporated to dryness. The residue was purified by column chromatography on silica gel to provide 4,4,7-trimethyl-2-oxochroman-5-yl trifluoromethanesulfonate. $^1$H NMR (300 MHz, Chloroform-d) δ 6.96-6.88 (m, 2H), 2.62 (s, 2H), 2.37 (s, 3H), 1.49 (s, 6H). $^{19}$F NMR (282 MHz, Chloroform-d) δ −73.74.

Example 11. Alternative Synthesis of tert-Butyl 2-(4,4,7-trimethyl-2-oxochroman-5-yl)acetate

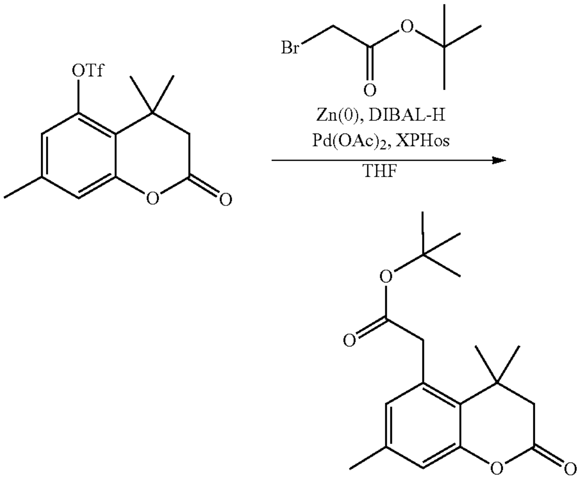

Formation of the zinc enolate: To a reactor, equipped with a magnetic stirring bar, $N_2$ inlet and outlet, and a condenser, was charged with Zn powder (1.70 equiv.). The flask was flushed with $N_2$ for about 15 minutes. Dry THE (100 volume) was added, and the slurry was heated to about 35° C. Tert-butyl-2-bromoacetate (0.050 equiv) was added in one portion, followed by dropwise addition of a solution of 25% DIBAL-H solution in toluene (0.040 equiv). The reaction mixture was stirred for about 15 minutes at about 35° C. Then the reaction mixture was heated to about 40° C. tert-butyl-2-bromoacetate (1.00 equiv, scaling factor) was added dropwise while keeping the content temperature below 50° C. Upon completion of addition, the reaction mixture was stirred at about 40° C. overnight. The agitation was turned off, and the mixture was cooled to about 22° C. Excess Zn powder settled at the bottom, and an aliquot of the upper clear solution was titrated with $I_2$—LiCl/THF solution.

Negishi coupling: To a reactor was charged 4,4,7-trimethyl-2-oxochroman-5-yl trifluoromethanesulfonate (1.00 equiv, scaling factor), $Pd(OAc)_2$ (0.050 eq), XPhos (0.050 equiv) and dry THE (11.8 volumes). The mixture was degassed under vacuum and refilled with $N_2$ for three times. Zinc enolate solution (2.50 equiv) was added dropwise at about 22° C. The reaction mixture was stirred at about 55° C. for about 2 hours. Upon reaction completion, the mixture was quenched with water, an aqueous solution of 1 M HCl, EtOAc and brine. The mixture was filtered. Aqueous layer was separated and extracted with EtOAc twice. The combined organic layer was washed with brine, dried with $Na_2SO_4$, filtered, and evaporated to dryness. The residue was purified by column chromatography on silica gel to afford tert-butyl 2-(4,4,7-trimethyl-2-oxochroman-5-yl)acetate. $^1H$ NMR (300 MHz, Chloroform-d) δ 6.83-6.80 (m, 1H), 6.80-6.77 (m, 1H), 3.70 (s, 2H), 2.58 (s, 2H), 2.30 (t, J=0.7 Hz, 3H), 1.47 (s, 9H), 1.42 (s, 6H). $^{13}C$ NMR (75 MHz, Chloroform-d) δ 170.97, 168.19, 151.59, 137.79, 132.35, 130.51, 127.18, 117.47, 81.23, 45.70, 41.58, 34.74, 27.99, 27.76, 20.57.

OTHER EMBODIMENTS

1. In some embodiments, the present disclosure provides a process of preparing a compound of Formula XIII:

XIII

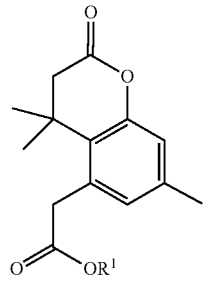

or a salt thereof, comprising reacting a compound of Formula XIV:

XIV

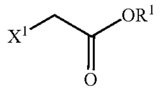

or a salt thereof, with an activator in the presence of zinc and an alkali metal halide to form a first mixture; and mixing the first mixture with a compound of Formula XI-a:

XI-a

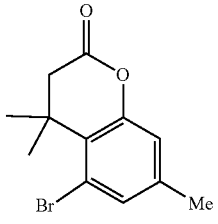

or a salt thereof, in the presence of a coupling catalyst, wherein:

$X^1$ is halo; and $R^1$ is $C_{1-6}$ alkyl.

2. The process of embodiment 1, wherein the activator is selected from the group consisting of diisobutylaluminium hydride, trimethylsilyl chloride, triethylsilyl chloride, trimethylsilyl iodide, dibromoethane, dichloroethane, and iodine.
3. The process of embodiment 1, wherein the activator is diisobutylaluminium hydride.
4. The process of any one of embodiments 1 to 3, wherein the alkali metal halide is lithium chloride.
5. The process of any one of embodiments 1 to 4, wherein the coupling catalyst comprises a palladium catalyst.
6. The process of any one of embodiments 1 to 5, wherein the coupling catalyst comprises a palladium catalyst and a phosphine ligand.
7. The process of embodiment 5 or 6, wherein the palladium catalyst is selected from the group consisting of palladium (II) chloride, palladium (II) bromide, palladium (II) acetate, palladium (II) trifluoroacetate, tris(dibenzylideneacetone)dipalladium(0), tetrakis(triphenylphosphine)palladium(0), (2-dicyclohexylphosphino-2',4',6'-triisopropyl-1,1'-biphenyl)[2-(2'-amino-1,1'-biphenyl)]palladium(II) methanesulfonate, and (SP-4-3)-[dicyclohexyl[2',4',6'-tris(1-methylethyl)[1,1'-biphenyl]-2-yl]phosphine] (methanesulfonato-κO)[2'-(methylamino-κN)[1,1'-biphenyl]-2-yl-κC]palladium.
8. The process of embodiment 6 or 7, wherein the phosphine ligand is selected from the group consisting of 2-dicyclohexylphosphino-2',4',6'-triisopropylbiphenyl, tricyclohexylphosphine, tri-tert-butyl phosphine, triphenyl phosphine, 2-dicyclohexylphosphino-2',6'-dimethoxybiphenyl, and ethylenebis(diphenylphosphine).
9. The process of any one of embodiments 1 to 6, wherein the coupling catalyst comprises palladium (II) acetate and 2-dicyclohexylphosphino-2',4',6'-triisopropylbiphenyl.
10. The process of any one of embodiments 1 to 9, wherein the mixing of the first mixture with the compound of Formula XI-a is performed at a temperature of from about 0° C. to about 100° C.
11. The process of any one of embodiments 1 to 10, wherein the mixing of the first mixture and the compound of Formula XI-a is performed in a solvent comprising tetrahydrofuran and 2-methyltetrahydrofuran.
12. The process of any one of embodiments 1 to 11, wherein the compound of Formula XIV is a compound of Formula XIV-a:

XIV-a

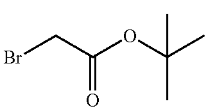

or a salt thereof.

13. The process of any one of embodiments 1 to 12, wherein the compound of Formula XIII is a compound of Formula XIII-a:

XIII-a

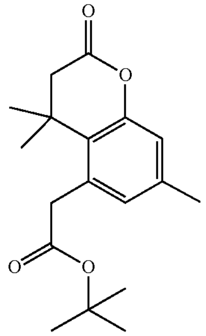

or a salt thereof.

14. The process of any one of embodiments 1 to 13, further comprising phosphorylating the compound of Formula XIII, or a salt thereof, to form a compound of Formula IV:

IV

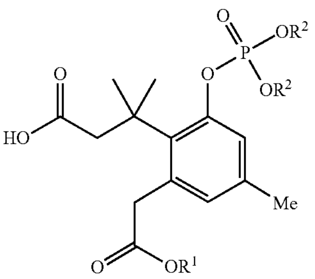

or a salt thereof, wherein each $R^2$ is independently selected from the group consisting of $C_{1-6}$ alkyl.

15. The process of embodiment 14, wherein the phosphorylating comprises reacting the compound of Formula XIII, or a salt thereof, with phorphorylating agent, optionally in the presence of an oxidizing agent and a base.

16. The process of embodiment 15, wherein the phosphorylating agent is selected from the group consisting of di-tert-butyl phosphite, di-tert-butyl phosphoryl chloride, di-tert-butyl phosphoryl bromide, di-ethyl phosphoryl chloride, di-isopropyl phosphoryl chloride, dibenzyl phosphorochloridate, and dibenzyl phosphorobromidate.

17. The process of embodiment 15, wherein the phosphorylating agent is di-tert-butyl phosphite.

18. The process of any one of embodiments 15 to 17, wherein the oxidizing agent is selected from the group consisting of bromoform, carbontetrabromide, carbon tetrachloride, dibromomethane, dibromoethane, bromotrichloromethane, N-chlorosuccinimide, N-bromosuccinimide, N-chlorotosylamide sodium salt, bromine, chlorine, iodine, and sodium hypochlorite.

19. The process of any one of embodiments 15 to 17, wherein the oxidizing agent is bromoform.

20. The process of any one of embodiments 15 to 19, wherein the base is selected from the group consisting of sodium trimethylsilanolate, potassium hydroxide, sodium hydroxide, lithium hydroxide, sodium tert-butoxide, sodium hydride, and cesium carbonate.

21. The process of any one of embodiments 15 to 19, wherein the base is sodium trimethylsilanolate.

22. The process of any one of embodiments 14 to 21, wherein the phosphorylating is performed at a temperature of from about 0° C. to about 40° C.

23. The process of any one of embodiments 14 to 22, wherein the phosphorylating is performed in a solvent comprising 2-methyltetrahydrofuran and water.

24. The process of any one of embodiments 14 to 23, wherein each $R^2$ is tert-butyl.

25. The process of any one of embodiments 14 to 24, wherein the compound of Formula IV is a compound of Formula IV-a:

IV-a

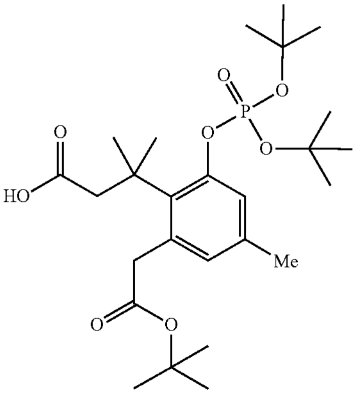

or a salt thereof.

26. In some embodiments, the present disclosure provides a process of preparing a compound of Formula VI:

VI

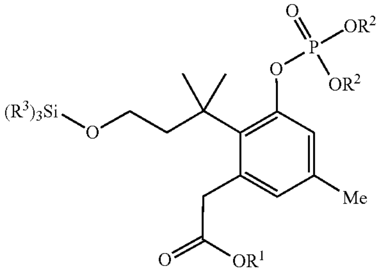

or a salt thereof, comprising reacting a compound of Formula VII:

VII

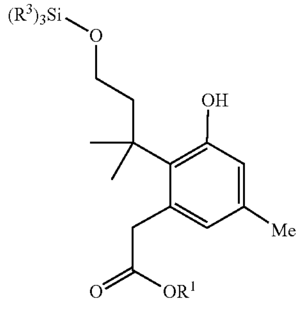

or a salt thereof, with di($C_{1-6}$ alkyl)phosphite in the presence of an oxidizing agent and a base, wherein:

$R^1$ is $C_{1-6}$ alkyl;

each $R^2$ is independently selected from the group consisting of $C_{1-6}$ alkyl; and each $R^3$ is independently selected from the group consisting of $C_{1-6}$ alkyl.

27. The process of embodiment 26, wherein the di($C_{1-6}$ alkyl)phosphite is di-tert-butyl phosphite.

28. The process of embodiment 26 or 27, wherein the oxidizing agent is selected from the group consisting of bromoform, carbontetrabromide, carbon tetrachloride, dibromomethane, dibromoethane, bromotrichloromethane, N-chlorosuccinimide, N-bromosuccinimide, N-chlorotosylamide sodium salt, bromine, chlorine, iodine, and sodium hypochlorite.

29. The process of embodiment 26 or 27, wherein the oxidizing agent is bromoform.

30. The process of any one of embodiments 26 to 29, wherein the base is selected from the group consisting of cesium carbonate, sodium hydroxide, potassium hydroxide, potassium phosphate dibasic, potassium phosphate tribasic, cesium carbonate, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, collidine, 1-methylimidazole, and sodium hydride.

31. The process of any one of embodiments 26 to 29, wherein the base is cesium carbonate.

32. The process of any one of embodiments 26 to 31, wherein the reacting is performed a temperature of from about −20° C. to about 100° C.

33. The process of any one of embodiments 26 to 32, wherein the reacting is performed in a solvent comprising tetrahydrofuran.

34. The process of any one of embodiments 26 to 33, wherein the compound of Formula VI is a compound of Formula VI-a:

VI-a

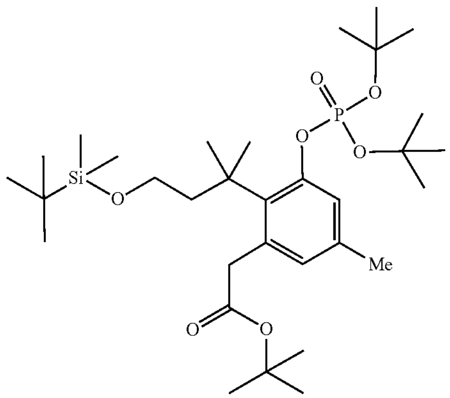

or a salt thereof.

35. In some embodiments, the present disclosure provides a process of preparing a compound of Formula VI:

VI

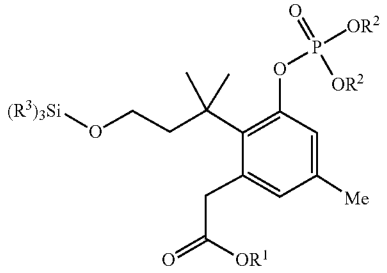

or a salt thereof, comprising reacting a compound of Formula VII:

VII

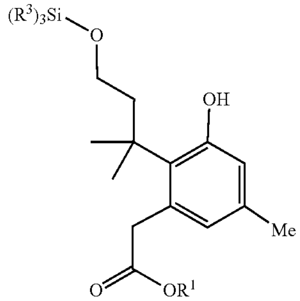

or a salt thereof, with tetra($C_{6-10}$ aryl-$C_{1-6}$ alkyl-)pyrophosphate or $(R^4O)_2P(=O)$-$LG^2$ in the presence of a base, wherein:

$R^1$ is $C_{1-6}$ alkyl;

each $R^2$ is independently selected from the group consisting of $C_{6-10}$ aryl-$C_{1-6}$ alkyl;

each $R^3$ is independently selected from the group consisting of $C_{1-6}$ alkyl, each $R^4$ is independently selected from the group consisting of $C_{6-10}$ aryl-$C_{1-6}$ alkyl; and $LG^2$ is selected from the group consisting of halo and 4-methylbenzylsulfonyloxy.

36. The process of embodiment 35, wherein the tetra($C_{6-10}$ aryl-$C_{1-6}$ alkyl-)pyrophosphate is tetrabenzyl pyrophosphate.

37. The process of embodiment 35, wherein each $R^4$ is benzyl.

38. The process of embodiment 35, wherein LG is selected from the group consisting of chloro, bromo, iodo, and 4-methylbenzylsulfonyloxy.

39. The process of any one of embodiments 35 to 38, wherein the base is selected from the group consisting of sodium hydride, sodium hydroxide, potassium hydroxide, potassium phosphate dibasic, potassium phosphate tribasic, cesium carbonate, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, collidine, and 1-methylimidazole.

40. The process of any one of embodiments 35 to 38, wherein the base is sodium hydride.

41. The process of any one of embodiments 35 to 40, wherein the reacting is performed at a temperature of from about −40° C. to about 100° C.

42. The process of any one of embodiments 35 to 41, wherein the reacting is performed in a solvent comprising tetrahydrofuran.

43. The process of any one of embodiments 35 to 42, wherein the compound of Formula VI is a compound of Formula VI-b:

VI-b

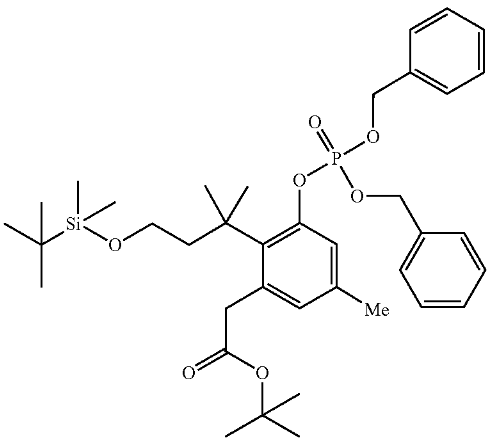

or a salt thereof.

44. In some embodiments, the present disclosure provides a process of preparing a compound of Formula VI:

VI

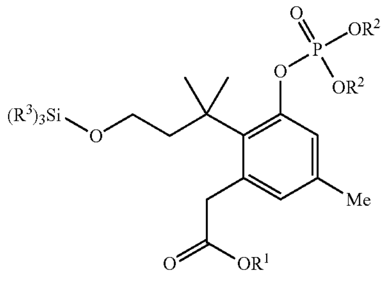

or a salt thereof, comprising reacting a compound of Formula VII:

VII

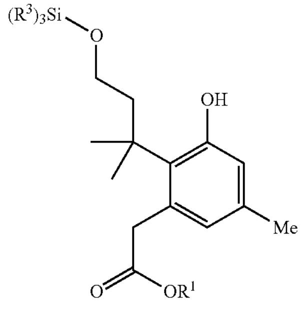

or a salt thereof, with a di($C_{1-6}$ alkyl), N,N-di($C_{1-6}$ alkyl) phosphoramidate in the presence of a base and an acid to form a first mixture; and mixing the first mixture with an oxidizing agent; wherein $R^1$ is $C_{1-6}$ alkyl;

each $R^2$ is independently selected from the group consisting of $C_{1-6}$ alkyl; and each $R^3$ is independently selected from the group consisting of $C_{1-6}$ alkyl.

45. The process of embodiment 44, wherein the di($C_{1-6}$ alkyl), N,N-di($C_{1-6}$ alkyl)phosphoramidate is di-tert-butyl N,N-diisopropylphosphoramidate.

46. The process of embodiment 44 or 45, wherein the base is selected from the group consisting of 1-methylimidazole, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, and collidine.

47. The process of embodiment 44 or 45, wherein the base is 1-methylimidazole.

48. The process of any one of embodiments 44 to 47, wherein the acid is selected from the group consisting of trifluoroacetic acid, trichloroacetic acid, formic acid, hydrofluoric acid, hydrochloric acid, sulfuric acid, phosphoric acid, methanesulfonic acid, p-toluenesulfonic acid, 1H-tetrazole, 5-phenyltetrazole, benzylthiotetrazole, ethylthiotetrazole, 2,4-dinitrophenol, 4-cyanophenol, 2-bromo-4,5-dicyanoimidazole, 4,5-dicyanoimidazole, and saccharin.

49. The process of any one of embodiments 44 to 47, wherein the acid is trifluoroacetic acid.

50. The process of any one of embodiments 44 to 49, wherein the oxidizing agent is selected from the group consisting of hydrogen peroxide, N-chlorosuccinimide, N-bromosuccinimide, N-chlorotosylamide sodium salt, bromine, chlorine, iodine, sodium hypochlorite), sodium peroxide, tert-butyl hydrogen peroxide, sodium perborate, and potassium peroxymonosulfate.

51. The process of any one of embodiments 44 to 49, wherein the oxidizing agent is hydrogen peroxide.

52. The process of any one of embodiments 44 to 51, wherein the reacting is performed a temperature of from about −20° C. to about 100° C.

53. The process of any one of embodiments 44 to 52, wherein the reacting is performed in a solvent comprising tetrahydrofuran and water.

54. The process of any one of embodiments 44 to 53, wherein the compound of Formula VI is a compound of Formula VI-a:

VI-a

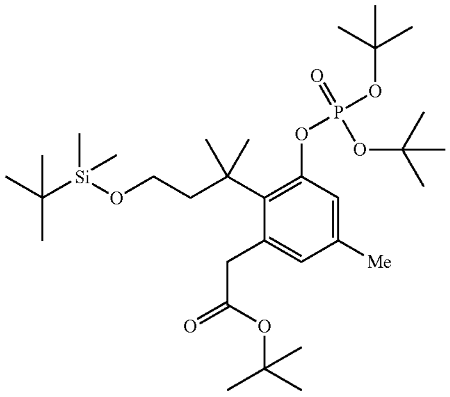

or a salt thereof.

55. The process of any one of embodiments 26 to 54, wherein the compound of Formula VII is a compound of Formula VII-a:

VII-a

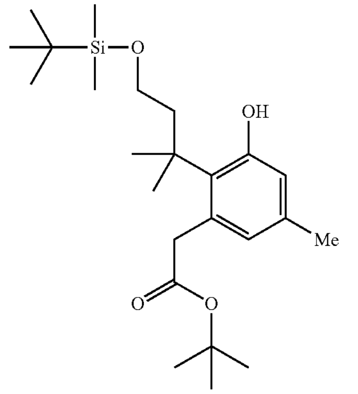

or a salt thereof.

56. The process of any one of embodiments 26 to 55, further comprising deprotecting the compound of Formula VI, or a salt thereof, to form a compound of Formula V:

V

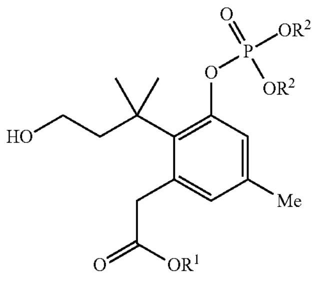

or a salt thereof.

57. The process of embodiment 56, wherein the deprotecting comprises reacting the compound of Formula VI, or a salt thereof, with a deprotecting agent selected from the group consisting of tetrabutylammonium fluoride, potassium hydrogen fluoride, potassium fluoride, sodium hydroxide, potassium hydroxide, potassium phosphate dibasic, potassium phosphate tribasic, cesium carbonate, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, collidine, 1-methylimidazole, hydrofluoric acid, hydrochloric acid, sulfuric acid, methanesulfonic acid, N-chlorosuccinimide, potassium peroxymonosulfate, and iodine.

58. The process of embodiment 56, wherein the deprotecting comprises reacting the compound of Formula VI, or a salt thereof, with tetrabutylammonium fluoride.

59. The process of any one of embodiments 56 to 58, wherein the deprotecting is performed a temperature of from about −20° C. to about 100° C.

60. The process of any one of embodiments 56 to 59, wherein the deprotecting is performed in a solvent comprising tetrahydrofuran.

61. The process of any one of embodiments 56 to 60, further comprising oxidizing the compound of Formula V, or a salt thereof, to form a compound of Formula IV:

IV

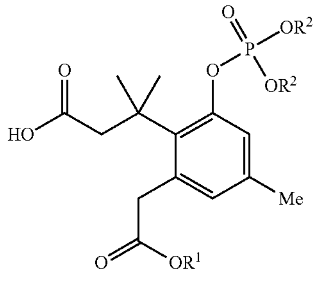

or a salt thereof.

62. The process of embodiment 61, wherein the oxidizing comprises reacting the compound of Formula V, or a salt thereof with an oxidizing agent in the presence of a base and an oxidation catalyst.

63. The process of embodiment 62, wherein the oxidizing agent is selected from the group consisting of (diacetoxyiodo)benzene, (bis(trifluoroacetoxy)iodo)benzene, 2-iodoxybenzoic acid, N-chlorosuccinimide, N-bromosuccinimide, N-chlorotosylamide sodium salt, bromine, chlorine, iodine, sodium hypochlorite, sodium chlorite, hydrogen peroxide, sodium peroxide, t-butyl hydrogen peroxide, sodium perborate, potassium peroxymonosulfate, and sodium periodate, or any combination thereof.

64. The process of embodiment 62, wherein the oxidizing agent is (diacetoxyiodo)benzene.

65. The process of any one of embodiments 61 to 64, wherein the base is selected from the group consisting of sodium phosphate dibasic, sodium hydroxide, potassium hydroxide, potassium phosphate monobasic, potassium phosphate dibasic, potassium phosphate tribasic, cesium carbonate, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, collidine, 1-methylimidazole, tetrabutylammonium bisulfate, and tetrabutylammonium chloride.

66. The process of any one of embodiments 61 to 64, wherein the base is sodium phosphate dibasic.

67. The process of any one of embodiments 61 to 66, wherein the oxidation catalyst is selected from the group consisting of 2,2,6,6-tetramethylpiperidine 1-oxyl, 2-azaadamantane N-oxyl, ruthenium trichloride, ruthenium tetraoxide, and osmium tetraoxide.

68. The process of any one of embodiments 61 to 66, wherein the oxidation catalyst is 2,2,6,6-tetramethylpiperidine 1-oxyl.

69. The process of any one of embodiments 61 to 68, wherein the oxidizing is performed a temperature of from about −20° C. to about 100° C.

70. The process of any one of embodiments 61 to 69, wherein the oxidizing is performed in a solvent comprising methyl tert-butyl ether, acetonitrile, and water.

71. The process of any one of embodiments 26 to 70, wherein the compound of Formula VII, or a salt thereof, is prepared by deprotecting a compound of Formula VIII:

VIII

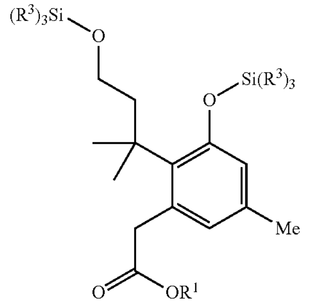

or a salt thereof, wherein each $R^3$ is independently $C_{1-6}$ alkyl.

72. The process of embodiment 71, wherein the deprotecting comprises reacting the compound of Formula VII with a deprotecting agent selected from the group consisting of lithium hydroxide, potassium hydrogen fluoride, tetrabutylammonium fluoride, potassium fluoride, sodium hydroxide, potassium hydroxide, potassium phosphate dibasic, potassium phosphate tribasic, cesium carbonate, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, collidine, 1-methylimidazole, hydrofluoric acid, hydrochloric acid, sulfuric acid, methanesulfonic acid, N-chlorosuccinimide, potassium peroxymonosulfate, and iodine, or any combination thereof in the presence of water.

73. The process of embodiment 72, wherein the deprotecting agent is lithium hydroxide.

74. The process of any one of embodiments 71 to 73, wherein the deprotecting is performed a temperature of from about 0° C. to about 100° C.

75. The process of any one of embodiments 71 to 74, wherein the deprotecting is performed in a solvent comprising tetrahydrofuran and water.

76. The process of any one of embodiments 71 to 75, wherein each $R^3$ is independently selected from the group consisting of methyl and tert-butyl.

77. The process of any one of embodiments 71 to 76, wherein the compound of Formula VIII is a compound of Formula VIII-a:

VIII-a

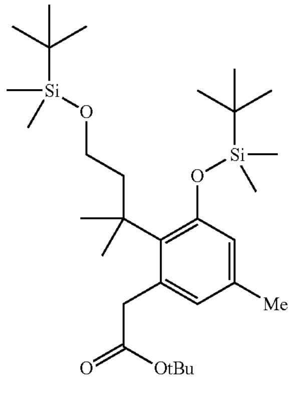

or a salt thereof.

78. The process of any one of embodiments 71 to 77, wherein the compound of Formula VIII, or a salt thereof, is prepared by a process comprising reacting a compound of Formula XIV:

XIV

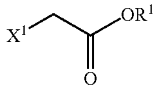

or a salt thereof, with an activator in the presence of zinc to form a first mixture; and mixing the first mixture with a compound of Formula IX:

IX

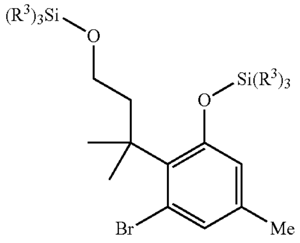

or a salt thereof, in the presence of a coupling catalyst, wherein $X^1$ is halo.

79. The process of embodiments 78, wherein the activator is selected from the group consisting of trimethylsilyl chloride, triethylsilyl chloride, trimethylsilyl iodide, dibromoethane, dichloroethane, diisobutylaluminium hydride, and iodine.

80. The process of embodiments 78, wherein the activator is trimethylsilyl chloride.

81. The process of any one of embodiments 78 to 80, wherein the coupling catalyst comprises a palladium catalyst.

82. The process of any one of embodiments 78 to 81, wherein the coupling catalyst comprises a palladium catalyst and a phosphine ligand.

83. The process of embodiment 81 or 82, wherein the palladium catalyst is selected from the group consisting of tris(dibenzylideneacetone)dipalladium(0), palladium (II) chloride, palladium (II) bromide, palladium (II) acetate, palladium (II) trifluoroacetate, tetrakis(triphenylphosphine)palladium(0)), (2-dicyclohexylphosphino-2',4',6'-triisopropyl-1,1'-biphenyl)[2-(2'-amino-1,1'-biphenyl)]palladium(II) methanesulfonate, and (SP-4-3)-[dicyclohexyl[2',4',6'-tris(1-methylethyl)[1,1'-biphenyl]-2-yl]phosphine] (methanesulfonato-κO) [2'-(methylamino-κN)[1,1'-biphenyl]-2-yl-κC]palladium.

84. The process of embodiment 82, wherein the phosphine ligand is selected from the group consisting of 2-dicyclohexylphosphino-2',4',6'-triisopropylbiphenyl, tricyclohexylphosphine, tri-tert-butyl phosphine, triphenyl phosphine), 2-dicyclohexylphosphino-2',6'-dimethoxybiphenyl, and ethylenebis(diphenylphosphine).

85. The process of any one of embodiments 78 to 80, wherein the coupling catalyst comprises tris(dibenzylideneacetone)dipalladium and 2-dicyclohexylphosphino-2',4',6'-triisopropylbiphenyl.

86. The process of any one of embodiments 78 to 85, wherein the mixing of the first mixture with the compound of Formula IX is performed at a temperature of from about 0° C. to about 100° C.

87. The process of any one of embodiments 78 to 86, wherein the mixing of the first mixture with the compound of Formula IX is performed in a solvent comprising tetrahydrofuran.

88. The process of any one of embodiments 78 to 87, wherein the compound of Formula IX, or a salt thereof, is prepared by silylating a compound of Formula X:

X

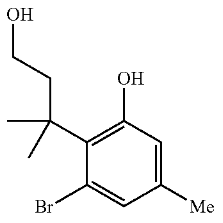

or a salt thereof.

89. The process of embodiment 88, wherein the silylating comprises reacting the compound of Formula IX, or a salt thereof, with a silylating agent of formula:

$Si(R^3)_3$-LG in the presence of a base and silylating catalyst, wherein each $R^3$ is independently $C_{1-6}$ alkyl; and LG is a leaving group.

90. The process of embodiment 89, wherein each $R^3$ is independently selected from the group consisting of methyl and tert-butyl.

91. The process of embodiment 89 or 90, wherein LG is selected from the group consisting of chloride, bromide, iodide, methanesulfonate, trifluoromethanesulfonate, and p-toluenesulfonate.

92. The process of embodiment 89, wherein the silylating agent is tert-butyl(chloro)dimethylsilane.

93. The process of any one of embodiments 89 to 92, wherein the base is selected from the group consisting of imidazole, triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, pyridine, 2,6-lutidine, collidine, 1-methylimidazole, lithium carbonate, sodium carbonate, potassium carbonate, calcium carbonate, potassium phosphate monobasic, potassium phosphate dibasic, potassium phosphate tribasic, sodium phosphate monobasic, sodium phosphate dibasic, and sodium phosphate tribasic.

94. The process of any one of embodiments 89 to 92, wherein the base is imidazole.

95. The process of any one of embodiments 89 to 94, wherein the silylating catalyst is selected from the group consisting of 4-dimethylaminopyridine, N-methylimidazole, 1-hydroxy-7-azabenzotriazole, 1-hydroxybenzotriazole, tetrabutyl ammonium bromide, and tetrabutyl ammonium iodide.

96. The process of any one of embodiments 89 to 94, wherein the silylating catalyst is 4-dimethylaminopyridine.

97. The process of any one of embodiments 88 to 96, wherein the silylating is performed at a temperature of from about 0° C. to about 100° C.

98. The process of any one of embodiments 88 to 97, wherein the silylating is performed in a solvent comprising N,N-dimethylformamide.

99. The process of any one of embodiments 88 to 98, wherein the compound of Formula X, or a salt thereof, is prepared by reducing a compound of Formula XI-a:

XI-a

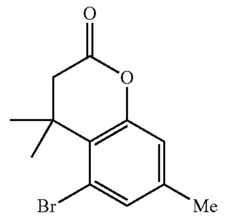

or a salt thereof.

100. The process of embodiment 99, wherein the reducing comprises reacting the compound of Formula X, or a salt thereof, in the presence of a reducing agent selected from the group consisting of lithium aluminum hydride, diisobutylaluminum hydride, aluminum hydride, sodium bis(2-methoxyethoxy)aluminum hydride, borane tetrahydrofuran complex, diborane, $I_2/NaBH_4$, and borane dimethyl sulfide complex.

101. The process of embodiment 100, wherein the reducing agent is lithium aluminum hydride.

102. The process of any one of embodiments 99 to 101, wherein the reducing is performed at a temperature of from about −20° C. to about 100° C.

103. The process of any one of embodiments 99 to 102, wherein the reducing is performed in a solvent comprising tetrahydrofuran.

104. The process of any one of embodiments 1 to 103, wherein the compound of Formula XI-a, or a salt thereof, is prepared by reacting 3-bromo-5-methylphenol with methyl 3,3-dimethylacrylate in the presence of an acid.

105. The process of embodiment 104, wherein the acid is selected from the group consisting of methane sulfonic acid, sulfuric acid, hydrochloric acid, hydrobromic acid, acetic acid, pivalic acid, phosphoric acid, p-toluenesulfonic acid, boron trichloride, lithium bromide, magnesium chloride, aluminum chloride, lithium triflate, magnesium triflate, and aluminum triflate.

106. The process of embodiment 104, wherein the acid is methane sulfonic acid.

107. The process of any one of embodiments 104 to 106, wherein the reacting is performed at a temperature of from about 0° C. to about 200° C.

108. The process of any one of embodiments 104 to 107, wherein the reacting is performed in the absence of a solvent.

109. The process of any one of embodiments 14 to 25 and 61 to 108, further comprising coupling the compound of Formula IV, or a salt thereof, with a compound of Formula III:

III

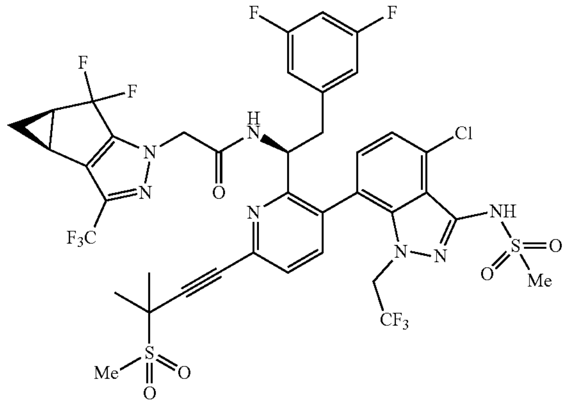

or a salt thereof, to form a compound of Formula II:

II

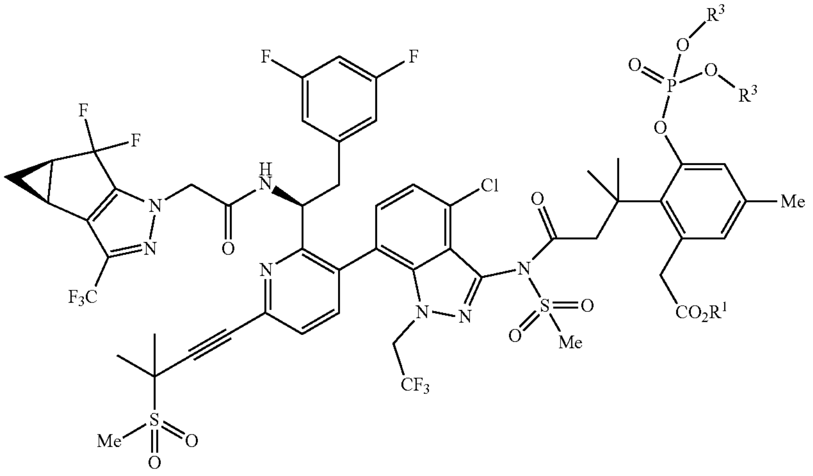

or a salt thereof.

110. The process of embodiment 109, wherein the coupling comprises reacting the compound of Formula IV, or a salt thereof, with the compound of Formula III, or a salt thereof, in the presence of a coupling agent and a base.

111. The process of embodiment 110, wherein the coupling agent is selected from the group consisting of N,N,N',N'-tetramethylchloroformamidinium hexafluorophosphate, 1,1'-carbonyldiimidazole, thionyl chloride, phosgene, triphosgene, ethyl chloroformate, isobutyl chloroformate, dicyclohexylcarbodiimide, diisopropylcarbodiimide, 1-ethyl-3-(3-dimethylaminopropyl)carbodiimide), propanephosphonic acid anhydride, HATU, HBTU, TATU, TBTU, HCTU, BOP, PyBOP, and COMU.

112. The process of embodiment 110, wherein the coupling agent is N,N,N',N'-tetramethylchloroformamidinium hexafluorophosphate or propanephosphonic acid anhydride.

113. The process of any one of embodiments 110 to 112, wherein the base is selected from the group consisting of 1-methylimidazole, diisopropylethylamine, 4-methylmorpholine, pyridine, 2,6-lutidine, imidazole, lithium carbonate, sodium carbonate, potassium carbonate, cesium carbonate, lithium bicarbonate, sodium bicarbonate, potassium bicarbonate, sodium phosphate, and potassium phosphate.

114. The process of any one of embodiments 110 to 112, wherein the base is 1-methylimidazole.

115. The process of any one of embodiments 109 to 114, wherein the coupling is performed at a temperature of from about −30° C. to about 60° C.

116. The process of any one of embodiments 109 to 115, wherein the coupling is performed in a solvent comprising acetonitrile.

117. The process of any one of embodiments 109 to 116, wherein the compound of Formula II is a compound of Formula II-a:

II-a

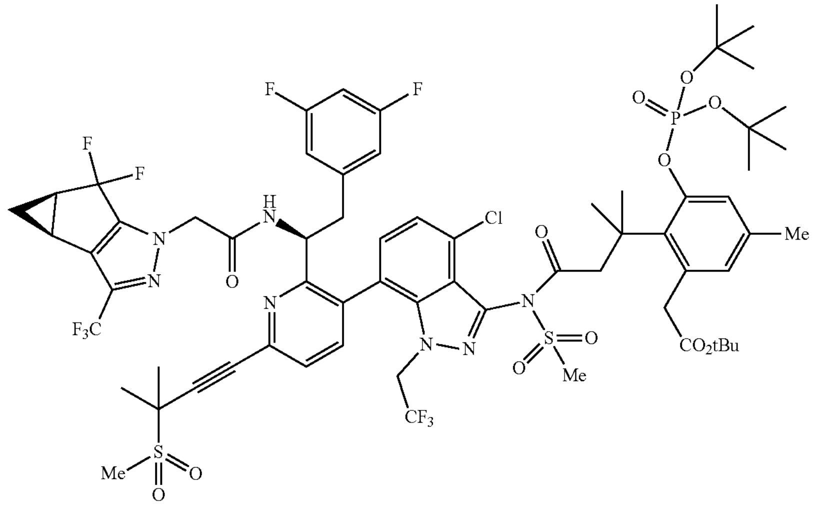

or a salt thereof.

118. The process of any one of embodiments 109 to 117, further comprising deprotecting the compound of Formula II, or a salt thereof, to form a compound of Formula I:

I

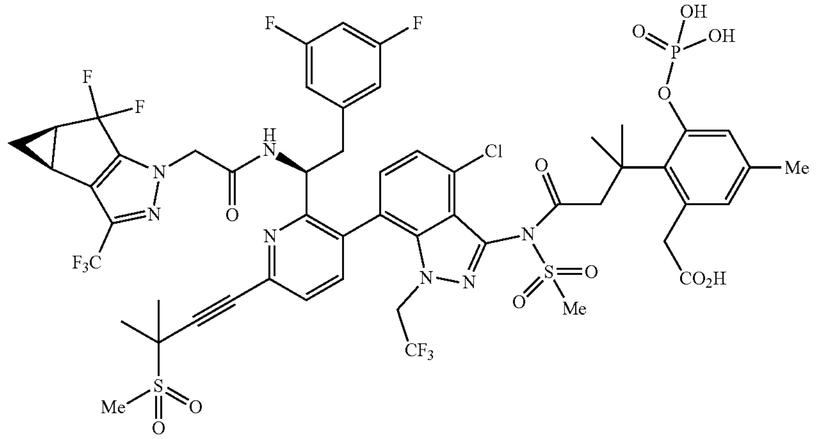

or a salt thereof

119. The process of embodiments 118, wherein the deprotecting comprises reacting the compound of Formula II, or a salt thereof, in the presence of an acid.

120. The process of embodiments 119, wherein the acid is selected from the group consisting of phosphoric acid, trifluoroacetic acid, trichloroacetic acid, formic acid, hydrofluoric acid, hydrochloric acid, sulfuric acid, methanesulfonic acid, p-toluenesulfonic acid, and camphorsulfonic acid.

121. The process of embodiments 119, wherein the acid is phosphoric acid.

122. The process of any one of embodiments 118 to 121, wherein the deprotecting is performed at a temperature of from about −20° C. to about 100° C.

123. The process of any one of embodiments 118 to 122, wherein the coupling is performed in a solvent comprising acetonitrile and water.

124. In some embodiments, the present disclosure provides a process of preparing a compound of Formula I:

I

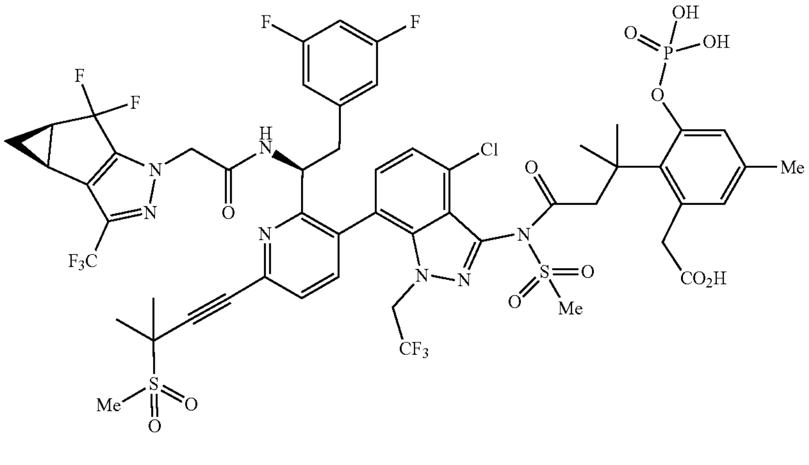

or a salt thereof, comprising:

reacting a compound of Formula XIV-a:

XIV-a

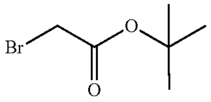

or a salt thereof, with diisobutylaluminium hydride in the presence of zinc and lithium chloride to form a first mixture; and mixing the first mixture with a compound of Formula XI-a:

XI-a

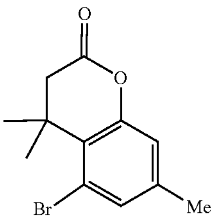

or a salt thereof, in the presence of palladium (II) acetate and 2-dicyclohexylphosphino-2',4',6'-triisopropylbiphenyl to form a compound of Formula XIII-a:

XIII-a

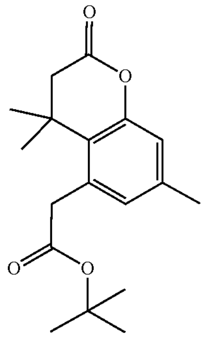

or a salt thereof;

reacting the compound of Formula XIII-a, or a salt thereof, with di-tert-butyl phosphite, bromoform, and trimethylsilanolate to form a compound of Formula IV-a:

IV-a

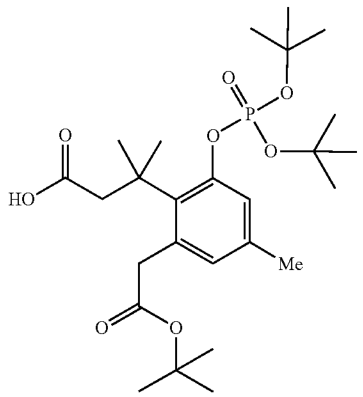

or a salt thereof, coupling the compound of Formula IV-a, or a salt thereof, with a compound of Formula III:

III

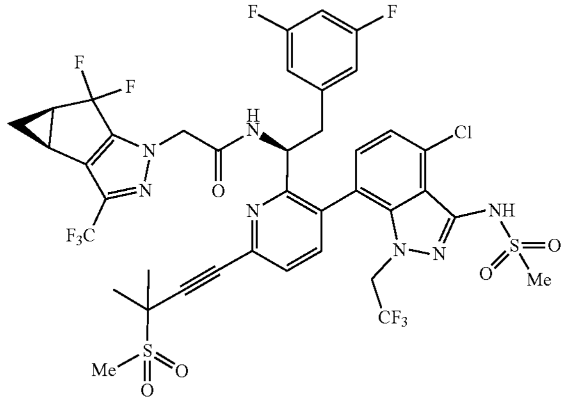

or a salt thereof, in the presence of N,N,N',N'-tetramethylchloroformamidinium hexafluorophosphate and 1-methylimidazole to form a compound of Formula II-a:

II-a

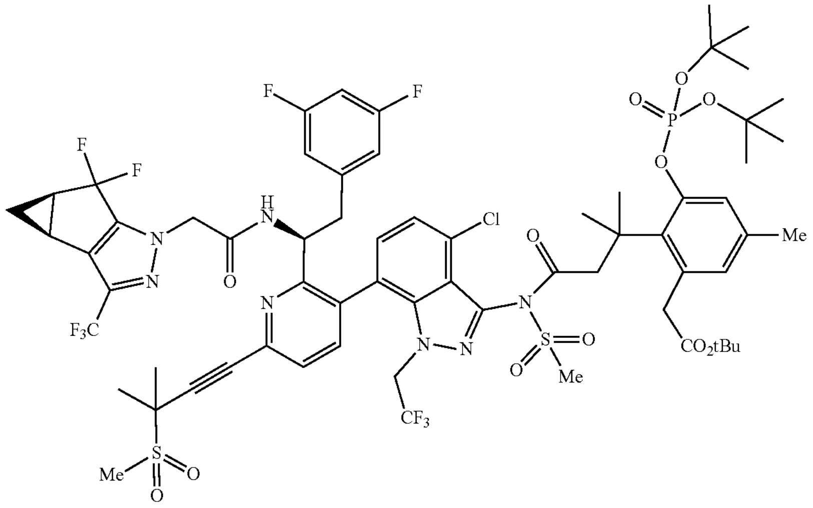

or a salt thereof, and deprotecting the compound of Formula II-a, or a salt thereof, with phosphoric acid to form the compound of Formula I, or a salt thereof.

125. In some embodiments, the present disclosure provides a process of preparing a compound of Formula I:

I

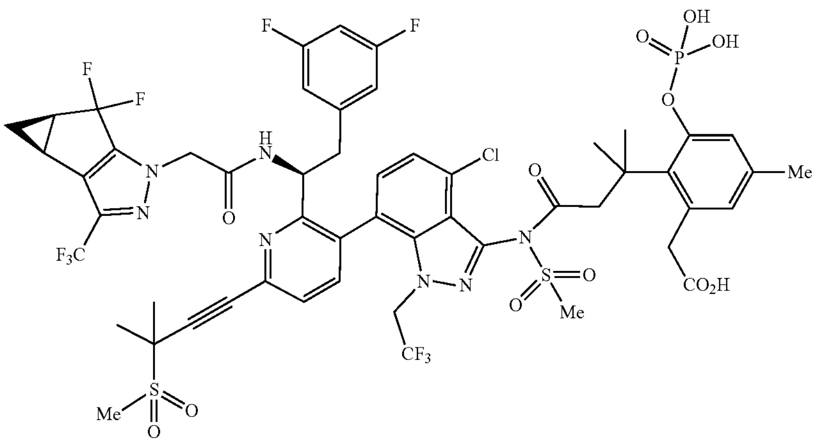

or a salt thereof, comprising:

reacting a compound of Formula VII-a:

VII-a

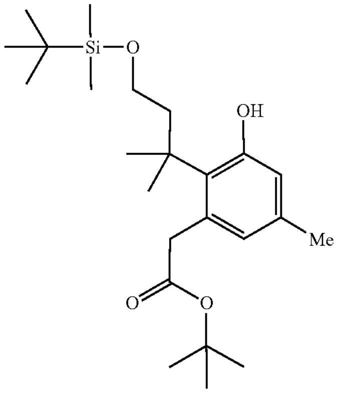

or a salt thereof, with di-tert-butyl phosphite in the presence of bromoform and cesium carbonate to form a compound of Formula VI-a:

VI-a

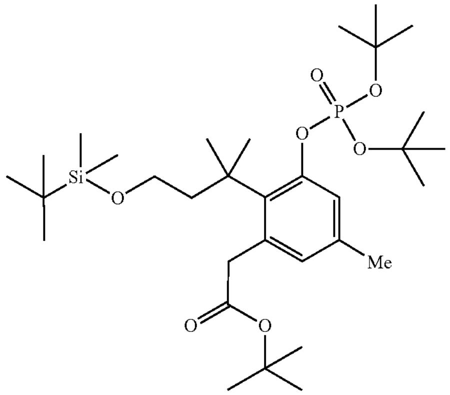

or a salt thereof;

deprotecting the compound of Formula VI-a, or a salt thereof, in the presence of tetrabutylammonium fluoride to form a compound of Formula V-a:

V-a

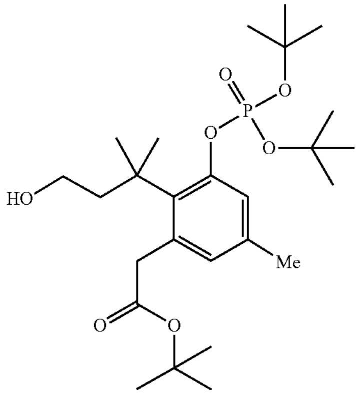

or a salt thereof;

oxidizing the compound of Formula V-a, or a salt thereof, in the presence of (diacetoxyiodo)benzene, sodium phosphate dibasic, and 2,2,6,6-tetramethylpiperidine 1-oxyl to form a compound of Formula IV-a:

IV-a

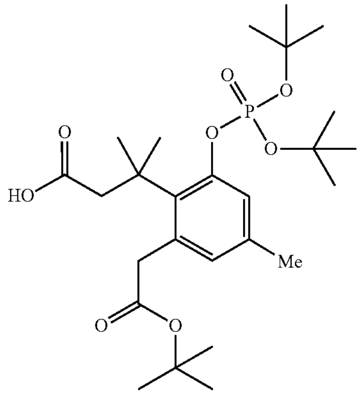

or a salt thereof;

coupling the compound of Formula IV-a, or a salt thereof, with a compound of Formula III:

III

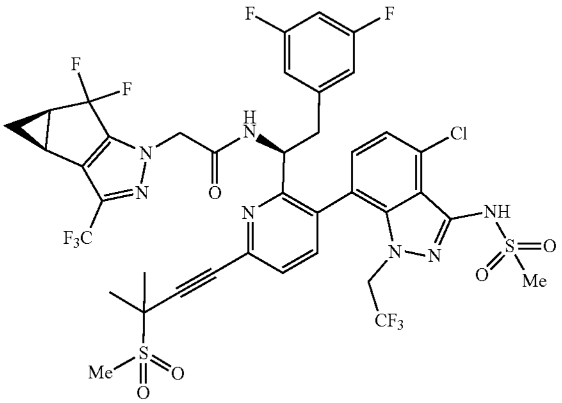

or a salt thereof, in the presence of N,N,N',N'-tetramethylchloroformamidinium hexafluorophosphate and 1-methylimidazole to form a compound of Formula II-a:

II-a
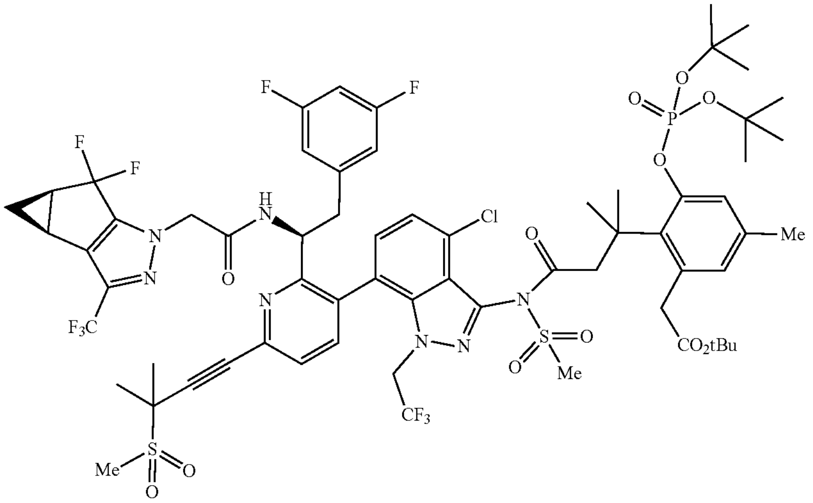
or a salt thereof; and
deprotecting the compound of Formula II-a, or a salt thereof, with phosphoric acid to form the compound of Formula I, or a salt thereof.
126. In some embodiments, the present disclosure provides a process of preparing a compound of Formula I:
I
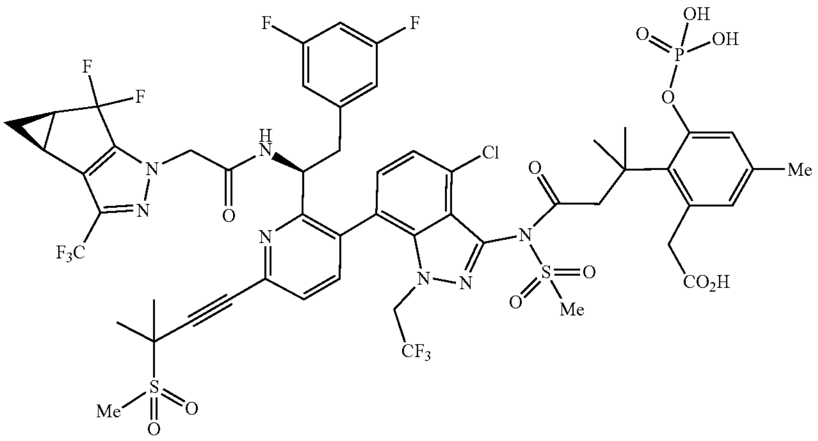

or a salt thereof, comprising:

reacting a compound of Formula VII-a:

VII-a

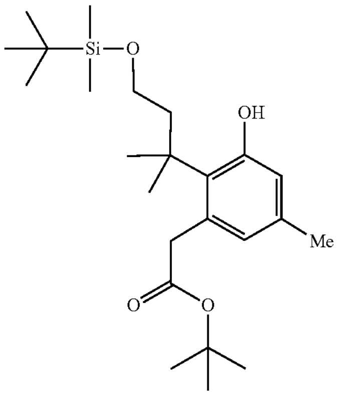

or a salt thereof, with tetrabenzyl pyrophosphate in the presence of sodium hydride to form a compound of Formula VI-b:

VI-b

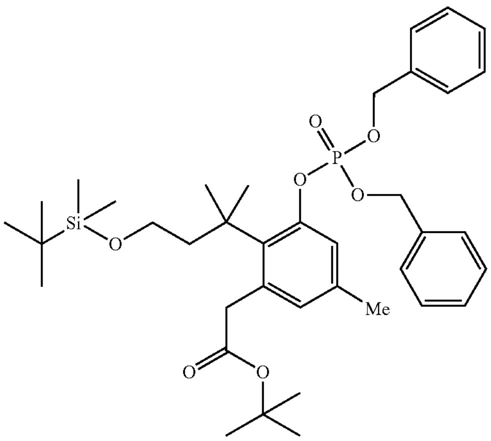

or a salt thereof;

deprotecting the compound of Formula VI-b, or a salt thereof, in the presence of tetrabutylammonium fluoride to form a compound of Formula V-b:

V-b

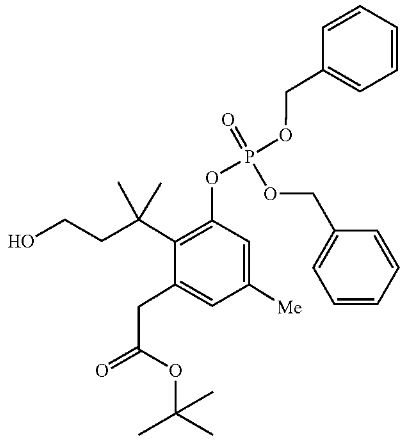

or a salt thereof;

oxidizing the compound of Formula V-b, or a salt thereof, in the presence of (diacetoxyiodo)benzene, sodium phosphate dibasic, and 2,2,6,6-tetramethylpiperidine 1-oxyl to form a compound of Formula IV-b:

IV-b

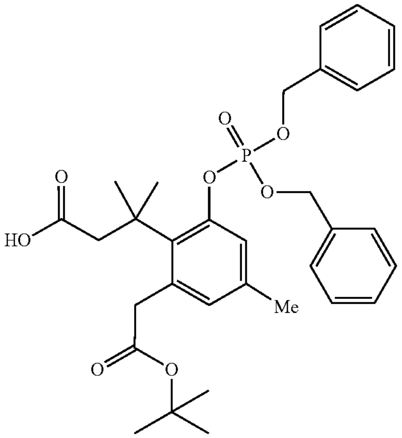

or a salt thereof;

coupling the compound of Formula IV-b, or a salt thereof, with a compound of Formula III:

III

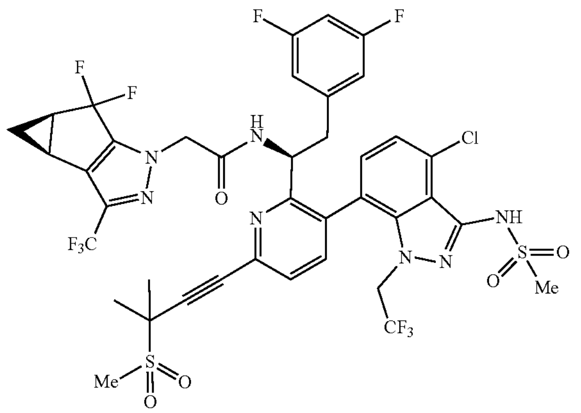

or a salt thereof, in the presence of N,N,N',N'-tetramethylchloroformamidinium hexafluorophosphate and 1-methylimidazole to form a compound of Formula II-b:

II-b

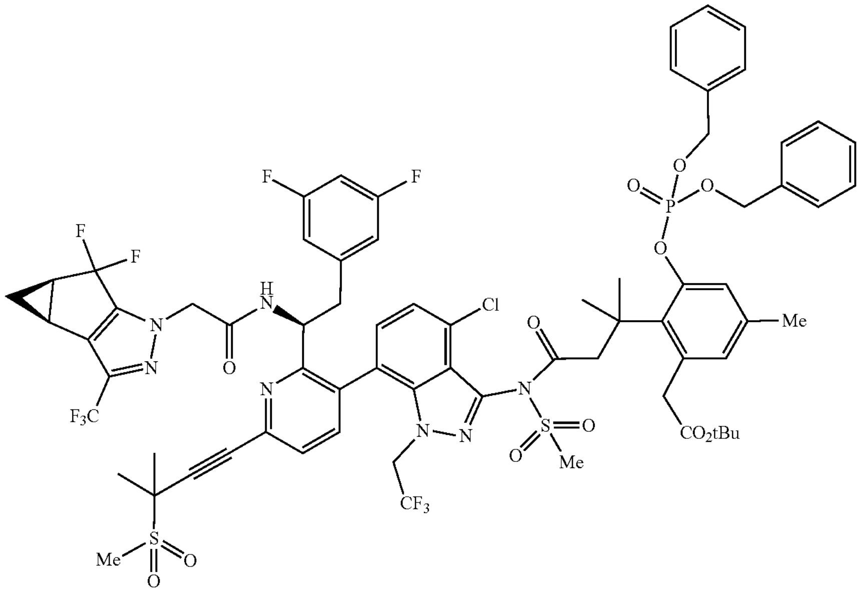

or a salt thereof, and deprotecting the compound of Formula II-b, or a salt thereof, with phosphoric acid to form the compound of Formula I, or a salt thereof.

127. In some embodiments, the present disclosure provides a process of preparing a compound of Formula I:

I

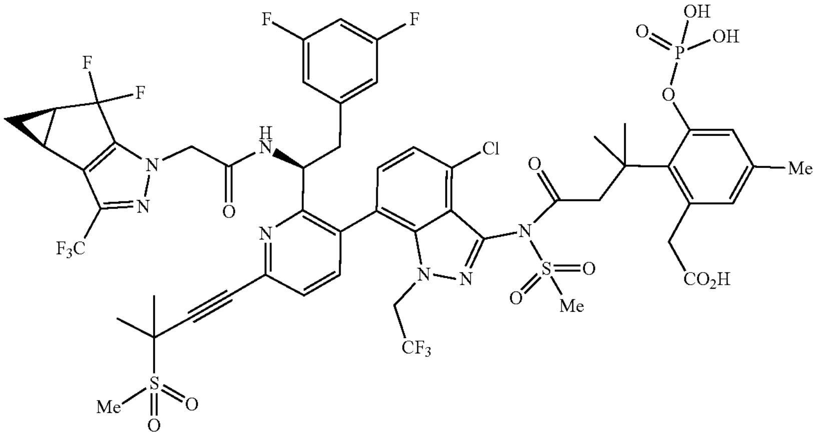

or a salt thereof, comprising:

reacting a compound of Formula VII-a:

VII-a

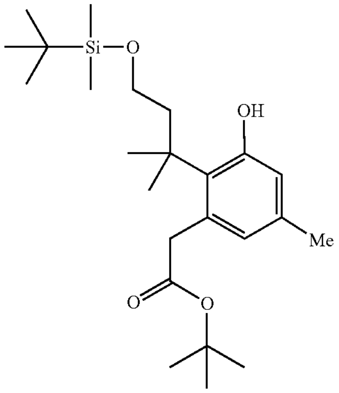

or a salt thereof, with di-tert-butyl N,N-diisopropylphosphoramidate in the presence of a 1-methylimidazole and trifluoroacetic acid to form a first mixture; and mixing the first mixture with hydrogen peroxide to form a compound of Formula VI-a:

VI-a

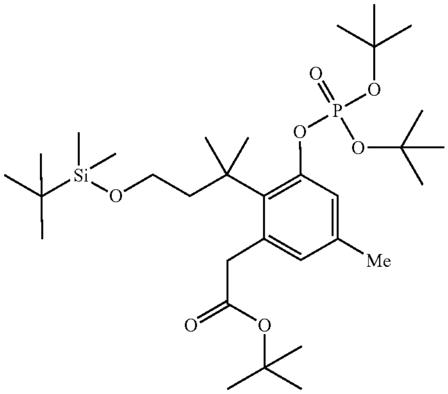

or a salt thereof;

deprotecting the compound of Formula VI-a, or a salt thereof, in the presence of tetrabutylammonium fluoride to form a compound of Formula V-a:

V-a

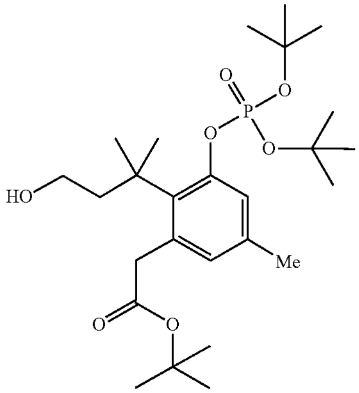

or a salt thereof;

oxidizing the compound of Formula V-a, or a salt thereof, in the presence of (diacetoxyiodo)benzene, sodium phosphate dibasic, and 2,2,6,6-tetramethylpiperidine 1-oxyl to form a compound of Formula IV-a:

IV-a
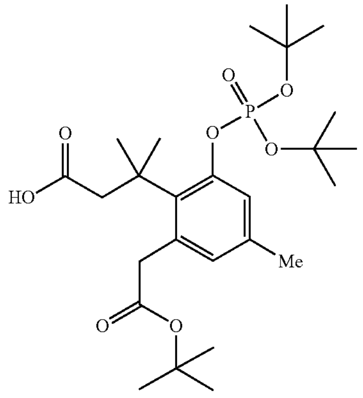
or a salt thereof;
coupling the compound of Formula IV-a, or a salt thereof, with a compound of Formula III:
III
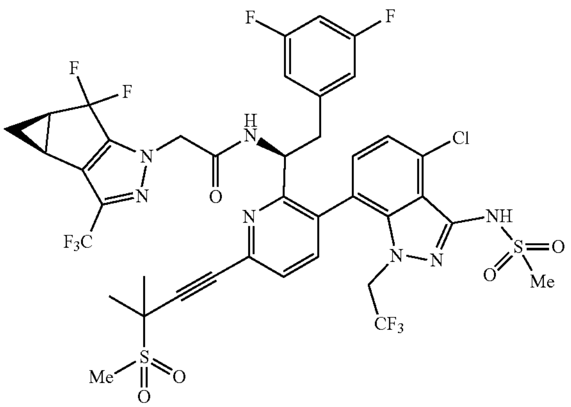
or a salt thereof, in the presence of N,N,N',N'-tetramethylchloroformamidinium hexafluorophosphate and 1-methylimidazole to form a compound of Formula II-a:
II-a
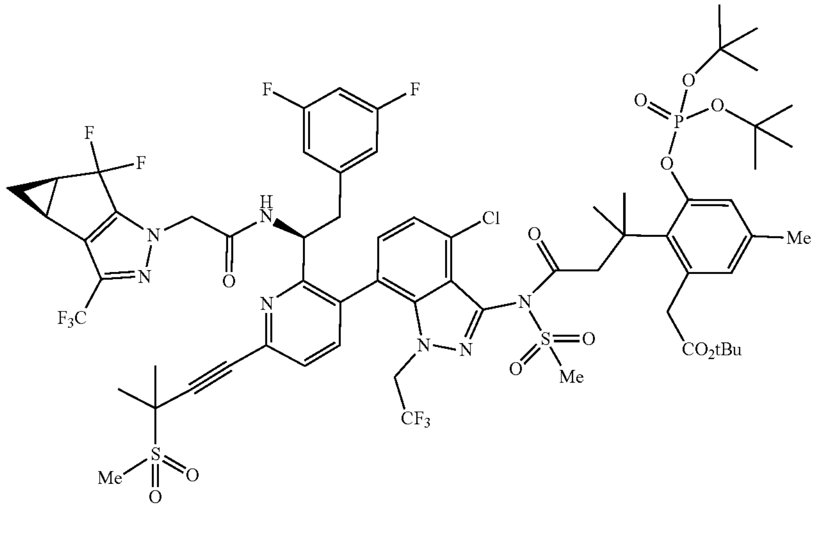

or a salt thereof; and deprotecting the compound of Formula II-a, or a salt thereof, with phosphoric acid to form the compound of Formula I, or a salt thereof.

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter, and is not intended to limit the appended claims to the specific embodiments illustrated.

What is claimed is:

1. A process of preparing a compound of Formula XIII:

XIII

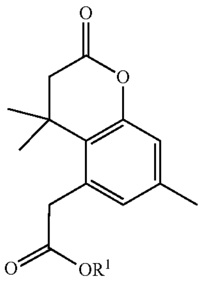

or a salt thereof, comprising reacting a compound of Formula XIV:

XIV

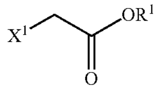

or a salt thereof, with an activator in the presence of zinc and optionally an alkali metal halide to form a first mixture; and mixing the first mixture with a compound of Formula XI-a:

XI-a

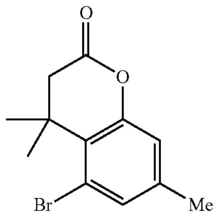

or a salt thereof, in the presence of a coupling catalyst, wherein:

$X^1$ is halo; and $R^1$ is $C_{1-6}$ alkyl.

2. The process of claim 1, wherein the activator is selected from the group consisting of diisobutylaluminium hydride, trimethylsilyl chloride, triethylsilyl chloride, trimethylsilyl iodide, dibromoethane, dichloroethane, and iodine.

3. The process of claim 1, wherein the coupling catalyst comprises a palladium catalyst and a phosphine ligand, wherein the palladium catalyst is selected from the group consisting of palladium (II) chloride, palladium (II) bromide, palladium (II) acetate, palladium (II) trifluoroacetate, bis(dibenzylideneacetone) palladium (0), tris (dibenzylideneacetone) dipalladium (0), tetrakis(triphenylphosphine) palladium (0), (2-dicyclohexylphosphino-2',4',6'-triisopropyl-1,1'-biphenyl)[2-(2'-amino-1,1'-biphenyl)]palladium (II) methanesulfonate, and (SP-4-3)-[dicyclohexyl[2',4',6'-tris(1-methylethyl) [1,1'-biphenyl]-2-yl]phosphine] (methanesulfonato-κO)[2'-(methylamino-κN) [1,1'-biphenyl]-2-yl-κC] palladium; and the phosphine ligand is selected from the group consisting of 2-dicyclohexylphosphino-2',4',6'-triisopropylbiphenyl, tricyclohexylphosphine, tri-tert-butyl phosphine, triphenyl phosphine, 2-dicyclohexylphosphino-2',6'-dimethoxybiphenyl, and ethylenebis(diphenylphosphine).

4. A process of preparing a compound of Formula XIII:

XIII

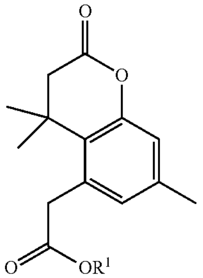

or a salt thereof, comprising reacting a compound of Formula XI-b:

XI-b

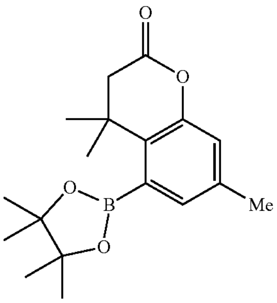

or a salt thereof, with a compound of Formula XIV:

XIV

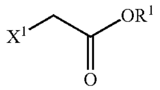

or a salt thereof, under Suzuki coupling conditions, wherein:

$X^1$ is halo; and $R^1$ is $C_{1-6}$ alkyl.

5. The process of claim 4, wherein the Suzuki coupling conditions comprise reacting the compound of Formula XI-b, or a salt thereof, with the compound of Formula XIV, or a salt thereof, in the presence of a palladium catalyst, a base, and optionally in the presence of a ligand.

6. The process of claim 5, wherein the palladium catalyst is selected from palladium (II) chloride, palladium (II) bromide, palladium (II) acetate, palladium (II) trifluoroacetate, bis(dibenzylideneacetone) palladium (0), tetrakis(triphenylphosphine) palladium (0)), (2-dicyclohexylphosphino-2',4',6'-triisopropyl-1,1'-biphenyl) [2-(2'-amino-1,1'-biphenyl)] palladium (II) methanesulfonate, (SP-4-3)-[dicyclohexyl[2',4',6'-tris(1-methylethyl) [1,1'-biphenyl]-2-yl] phosphine] (methanesulfonato-κO) [2'-(methylamino-κN) [1,1'-biphenyl]-2-yl-KC] palladium;

the base is selected from sodium hydroxide, potassium hydroxide, potassium phosphate dibasic, potassium phosphate tribasic, cesium carbonate, potassium propionate, triethylamine, N-methylmorpholine, tripropylamine, and N,N-diisopropylethylamine; and the ligand is selected from tricyclohexylphosphine, tri-tert-butyl phosphine, triphenyl phosphine, 2-dicyclohexylphosphino-2',6'-dimethoxybiphenyl, ethylenebis (diphenylphosphine), and 1,3,5,7-tetramethyl-6-phenyl-2,4,8-trioxa-6-phosphaadamantane.

7. The process of claim 4, wherein the compound of Formula XI-b, or a salt thereof, is prepared by borylating a compound of Formula XI-a:

XI-a

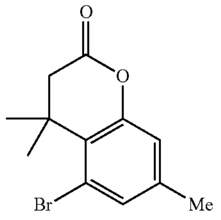

or a salt thereof, with a diboron reagent in the presence of a palladium catalyst, a base, and optionally in the presence of a ligand.

8. The process of claim 7, wherein the diboron reagent is bis(pinacolato)diboron.

9. The process of claim 7, wherein the palladium catalyst is selected from palladium (II) chloride, palladium (II) bromide, palladium (II) acetate, palladium (II) trifluoroacetate, bis(dibenzylideneacetone) palladium (0), tetrakis(triphenylphosphine) palladium (0), (2-dicyclohexylphosphino-2',4',6'-triisopropyl-1,1'-biphenyl) [2-(2'-amino-1,1'-biphenyl)] palladium (II) methanesulfonate, and (SP-4-3)-[dicyclohexyl[2',4',6'-tris(1-methylethyl) [1,1'-biphenyl]-2-yl] phosphine] (methanesulfonato-κO) [2'-(methylamino-κN) [1,1'-biphenyl]-2-yl-KC] palladium;

the ligand is selected from tricyclohexylphosphine, tri-tert-butyl phosphine, triphenylphosphine, tri (o-tolyl) phosphine, 2-dicyclohexylphosphino-2',6'-dimethoxybiphenyl, ethylenebis(diphenylphosphine); and the base is selected from sodium acetate, sodium hydroxide, potassium hydroxide, potassium phosphate dibasic, potassium phosphate tribasic, cesium carbonate, potassium propionate, triethylamine, N-methylmorpholine, tripropylamine, and N,N-diisopropylethylamine.

10. The process of claim 1, wherein the compound of Formula XIV is a compound of Formula XIV-a:

XIV-a

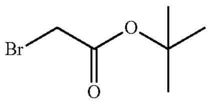

or a salt thereof.

11. The process of claim 1, wherein the compound of Formula XIII is a compound of Formula XIII-a:

XIII-a

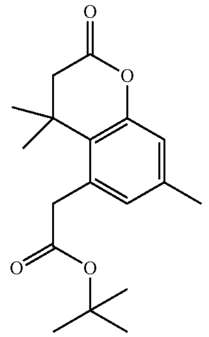

or a salt thereof.

12. The process of claim 1, further comprising phosphorylating the compound of Formula XIII, or a salt thereof, to form a compound of Formula IV:

IV

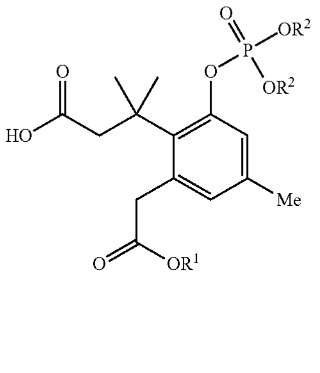

or a salt thereof, wherein each $R^2$ is independently selected from the group consisting of $C_{1-6}$ alkyl.

13. The process of claim 12, wherein the phosphorylating comprises reacting the compound of Formula XIII, or a salt thereof, with a phosphorylating agent, optionally in the presence of an oxidizing agent and a base.

14. The process of claim 13, wherein the phosphorylating agent is selected from the group consisting of di-tert-butyl phosphite, di-tert-butyl phosphoryl chloride, di-tert-butyl phosphoryl bromide, di-ethyl phosphoryl chloride, di-isopropyl phosphoryl chloride, dibenzyl phosphorochloridate, and dibenzyl phosphorobromidate;

the oxidizing agent is selected from the group consisting of bromoform, carbon tetrabromide, carbon tetrachloride, dibromomethane, dibromoethane, bromotrichloromethane, N-chlorosuccinimide, N-bromosuccinimide, N-chlorotosylamide sodium salt, bromine, chlorine, iodine, and sodium hypochlorite; and the base is selected from the group consisting of sodium trimethylsilanolate, potassium hydroxide, sodium hydroxide, lithium hydroxide, sodium tert-butoxide, sodium hydride, and cesium carbonate.

15. The process of claim 12, wherein the compound of Formula IV is a compound of Formula IV-a:

IV-a

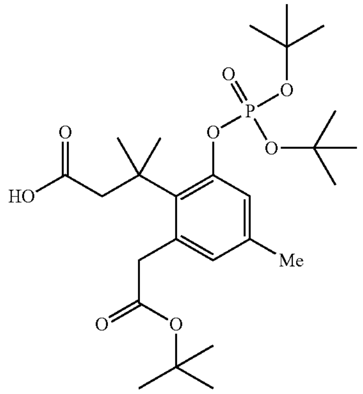

or a salt thereof.

16. The process of claim 1, wherein the compound of Formula XI-a, or a salt thereof, is prepared by reacting 3-bromo-5-methylphenol with methyl 3,3-dimethylacrylate in the presence of an acid selected from the group consisting of methane sulfonic acid, sulfuric acid, hydrochloric acid, hydrobromic acid, acetic acid, pivalic acid, phosphoric acid, p-toluenesulfonic acid, boron trichloride, lithium bromide, magnesium chloride, aluminum chloride, lithium triflate, magnesium triflate, and aluminum triflate.

17. The process of claim 12, further comprising coupling the compound of Formula IV, or a salt thereof, with a compound of Formula III:

III

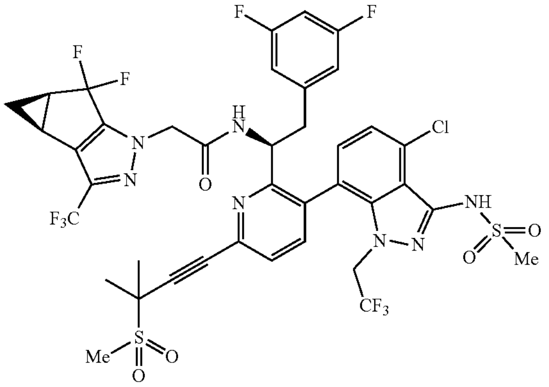

or a salt thereof, to form a compound of Formula II:

II

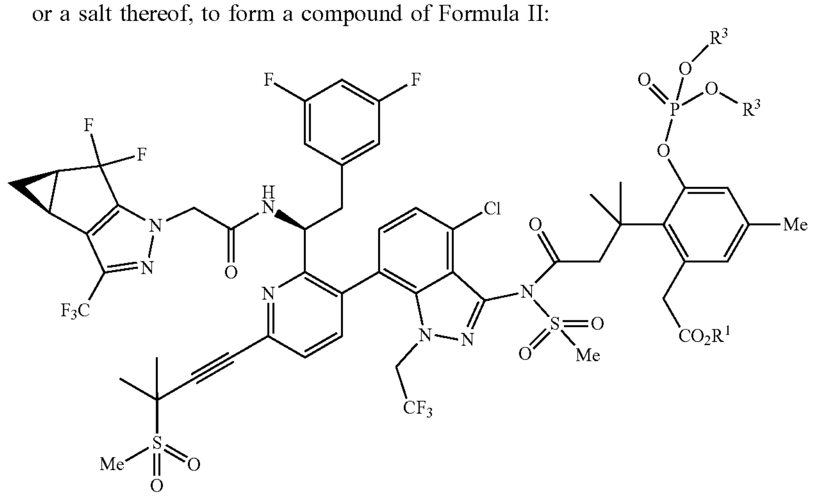

or a salt thereof.

18. The process of claim 17, wherein the coupling comprises reacting the compound of Formula IV, or a salt thereof, with the compound of Formula III, or a salt thereof, in the presence of a coupling agent and a base.

19. The process of claim 18, wherein the coupling agent is selected from the group consisting of N,N,N',N'-tetramethylchloroformamidinium hexafluorophosphate, 1,1'-carbonyldiimidazole, thionyl chloride, phosgene, triphosgene, ethyl chloroformate, isobutyl chloroformate, dicyclohexylcarbodiimide, diisopropylcarbodiimide, 1-ethyl-3-(3-dimethylaminopropyl) carbodiimide), propanephosphonic acid anhydride, HATU, HBTU, TATU, TBTU, HCTU, BOP, PyBOP, and COMU; and the base is selected from the group consisting of 1-methylimidazole, diisopropylethylamine, 4-methylmorpholine, pyridine, 2,6-lutidine, imidazole, lithium carbonate, sodium carbonate, potassium carbonate, cesium carbonate, lithium bicarbonate, sodium bicarbonate, potassium bicarbonate, sodium phosphate, and potassium phosphate.

20. The process of claim 17, wherein the compound of Formula II is a compound of Formula II-a:

II-a

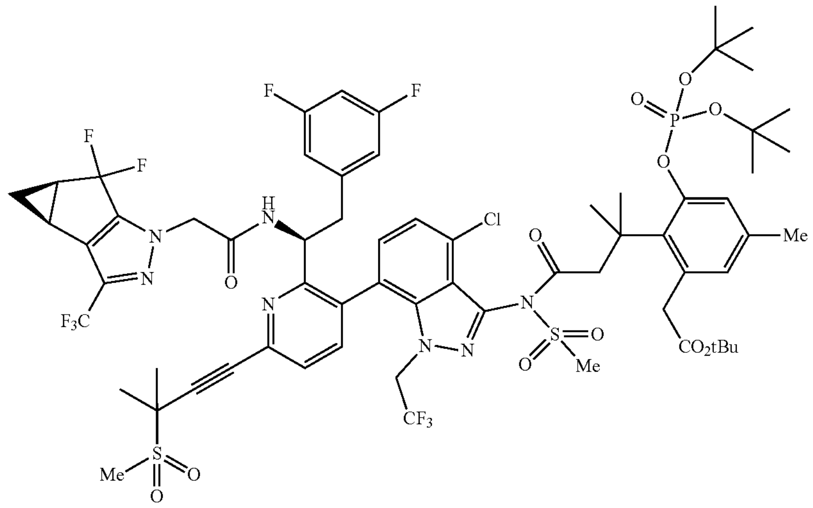

or a salt thereof.

21. The process of claim 18, further comprising deprotecting the compound of Formula II, or a salt thereof, to form a compound of Formula I:

I

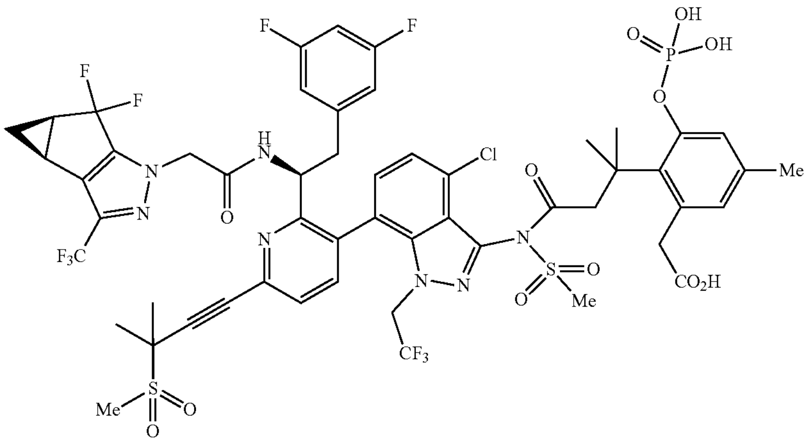

or a salt thereof.

22. The process of claim 21, wherein the deprotecting comprises reacting the compound of Formula II, or a salt thereof, in the presence of an acid selected from the group consisting of phosphoric acid, trifluoroacetic acid, trichloroacetic acid, formic acid, hydrofluoric acid, hydrochloric acid, sulfuric acid, methanesulfonic acid, p-toluenesulfonic acid, and camphorsulfonic acid.

23. A process of preparing a compound of Formula I:

I

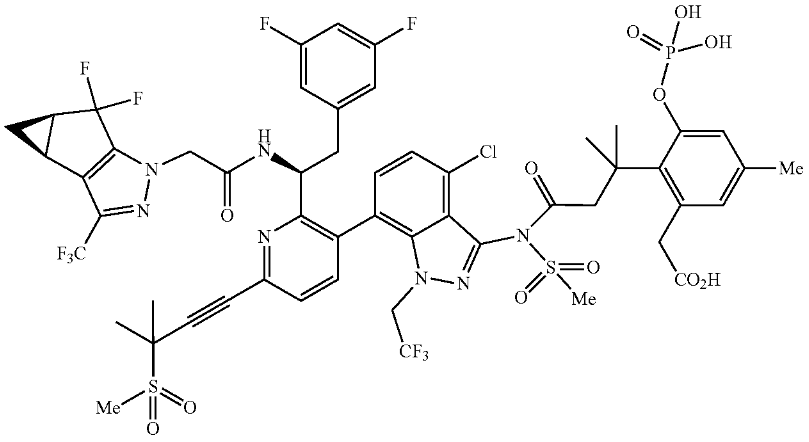

or a salt thereof, comprising:

reacting 3-bromo-5-methylphenol with methyl 3,3-dimethylacrylate in the presence of sulfuric acid to form a compound of Formula XI-a:

XI-a

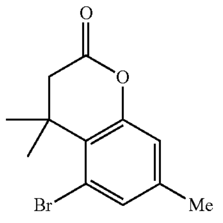

or a salt thereof;

reacting a compound of Formula XIV-a:

XIV-a

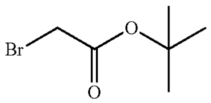

or a salt thereof, with trimethylsilyl chloride in the presence of zinc to form a first mixture; and mixing the first mixture with the compound of Formula XI-a, or a salt thereof, in the presence of bis(dibenzylideneacetone) palladium (0) and 2-dicyclohexylphosphino-2',4',6'-triisopropylbiphenyl to form a compound of Formula XIII-a:

XIII-a

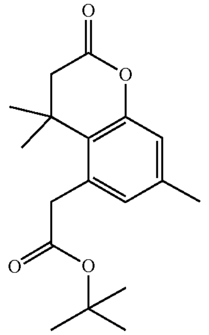

or a salt thereof;

reacting the compound of Formula XIII-a, or a salt thereof, with di-tert-butyl phosphite, bromoform, and sodium trimethylsilanolate to form a compound of Formula IV-a:

IV-a

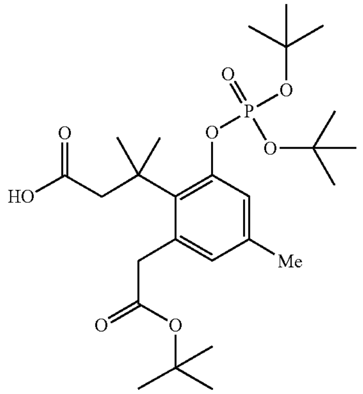

or a salt thereof, coupling the compound of Formula IV-a, or a salt thereof, with a compound of Formula III:

III

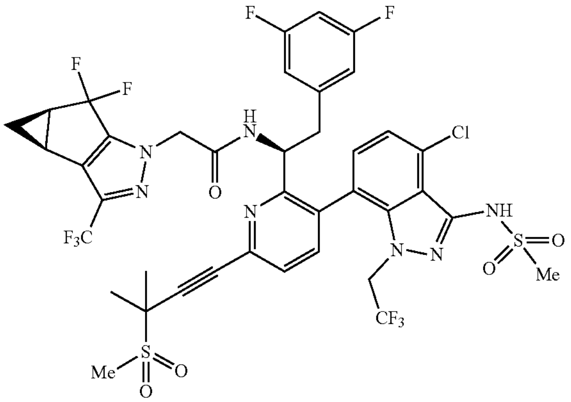

or a salt thereof, in the presence of propanephosphonic acid anhydride and 1-methylimidazole to form a compound of Formula II-a:

II-a
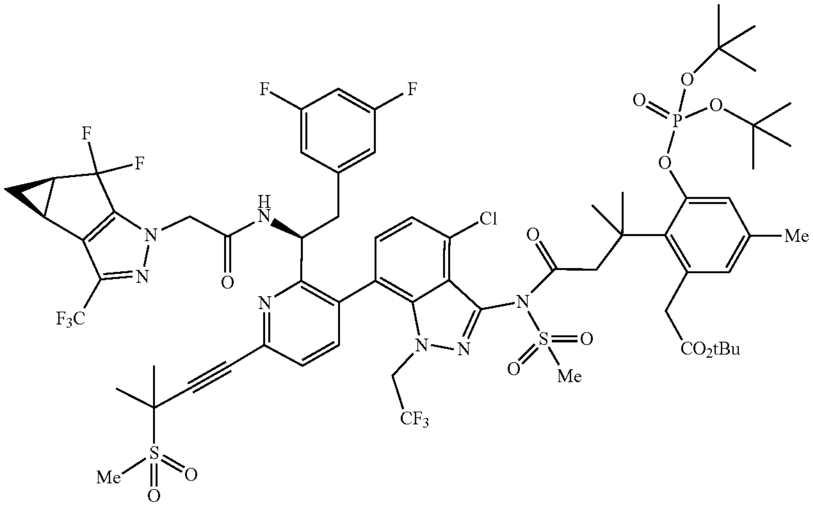
or a salt thereof; and
deprotecting the compound of Formula II-a, or a salt thereof, with phosphoric acid to form the compound of Formula I, or a salt thereof.
24. A process of preparing a compound of Formula I:
I
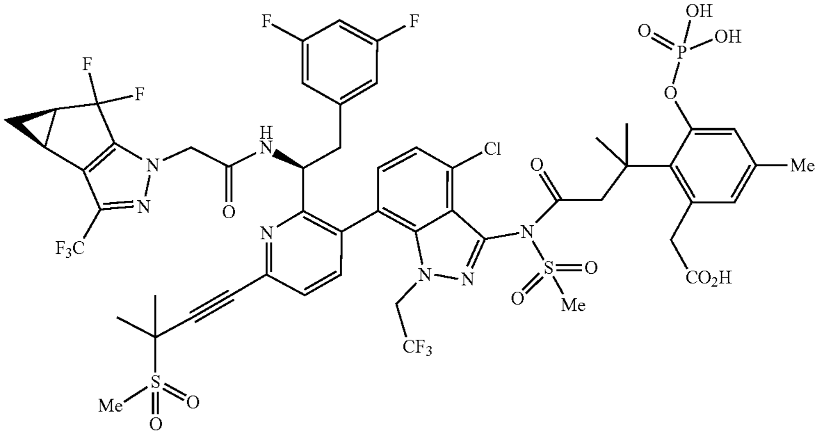

or a salt thereof, comprising:

reacting 3-bromo-5-methylphenol with methyl 3,3-dimethylacrylate in the presence of sulfuric acid to form a compound of Formula XI-a:

XI-a

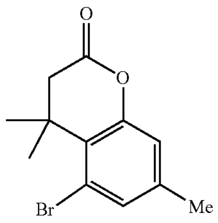

or a salt thereof;

reacting the compound of Formula XI-a, or a salt thereof, with bis(pinacolato)diboron in the presence of bis(dibenzylideneacetone) palladium (0), triphenylphosphine, and potassium propionate to form a compound of Formula XI-b:

XI-b

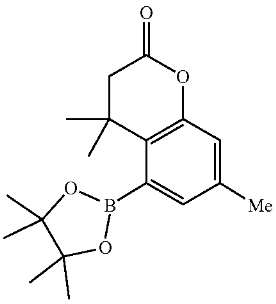

or a salt thereof;

reacting the compound of Formula XI-b, or a salt thereof, with a compound of Formula XIV-a:

XIV-a

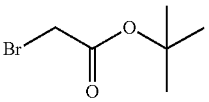

or a salt thereof, in the presence of bis(dibenzylideneacetone) palladium (0), potassium phosphate tribasic, and 1,3,5,7-tetramethyl-6-phenyl-2,4,8-trioxa-6-phospha-adamantane to form a compound of Formula XIII-a:

XIII-a

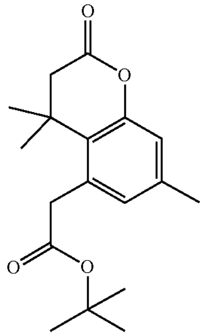

or a salt thereof;

reacting the compound of Formula XIII-a, or a salt thereof, with di-tert-butyl phosphite, bromoform, and sodium trimethylsilanolate to form a compound of Formula IV-a:

IV-a

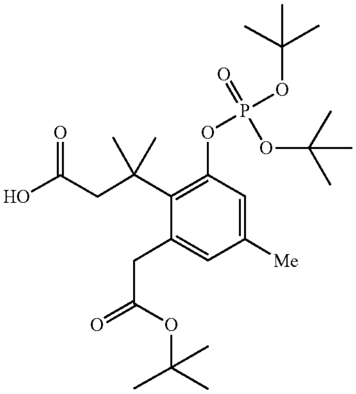

or a salt thereof, coupling the compound of Formula IV-a, or a salt thereof, with a compound of Formula III:

III

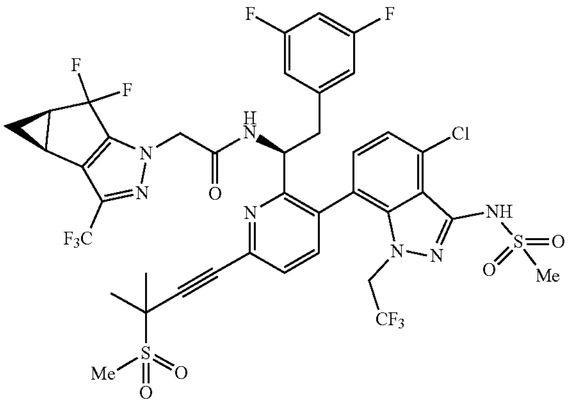

or a salt thereof, in the presence of propanephosphonic acid anhydride and 1-methylimidazole to form a compound of Formula II-a:

II-a

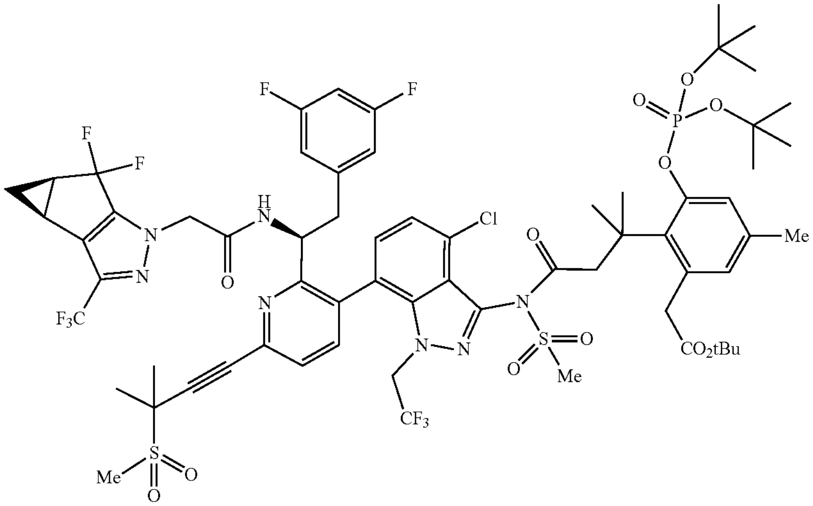

or a salt thereof; and deprotecting the compound of Formula II-a, or a salt thereof, with phosphoric acid to form the compound of Formula I, or a salt thereof.

25. The process of claim 23, wherein the compound of Formula III, or a salt thereof, is a sodium salt of the compound of Formula III.

26. A process of preparing a compound of Formula VI-a:

VI-a

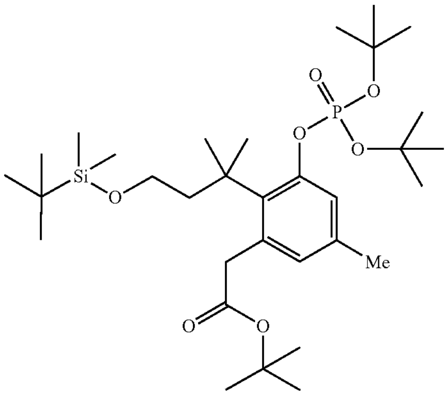

or a salt thereof, comprising reacting a compound of Formula VII-a:

VII-a

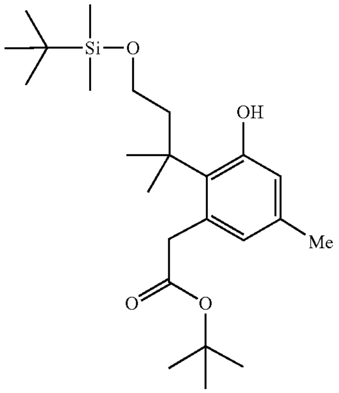

or a salt thereof, with di-tert-butyl N,N-diisopropylphosphoramidate in the presence of 1-methylimidazole and trifluoroacetic acid to form a first mixture; and mixing the first mixture with hydrogen peroxide to form the compound of Formula VI-a, or a salt thereof.

* * * * *